US012539364B2

(12) United States Patent
DiPerna et al.

(10) Patent No.: US 12,539,364 B2
(45) **Date of Patent: *Feb. 3, 2026**

(54) INFUSION PUMP SYSTEMS WITH DISPOSABLE CARTRIDGE HAVING PRESSURE VENTING AND PRESSURE FEEDBACK

(71) Applicant: Tandem Diabetes Care, Inc., San Diego, CA (US)

(72) Inventors: Paul M. DiPerna, Cardiff, CA (US); Michael J. Rosinko, Anaheim, CA (US); Geoffrey A. Kruse, San Diego, CA (US); Thomas R. Ulrich, Rancho Santa Margarita, CA (US); Christopher Dabrow, Santa Ana, CA (US); Mark Williamson, Wonder Lake, IL (US); Brian Bureson, San Diego, CA (US); Kathryn Rieger, Malvern, PA (US)

(73) Assignee: TANDEM DIABETES CARE, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/668,929

(22) Filed: May 20, 2024

(65) Prior Publication Data

US 2024/0299655 A1 Sep. 12, 2024

Related U.S. Application Data

(63) Continuation of application No. 17/478,530, filed on Sep. 17, 2021, now Pat. No. 12,042,627, which is a (Continued)

(51) Int. Cl.
*A61M 5/172* (2006.01)
*A61M 5/14* (2006.01)
(Continued)

(52) U.S. Cl.
CPC .......... *A61M 5/172* (2013.01); *A61M 5/1413* (2013.01); *A61M 5/14244* (2013.01);
(Continued)

(58) Field of Classification Search
CPC ................ A61M 5/172; A61M 5/1723; A61M 5/14244; G16H 20/17
See application file for complete search history.

(56) References Cited

U.S. PATENT DOCUMENTS 278,355 A 5/1883 Molera et al.
318,856 A 5/1885 Bliz
(Continued)

FOREIGN PATENT DOCUMENTS

CN 1229347 9/1999
CN 2668155 1/2005
(Continued)

OTHER PUBLICATIONS

Angiodynamics, “Smart Port, Power-Injectable Ports,” Product Bronchure, 2010, 4 pages.
(Continued)

*Primary Examiner* — Laura A Bouchelle
(74) *Attorney, Agent, or Firm* — Merchant & Gould P.C.

(57) ABSTRACT

Embodiments are directed to portable infusion devices, systems, and methods of using the same for dispensing materials. In some cases, the devices, systems and methods may be used for infusing a material such as medicament, e.g., insulin, into a body in need thereof.

20 Claims, 58 Drawing Sheets

Related U.S. Application Data continuation of application No. 16/502,248, filed on Jul. 3, 2019, now Pat. No. 11,135,362, which is a continuation of application No. 15/340,417, filed on Nov. 1, 2016, now Pat. No. 10,434,253, which is a continuation of application No. 12/846,688, filed on Jul. 29, 2010, now abandoned.

(60) Provisional application No. 61/230,061, filed on Jul. 30, 2009.

(51) Int. Cl.

| | |
|---|---|
| ***A61M 5/142*** | (2006.01) |
| ***A61M 5/315*** | (2006.01) |
| ***F04B 43/113*** | (2006.01) |
| ***F04B 53/14*** | (2006.01) |
| ***F16J 15/32*** | (2016.01) |
| ***F16J 15/56*** | (2006.01) |
| ***G16H 40/63*** | (2018.01) |
| *A61M 5/168* | (2006.01) |
| *G06F 3/0488* | (2022.01) |

(52) U.S. Cl.

CPC ...... *A61M 5/14248* (2013.01); *A61M 5/1723* (2013.01); *A61M 5/31513* (2013.01); *F04B 43/113* (2013.01); *F04B 53/143* (2013.01); *F16J 15/32* (2013.01); *F16J 15/56* (2013.01); *G16H 40/63* (2018.01); *A61M 2005/14268* (2013.01); *A61M 5/16804* (2013.01); *A61M 2205/3389* (2013.01); *A61M 2205/50* (2013.01); *A61M 2205/505* (2013.01); *A61M 2205/52* (2013.01); *A61M 2230/201* (2013.01); *A61M 2230/63* (2013.01); *G06F 3/0488* (2013.01)

(56) References Cited

U.S. PATENT DOCUMENTS

| | | | |
|---|---|---|---|
| 329,881 | A | 11/1885 | Benton |
| 332,402 | A | 12/1885 | Leadley |
| 596,062 | A | 12/1897 | Firey |
| 722,431 | A | 3/1903 | Packard et al. |
| 779,183 | A | 1/1905 | Renz |
| 818,938 | A | 4/1906 | Clarence |
| 926,092 | A | 6/1909 | William |
| 1,079,522 | A | 11/1913 | Paul |
| 1,274,884 | A | 8/1918 | Hudson et al. |
| 1,304,036 | A | 5/1919 | Eshielby |
| 1,314,987 | A | 9/1919 | Smith |
| 1,643,021 | A | 9/1927 | Ridder et al. |
| 1,657,663 | A | 1/1928 | Devereux |
| 1,866,061 | A | 7/1932 | Schoel et al. |
| 1,910,032 | A | 5/1933 | Mills |
| 2,018,316 | A | 10/1935 | Owings |
| 2,029,630 | A | 2/1936 | McMichael |
| 2,147,164 | A | 2/1939 | Kent |
| 2,398,234 | A | 4/1946 | Long |
| 2,412,397 | A | 12/1946 | Harper et al. |
| 2,444,677 | A | 7/1948 | Rosenblum |
| 2,454,929 | A | 11/1948 | Kempton |
| 2,462,596 | A | 2/1949 | Bent et al. |
| 2,495,693 | A | 1/1950 | Byrd et al. |
| 2,497,020 | A | 2/1950 | Singer |
| 2,568,519 | A | 9/1951 | Smith |
| 2,599,325 | A | 6/1952 | Fritzberg |
| 2,629,376 | A | 2/1953 | Pierre et al. |
| 2,629,402 | A | 2/1953 | Cook |
| 2,667,900 | A | 2/1954 | Cantalupo |
| 2,674,262 | A | 4/1954 | Bradshaw |
| 2,679,954 | A | 6/1954 | Barnes |
| 2,691,542 | A | 10/1954 | Chenoweth et al. |
| 2,701,583 | A | 2/1955 | Rux |
| 2,706,612 | A | 4/1955 | Ratelband |
| 2,735,642 | A | 2/1956 | Norman |
| 2,736,463 | A | 2/1956 | Levine |
| 2,746,709 | A | 5/1956 | Minor |
| 2,764,183 | A | 9/1956 | Gollehon |
| 2,781,058 | A | 2/1957 | Warhus |
| 2,834,379 | A | 5/1958 | Fields |
| 2,841,237 | A | 7/1958 | Slayter |
| 2,852,033 | A | 9/1958 | Orser |
| 2,878,836 | A | 3/1959 | Binks |
| 2,891,578 | A | 6/1959 | Dahl et al. |
| 2,898,078 | A | 8/1959 | Stephenson et al. |
| 2,898,088 | A | 8/1959 | Alder |
| 2,899,979 | A | 8/1959 | Dahl et al. |
| 2,936,788 | A | 5/1960 | Dahl et al. |
| 2,939,487 | A | 6/1960 | Fraser et al. |
| 2,960,109 | A | 11/1960 | Wilson |
| 2,968,318 | A | 1/1961 | Bauman |
| 2,971,466 | A | 2/1961 | Corebett et al. |
| 2,989,086 | A | 6/1961 | Dahl |
| 3,017,903 | A | 1/1962 | Steffens |
| 3,023,750 | A | 3/1962 | Baron |
| 3,035,613 | A | 5/1962 | Beatty |
| 3,059,639 | A | 10/1962 | Blackman et al. |
| 3,060,966 | A | 10/1962 | Ratelband |
| 3,061,039 | A | 10/1962 | Peters |
| 3,070,132 | A | 12/1962 | Sheridan |
| 3,072,151 | A | 1/1963 | Quercia |
| 3,077,903 | A | 2/1963 | Honsinger |
| 3,095,120 | A | 6/1963 | Steiner et al. |
| 3,095,175 | A | 6/1963 | Iketani |
| 3,118,646 | A | 1/1964 | Markey |
| 3,121,445 | A | 2/1964 | Wisniewski |
| 3,123,900 | A | 3/1964 | Millar |
| 3,133,678 | A | 5/1964 | Marwell et al. |
| 3,143,861 | A | 8/1964 | Dumas |
| 3,153,414 | A | 10/1964 | Beall et al. |
| 3,174,694 | A | 3/1965 | Kitabayashi |
| 3,187,562 | A | 6/1965 | Rolfson |
| 3,189,125 | A | 6/1965 | Windsor et al. |
| 3,195,586 | A | 7/1965 | Vogt |
| 3,202,178 | A | 8/1965 | Wolfe |
| 3,203,662 | A | 8/1965 | Lau |
| 3,214,903 | A | 11/1965 | Cochran |
| 3,216,451 | A | 11/1965 | Smallpeice |
| 3,227,311 | A | 1/1966 | Rowell |
| 3,298,394 | A | 1/1967 | Chorkey |
| 3,302,578 | A | 2/1967 | Anderson et al. |
| 3,318,138 | A | 5/1967 | Rolfson |
| 3,338,049 | A | 8/1967 | Fernberger |
| 3,347,418 | A | 10/1967 | Ferfferman |
| 3,376,625 | A | 4/1968 | McCulloch |
| 3,409,050 | A | 11/1968 | Weese |
| 3,428,223 | A | 2/1969 | Edward et al. |
| 3,430,659 | A | 3/1969 | Homer |
| 3,455,147 | A | 7/1969 | Adrian et al. |
| 3,464,359 | A | 9/1969 | King et al. |
| 3,471,079 | A | 10/1969 | Myers et al. |
| 3,479,002 | A | 11/1969 | Gene |
| 3,493,496 | A | 2/1970 | Bray et al. |
| 3,508,587 | A | 4/1970 | Hans |
| 3,532,125 | A | 10/1970 | Wilhelm et al. |
| 3,556,159 | A | 1/1971 | William |
| 3,568,847 | A | 3/1971 | Wayne |
| 3,583,603 | A | 6/1971 | Heinz et al. |
| 3,586,040 | A | 6/1971 | Leonard |
| 3,586,129 | A | 6/1971 | Cass et al. |
| 3,596,939 | A | 8/1971 | Glenn |
| 3,599,812 | A | 8/1971 | Hasstedt |
| 3,620,500 | A | 11/1971 | Louis |
| 3,621,882 | A | 11/1971 | Harry |
| 3,648,694 | A | 3/1972 | Ion et al. |
| 3,654,959 | A | 4/1972 | Aaron |
| 3,665,967 | A | 5/1972 | Joseph |
| 3,673,853 | A | 7/1972 | Griswold et al. |
| 3,674,183 | A | 7/1972 | Venable et al. |
| 3,675,672 | A | 7/1972 | Freeman |
| 3,693,484 | A | 9/1972 | Sanderson, Jr. |
| 3,696,958 | A | 10/1972 | Hong |

(56) References Cited

U.S. PATENT DOCUMENTS

| | | | |
|---|---|---|---|
| 3,717,174 | A | 2/1973 | Dewall |
| 3,724,234 | A | 4/1973 | Garavelli |
| 3,756,459 | A | 9/1973 | Bannister et al. |
| 3,833,019 | A | 9/1974 | Diggs |
| 3,836,113 | A | 9/1974 | Johnson |
| 3,836,794 | A | 9/1974 | Shimizu et al. |
| 3,837,363 | A | 9/1974 | Meronek |
| 3,847,178 | A | 11/1974 | Keppel |
| 3,860,353 | A | 1/1975 | Lukasik et al. |
| 3,894,538 | A | 7/1975 | Richter et al. |
| 3,899,135 | A | 8/1975 | O'Brian |
| 3,918,674 | A | 11/1975 | Sutter |
| 3,946,761 | A | 3/1976 | Thompson et al. |
| RE28,890 | E | 7/1976 | Ingram et al. |
| 3,970,105 | A | 7/1976 | Pelton et al. |
| 3,985,133 | A | 10/1976 | Jenkins et al. |
| 3,991,972 | A | 11/1976 | Eaton |
| 4,000,857 | A | 1/1977 | Moen |
| 4,003,398 | A | 1/1977 | Duveau |
| 4,023,772 | A | 5/1977 | Ratelband |
| 4,028,931 | A | 6/1977 | Bisera et al. |
| 4,032,265 | A | 6/1977 | Miller |
| 4,042,153 | A | 8/1977 | Callahan et al. |
| 4,076,872 | A | 2/1978 | Lewicki et al. |
| 4,087,301 | A | 5/1978 | Steadman |
| 4,089,206 | A | 5/1978 | Raffel et al. |
| 4,103,689 | A | 8/1978 | Leighton |
| 4,105,050 | A | 8/1978 | Hendrickson et al. |
| 4,106,510 | A | 8/1978 | Hakim et al. |
| 4,111,391 | A | 9/1978 | Pilolla |
| 4,137,913 | A | 2/1979 | Georgi |
| 4,156,127 | A | 5/1979 | Honda et al. |
| 4,178,938 | A | 12/1979 | Au |
| 4,191,184 | A | 3/1980 | Carlisle |
| 4,191,204 | A | 3/1980 | Nehring |
| 4,191,358 | A | 3/1980 | Ferri |
| 4,193,552 | A | 3/1980 | Ishikawa |
| 4,195,810 | A | 4/1980 | Lavin |
| 4,215,726 | A | 8/1980 | Tagami |
| 4,228,956 | A | 10/1980 | Varner |
| 4,248,270 | A | 2/1981 | Ostrowski |
| 4,250,872 | A | 2/1981 | Tamari |
| 4,254,791 | A | 3/1981 | Bron |
| 4,265,241 | A | 5/1981 | Portner et al. |
| 4,271,989 | A | 6/1981 | O'Neill et al. |
| 4,275,727 | A | 6/1981 | Keeri-Szanto |
| 4,306,556 | A | 12/1981 | Zelman |
| 4,314,621 | A | 2/1982 | Hansen |
| 4,314,979 | A | 2/1982 | Deabriges et al. |
| 4,327,845 | A | 5/1982 | Keyes et al. |
| 4,330,071 | A | 5/1982 | Ohlson |
| 4,344,459 | A | 8/1982 | Nelson |
| 4,356,935 | A | 11/1982 | Kamin |
| 4,367,786 | A | 1/1983 | Haefner et al. |
| 4,382,453 | A | 5/1983 | Bujan et al. |
| 4,403,984 | A | 9/1983 | Ash et al. |
| 4,405,294 | A | 9/1983 | Albarda et al. |
| 4,406,656 | A | 9/1983 | Hattler et al. |
| 4,411,651 | A | 10/1983 | Schulman et al. |
| 4,416,596 | A | 11/1983 | Lichtenstein et al. |
| 4,432,468 | A | 2/1984 | Siff et al. |
| 4,440,154 | A | 4/1984 | Bellows |
| 4,440,323 | A | 4/1984 | Benson |
| 4,443,218 | A | 4/1984 | Decant et al. |
| 4,444,546 | A | 4/1984 | Pazemenas |
| 4,445,885 | A | 5/1984 | Kifune |
| 4,448,538 | A | 5/1984 | Mantel |
| 4,457,343 | A | 7/1984 | Zukausky |
| 4,469,481 | A | 9/1984 | Kobayashi |
| 4,481,808 | A | 11/1984 | Sakata et al. |
| 4,492,339 | A | 1/1985 | Kreitzberg |
| 4,498,843 | A | 2/1985 | Schneider et al. |
| 4,508,144 | A | 4/1985 | Bernett |
| 4,515,536 | A | 5/1985 | van Os |
| 4,520,948 | A | 6/1985 | Hampel et al. |
| 4,527,595 | A | 7/1985 | Jorgensen et al. |
| 4,529,106 | A | 7/1985 | Broadfoot et al. |
| 4,529,401 | A | 7/1985 | Leslie et al. |
| 4,538,616 | A | 9/1985 | Rogoff |
| 4,557,726 | A | 12/1985 | Reinicke |
| 4,559,036 | A | 12/1985 | Wunsch |
| 4,559,038 | A | 12/1985 | Berg et al. |
| 4,562,751 | A | 1/1986 | Nason et al. |
| 4,562,960 | A | 1/1986 | Marty et al. |
| 4,565,542 | A | 1/1986 | Berg et al. |
| 4,570,745 | A | 2/1986 | Sparks et al. |
| 4,573,994 | A | 3/1986 | Fischell et al. |
| 4,592,390 | A | 6/1986 | Boyd |
| 4,609,014 | A | 9/1986 | Jurjevic et al. |
| 4,620,648 | A | 11/1986 | Schwartzman |
| 4,624,661 | A | 11/1986 | Arimond |
| 4,627,573 | A | 12/1986 | Havens et al. |
| 4,628,928 | A | 12/1986 | Lowell et al. |
| 4,636,226 | A | 1/1987 | Canfora et al. |
| 4,646,945 | A | 3/1987 | Steiner et al. |
| 4,649,959 | A | 3/1987 | Wadleigh |
| 4,650,469 | A | 3/1987 | Berg et al. |
| 4,650,471 | A | 3/1987 | Tamari |
| 4,651,781 | A | 3/1987 | Kandelman |
| 4,657,486 | A | 4/1987 | Stempfle et al. |
| 4,666,430 | A | 5/1987 | Brown et al. |
| 4,667,700 | A | 5/1987 | Buzzi |
| 4,673,415 | A | 6/1987 | Stanford et al. |
| 4,678,408 | A | 7/1987 | Nason et al. |
| 4,678,460 | A | 7/1987 | Rosner et al. |
| 4,684,364 | A | 8/1987 | Sawyer et al. |
| 4,684,367 | A | 8/1987 | Schaffer et al. |
| 4,685,903 | A | 8/1987 | Cable et al. |
| 4,687,423 | A | 8/1987 | Maget et al. |
| 4,699,615 | A | 10/1987 | Fischell et al. |
| 4,713,063 | A | 12/1987 | Krumme |
| 4,718,430 | A | 1/1988 | Holzer et al. |
| 4,718,893 | A | 1/1988 | Dorman et al. |
| 4,723,947 | A | 2/1988 | Konopka |
| 4,724,870 | A | 2/1988 | Molb et al. |
| 4,741,736 | A | 5/1988 | Brown et al. |
| 4,770,211 | A | 9/1988 | Olsson |
| 4,773,448 | A | 9/1988 | Francis |
| 4,776,842 | A | 10/1988 | Franetzki et al. |
| 4,778,451 | A | 10/1988 | Kamen |
| 4,779,762 | A | 10/1988 | Klein et al. |
| 4,787,408 | A | 11/1988 | Twerdochlib |
| 4,793,486 | A | 12/1988 | Konopka et al. |
| 4,808,167 | A | 2/1989 | Mann et al. |
| 4,810,243 | A | 3/1989 | Howson |
| 4,823,844 | A | 4/1989 | Bartholomew |
| 4,826,482 | A | 5/1989 | Kamen |
| 4,840,191 | A | 6/1989 | Gausman et al. |
| 4,850,972 | A | 7/1989 | Schulman et al. |
| 4,869,431 | A | 9/1989 | Jubert et al. |
| 4,871,093 | A | 10/1989 | Burshtain et al. |
| 4,878,896 | A | 11/1989 | Garrison et al. |
| 4,883,093 | A | 11/1989 | Miles et al. |
| 4,886,499 | A | 12/1989 | Cirelli et al. |
| 4,886,514 | A | 12/1989 | Maget |
| 4,893,966 | A | 1/1990 | Roehl |
| 4,897,906 | A | 2/1990 | Bartholomew |
| 4,902,278 | A | 2/1990 | Maget et al. |
| 4,908,017 | A | 3/1990 | Howson et al. |
| 4,919,596 | A | 4/1990 | Slate et al. |
| 4,931,050 | A | 6/1990 | Idriss et al. |
| 4,938,259 | A | 7/1990 | Schmidt |
| 4,938,832 | A | 7/1990 | Schmalz |
| 4,955,860 | A | 9/1990 | Ruano |
| 4,969,884 | A | 11/1990 | Yum |
| 4,973,402 | A | 11/1990 | Johnson et al. |
| 4,976,162 | A | 12/1990 | Kamen et al. |
| 4,985,015 | A | 1/1991 | Obermann et al. |
| 4,986,312 | A | 1/1991 | Gute |
| 4,989,456 | A | 2/1991 | Stupecky |
| 4,995,258 | A | 2/1991 | Frank |
| 5,000,739 | A | 3/1991 | Kulisz et al. |
| 5,002,527 | A | 3/1991 | Reller et al. |
| 5,005,403 | A | 4/1991 | Steudle et al. |

(56) References Cited

U.S. PATENT DOCUMENTS

| | | | |
|---|---|---|---|
| 5,006,997 | A | 4/1991 | Reich |
| 5,011,477 | A | 4/1991 | Winchell et al. |
| 5,020,562 | A | 6/1991 | Richmond et al. |
| 5,027,861 | A | 7/1991 | Gute |
| 5,035,865 | A | 7/1991 | Inaba et al. |
| 5,038,821 | A | 8/1991 | Maget |
| 5,041,086 | A | 8/1991 | Koenig et al. |
| 5,044,900 | A | 9/1991 | Cavallaro |
| 5,047,044 | A | 9/1991 | Smith et al. |
| 5,049,141 | A | 9/1991 | Olive |
| 5,050,612 | A | 9/1991 | Matsumura |
| 5,053,001 | A | 10/1991 | Reller et al. |
| 5,053,189 | A | 10/1991 | Chrise et al. |
| 5,059,171 | A | 10/1991 | Bridge et al. |
| 5,059,182 | A | 10/1991 | Laing |
| 5,062,834 | A | 11/1991 | Gross et al. |
| 5,062,841 | A | 11/1991 | Seigel |
| 5,076,911 | A | 12/1991 | Brown et al. |
| 5,078,683 | A | 1/1992 | Sancoff et al. |
| 5,080,653 | A | 1/1992 | Voss et al. |
| 5,082,240 | A | 1/1992 | Richmond |
| 5,082,503 | A | 1/1992 | Sluga et al. |
| 5,083,908 | A | 1/1992 | Gagnebin et al. |
| 5,084,021 | A | 1/1992 | Baldwin et al. |
| 5,085,644 | A | 2/1992 | Watson et al. |
| 5,087,245 | A | 2/1992 | Doan |
| 5,090,963 | A | 2/1992 | Gross et al. |
| 5,091,091 | A | 2/1992 | Terman |
| 5,091,094 | A | 2/1992 | Veech |
| 5,096,385 | A | 3/1992 | Georgi et al. |
| 5,097,122 | A | 3/1992 | Colman et al. |
| 5,103,211 | A | 4/1992 | Daoud et al. |
| 5,104,374 | A | 4/1992 | Bishko |
| 5,104,526 | A | 4/1992 | Brown et al. |
| 5,104,813 | A | 4/1992 | Besemer et al. |
| 5,108,363 | A | 4/1992 | Tuttle et al. |
| 5,125,781 | A | 6/1992 | Breunig et al. |
| 5,126,324 | A | 6/1992 | Clark et al. |
| 5,127,258 | A | 7/1992 | Brown et al. |
| 5,128,145 | A | 7/1992 | Edgren et al. |
| 5,131,816 | A | 7/1992 | Brown et al. |
| 5,135,491 | A | 8/1992 | Baldwin |
| 5,135,498 | A | 8/1992 | Kam et al. |
| 5,135,499 | A | 8/1992 | Tafani et al. |
| 5,148,154 | A | 9/1992 | MacKay et al. |
| 5,149,413 | A | 9/1992 | Maget |
| 5,154,712 | A | 10/1992 | Herweck et al. |
| 5,156,591 | A | 10/1992 | Gross et al. |
| 5,156,598 | A | 10/1992 | Skakoon et al. |
| 5,157,960 | A | 10/1992 | Brehm et al. |
| 5,158,230 | A | 10/1992 | Curran |
| 5,167,633 | A | 12/1992 | Mann et al. |
| 5,170,912 | A | 12/1992 | Du et al. |
| 5,170,986 | A | 12/1992 | Zelczer et al. |
| 5,173,302 | A | 12/1992 | Holmbald et al. |
| 5,176,502 | A | 1/1993 | Sanderson et al. |
| 5,176,644 | A | 1/1993 | Srisathapat et al. |
| 5,176,662 | A | 1/1993 | Bartholomew et al. |
| 5,178,603 | A | 1/1993 | Prince |
| 5,181,910 | A | 1/1993 | Scanlon |
| 5,182,258 | A | 1/1993 | Chiou |
| 5,184,359 | A | 2/1993 | Tsukamura et al. |
| 5,186,431 | A | 2/1993 | Tamari et al. |
| 5,186,805 | A | 2/1993 | Gross et al. |
| 5,188,258 | A | 2/1993 | Iwashita |
| 5,190,522 | A | 3/1993 | Wojcicki et al. |
| 5,191,719 | A | 3/1993 | Kitt |
| 5,192,264 | A | 3/1993 | Fossel |
| 5,192,272 | A | 3/1993 | Faure et al. |
| 5,197,322 | A | 3/1993 | Indravudh |
| 5,203,506 | A | 4/1993 | Gross et al. |
| 5,207,642 | A | 5/1993 | Orkin et al. |
| 5,207,645 | A | 5/1993 | Ross et al. |
| 5,207,666 | A | 5/1993 | Idriss et al. |
| 5,209,265 | A | 5/1993 | Taguri et al. |
| 5,215,450 | A | 6/1993 | Tamari et al. |
| 5,217,440 | A | 6/1993 | Frassica |
| 5,217,442 | A | 6/1993 | Davis |
| 5,218,987 | A | 6/1993 | Heil et al. |
| 5,220,515 | A | 6/1993 | Freerks et al. |
| 5,224,796 | A | 7/1993 | Zeman |
| 5,226,446 | A | 7/1993 | Cooper |
| 5,228,291 | A | 7/1993 | Meyering |
| 5,228,842 | A | 7/1993 | Guebeli et al. |
| 5,231,616 | A | 7/1993 | Oliver et al. |
| 5,232,437 | A | 8/1993 | Lysaght et al. |
| 5,232,449 | A | 8/1993 | Stern et al. |
| 5,240,603 | A | 8/1993 | Frank et al. |
| 5,241,935 | A | 9/1993 | Beck et al. |
| 5,242,406 | A | 9/1993 | Gross et al. |
| 5,242,408 | A | 9/1993 | Jhuboo et al. |
| 5,243,983 | A | 9/1993 | Tarr et al. |
| 5,246,147 | A | 9/1993 | Gross |
| 5,246,157 | A | 9/1993 | Siegel |
| 5,247,434 | A | 9/1993 | Peterson et al. |
| 5,254,096 | A | 10/1993 | Rondelet et al. |
| 5,257,971 | A | 11/1993 | Lord et al. |
| 5,257,980 | A | 11/1993 | Van et al. |
| 5,259,399 | A | 11/1993 | Brown |
| 5,259,732 | A | 11/1993 | Stern |
| 5,261,459 | A | 11/1993 | Atkinson et al. |
| 5,261,884 | A | 11/1993 | Stern et al. |
| 5,266,265 | A | 11/1993 | Raible |
| 5,270,005 | A | 12/1993 | Raible |
| 5,271,724 | A | 12/1993 | van Lintel |
| 5,272,294 | A | 12/1993 | Charboneau et al. |
| 5,272,909 | A | 12/1993 | Nguyen et al. |
| 5,273,406 | A | 12/1993 | Feygin |
| 5,273,518 | A | 12/1993 | Lee et al. |
| 5,278,142 | A | 1/1994 | Chiou |
| 5,279,543 | A | 1/1994 | Glikfeld et al. |
| 5,279,556 | A | 1/1994 | Goi et al. |
| 5,279,585 | A | 1/1994 | Balkwill |
| 5,279,586 | A | 1/1994 | Balkwill |
| 5,290,684 | A | 3/1994 | Kelly |
| 5,291,086 | A | 3/1994 | Shekalim |
| 5,294,133 | A | 3/1994 | Dutta |
| 5,295,966 | A | 3/1994 | Stern et al. |
| 5,295,967 | A | 3/1994 | Rondelet et al. |
| 5,295,976 | A | 3/1994 | Harris et al. |
| 5,303,843 | A | 4/1994 | Zink et al. |
| 5,304,126 | A | 4/1994 | Epstein et al. |
| 5,304,163 | A | 4/1994 | Bonnici et al. |
| 5,308,340 | A | 5/1994 | Harris |
| 5,312,233 | A | 5/1994 | Tanny et al. |
| 5,320,250 | A | 6/1994 | La et al. |
| 5,321,392 | A | 6/1994 | Skakoon et al. |
| 5,322,418 | A | 6/1994 | Comer et al. |
| 5,322,620 | A | 6/1994 | Brown et al. |
| 5,322,626 | A | 6/1994 | Frank et al. |
| 5,327,777 | A | 7/1994 | Kaye et al. |
| 5,328,460 | A | 7/1994 | Lord et al. |
| 5,328,464 | A | 7/1994 | Kriesel et al. |
| 5,334,144 | A | 8/1994 | Alchas et al. |
| 5,334,162 | A | 8/1994 | Harris |
| 5,335,705 | A | 8/1994 | Morishita et al. |
| 5,335,852 | A | 8/1994 | Muntean et al. |
| 5,336,051 | A | 8/1994 | Tamari et al. |
| 5,336,174 | A | 8/1994 | Daoud et al. |
| 5,336,180 | A | 8/1994 | Kriesel et al. |
| 5,336,188 | A | 8/1994 | Kriesel et al. |
| 5,337,747 | A | 8/1994 | Neftel |
| 5,338,157 | A | 8/1994 | Blomquist |
| 5,339,393 | A | 8/1994 | Duffy et al. |
| 5,339,865 | A | 8/1994 | Asghar et al. |
| 5,341,783 | A | 8/1994 | Beck et al. |
| 5,342,180 | A | 8/1994 | Daoud |
| 5,345,273 | A | 9/1994 | Sun |
| 5,345,488 | A | 9/1994 | Skipper et al. |
| 5,348,197 | A | 9/1994 | Mizzi et al. |
| 5,348,548 | A | 9/1994 | Meyer et al. |
| 5,349,933 | A | 9/1994 | Hasegawa et al. |
| 5,350,224 | A | 9/1994 | Nell et al. |
| 5,352,201 | A | 10/1994 | Jemmott |

(56) References Cited

U.S. PATENT DOCUMENTS 5,354,273 A 10/1994 Hagen
5,356,375 A 10/1994 Higley et al.
5,356,378 A 10/1994 Doan
5,356,632 A 10/1994 Gross et al.
5,358,489 A 10/1994 Wyrick
5,358,635 A 10/1994 Frank et al.
5,360,062 A 11/1994 White
5,360,734 A 11/1994 Chapman et al.
5,362,213 A 11/1994 Komatsu et al.
5,362,307 A 11/1994 Guy et al.
5,364,242 A 11/1994 Olsen et al.
5,364,387 A 11/1994 Sweeney
5,366,904 A 11/1994 Qureshi et al.
5,367,910 A 11/1994 Woodward et al.
5,368,555 A 11/1994 Sussman et al.
5,368,562 A 11/1994 Blomquist et al.
5,369,976 A 12/1994 Ratton
5,370,622 A 12/1994 Livingston et al.
5,370,870 A 12/1994 Wong
5,373,865 A 12/1994 Jung et al.
5,376,070 A 12/1994 Purvis et al.
5,381,823 A 1/1995 Dibartolo
5,384,709 A 1/1995 Seder et al.
5,387,192 A 2/1995 Glantz et al.
5,387,327 A 2/1995 Khan
5,388,453 A 2/1995 Ratton et al.
5,389,071 A 2/1995 Kawahara et al.
5,389,078 A 2/1995 Zalesky et al.
5,389,091 A 2/1995 Moorehead
5,390,671 A 2/1995 Lord et al.
5,391,250 A 2/1995 Cheney, II et al.
5,395,320 A 3/1995 Padda et al.
5,395,324 A 3/1995 Hinrichs et al.
5,395,326 A 3/1995 Haber et al.
5,399,166 A 3/1995 Laing
5,403,551 A 4/1995 Galloway et al.
5,407,444 A 4/1995 Kroll
5,410,908 A 5/1995 Erichsen
5,411,685 A 5/1995 Burgis
5,415,024 A 5/1995 Proffitt et al.
5,418,154 A 5/1995 Aebischer et al.
5,421,208 A 6/1995 Packard et al.
5,423,743 A 6/1995 Butterfield
5,425,374 A 6/1995 Ueda et al.
5,425,706 A 6/1995 Gross et al.
5,425,742 A 6/1995 Joy
5,427,870 A 6/1995 Joshi et al.
5,429,483 A 7/1995 Tamari
5,429,601 A 7/1995 Conley et al.
5,431,171 A 7/1995 Harrison et al.
5,431,208 A 7/1995 Aoki et al.
5,431,627 A 7/1995 Pastrone et al.
5,433,710 A 7/1995 Vanantwerp et al.
5,435,465 A 7/1995 El-Amin
5,435,697 A 7/1995 Guebeli et al.
5,435,797 A 7/1995 Harris
5,438,510 A 8/1995 Bryant et al.
5,441,027 A 8/1995 Buchanon et al.
5,442,948 A 8/1995 Cowing
5,442,950 A 8/1995 Unalmiser et al.
5,443,450 A 8/1995 Kratoska et al.
5,445,506 A 8/1995 Afflerbaugh et al.
5,445,616 A 8/1995 Kratoska et al.
5,447,509 A 9/1995 Mills et al.
5,447,863 A 9/1995 Langley
5,448,034 A 9/1995 Skipper et al.
5,448,978 A 9/1995 Hasegawa et al.
5,450,750 A 9/1995 Abler
5,454,922 A 10/1995 Joshi et al.
5,458,469 A 10/1995 Hauser
5,460,030 A 10/1995 Bloxsom et al.
5,460,605 A 10/1995 Tuttle et al.
5,460,618 A 10/1995 Harreld
5,460,945 A 10/1995 Springer et al.
5,462,417 A 10/1995 Chapman
5,462,525 A 10/1995 Srisathapat et al.
5,462,535 A 10/1995 Bonnichsen et al.
5,464,392 A 11/1995 Epstein et al.
5,464,398 A 11/1995 Haindl
5,466,218 A 11/1995 Srisathapat et al.
5,466,229 A 11/1995 Elson et al.
5,469,846 A 11/1995 Khan
5,470,318 A 11/1995 Griffith, III et al.
5,472,577 A 12/1995 Porter et al.
5,476,444 A 12/1995 Keeling et al.
5,476,449 A 12/1995 Richmond
5,476,460 A 12/1995 Montalvo
5,478,316 A 12/1995 Bitdinger et al.
5,478,751 A 12/1995 Oosta et al.
5,480,294 A 1/1996 DiPerna et al.
5,480,381 A 1/1996 Weston et al.
5,482,446 A 1/1996 Williamson et al.
5,482,745 A 1/1996 Cuellar et al.
5,483,930 A 1/1996 Moriya et al.
5,485,408 A 1/1996 Blomquist
5,487,528 A 1/1996 Richmond
5,489,265 A 2/1996 Montalvo et al.
5,492,534 A 2/1996 Athayde et al.
5,494,578 A 2/1996 Brown et al.
5,497,772 A 3/1996 Schulman et al.
5,498,421 A 3/1996 Grinstaff et al.
5,503,538 A 4/1996 Wiernicki et al.
5,505,709 A 4/1996 Funderburk et al.
5,505,777 A 4/1996 Ciardella et al.
5,509,294 A 4/1996 Gowing
5,510,336 A 4/1996 Saven et al.
5,514,103 A 5/1996 Srisathapat et al.
5,518,730 A 5/1996 Suisz
5,522,798 A 6/1996 Johnson et al.
5,526,675 A 6/1996 Ratton
5,527,288 A 6/1996 Gross et al.
5,527,307 A 6/1996 Srisathapat et al.
5,527,704 A 6/1996 Wolf, Jr. et al.
5,528,624 A 6/1996 Kaku et al.
5,531,697 A 7/1996 Olsen et al.
5,531,698 A 7/1996 Olsen et al.
5,533,876 A 7/1996 Nelson, II
5,533,981 A 7/1996 Mandro et al.
5,536,249 A 7/1996 Castellano et al.
5,538,002 A 7/1996 Boussignac et al.
5,538,043 A 7/1996 Salazar
5,538,399 A 7/1996 Johnson
5,540,562 A 7/1996 Giter
5,544,519 A 8/1996 Hammarberg et al.
5,545,140 A 8/1996 Conero et al.
5,545,252 A 8/1996 Hinshaw et al.
5,549,458 A 8/1996 Chapman et al.
5,551,391 A 9/1996 Beck et al.
5,551,850 A 9/1996 Williamson et al.
5,554,177 A 9/1996 Kieval et al.
5,556,421 A 9/1996 Prutchi et al.
5,558,638 A 9/1996 Evers et al.
5,562,079 A 10/1996 Gray
5,562,618 A 10/1996 Cai et al.
5,563,347 A 10/1996 Martin et al.
5,564,915 A 10/1996 Johnson
5,566,865 A 10/1996 Jouillat et al.
5,567,136 A 10/1996 Johnson
5,567,287 A 10/1996 Joshi et al.
5,568,038 A 10/1996 Tatsumi
5,568,806 A 10/1996 Cheney, II et al.
5,568,884 A 10/1996 Bruna
5,569,186 A 10/1996 Lord et al.
5,575,310 A 11/1996 Kamen et al.
5,575,632 A 11/1996 Morris et al.
5,575,770 A 11/1996 Melsky et al.
5,578,005 A 11/1996 Sancoff et al.
5,578,014 A 11/1996 Erez et al.
5,578,832 A 11/1996 Trulson et al.
5,582,168 A 12/1996 Samuels et al.
5,584,667 A 12/1996 Davis
5,584,815 A 12/1996 Pawelka et al.
5,586,553 A 12/1996 Halili et al.
5,586,727 A 12/1996 Shekalim

(56) References Cited

U.S. PATENT DOCUMENTS

| | | | |
|---|---|---|---|
| 5,590,648 | A | 1/1997 | Mitchell et al. |
| 5,593,552 | A | 1/1997 | Joshi et al. |
| 5,602,040 | A | 2/1997 | May et al. |
| 5,603,729 | A | 2/1997 | Brown et al. |
| 5,605,152 | A | 2/1997 | Slate et al. |
| 5,605,701 | A | 2/1997 | Bymaster et al. |
| 5,606,131 | A | 2/1997 | Pope |
| 5,607,418 | A | 3/1997 | Arzbaecher |
| 5,613,945 | A | 3/1997 | Cai et al. |
| 5,615,671 | A | 4/1997 | Schoonen et al. |
| 5,616,123 | A | 4/1997 | Cheikh |
| 5,616,132 | A | 4/1997 | Newman |
| 5,617,650 | A | 4/1997 | Grim |
| 5,621,797 | A | 4/1997 | Rosen |
| RE35,501 | E | 5/1997 | Ross et al. |
| 5,626,566 | A | 5/1997 | Petersen et al. |
| 5,628,324 | A | 5/1997 | Sarbach |
| 5,628,349 | A | 5/1997 | Diggins et al. |
| 5,628,922 | A | 5/1997 | Chen |
| 5,634,491 | A | 6/1997 | Benedict |
| 5,634,779 | A | 6/1997 | Eysymontt |
| 5,634,896 | A | 6/1997 | Bryant et al. |
| 5,637,095 | A | 6/1997 | Nason et al. |
| 5,639,220 | A | 6/1997 | Hayakawa |
| 5,639,441 | A | 6/1997 | Sievers et al. |
| 5,639,473 | A | 6/1997 | Grinstaff et al. |
| 5,641,405 | A | 6/1997 | Keshaviah et al. |
| 5,643,773 | A | 7/1997 | Aebischer et al. |
| 5,645,526 | A | 7/1997 | Flower |
| 5,647,853 | A | 7/1997 | Feldmann et al. |
| 5,647,854 | A | 7/1997 | Olsen et al. |
| 5,651,980 | A | 7/1997 | Lanza et al. |
| 5,653,386 | A | 8/1997 | Hennessee et al. |
| 5,656,032 | A | 8/1997 | Kriesel et al. |
| 5,656,501 | A | 8/1997 | Yedgar et al. |
| 5,656,503 | A | 8/1997 | May et al. |
| 5,658,250 | A | 8/1997 | Blomquist et al. |
| 5,658,252 | A | 8/1997 | Johnson |
| 5,659,126 | A | 8/1997 | Farber |
| 5,660,150 | A | 8/1997 | Andersen et al. |
| 5,660,163 | A | 8/1997 | Schulman et al. |
| 5,665,065 | A | 9/1997 | Colman et al. |
| 5,665,070 | A | 9/1997 | McPhee |
| 5,669,877 | A | 9/1997 | Blomquist |
| 5,671,874 | A | 9/1997 | Behar et al. |
| 5,676,651 | A | 10/1997 | Larson et al. |
| 5,681,285 | A | 10/1997 | Ford et al. |
| 5,681,435 | A | 10/1997 | Joshi et al. |
| 5,685,844 | A | 11/1997 | Marttila |
| 5,688,113 | A | 11/1997 | Bareiss et al. |
| 5,688,225 | A | 11/1997 | Walker |
| 5,688,232 | A | 11/1997 | Flower |
| 5,693,018 | A | 12/1997 | Kriesel et al. |
| 5,694,961 | A | 12/1997 | Begemann et al. |
| 5,695,464 | A | 12/1997 | Viallet |
| 5,695,472 | A | 12/1997 | Wyrick |
| 5,695,473 | A | 12/1997 | Olsen |
| 5,697,092 | A | 12/1997 | Mourant et al. |
| 5,700,244 | A | 12/1997 | Kriesel |
| 5,702,384 | A | 12/1997 | Umeyama et al. |
| 5,704,366 | A | 1/1998 | Tacklind et al. |
| 5,704,520 | A | 1/1998 | Gross |
| 5,707,212 | A | 1/1998 | Matthews |
| 5,707,361 | A | 1/1998 | Slettenmark |
| 5,711,989 | A | 1/1998 | Ciardella et al. |
| 5,712,795 | A | 1/1998 | Layman et al. |
| 5,713,856 | A | 2/1998 | Eggers et al. |
| 5,713,858 | A | 2/1998 | Heruth et al. |
| 5,718,562 | A | 2/1998 | Lawless et al. |
| 5,719,761 | A | 2/1998 | Gatti et al. |
| 5,720,241 | A | 2/1998 | Gail |
| 5,720,921 | A | 2/1998 | Meserol |
| 5,722,367 | A | 3/1998 | Izydorek et al. |
| 5,728,396 | A | 3/1998 | Peery et al. |
| 5,730,149 | A | 3/1998 | Nakayama et al. |
| 5,730,723 | A | 3/1998 | Castellano et al. |
| 5,735,618 | A | 4/1998 | Kriesel et al. |
| 5,738,650 | A | 4/1998 | Gregg |
| 5,740,718 | A | 4/1998 | Renirie et al. |
| 5,741,242 | A | 4/1998 | Kriesel |
| 5,743,291 | A | 4/1998 | Nehm et al. |
| 5,743,873 | A | 4/1998 | Cai et al. |
| 5,746,733 | A | 5/1998 | Capaccio et al. |
| 5,755,683 | A | 5/1998 | Houle et al. |
| 5,755,696 | A | 5/1998 | Caizza |
| 5,759,018 | A | 6/1998 | Thanscheidt |
| 5,759,199 | A | 6/1998 | Snell et al. |
| 5,762,931 | A | 6/1998 | Talwar et al. |
| 5,763,267 | A | 6/1998 | Kurjan et al. |
| 5,763,398 | A | 6/1998 | Bengtsson |
| 5,765,464 | A | 6/1998 | Morita |
| 5,765,729 | A | 6/1998 | Miller et al. |
| 5,769,615 | A | 6/1998 | Giter |
| 5,770,149 | A | 6/1998 | Raible |
| 5,770,160 | A | 6/1998 | Smith et al. |
| 5,771,770 | A | 6/1998 | Mueller |
| 5,772,409 | A | 6/1998 | Johnson |
| 5,772,635 | A | 6/1998 | Dastur et al. |
| 5,782,805 | A | 7/1998 | Meinzer et al. |
| 5,785,681 | A | 7/1998 | Indravudh |
| 5,785,688 | A | 7/1998 | Joshi et al. |
| 5,788,642 | A | 8/1998 | Hamatake et al. |
| 5,788,669 | A | 8/1998 | Peterson |
| 5,788,671 | A | 8/1998 | Johnson |
| 5,788,682 | A | 8/1998 | Maget, Jr. |
| 5,792,603 | A | 8/1998 | Dunkelman et al. |
| 5,794,505 | A | 8/1998 | Fischer et al. |
| 5,794,515 | A | 8/1998 | Bethke |
| 5,795,327 | A | 8/1998 | Wilson et al. |
| 5,797,867 | A | 8/1998 | Guerrera et al. |
| 5,798,114 | A | 8/1998 | Elsberry et al. |
| 5,800,387 | A | 9/1998 | Duffy et al. |
| 5,800,420 | A | 9/1998 | Gross et al. |
| 5,803,319 | A | 9/1998 | Smith et al. |
| 5,803,917 | A | 9/1998 | Butterfield et al. |
| 5,807,315 | A | 9/1998 | Van et al. |
| 5,807,335 | A | 9/1998 | Kriesel et al. |
| 5,807,336 | A | 9/1998 | Russo et al. |
| 5,807,374 | A | 9/1998 | Caizza et al. |
| 5,807,375 | A | 9/1998 | Gross et al. |
| 5,810,737 | A | 9/1998 | Dardik |
| 5,810,771 | A | 9/1998 | Blomquist |
| 5,810,783 | A | 9/1998 | Claro et al. |
| 5,814,020 | A | 9/1998 | Gross |
| 5,814,100 | A | 9/1998 | Carpentier et al. |
| 5,820,587 | A | 10/1998 | Place |
| 5,820,589 | A | 10/1998 | Torgerson et al. |
| 5,820,622 | A | 10/1998 | Gross et al. |
| 5,822,715 | A | 10/1998 | Worthington et al. |
| 5,823,388 | A | 10/1998 | Green |
| 5,823,746 | A | 10/1998 | Johnson et al. |
| 5,823,998 | A | 10/1998 | Yamagata |
| 5,826,621 | A | 10/1998 | Jemmott |
| 5,830,175 | A | 11/1998 | Flower et al. |
| 5,830,187 | A | 11/1998 | Kriesel et al. |
| 5,837,220 | A | 11/1998 | Blake et al. |
| 5,837,444 | A | 11/1998 | Shah |
| 5,840,069 | A | 11/1998 | Robinson |
| 5,840,071 | A | 11/1998 | Kriesel et al. |
| 5,840,770 | A | 11/1998 | Hill |
| 5,848,593 | A | 12/1998 | McGrady et al. |
| 5,848,880 | A | 12/1998 | Helmig |
| 5,848,990 | A | 12/1998 | Cirelli et al. |
| 5,848,991 | A | 12/1998 | Gross et al. |
| 5,849,031 | A | 12/1998 | Martinez et al. |
| 5,849,737 | A | 12/1998 | Chaplan et al. |
| 5,851,197 | A | 12/1998 | Marano et al. |
| 5,851,198 | A | 12/1998 | Castellano et al. |
| 5,851,549 | A | 12/1998 | Svec |
| 5,851,985 | A | 12/1998 | Tepic et al. |
| 5,854,074 | A | 12/1998 | Charlton et al. |
| 5,854,719 | A | 12/1998 | Ginosar et al. |
| 5,858,001 | A | 1/1999 | Tsals et al. |
| 5,858,201 | A | 1/1999 | Otsuka et al. |

(56) References Cited

U.S. PATENT DOCUMENTS 5,858,388 A 1/1999 Grossman et al.
5,858,393 A 1/1999 Bymaster et al.
5,859,365 A 1/1999 Kataoka et al.
5,860,957 A 1/1999 Jacobsen et al.
5,863,187 A 1/1999 Bensley et al.
5,865,603 A 2/1999 Francart
5,871,125 A 2/1999 Gross
5,871,515 A 2/1999 Wiklund et al.
5,873,857 A 2/1999 Kriesel
5,876,189 A 3/1999 Lukas et al.
5,876,368 A 3/1999 Flower
5,876,370 A 3/1999 Blomquist
5,877,146 A 3/1999 McKenzie et al.
5,877,216 A 3/1999 Place et al.
5,878,992 A 3/1999 Edwards et al.
5,879,143 A 3/1999 Cote et al.
5,879,144 A 3/1999 Johnson
5,880,101 A 3/1999 Stankov
5,882,494 A 3/1999 Van Antwerp
5,883,138 A 3/1999 Hershkowitz et al.
5,885,211 A 3/1999 Eppstein et al.
5,885,250 A 3/1999 Kriesel et al.
5,885,614 A 3/1999 Hirsch
5,886,056 A 3/1999 Hershkowitz et al.
5,887,793 A 3/1999 Kieffer
5,890,413 A 4/1999 Bayer et al.
5,891,097 A 4/1999 Saito et al.
5,893,708 A 4/1999 Nelson, II
5,894,992 A 4/1999 Liu et al.
5,895,369 A 4/1999 Flower
5,897,530 A 4/1999 Jackson
5,902,336 A 5/1999 Mishkin et al.
5,903,710 A 5/1999 Wefler et al.
5,912,005 A 6/1999 Lanza et al.
5,916,191 A 6/1999 Plunkett et al.
5,919,156 A 7/1999 Stropkay et al.
5,919,209 A 7/1999 Schouten
5,919,216 A 7/1999 Houben et al.
5,924,448 A 7/1999 West et al.
5,924,456 A 7/1999 Simon
5,925,629 A 7/1999 Place
5,928,194 A 7/1999 Maget et al.
5,928,196 A 7/1999 Johnson et al.
5,928,201 A 7/1999 Poulsen et al.
5,928,281 A 7/1999 Huynh et al.
5,931,814 A 8/1999 Alex et al.
5,933,287 A 8/1999 Mueller
5,935,099 A 8/1999 Peterson et al.
5,935,106 A 8/1999 Olsen
5,935,168 A 8/1999 Yang et al.
5,935,598 A 8/1999 Sage et al.
5,938,636 A 8/1999 Kramer et al.
5,938,640 A 8/1999 Maget et al.
5,938,642 A 8/1999 Burroughs et al.
5,941,846 A 8/1999 Duffy et al.
5,944,694 A 8/1999 Hitchins et al.
5,948,367 A 9/1999 Gmeiner et al.
5,950,879 A 9/1999 Ritsche
5,951,521 A 9/1999 Mastrototaro et al.
5,951,523 A 9/1999 Oesterlind et al.
5,954,485 A 9/1999 Johnson et al.
5,954,643 A 9/1999 Vanantwerp et al.
5,954,685 A 9/1999 Tierney et al.
5,954,696 A 9/1999 Ryan et al.
5,954,697 A 9/1999 Srisathapat et al.
5,954,700 A 9/1999 Kovelman
5,954,752 A 9/1999 Mongeon et al.
5,957,861 A 9/1999 Combs et al.
5,957,885 A 9/1999 Bollish et al.
5,957,889 A 9/1999 Poulsen et al.
5,957,890 A 9/1999 Mann et al.
5,957,895 A 9/1999 Sage et al.
5,958,760 A 9/1999 Freeman
5,959,598 A 9/1999 McKnight
5,960,403 A 9/1999 Brown
5,961,305 A 10/1999 Eek et al.
5,961,483 A 10/1999 Sage et al.
5,962,566 A 10/1999 Grandfils et al.
5,962,794 A 10/1999 Kriesel et al.
5,964,377 A 10/1999 Demarest et al.
5,964,724 A 10/1999 Rivera et al.
5,971,722 A 10/1999 Maget et al.
5,973,012 A 10/1999 Behrmann et al.
5,976,109 A 11/1999 Heruth et al.
5,980,489 A 11/1999 Kriesel
5,980,596 A 11/1999 Hershkowitz et al.
5,983,976 A 11/1999 Kono
5,984,894 A 11/1999 Poulsen et al.
5,984,897 A 11/1999 Petersen et al.
5,984,906 A 11/1999 Bonnichsen et al.
5,985,305 A 11/1999 Peery et al.
5,988,165 A 11/1999 Richey, II et al.
5,988,851 A 11/1999 Gent
5,988,998 A 11/1999 Glover
5,989,216 A 11/1999 Johnson et al.
5,989,222 A 11/1999 Cole et al.
5,989,238 A 11/1999 Ginsburg
5,989,409 A 11/1999 Kurnik et al.
5,990,809 A 11/1999 Howard
5,992,695 A 11/1999 Start
5,993,421 A 11/1999 Kriesel
5,993,425 A 11/1999 Kriesel
5,995,860 A 11/1999 Sun et al.
5,997,475 A 12/1999 Bortz
5,997,501 A 12/1999 Gross et al.
5,997,518 A 12/1999 Laibovitz et al.
6,001,089 A 12/1999 Burroughs et al.
6,001,585 A 12/1999 Gramer
6,003,566 A 12/1999 Thibault et al.
6,003,736 A 12/1999 Ljunggren
6,006,800 A 12/1999 Nakano
6,007,314 A 12/1999 Nelson, II
6,007,518 A 12/1999 Kriesel et al.
6,012,034 A 1/2000 Hamparian et al.
6,012,492 A 1/2000 Kozyuk
6,013,020 A 1/2000 Meloul et al.
6,016,044 A 1/2000 Holdaway
6,017,318 A 1/2000 Gauthier et al.
6,017,545 A 1/2000 Modi
6,019,747 A 2/2000 McPhee
6,023,629 A 2/2000 Tamada
6,023,641 A 2/2000 Thompson
6,024,009 A 2/2000 Morita
6,024,539 A 2/2000 Blomquist
6,024,699 A 2/2000 Surwit et al.
6,030,358 A 2/2000 Odland
6,030,363 A 2/2000 Kriesel
6,033,377 A 3/2000 Rasmussen et al.
6,034,054 A 3/2000 Defelippis et al.
6,035,639 A 3/2000 Kolmanovsky et al.
6,037,346 A 3/2000 Doherty, Jr. et al.
6,038,960 A 3/2000 Fukushima et al.
6,040,834 A 3/2000 Jain et al.
6,042,561 A 3/2000 Ash et al.
RE36,654 E 4/2000 Conner et al.
6,045,537 A 4/2000 Klitmose
6,048,337 A 4/2000 Svedman et al.
6,051,256 A 4/2000 Platz et al.
6,053,887 A 4/2000 Levitas et al.
6,056,522 A 5/2000 Johnson
6,056,718 A 5/2000 Funderburk et al.
6,059,507 A 5/2000 Adams
6,059,753 A 5/2000 Faust et al.
6,062,022 A 5/2000 Folsom et al.
6,062,531 A 5/2000 Rapp et al.
6,063,053 A 5/2000 Castellano et al.
6,063,059 A 5/2000 Kriesel
6,065,279 A 5/2000 Kuromitsu et al.
6,065,289 A 5/2000 Phillips
6,065,941 A 5/2000 Gray et al.
6,070,761 A 6/2000 Bloom et al.
6,071,423 A 6/2000 Brown et al.
6,073,048 A 6/2000 Kieval et al.
6,074,359 A 6/2000 Keshaviah et al.

(56) References Cited

U.S. PATENT DOCUMENTS

| | | | |
|---|---|---|---|
| 6,077,055 | A | 6/2000 | Vilks |
| 6,077,246 | A | 6/2000 | Kullas et al. |
| 6,080,130 | A | 6/2000 | Castellano et al. |
| 6,083,710 | A | 7/2000 | Heller et al. |
| 6,086,561 | A | 7/2000 | Kriesel et al. |
| 6,086,562 | A | 7/2000 | Jacobsen et al. |
| 6,093,167 | A | 7/2000 | Houben et al. |
| 6,093,172 | A | 7/2000 | Funderburk et al. |
| 6,093,312 | A | 7/2000 | Boulter et al. |
| 6,095,134 | A | 8/2000 | Sievers et al. |
| 6,096,216 | A | 8/2000 | Shanbrom et al. |
| 6,099,293 | A | 8/2000 | Kern et al. |
| 6,099,495 | A | 8/2000 | Kinghorn et al. |
| 6,099,604 | A | 8/2000 | Gross et al. |
| 6,102,127 | A | 8/2000 | Pierce |
| 6,103,033 | A | 8/2000 | Say et al. |
| 6,103,275 | A | 8/2000 | Seitz et al. |
| 6,105,442 | A | 8/2000 | Kriesel et al. |
| 6,106,477 | A | 8/2000 | Miesel et al. |
| 6,109,896 | A | 8/2000 | Schuller et al. |
| 6,110,148 | A | 8/2000 | Brown et al. |
| 6,110,149 | A | 8/2000 | Klitgaard et al. |
| 6,110,152 | A | 8/2000 | Kovelman |
| 6,110,427 | A | 8/2000 | Uffenheimer |
| RE36,871 | E | 9/2000 | Epstein et al. |
| 6,113,782 | A | 9/2000 | Leonard |
| 6,117,122 | A | 9/2000 | Din et al. |
| 6,120,460 | A | 9/2000 | Abreu |
| 6,122,536 | A | 9/2000 | Sun et al. |
| 6,123,175 | A | 9/2000 | Fett |
| 6,123,686 | A | 9/2000 | Olsen et al. |
| 6,126,642 | A | 10/2000 | Kriesel et al. |
| 6,126,956 | A | 10/2000 | Grossman et al. |
| 6,127,363 | A | 10/2000 | Doherty, Jr. et al. |
| 6,132,686 | A | 10/2000 | Gallup et al. |
| 6,135,196 | A | 10/2000 | Kono |
| 6,135,949 | A | 10/2000 | Russo et al. |
| 6,135,978 | A | 10/2000 | Houben et al. |
| D433,755 | S | 11/2000 | Mastrototaro et al. |
| 6,142,939 | A | 11/2000 | Eppstein et al. |
| 6,143,238 | A | 11/2000 | Konishi et al. |
| 6,143,252 | A | 11/2000 | Haxo, Jr. et al. |
| 6,144,866 | A | 11/2000 | Miesel et al. |
| 6,144,869 | A | 11/2000 | Berner et al. |
| 6,145,625 | A | 11/2000 | Prokop et al. |
| 6,146,361 | A | 11/2000 | Dibiasi et al. |
| 6,147,070 | A | 11/2000 | Facchini |
| 6,147,109 | A | 11/2000 | Liao et al. |
| 6,152,898 | A | 11/2000 | Olsen et al. |
| 6,155,748 | A | 12/2000 | Allen et al. |
| 6,156,753 | A | 12/2000 | Doherty, Jr. et al. |
| 6,158,431 | A | 12/2000 | Poole |
| 6,158,965 | A | 12/2000 | Butterfield et al. |
| 6,163,721 | A | 12/2000 | Thompson |
| 6,164,924 | A | 12/2000 | Gruett et al. |
| 6,165,155 | A | 12/2000 | Jacobsen et al. |
| 6,165,460 | A | 12/2000 | Schlom |
| 6,167,290 | A | 12/2000 | Yang et al. |
| 6,168,575 | B1 | 1/2001 | Soltanpour |
| 6,175,752 | B1 | 1/2001 | Say et al. |
| 6,176,692 | B1 | 1/2001 | Reinartz et al. |
| 6,178,996 | B1 | 1/2001 | Suzuki |
| 6,179,583 | B1 | 1/2001 | Weston |
| 6,180,416 | B1 | 1/2001 | Kurnik et al. |
| 6,180,597 | B1 | 1/2001 | Liao |
| 6,186,982 | B1 | 2/2001 | Gross et al. |
| 6,190,359 | B1 | 2/2001 | Heruth et al. |
| 6,198,383 | B1 | 3/2001 | Sekura et al. |
| 6,202,708 | B1 | 3/2001 | Bynum et al. |
| 6,205,961 | B1 | 3/2001 | Bailey et al. |
| 6,210,135 | B1 | 4/2001 | Rassin et al. |
| 6,210,361 | B1 | 4/2001 | Kamen et al. |
| 6,210,368 | B1 | 4/2001 | Rogers et al. |
| 6,210,957 | B1 | 4/2001 | Carpentier et al. |
| 6,211,147 | B1 | 4/2001 | Unemori |
| 6,211,426 | B1 | 4/2001 | Abrams |
| 6,212,948 | B1 | 4/2001 | Ekdahl et al. |
| 6,213,120 | B1 | 4/2001 | Block et al. |
| 6,213,408 | B1 | 4/2001 | Shekalim |
| 6,217,826 | B1 | 4/2001 | Reeder et al. |
| 6,218,666 | B1 | 4/2001 | Lukica et al. |
| 6,221,378 | B1 | 4/2001 | Modi |
| 6,223,080 | B1 | 4/2001 | Thompson |
| 6,223,703 | B1 | 5/2001 | Galvin |
| 6,223,746 | B1 | 5/2001 | Jewett et al. |
| 6,224,347 | B1 | 5/2001 | Clark et al. |
| 6,224,352 | B1 | 5/2001 | Hauser et al. |
| 6,225,999 | B1 | 5/2001 | Jain et al. |
| 6,227,818 | B1 | 5/2001 | Falk et al. |
| 6,228,044 | B1 | 5/2001 | Jensen et al. |
| 6,229,584 | B1 | 5/2001 | Chuo et al. |
| 6,231,545 | B1 | 5/2001 | Kriesel et al. |
| 6,231,560 | B1 | 5/2001 | Bui et al. |
| 6,231,882 | B1 | 5/2001 | Modi |
| 6,232,609 | B1 | 5/2001 | Snyder et al. |
| 6,233,471 | B1 | 5/2001 | Berner et al. |
| 6,236,887 | B1 | 5/2001 | Ben-Haim et al. |
| 6,238,423 | B1 | 5/2001 | Bardy |
| 6,241,704 | B1 | 6/2001 | Peterson et al. |
| 6,241,743 | B1 | 6/2001 | Levin et al. |
| 6,245,347 | B1 | 6/2001 | Zhang et al. |
| 6,247,493 | B1 | 6/2001 | Henderson |
| 6,248,067 | B1 | 6/2001 | Causey, III et al. |
| 6,248,093 | B1 | 6/2001 | Moberg et al. |
| 6,248,280 | B1 | 6/2001 | Kern et al. |
| 6,251,098 | B1 | 6/2001 | Rake et al. |
| 6,251,293 | B1 | 6/2001 | Snodgrass et al. |
| 6,251,932 | B1 | 6/2001 | Reichelt et al. |
| 6,254,355 | B1 | 7/2001 | Gharib |
| 6,254,569 | B1 | 7/2001 | O'Donnell et al. |
| 6,254,576 | B1 | 7/2001 | Shekalim |
| 6,254,586 | B1 | 7/2001 | Mann et al. |
| 6,256,533 | B1 | 7/2001 | Yuzhakov et al. |
| 6,257,178 | B1 | 7/2001 | Laimboeck |
| 6,257,191 | B1 | 7/2001 | Kutlucinar |
| 6,261,272 | B1 | 7/2001 | Gross et al. |
| 6,261,280 | B1 | 7/2001 | Houben et al. |
| 6,264,439 | B1 | 7/2001 | Falk et al. |
| 6,264,680 | B1 | 7/2001 | Ash |
| 6,266,564 | B1 | 7/2001 | Hill et al. |
| 6,267,564 | B1 | 7/2001 | Rapheal |
| 6,269,340 | B1 | 7/2001 | Ford et al. |
| 6,270,478 | B1 | 8/2001 | Mernoee |
| 6,272,364 | B1 | 8/2001 | Kurnik |
| 6,275,717 | B1 | 8/2001 | Gross et al. |
| 6,276,434 | B1 | 8/2001 | Kono |
| 6,277,095 | B1 | 8/2001 | Kriesel et al. |
| 6,277,097 | B1 | 8/2001 | Mikkelsen et al. |
| 6,277,819 | B1 | 8/2001 | Efendic |
| 6,280,408 | B1 | 8/2001 | Sipin et al. |
| 6,280,409 | B1 | 8/2001 | Stone et al. |
| 6,280,416 | B1 | 8/2001 | Van et al. |
| 6,283,197 | B1 | 9/2001 | Kono |
| 6,283,680 | B1 | 9/2001 | Vidal |
| 6,283,943 | B1 | 9/2001 | Dy et al. |
| 6,283,944 | B1 | 9/2001 | McMullen et al. |
| 6,283,949 | B1 | 9/2001 | Roorda et al. |
| 6,284,725 | B1 | 9/2001 | Coolidge et al. |
| 6,288,518 | B1 | 9/2001 | Yang et al. |
| 6,289,248 | B1 | 9/2001 | Conley et al. |
| 6,290,683 | B1 | 9/2001 | Erez et al. |
| 6,293,159 | B1 | 9/2001 | Kriesel et al. |
| 6,293,242 | B1 | 9/2001 | Kutlucinar |
| 6,293,429 | B2 | 9/2001 | Sadler et al. |
| 6,293,756 | B1 | 9/2001 | Andersson |
| 6,294,550 | B1 | 9/2001 | Place et al. |
| 6,296,456 | B1 | 10/2001 | Thornelow et al. |
| 6,296,623 | B2 | 10/2001 | Spinello |
| 6,298,254 | B2 | 10/2001 | Tamada |
| 6,298,760 | B1 | 10/2001 | Truttmann et al. |
| 6,298,941 | B1 | 10/2001 | Spadafora |
| 6,299,415 | B1 | 10/2001 | Bahrton |
| 6,299,578 | B1 | 10/2001 | Kurnik et al. |
| 6,302,107 | B1 | 10/2001 | Richey, II et al. |

(56) References Cited

U.S. PATENT DOCUMENTS 6,302,653 B1 10/2001 Bryant et al.
6,302,855 B1 10/2001 Lav et al.
6,304,911 B1 10/2001 Brcich et al.
6,306,420 B1 10/2001 Cheikh
6,306,841 B1 10/2001 Place et al.
6,309,351 B1 10/2001 Kurnik et al.
6,309,371 B1 10/2001 Deboer et al.
6,310,270 B1 10/2001 Huang et al.
6,312,409 B1 11/2001 Gross
6,314,317 B1 11/2001 Willis et al.
6,315,769 B1 11/2001 Peer et al.
6,319,215 B1 11/2001 Manor et al.
6,319,245 B1 11/2001 Berrigan
6,323,022 B1 11/2001 Chang et al.
6,325,999 B1 12/2001 Bellgrau et al.
6,327,964 B1 12/2001 Schuller et al.
6,328,004 B1 12/2001 Rynhart
6,331,172 B1 12/2001 Epstein et al.
6,334,761 B1 1/2002 Tai et al.
6,338,942 B2 1/2002 Kraus et al.
6,340,357 B1 1/2002 Poulsen et al.
6,340,421 B1 1/2002 Vachon et al.
6,340,783 B1 1/2002 Snow
6,341,232 B1 1/2002 Conn et al.
6,342,037 B1 1/2002 Roe et al.
6,342,484 B1 1/2002 Kulkarni et al.
6,344,457 B1 2/2002 Jeanpetit et al.
6,346,095 B1 2/2002 Gross et al.
6,350,589 B1 2/2002 Morris et al.
6,355,030 B1 3/2002 Aldrich et al.
6,358,225 B1 3/2002 Butterfield
6,358,519 B1 3/2002 Waterman
6,360,888 B1 3/2002 McIvor et al.
6,362,591 B1 3/2002 Moberg
6,364,865 B1 4/2002 Lavi et al.
6,365,185 B1 4/2002 Ritschel et al.
6,365,628 B1 4/2002 Berge
6,366,808 B1 4/2002 Schroeppel et al.
6,368,272 B1 4/2002 Porumbescu
6,368,314 B1 4/2002 Kipfer et al.
6,371,732 B1 4/2002 Moubayed et al.
6,372,182 B1 4/2002 Mauro et al.
6,372,508 B1 4/2002 Shnizer et al.
6,374,683 B1 4/2002 Hunicke-Smith et al.
6,374,876 B2 4/2002 Bynum et al.
6,375,638 B2 4/2002 Nason et al.
6,381,493 B1 4/2002 Stadler et al.
6,382,923 B1 5/2002 Gray
6,393,318 B1 5/2002 Conn et al.
6,393,893 B1 5/2002 Fetz et al.
6,394,981 B2 5/2002 Heruth et al.
6,395,292 B2 5/2002 Peery et al.
6,395,536 B2 5/2002 Freeman
6,397,199 B1 5/2002 Goodwin, III
6,398,718 B1 6/2002 Yachia et al.
6,398,760 B1 6/2002 Danby et al.
6,399,024 B1 6/2002 Bevirt et al.
6,402,689 B1 6/2002 Scarantino et al.
6,406,455 B1 6/2002 Willis et al.
6,409,698 B1 6/2002 Robinson et al.
6,412,273 B1 7/2002 Rohs
6,413,238 B1 7/2002 Maget
6,413,254 B1 7/2002 Hissong et al.
6,415,961 B2 7/2002 Bonningue
6,416,215 B1 7/2002 Terentiev
6,416,291 B1 7/2002 Butterfield et al.
6,416,293 B1 7/2002 Bouchard et al.
6,420,169 B1 7/2002 Read et al.
6,422,057 B1 7/2002 Anderson
6,422,256 B1 7/2002 Balazy et al.
6,423,029 B1 7/2002 Elsberry
6,423,035 B1 7/2002 Das et al.
6,423,344 B1 7/2002 Platz et al.
6,424,847 B1 7/2002 Mastrototaro et al.
6,425,740 B1 7/2002 Jacobsen et al.
6,425,878 B1 7/2002 Shekalim
6,427,088 B1 7/2002 Bowman, IV et al.
6,428,491 B1 8/2002 Weiss
6,429,197 B1 8/2002 Coolidge et al.
6,429,230 B1 8/2002 Cavazza
6,429,232 B1 8/2002 Kinsella et al.
6,433,040 B1 8/2002 Dellamary et al.
6,436,072 B1 8/2002 Kullas et al.
6,436,078 B1 8/2002 Svedman et al.
6,438,408 B1 8/2002 Mulligan et al.
6,438,414 B1 8/2002 Conn et al.
6,440,096 B1 8/2002 Lastovich et al.
6,441,036 B1 8/2002 Berge
6,442,433 B1 8/2002 Linberg
6,443,097 B1 9/2002 Zohar et al.
6,443,942 B2 9/2002 Van et al.
6,446,513 B1 9/2002 Henderson
6,447,443 B1 9/2002 Keogh et al.
6,447,446 B1 9/2002 Smith et al.
6,447,475 B1 9/2002 Castellano
6,447,522 B2 9/2002 Gambale et al.
6,450,942 B1 9/2002 Lapanashvili et al.
6,450,953 B1 9/2002 Place et al.
6,454,707 B1 9/2002 Casscells, III et al.
6,454,785 B2 9/2002 De et al.
6,457,958 B1 10/2002 Hauser et al.
6,458,102 B1 10/2002 Mann et al.
6,458,109 B1 10/2002 Henley et al.
6,458,256 B1 10/2002 Zhong
6,458,762 B1 10/2002 McKenzie et al.
6,461,329 B1 10/2002 Van et al.
6,461,331 B1 10/2002 Van
6,461,334 B1 10/2002 Buch-Rasmussen et al.
6,461,828 B1 10/2002 Stanton et al.
6,463,794 B1 10/2002 Moshe et al.
6,464,667 B1 10/2002 Kamen et al.
6,467,267 B2 10/2002 Kanazawa et al.
6,468,200 B1 10/2002 Fischi
6,468,242 B1 10/2002 Wilson et al.
6,469,016 B1 10/2002 Place et al.
6,470,234 B1 10/2002 McGrady
6,471,496 B1 10/2002 Merklein et al.
6,471,689 B1 10/2002 Joseph et al.
6,471,855 B1 10/2002 Odak et al.
6,472,434 B1 10/2002 Place et al.
6,474,219 B2 11/2002 Klitmose et al.
6,475,180 B2 11/2002 Peterson et al.
6,475,750 B1 11/2002 Han et al.
6,477,774 B1 11/2002 Marando et al.
6,478,385 B2 11/2002 Nishii et al.
6,478,771 B1 11/2002 Lavi et al.
6,482,186 B1 11/2002 Douglas
6,484,906 B2 11/2002 Bonningue
6,485,263 B1 11/2002 Bryant et al.
6,485,452 B1 11/2002 French et al.
6,485,461 B1 11/2002 Mason et al.
6,485,463 B1 11/2002 Yeh
6,485,464 B1 11/2002 Christenson et al.
6,485,465 B2 11/2002 Moberg et al.
6,485,471 B1 11/2002 Zivitz et al.
6,488,652 B1 12/2002 Weijand et al.
6,488,697 B1 12/2002 Ariura et al.
6,489,346 B1 12/2002 Phillips
6,490,483 B2 12/2002 Willis et al.
6,494,865 B1 12/2002 Alchas et al.
6,500,150 B1 12/2002 Gross et al.
6,505,059 B1 1/2003 Kollias et al.
6,506,594 B1 1/2003 Barany et al.
6,508,788 B2 1/2003 Preuthun
6,511,435 B1 1/2003 Bluth et al.
6,512,949 B1 1/2003 Combs et al.
6,514,689 B2 2/2003 Han et al.
6,517,482 B1 2/2003 Elden et al.
6,520,936 B1 2/2003 Mann et al.
6,520,938 B1 2/2003 Funderburk et al.
6,522,980 B1 2/2003 Arnold
6,530,900 B1 3/2003 Daily et al.
6,533,183 B2 3/2003 Aasmul et al.
6,535,714 B2 3/2003 Melker et al.

(56) References Cited

U.S. PATENT DOCUMENTS 6,537,241 B1 3/2003 Klitmose
6,537,268 B1 3/2003 Gibson et al.
6,537,272 B2 3/2003 Christopherson et al.
6,540,008 B1 4/2003 Kono
6,540,161 B1 4/2003 Gordon
6,540,727 B2 4/2003 Harper et al.
6,540,996 B1 4/2003 Zwaal et al.
6,541,021 B1 4/2003 Johnson et al.
6,542,774 B2 4/2003 Hill et al.
6,542,775 B2 4/2003 Ding et al.
6,544,212 B2 4/2003 Galley et al.
6,544,229 B1 4/2003 Danby et al.
6,544,233 B1 4/2003 Fukui et al.
6,546,269 B1 4/2003 Kurnik
6,547,775 B1 4/2003 Blyakhman
6,550,245 B2 4/2003 Nishii et al.
6,551,276 B1 4/2003 Mann et al.
6,551,277 B1 4/2003 Ford
6,551,992 B1 4/2003 Defelippis et al.
6,553,244 B2 4/2003 Lesho et al.
6,553,245 B1 4/2003 Grace et al.
6,554,798 B1 4/2003 Mann et al.
6,554,800 B1 4/2003 Nezhadian et al.
6,555,986 B2 4/2003 Moberg
6,557,454 B2 5/2003 Miyazawa
6,558,320 B1 5/2003 Causey, III et al.
6,558,345 B1 5/2003 Houben et al.
6,558,351 B1 5/2003 Steil et al.
6,558,665 B1 5/2003 Cohen et al.
6,558,902 B1 5/2003 Hillenkamp
6,560,478 B1 5/2003 Alfano et al.
6,561,978 B1 5/2003 Conn et al.
6,562,001 B2 5/2003 Lebel et al.
6,564,093 B1 5/2003 Ostrow et al.
6,564,104 B2 5/2003 Nelson et al.
6,564,105 B2 5/2003 Starkweather et al.
6,565,802 B1 5/2003 Hanley et al.
6,565,872 B2 5/2003 Wu et al.
6,568,898 B2 5/2003 Nishimura et al.
6,568,922 B1 5/2003 Winsel
6,569,123 B2 5/2003 Alchas et al.
6,569,143 B2 5/2003 Alchas et al.
6,569,456 B2 5/2003 Faour et al.
6,571,128 B2 5/2003 Lebel et al.
6,571,831 B1 6/2003 Houben et al.
6,572,542 B1 6/2003 Effenhauser et al.
6,572,586 B1 6/2003 Wojcik
6,575,935 B1 6/2003 Oliver et al.
6,577,899 B2 6/2003 Lebel et al.
6,579,496 B1 6/2003 Fausset et al.
6,582,366 B1 6/2003 Porumbescu
6,582,393 B2 6/2003 Sage et al.
6,582,418 B1 6/2003 Verbeek et al.
6,583,111 B1 6/2003 Dimarchi et al.
6,585,644 B2 7/2003 Lebel et al.
6,585,695 B1 7/2003 Adair et al.
6,585,707 B2 7/2003 Cabiri et al.
6,587,705 B1 7/2003 Kim et al.
6,589,158 B2 7/2003 Winkler et al.
6,589,229 B1 7/2003 Connelly et al.
6,592,544 B1 7/2003 Mooney et al.
6,592,572 B1 7/2003 Verbeek et al.
6,592,860 B1 7/2003 Levy et al.
6,592,904 B2 7/2003 Platz et al.
6,593,313 B2 7/2003 Place et al.
6,594,514 B2 7/2003 Berner et al.
6,594,634 B1 7/2003 Hampton et al.
6,595,756 B2 7/2003 Gray et al.
6,595,919 B2 7/2003 Berner et al.
6,595,948 B2 7/2003 Suzuki et al.
6,595,956 B1 7/2003 Gross et al.
6,599,281 B1 7/2003 Struys et al.
6,602,241 B2 8/2003 Makower et al.
6,604,908 B1 8/2003 Bryant et al.
6,605,072 B2 8/2003 Struys et al.
6,607,513 B1 8/2003 Down et al.
6,607,658 B1 8/2003 Heller et al.
6,607,739 B1 8/2003 Wallo
6,609,653 B1 8/2003 Lapstun et al.
6,610,003 B1 8/2003 Meloul et al.
6,612,535 B1 9/2003 Tai et al.
6,613,019 B2 9/2003 Munk
6,616,196 B1 9/2003 Weh et al.
6,616,627 B2 9/2003 Willis et al.
6,618,603 B2 9/2003 Varalli et al.
6,620,140 B1 9/2003 Metzger
6,620,379 B1 9/2003 Piuk et al.
6,623,698 B2 9/2003 Kuo
6,625,479 B1 9/2003 Weber et al.
6,626,644 B2 9/2003 Ozaki
6,629,934 B2 10/2003 Mault et al.
6,629,938 B1 10/2003 Engvall et al.
6,629,949 B1 10/2003 Douglas
6,629,954 B1 10/2003 Heruth et al.
6,634,939 B2 10/2003 Johnson et al.
6,635,014 B2 10/2003 Starkweather et al.
6,635,048 B1 10/2003 Ullestad et al.
6,636,796 B2 10/2003 Kolmanovsky et al.
6,639,381 B2 10/2003 Tamura et al.
6,641,533 B2 11/2003 Causey, III et al.
6,641,562 B1 11/2003 Peterson et al.
6,641,565 B1 11/2003 Lavi et al.
6,641,566 B2 11/2003 Douglas
6,642,019 B1 11/2003 Anderson et al.
6,645,176 B1 11/2003 Christenson et al.
6,645,181 B1 11/2003 Lavi et al.
6,645,448 B2 11/2003 Cho et al.
6,648,821 B2 11/2003 Lebel et al.
6,648,859 B2 11/2003 Bitdinger et al.
6,648,861 B2 11/2003 Platt et al.
6,649,403 B1 11/2003 McDevitt et al.
6,650,919 B2 11/2003 Edelberg et al.
6,650,951 B1 11/2003 Jones et al.
6,651,546 B2 11/2003 Sandlin et al.
6,652,493 B1 11/2003 Das
6,652,510 B2 11/2003 Lord et al.
6,653,091 B1 11/2003 Dunn et al.
6,656,114 B1 12/2003 Poulsen et al.
6,656,148 B2 12/2003 Das et al.
6,656,158 B2 12/2003 Mahoney et al.
6,656,159 B2 12/2003 Flaherty et al.
6,659,948 B2 12/2003 Lebel et al.
6,659,978 B1 12/2003 Kasuga et al.
6,659,980 B2 12/2003 Moberg et al.
6,662,466 B2 12/2003 Gurer
6,663,359 B2 12/2003 Gray et al.
6,663,602 B2 12/2003 Moller et al.
6,666,665 B1 12/2003 Nguyen et al.
6,666,821 B2 12/2003 Keimel
6,668,196 B1 12/2003 Villegas et al.
6,668,701 B1 12/2003 Everitt
6,669,663 B1 12/2003 Thompson
6,669,669 B2 12/2003 Flaherty et al.
6,673,033 B1 1/2004 Sciulli et al.
6,676,387 B1 1/2004 Penn et al.
6,677,320 B2 1/2004 Diederich et al.
6,679,865 B2 1/2004 Shikalim
6,682,497 B2 1/2004 Jensen et al.
6,683,690 B1 1/2004 Tobias
6,687,522 B2 2/2004 Tamada
6,687,546 B2 2/2004 Lebel et al.
6,689,100 B2 2/2004 Connelly et al.
6,689,108 B2 2/2004 Lavi et al.
6,689,118 B2 2/2004 Alchas et al.
6,689,373 B2 2/2004 Johnson et al.
6,692,456 B1 2/2004 Eppstein et al.
6,692,457 B2 2/2004 Flaherty
6,692,472 B2 2/2004 Hansen et al.
6,692,473 B2 2/2004 St. Cyr et al.
6,694,191 B2 2/2004 Starkweather et al.
6,695,011 B2 2/2004 Sochtig
6,696,090 B1 2/2004 Nilsson et al.
6,696,493 B2 2/2004 Cavazza
6,699,218 B2 3/2004 Flaherty et al.

(56) References Cited

U.S. PATENT DOCUMENTS 6,699,234 B2 3/2004 Yeh et al.
6,699,665 B1 3/2004 Phillips
6,702,779 B2 3/2004 Connelly et al.
6,702,857 B2 3/2004 Brauker et al.
6,705,845 B2 3/2004 Krieger et al.
6,706,008 B2 3/2004 Vishnoi et al.
6,706,009 B2 3/2004 Diermann et al.
6,706,689 B2 3/2004 Coolidge et al.
6,710,051 B1 3/2004 Trier
6,711,489 B2 3/2004 Haskara et al.
6,712,095 B2 3/2004 Williamson et al.
6,715,516 B2 4/2004 Ohms et al.
6,716,190 B1 4/2004 Glines et al.
6,716,198 B2 4/2004 Larsen
6,718,206 B2 4/2004 Casavant
6,719,302 B2 4/2004 Andrick
6,723,068 B2 4/2004 Lavi et al.
6,723,072 B2 4/2004 Flaherty et al.
6,726,920 B1 4/2004 Theeuwes et al.
6,732,573 B2 5/2004 Shin et al.
6,733,446 B2 5/2004 Lebel et al.
6,734,186 B1 5/2004 Maw et al.
6,736,796 B2 5/2004 Shekalim
6,738,663 B2 5/2004 Schroeppel et al.
6,738,707 B2 5/2004 Kotwicki et al.
6,740,059 B2 5/2004 Flaherty
6,740,072 B2 5/2004 Starkweather et al.
6,740,075 B2 5/2004 Lebel et al.
6,743,201 B1 6/2004 Doenig et al.
6,743,202 B2 6/2004 Hirschman et al.
6,744,152 B2 6/2004 Kroll
6,744,350 B2 6/2004 Blomquist
6,745,079 B2 6/2004 King
6,746,438 B1 6/2004 Arnissolle
6,748,930 B2 6/2004 Bofinger et al.
6,749,403 B2 6/2004 Bryant et al.
6,749,587 B2 6/2004 Flaherty
6,752,785 B2 6/2004 Van et al.
6,752,787 B1 6/2004 Causey, III et al.
6,755,628 B1 6/2004 Howell
6,755,810 B1 6/2004 Bush-Rasmussen et al.
6,758,593 B1 7/2004 Terentiev
6,758,810 B2 7/2004 Lebel et al.
6,759,386 B2 7/2004 Franco
6,767,188 B2 7/2004 Vrane et al.
6,767,896 B1 7/2004 McIntosh et al.
6,768,425 B2 7/2004 Flaherty et al.
6,769,364 B2 8/2004 Dougherty
6,770,054 B1 8/2004 Smolyarov et al.
6,770,067 B2 8/2004 Lorenzen et al.
6,773,669 B1 8/2004 Holaday et al.
6,773,739 B2 8/2004 Hauck et al.
6,775,577 B2 8/2004 Crnkovich et al.
6,776,776 B2 8/2004 Alchas et al.
6,780,156 B2 8/2004 Haueter et al.
6,780,171 B2 8/2004 Gabel et al.
6,780,426 B2 8/2004 Zhang et al.
6,780,770 B2 8/2004 Larson
6,780,836 B2 8/2004 Unemori
6,783,107 B2 8/2004 Chatufale
6,783,328 B2 8/2004 Lucke et al.
6,786,246 B2 9/2004 Ohms et al.
6,790,670 B2 9/2004 Munagavalasa et al.
6,796,956 B2 9/2004 Hartlaub et al.
6,801,420 B2 10/2004 Talbot et al.
6,804,002 B2 10/2004 Fine et al.
6,804,555 B2 10/2004 Warkentin
6,805,687 B2 10/2004 Dextradeur et al.
6,808,122 B2 10/2004 Richey, II et al.
6,808,506 B2 10/2004 Lastovich et al.
6,810,290 B2 10/2004 Lebel et al.
6,811,533 B2 11/2004 Lebel et al.
6,811,534 B2 11/2004 Bowman et al.
6,811,792 B2 11/2004 Roser et al.
6,813,519 B2 11/2004 Lebel et al.
6,813,964 B1 11/2004 Clark et al.
6,814,547 B2 11/2004 Childers et al.
6,821,249 B2 11/2004 Casscells et al.
6,821,484 B1 11/2004 Gregersen
6,824,529 B2 11/2004 Gross et al.
6,827,524 B2 12/2004 Starry et al.
6,827,702 B2 12/2004 Lebel et al.
6,827,710 B1 12/2004 Mooney et al.
6,827,898 B1 12/2004 Fausset et al.
6,828,552 B2 12/2004 Hartley
6,830,558 B2 12/2004 Flaherty et al.
6,830,560 B1 12/2004 Gross et al.
6,835,175 B1 12/2004 Porumbescu
6,835,194 B2 12/2004 Johnson et al.
6,842,642 B2 1/2005 Vanhout
6,843,782 B2 1/2005 Gross et al.
6,847,898 B1 1/2005 Chen et al.
6,851,449 B2 2/2005 Kleibrink
6,852,104 B2 2/2005 Blomquist
6,852,487 B1 2/2005 Barany et al.
6,854,432 B2 2/2005 Hirano et al.
6,854,620 B2 2/2005 Ramey
6,858,011 B2 2/2005 Sehgal
6,858,403 B2 2/2005 Han et al.
6,859,673 B2 2/2005 Steffen
6,864,101 B1 3/2005 Winkler et al.
6,867,196 B1 3/2005 Wolff et al.
6,868,358 B2 3/2005 Brown et al.
6,872,200 B2 3/2005 Mann et al.
6,873,268 B2 3/2005 Lebel et al.
6,876,885 B2 4/2005 Swoyer et al.
6,877,713 B1 4/2005 Gray et al.
6,880,564 B2 4/2005 Erickson
6,882,940 B2 4/2005 Potts et al.
6,884,122 B2 4/2005 Robinson et al.
6,884,228 B2 4/2005 Brown et al.
6,885,881 B2 4/2005 Leonardt
6,885,888 B2 4/2005 Rezai
6,886,556 B2 5/2005 Fuchs
6,892,755 B2 5/2005 Black et al.
6,892,900 B2 5/2005 Drechsel
6,893,415 B2 5/2005 Madsen et al.
6,894,024 B2 5/2005 Coolidge et al.
6,895,263 B2 5/2005 Shin et al.
6,896,666 B2 5/2005 Kochamba
6,899,699 B2 5/2005 Enggaard
RE38,749 E 6/2005 Dardik
6,902,905 B2 6/2005 Burson et al.
6,905,314 B2 6/2005 Danby
6,905,479 B1 6/2005 Bouchard et al.
6,906,028 B2 6/2005 Defelippis et al.
6,908,591 B2 6/2005 MacPhee et al.
6,909,840 B2 6/2005 Harwig et al.
6,912,425 B2 6/2005 Nova et al.
6,913,933 B2 7/2005 Jacobs et al.
6,914,076 B2 7/2005 Cavazza
6,916,010 B2 7/2005 Beck et al.
6,916,159 B2 7/2005 Rush et al.
6,918,542 B2 7/2005 Silverbrook et al.
6,923,006 B2 8/2005 Walton et al.
6,923,180 B2 8/2005 Richey, II et al.
6,923,764 B2 8/2005 Aceti et al.
6,926,694 B2 8/2005 Marano-Ford et al.
6,928,338 B1 8/2005 Buchser et al.
6,930,093 B2 8/2005 Brantl
6,931,845 B2 8/2005 Schaeffer
6,931,925 B2 8/2005 Huemer et al.
6,932,114 B2 8/2005 Sparks
6,932,584 B2 8/2005 Gray et al.
6,932,796 B2 8/2005 Sage et al.
6,935,531 B1 8/2005 Clayton et al.
6,935,539 B2 8/2005 Krieger et al.
6,936,026 B2 8/2005 Diermann et al.
6,936,029 B2 8/2005 Mann et al.
6,936,035 B2 8/2005 Rake et al.
6,936,046 B2 8/2005 Hissong et al.
6,939,323 B2 9/2005 Angel et al.
6,939,324 B2 9/2005 Gonnelli et al.
6,942,636 B2 9/2005 Holst et al.

(56) References Cited

U.S. PATENT DOCUMENTS 6,943,034 B1 9/2005 Winkler et al.
6,945,760 B2 9/2005 Gray et al.
6,946,117 B1 9/2005 Schutt et al.
6,948,918 B2 9/2005 Hansen et al.
6,949,081 B1 9/2005 Chance
6,950,708 B2 9/2005 Bowman et al.
6,951,165 B2 10/2005 Kuhn et al.
6,951,553 B2 10/2005 Bubb et al.
6,952,604 B2 10/2005 Denuzzio et al.
6,952,963 B2 10/2005 Delnevo
6,953,323 B2 10/2005 Childers et al.
6,955,819 B2 10/2005 Zhang et al.
6,955,915 B2 10/2005 Fodor et al.
6,956,204 B2 10/2005 Dong et al.
6,957,655 B2 10/2005 Erickson et al.
6,957,924 B1 10/2005 McMeekin et al.
6,958,073 B2 10/2005 Rogers et al.
6,958,691 B1 10/2005 Anderson et al.
6,958,705 B2 10/2005 Lebel et al.
6,960,184 B2 11/2005 Willis et al.
6,960,192 B1 11/2005 Flaherty et al.
6,962,103 B2 11/2005 Sandlin
6,962,151 B1 11/2005 Knoch et al.
6,963,770 B2 11/2005 Knoch et al.
6,966,325 B2 11/2005 Erickson
6,966,895 B2 11/2005 Tribe
6,969,369 B2 11/2005 Struble et al.
6,970,741 B1 11/2005 Whitehurst et al.
6,970,742 B2 11/2005 Mann et al.
6,971,999 B2 12/2005 Py et al.
6,973,374 B2 12/2005 Ader
6,974,055 B2 12/2005 Moore et al.
6,974,115 B2 12/2005 Silva et al.
6,974,437 B2 12/2005 Lebel et al.
6,974,438 B2 12/2005 Shekalim
6,974,588 B1 12/2005 Miranda et al.
6,979,308 B1 12/2005 MacDonald et al.
6,979,315 B2 12/2005 Rogers et al.
6,979,316 B1 12/2005 Rubin et al.
6,979,326 B2 12/2005 Mann et al.
6,980,855 B2 12/2005 Cho
6,981,499 B2 1/2006 Anderson et al.
6,981,967 B2 1/2006 Massengale et al.
6,982,248 B2 1/2006 Coolidge et al.
6,983,209 B2 1/2006 Jaynes
6,985,770 B2 1/2006 Nyhart et al.
6,985,771 B2 1/2006 Fischell et al.
6,986,867 B2 1/2006 Hanley et al.
6,987,129 B2 1/2006 Mak et al.
6,991,619 B2 1/2006 Marano-Ford et al.
6,991,620 B2 1/2006 Marano-Ford et al.
6,993,795 B2 2/2006 Prineppi et al.
6,994,691 B2 2/2006 Ejlersen
6,994,700 B2 2/2006 Elkins et al.
6,997,202 B2 2/2006 Olander
6,997,905 B2 2/2006 Gillespie et al.
6,997,911 B2 2/2006 Klitmose
6,997,916 B2 2/2006 Simas et al.
6,997,920 B2 2/2006 Mann et al.
6,997,921 B2 2/2006 Gray et al.
6,998,387 B1 2/2006 Goke et al.
6,998,404 B2 2/2006 Moskowitz
6,999,810 B2 2/2006 Berner et al.
6,999,854 B2 2/2006 Roth
7,003,336 B2 2/2006 Holker et al.
7,004,928 B2 2/2006 Aceti et al.
7,008,399 B2 3/2006 Larsen et al.
7,008,403 B1 3/2006 Mallett et al.
7,008,413 B2 3/2006 Kovach et al.
7,010,340 B2 3/2006 Scarantino et al.
7,011,630 B2 3/2006 Desai et al.
7,011,647 B2 3/2006 Purdy et al.
7,011,682 B2 3/2006 Lashinski et al.
7,013,727 B2 3/2006 Delnevo
7,015,782 B2 3/2006 Kincaid et al.
7,018,336 B2 3/2006 Enegren et al.
7,018,360 B2 3/2006 Flaherty et al.
7,018,361 B2 3/2006 Gillespie et al.
7,018,630 B2 3/2006 Takaoka
7,022,067 B2 4/2006 Dempster et al.
7,022,071 B2 4/2006 Schaupp et al.
7,022,072 B2 4/2006 Fox et al.
7,022,108 B2 4/2006 Marano-Ford
7,024,244 B2 4/2006 Muhlenberg et al.
7,024,245 B2 4/2006 Lebel et al.
7,025,716 B1 4/2006 Meloul et al.
7,025,743 B2 4/2006 Mann et al.
7,027,478 B2 4/2006 Ackley
7,027,871 B2 4/2006 Burnes et al.
7,029,455 B2 4/2006 Flaherty
7,031,772 B2 4/2006 Condie et al.
7,033,338 B2 4/2006 Vilks et al.
7,033,539 B2 4/2006 Krensky et al.
7,033,843 B2 4/2006 Hasegawa et al.
7,041,082 B2 5/2006 Blomquist et al.
7,047,070 B2 5/2006 Wilkinson et al.
7,048,193 B2 5/2006 Tsukada et al.
7,048,951 B1 5/2006 Seitz et al.
7,052,251 B2 5/2006 Nason et al.
7,052,483 B2 5/2006 Wojcik
7,053,761 B2 5/2006 Schofield et al.
7,056,179 B2 6/2006 Courtney
7,056,302 B2 6/2006 Douglas
7,056,494 B2 6/2006 Adjei et al.
7,056,887 B2 6/2006 Coolidge et al.
7,058,438 B2 6/2006 Grace et al.
7,059,348 B2 6/2006 Nat et al.
7,060,856 B2 6/2006 Macikenas et al.
7,063,684 B2 6/2006 Moberg et al.
7,064,472 B2 6/2006 Pelrine et al.
7,066,359 B2 6/2006 Greiner-Perth
7,066,910 B2 6/2006 Bauhahn et al.
7,066,915 B2 6/2006 Olsen
7,066,922 B2 6/2006 Angel et al.
7,069,075 B2 6/2006 Olson
7,070,577 B1 7/2006 Haller et al.
7,072,802 B2 7/2006 Hartlaub
7,073,485 B2 7/2006 Truscott et al.
7,073,713 B2 7/2006 Silverbrook et al.
7,074,200 B1 7/2006 Lewis
7,077,822 B1 7/2006 Howard, III
7,078,163 B2 7/2006 Torrianni
7,081,105 B2 7/2006 Reilly et al.
7,082,333 B1 7/2006 Bauhahn et al.
7,082,812 B2 8/2006 Lenormand et al.
7,083,108 B2 8/2006 Silverbrook et al.
7,083,592 B2 8/2006 Lastovich et al.
7,083,599 B2 8/2006 Alchas et al.
7,089,608 B2 8/2006 Erb et al.
7,090,648 B2 8/2006 Sackner et al.
7,091,179 B2 8/2006 Franco
7,092,011 B2 8/2006 Silverbrook et al.
7,092,796 B2 8/2006 Vanderveen
7,095,210 B2 8/2006 Tamura et al.
7,096,889 B1 8/2006 Roys
7,097,104 B2 8/2006 Silverbrook et al.
7,098,803 B2 8/2006 Mann et al.
7,104,973 B2 9/2006 Woolston et al.
7,104,981 B2 9/2006 Elkins et al.
7,107,706 B1 9/2006 Bailey, Sr. et al.
7,107,837 B2 9/2006 Lauman et al.
7,108,491 B2 9/2006 Ganser
7,108,679 B2 9/2006 Alchas
7,109,878 B2 9/2006 Mann et al.
7,111,346 B2 9/2006 Inman et al.
7,115,108 B2 10/2006 Wilkinson et al.
7,118,351 B2 10/2006 Effenhauser et al.
7,118,676 B2 10/2006 Mueth et al.
7,122,151 B2 10/2006 Reeder et al.
7,127,292 B2 10/2006 Warman et al.
7,128,727 B2 10/2006 Flaherty et al.
7,128,730 B2 10/2006 Marano-Ford et al.
7,131,967 B2 11/2006 Gray et al.
7,133,329 B2 11/2006 Skyggebjerg et al.

(56) References Cited

U.S. PATENT DOCUMENTS 7,136,701 B2 11/2006 Greatbatch et al.
7,137,951 B2 11/2006 Pilarski
7,137,964 B2 11/2006 Flaherty
7,138,141 B2 11/2006 Platz et al.
7,140,332 B2 11/2006 Klein et al.
7,141,425 B2 11/2006 Dzekunov et al.
7,141,812 B2 11/2006 Appleby et al.
7,144,384 B2 12/2006 Gorman et al.
7,144,729 B2 12/2006 Rolland et al.
7,147,386 B2 12/2006 Zhang et al.
7,147,839 B2 12/2006 Sampath et al.
7,150,409 B2 12/2006 Gonnelli et al.
7,150,724 B2 12/2006 Morris et al.
7,150,726 B2 12/2006 Dalton
7,150,737 B2 12/2006 Purdy et al.
7,150,741 B2 12/2006 Erickson et al.
7,152,673 B2 12/2006 Lohbeck
7,153,286 B2 12/2006 Busby et al.
7,153,823 B2 12/2006 Franco
7,156,808 B2 1/2007 Quy
7,156,838 B2 1/2007 Gabel et al.
7,159,271 B2 1/2007 Sepke et al.
7,162,303 B2 1/2007 Levin et al.
7,163,385 B2 1/2007 Gharib et al.
7,163,520 B2 1/2007 Bernard et al.
7,166,280 B2 1/2007 Franco
7,171,274 B2 1/2007 Starkweather et al.
7,174,199 B2 2/2007 Berner et al.
7,179,226 B2 2/2007 Crothall et al.
7,181,505 B2 2/2007 Haller et al.
7,183,066 B2 2/2007 Burson et al.
7,186,236 B2 3/2007 Gibson et al.
7,187,404 B2 3/2007 Silverbrook et al.
7,187,528 B2 3/2007 Talbot et al.
7,187,969 B2 3/2007 Willis et al.
7,189,352 B2 3/2007 Carpenter et al.
7,193,521 B2 3/2007 Moberg et al.
7,194,890 B2 3/2007 Tanaka et al.
7,195,616 B2 3/2007 Atterbury et al.
7,198,603 B2 4/2007 Penner et al.
7,198,637 B2 4/2007 Deshmukh et al.
7,198,751 B2 4/2007 Carpenter et al.
7,198,940 B2 4/2007 Vellinger et al.
7,201,319 B2 4/2007 Silverbrook et al.
7,201,730 B2 4/2007 Davidner et al.
7,204,823 B2 4/2007 Estes et al.
7,204,958 B2 4/2007 Olsen et al.
7,207,952 B2 4/2007 Takinami et al.
7,207,964 B2 4/2007 Davidner et al.
7,208,119 B1 4/2007 Kurtock et al.
7,208,120 B2 4/2007 Bitensky et al.
7,214,207 B2 5/2007 Lynch et al.
7,214,221 B2 5/2007 Fentress et al.
7,214,658 B2 5/2007 Tobinick et al.
7,217,699 B2 5/2007 Yakubov
7,217,796 B2 5/2007 Wang et al.
7,220,109 B2 5/2007 Kultgen
7,220,236 B2 5/2007 Pan
7,220,248 B2 5/2007 Mernoe et al.
7,220,365 B2 5/2007 Qu et al.
7,224,815 B2 5/2007 Maltan et al.
7,225,807 B2 6/2007 Papania et al.
7,226,278 B2 6/2007 Nason et al.
7,226,910 B2 6/2007 Wilson et al.
7,229,288 B2 6/2007 Stuart et al.
7,229,430 B2 6/2007 Hickle et al.
7,231,263 B2 6/2007 Choi
7,232,423 B2 6/2007 Mernoe et al.
7,232,430 B2 6/2007 Carlisle et al.
7,232,435 B2 6/2007 Hildebrand et al.
7,234,645 B2 6/2007 Silverbrook et al.
7,235,164 B2 6/2007 Anex et al.
7,235,583 B1 6/2007 Webb et al.
7,237,694 B2 7/2007 Freudinger
7,238,165 B2 7/2007 Vincent et al.
7,239,941 B2 7/2007 Mori et al.
7,244,225 B2 7/2007 Loeb et al.
7,244,354 B2 7/2007 Burris et al.
7,247,138 B2 7/2007 Reghabi et al.
7,247,426 B2 7/2007 Makrigiorgos
7,247,702 B2 7/2007 Gardner et al.
7,250,037 B2 7/2007 Shermer et al.
7,251,516 B2 7/2007 Walker et al.
7,252,014 B1 8/2007 Mayer et al.
7,252,651 B2 8/2007 Haider et al.
7,254,782 B1 8/2007 Sherer
7,255,690 B2 8/2007 Gray et al.
7,256,771 B2 8/2007 Novak et al.
7,256,824 B2 8/2007 Silverbrook et al.
7,256,888 B2 8/2007 Staehr et al.
7,258,864 B2 8/2007 Clark
RE39,816 E 9/2007 Stanton et al.
7,264,730 B2 9/2007 Connell et al.
7,265,091 B2 9/2007 Lue et al.
7,267,665 B2 9/2007 Steil et al.
7,267,753 B2 9/2007 Anex et al.
7,267,771 B2 9/2007 Gorsuch et al.
7,268,859 B2 9/2007 Sage et al.
7,272,544 B2 9/2007 Gopal et al.
7,276,027 B2 10/2007 Haar et al.
7,276,028 B2 10/2007 Ellingsen et al.
7,276,057 B2 10/2007 Gerber et al.
7,278,983 B2 10/2007 Ireland et al.
7,281,519 B2 10/2007 Schroeder et al.
7,282,029 B1 10/2007 Poulsen et al.
7,285,293 B2 10/2007 Castillo et al.
7,287,289 B1 10/2007 Hagopian
7,287,485 B2 10/2007 Petrakis
7,288,085 B2 10/2007 Olsen
7,288,760 B2 10/2007 Weitz
7,289,142 B2 10/2007 Silverbrook
7,291,107 B2 11/2007 Hellwig et al.
7,291,126 B2 11/2007 Shekalim et al.
7,291,132 B2 11/2007 Deruntz et al.
7,291,133 B1 11/2007 Kindler et al.
7,295,867 B2 11/2007 Berner et al.
7,297,151 B2 11/2007 Boecker et al.
7,302,295 B2 11/2007 Stahmann et al.
7,303,543 B1 12/2007 Maule et al.
7,303,549 B2 12/2007 Flaherty et al.
7,303,680 B2 12/2007 Connell et al.
7,304,033 B2 12/2007 Larsen et al.
7,305,975 B2 12/2007 Reddy
7,306,555 B2 12/2007 Dolecek et al.
7,306,576 B2 12/2007 Gray et al.
7,311,693 B2 12/2007 Shekalim et al.
7,316,700 B2 1/2008 Alden et al.
7,316,899 B2 1/2008 McDevitt et al.
7,318,892 B2 1/2008 Connell et al.
7,320,675 B2 1/2008 Pastore et al.
7,320,677 B2 1/2008 Brouillette et al.
7,322,321 B2 1/2008 Robinson et al.
7,323,141 B2 1/2008 Kirchhevel et al.
7,323,543 B2 1/2008 Van Antwerp et al.
7,324,012 B2 1/2008 Mann et al.
7,324,949 B2 1/2008 Bristol
7,334,556 B2 2/2008 Wachigai et al.
7,335,377 B2 2/2008 Stern et al.
7,338,464 B2 3/2008 Blischak et al.
7,341,577 B2 3/2008 Gill
7,341,581 B2 3/2008 Mallett et al.
7,344,500 B2 3/2008 Talbot et al.
7,344,507 B2 3/2008 Briggs et al.
7,344,894 B2 3/2008 Greenstein et al.
7,347,201 B2 3/2008 Djupesland
7,347,836 B2 3/2008 Peterson et al.
7,347,854 B2 3/2008 Shelton et al.
7,348,176 B2 3/2008 Dimilla et al.
7,350,190 B2 3/2008 Torres et al.
7,351,239 B2 4/2008 Gill et al.
7,351,340 B2 4/2008 Connell et al.
7,351,411 B2 4/2008 Holash et al.
7,351,695 B2 4/2008 Almarssoo et al.
7,354,420 B2 4/2008 Steil et al.

(56) References Cited

U.S. PATENT DOCUMENTS

| | | | |
|---|---|---|---|
| 7,356,382 | B2 | 4/2008 | Vanderveen |
| 7,357,794 | B2 | 4/2008 | Makower et al. |
| 7,357,899 | B2 | 4/2008 | Gaillard et al. |
| 7,358,091 | B2 | 4/2008 | Phillips et al. |
| 7,361,155 | B2 | 4/2008 | Sage et al. |
| 7,362,971 | B2 | 4/2008 | Silverbrook et al. |
| 7,363,072 | B2 | 4/2008 | Movahed |
| 7,363,075 | B2 | 4/2008 | Stern et al. |
| 7,364,566 | B2 | 4/2008 | Elkins et al. |
| 7,364,568 | B2 | 4/2008 | Angel et al. |
| 7,366,925 | B2 | 4/2008 | Keely et al. |
| 7,368,003 | B2 | 5/2008 | Crapser et al. |
| 7,371,418 | B2 | 5/2008 | Sheabar et al. |
| 7,373,083 | B2 | 5/2008 | Silverbrook et al. |
| 7,373,690 | B2 | 5/2008 | Sepke et al. |
| 7,373,826 | B2 | 5/2008 | Weber et al. |
| 7,374,544 | B2 | 5/2008 | Boecker et al. |
| 7,374,556 | B2 | 5/2008 | Mallett et al. |
| 7,377,706 | B2 | 5/2008 | Silverbrook et al. |
| 7,377,907 | B2 | 5/2008 | Shekalim |
| 7,378,270 | B2 | 5/2008 | Azarnia et al. |
| 7,378,443 | B2 | 5/2008 | Berge |
| 7,380,447 | B2 | 6/2008 | Rollinger et al. |
| 7,384,397 | B2 | 6/2008 | Zhang et al. |
| 7,384,410 | B2 | 6/2008 | Eggers et al. |
| 7,384,413 | B2 | 6/2008 | Gross et al. |
| 7,384,912 | B2 | 6/2008 | Stewart |
| 7,385,443 | B1 | 6/2008 | Denison |
| 7,386,346 | B2 | 6/2008 | Struble et al. |
| 7,390,311 | B2 | 6/2008 | Hildebrand et al. |
| 7,390,314 | B2 | 6/2008 | Stutz et al. |
| 7,390,458 | B2 | 6/2008 | Burow et al. |
| 7,394,182 | B2 | 7/2008 | Pelrine et al. |
| 7,396,353 | B2 | 7/2008 | Lorenzen et al. |
| 7,399,277 | B2 | 7/2008 | Saidara et al. |
| 7,399,304 | B2 | 7/2008 | Gambale et al. |
| 7,399,401 | B2 | 7/2008 | Rush |
| 7,399,772 | B2 | 7/2008 | Phillips et al. |
| 7,402,153 | B2 | 7/2008 | Steil et al. |
| 7,402,154 | B2 | 7/2008 | Holst et al. |
| 7,405,055 | B2 | 7/2008 | Dunn et al. |
| 7,407,489 | B2 | 8/2008 | Holst et al. |
| 7,407,490 | B2 | 8/2008 | Bendsen et al. |
| 7,410,468 | B2 | 8/2008 | Boecker et al. |
| 7,410,475 | B2 | 8/2008 | Krensky et al. |
| 7,411,204 | B2 | 8/2008 | Appleby et al. |
| 7,416,644 | B2 | 8/2008 | Bonde |
| 7,421,316 | B2 | 9/2008 | Gray et al. |
| 7,421,882 | B2 | 9/2008 | Leddy et al. |
| 7,425,204 | B2 | 9/2008 | Angel et al. |
| 7,426,408 | B2 | 9/2008 | Denuzzio et al. |
| 7,427,275 | B2 | 9/2008 | Deruntz et al. |
| 7,429,255 | B2 | 9/2008 | Thompson |
| 7,429,258 | B2 | 9/2008 | Angel et al. |
| 7,429,269 | B2 | 9/2008 | Schwammenthal et al. |
| 7,435,250 | B2 | 10/2008 | Francischelli et al. |
| 7,435,717 | B2 | 10/2008 | Bisgaier et al. |
| 7,440,606 | B2 | 10/2008 | Whitehurst et al. |
| 7,442,186 | B2 | 10/2008 | Blomquist |
| 7,442,682 | B2 | 10/2008 | Kitaura et al. |
| 7,444,436 | B2 | 10/2008 | Wille |
| RE40,570 | E | 11/2008 | Carpentier et al. |
| 7,445,616 | B2 | 11/2008 | Petrakis et al. |
| 7,446,091 | B2 | 11/2008 | Van Den Berghe |
| 7,449,333 | B2 | 11/2008 | Rolland et al. |
| 7,452,301 | B2 | 11/2008 | Yoshioka |
| 7,455,663 | B2 | 11/2008 | Bikovsky |
| 7,455,835 | B2 | 11/2008 | Cohen et al. |
| 7,459,305 | B2 | 12/2008 | Levy |
| 7,460,152 | B2 | 12/2008 | Silverbrook et al. |
| 7,460,350 | B2 | 12/2008 | Talbot et al. |
| 7,460,895 | B2 | 12/2008 | Arnold et al. |
| 7,462,166 | B2 | 12/2008 | Cowan et al. |
| 7,463,934 | B2 | 12/2008 | Tronnes et al. |
| 7,464,010 | B2 | 12/2008 | Yang et al. |
| 7,464,580 | B2 | 12/2008 | Zeng et al. |
| 7,464,704 | B2 | 12/2008 | Braithwaite |
| 7,465,285 | B2 | 12/2008 | Hutchinson et al. |
| 7,465,375 | B2 | 12/2008 | Demers et al. |
| 7,467,027 | B2 | 12/2008 | Ding et al. |
| 7,467,613 | B2 | 12/2008 | Taylor et al. |
| 7,468,033 | B2 | 12/2008 | Van Antwerp et al. |
| 7,469,383 | B2 | 12/2008 | Busch |
| 7,469,697 | B2 | 12/2008 | Lee et al. |
| 7,469,844 | B2 | 12/2008 | Conway et al. |
| 7,470,246 | B2 | 12/2008 | Mori et al. |
| 7,471,994 | B2 | 12/2008 | Ford et al. |
| 7,473,239 | B2 | 1/2009 | Wang et al. |
| 7,473,247 | B2 | 1/2009 | Mikszta et al. |
| 7,474,968 | B2 | 1/2009 | Ding et al. |
| 7,475,825 | B2 | 1/2009 | Silverbrook et al. |
| 7,476,200 | B2 | 1/2009 | Yair et al. |
| 7,476,209 | B2 | 1/2009 | Gara et al. |
| 7,479,123 | B2 | 1/2009 | Griggs |
| 7,481,218 | B2 | 1/2009 | Djupesland |
| 7,481,759 | B2 | 1/2009 | Whitehurst et al. |
| 7,481,776 | B2 | 1/2009 | Boecker et al. |
| 7,481,792 | B2 | 1/2009 | Gonnelli et al. |
| 7,483,050 | B2 | 1/2009 | Silverbrook et al. |
| 7,483,743 | B2 | 1/2009 | Mann et al. |
| 7,485,296 | B2 | 2/2009 | Powell |
| 7,491,178 | B2 | 2/2009 | Boecker et al. |
| 7,491,187 | B2 | 2/2009 | Van et al. |
| 7,491,335 | B2 | 2/2009 | Reddy et al. |
| 7,493,154 | B2 | 2/2009 | Bonner et al. |
| 7,493,171 | B1 | 2/2009 | Whitehurst et al. |
| 7,494,481 | B2 | 2/2009 | Moberg et al. |
| 7,497,841 | B2 | 3/2009 | Alchas |
| 7,498,563 | B2 | 3/2009 | Mandro et al. |
| 7,500,959 | B2 | 3/2009 | Munk |
| 7,503,903 | B2 | 3/2009 | Carlisle et al. |
| 7,505,869 | B2 | 3/2009 | Hartlaub |
| 7,507,220 | B2 | 3/2009 | Childers et al. |
| 7,507,235 | B2 | 3/2009 | Keogh et al. |
| 7,509,169 | B2 | 3/2009 | Eigler et al. |
| 7,510,544 | B2 | 3/2009 | Vilks et al. |
| 7,510,552 | B2 | 3/2009 | Lebel et al. |
| 7,511,914 | B2 | 3/2009 | Hiller et al. |
| 7,514,075 | B2 | 4/2009 | Hedrick et al. |
| 7,514,401 | B2 | 4/2009 | Franco |
| 7,515,060 | B2 | 4/2009 | Tonelli et al. |
| 7,517,335 | B2 | 4/2009 | Gravesen et al. |
| 7,517,440 | B2 | 4/2009 | Anex et al. |
| 7,517,498 | B2 | 4/2009 | Fredrick |
| 7,517,530 | B2 | 4/2009 | Clark |
| 7,520,867 | B2 | 4/2009 | Bowman et al. |
| 7,524,045 | B2 | 4/2009 | Silverbrook et al. |
| 7,524,287 | B2 | 4/2009 | Bharmi |
| 7,524,293 | B2 | 4/2009 | Boecker et al. |
| 7,524,304 | B2 | 4/2009 | Genosar |
| 7,530,968 | B2 | 5/2009 | Gonnelli et al. |
| 7,530,975 | B2 | 5/2009 | Hunter |
| 7,534,221 | B2 | 5/2009 | Pile-Spellman |
| 7,534,226 | B2 | 5/2009 | Mernoe et al. |
| 7,536,983 | B2 | 5/2009 | Layher et al. |
| 7,537,571 | B2 | 5/2009 | Freeman et al. |
| 7,540,859 | B2 | 6/2009 | Claude et al. |
| 7,540,880 | B2 | 6/2009 | Nolting et al. |
| 7,543,581 | B2 | 6/2009 | Djupesland |
| 7,547,281 | B2 | 6/2009 | Hayes et al. |
| 7,547,287 | B2 | 6/2009 | Boecker et al. |
| 7,548,314 | B2 | 6/2009 | Altobelli et al. |
| 7,551,202 | B2 | 6/2009 | Silverbrook et al. |
| 7,553,281 | B2 | 6/2009 | Hellwig et al. |
| 7,553,291 | B2 | 6/2009 | Duffy et al. |
| 7,553,813 | B2 | 6/2009 | Linemori |
| 7,556,613 | B2 | 7/2009 | Wittmann et al. |
| 7,556,841 | B2 | 7/2009 | Kimball et al. |
| 7,558,629 | B2 | 7/2009 | Keimel et al. |
| 7,559,223 | B2 | 7/2009 | Chen et al. |
| 7,559,524 | B2 | 7/2009 | Gray et al. |
| 7,563,232 | B2 | 7/2009 | Boecker et al. |
| 7,563,253 | B2 | 7/2009 | Tanner et al. |
| 7,563,255 | B2 | 7/2009 | Adamis et al. |

(56) References Cited

U.S. PATENT DOCUMENTS

D598,109 S 8/2009 Collins et al.
7,569,030 B2 8/2009 Lebel et al.
7,569,036 B2 8/2009 Domkowski et al.
7,569,050 B2 8/2009 Moberg et al.
7,571,635 B2 8/2009 Lyon
7,572,789 B2 8/2009 Cowen et al.
7,577,477 B2 8/2009 Allen et al.
7,582,063 B2 9/2009 Wurster et al.
7,582,099 B2 9/2009 Boecker et al.
7,583,190 B2 9/2009 Reggiardo et al.
7,584,846 B2 9/2009 Senter
7,588,046 B1 9/2009 Erickson
7,588,550 B2 9/2009 Leonard et al.
7,588,784 B2 9/2009 Attila et al.
7,589,059 B2 9/2009 Wolff et al.
7,590,443 B2 9/2009 Bharmi
7,591,801 B2 9/2009 Brauker et al.
7,594,889 B2 9/2009 St. Ores et al.
7,597,682 B2 10/2009 Moberg et al.
7,598,031 B2 10/2009 Liew
7,602,310 B2 10/2009 Mann et al.
7,603,174 B2 10/2009 Ridder et al.
7,604,592 B2 10/2009 Freeman et al.
7,604,593 B2 10/2009 Parris et al.
7,604,619 B2 10/2009 Eich et al.
7,605,710 B2 10/2009 Crnkovich et al.
7,606,274 B2 10/2009 Mirov et al.
7,606,615 B2 10/2009 Makower et al.
7,607,965 B1 10/2009 Frazier
7,608,060 B2 10/2009 Gillespie et al.
7,608,640 B2 10/2009 Messadek
7,615,046 B2 11/2009 Shehata
7,618,369 B2 11/2009 Hayter et al.
7,618,615 B2 11/2009 Frey, II et al.
7,618,954 B2 11/2009 Nicolau et al.
7,621,893 B2 11/2009 Moberg et al.
7,624,409 B2 11/2009 Whymark
7,625,354 B2 12/2009 Hochman
7,625,358 B2 12/2009 Mernoe
7,625,369 B2 12/2009 Abboud et al.
7,628,590 B2 12/2009 Jacobsen et al.
7,628,772 B2 12/2009 McConnell et al.
7,628,782 B2 12/2009 Adair et al.
7,630,748 B2 12/2009 Budiman
7,630,773 B2 12/2009 Seeberger et al.
7,630,791 B2 12/2009 Nguyen et al.
7,632,228 B2 12/2009 Brauker et al.
7,632,247 B2 12/2009 Adams et al.
7,632,248 B2 12/2009 Delk et al.
7,635,349 B2 12/2009 Tribe et al.
7,635,575 B2 12/2009 Scherze et al.
7,637,279 B2 12/2009 Amley et al.
7,637,931 B2 12/2009 Heaton et al.
7,638,095 B2 12/2009 Sabol
7,641,649 B2 1/2010 Moberg et al.
7,642,232 B2 1/2010 Green et al.
7,644,203 B2 1/2010 Ingles
7,645,253 B2 1/2010 Gura et al.
7,645,264 B2 1/2010 Marsh et al.
7,647,107 B2 1/2010 Warman et al.
7,647,115 B2 1/2010 Levin et al.
7,647,237 B2 1/2010 Malave et al.
7,650,181 B2 1/2010 Freeman et al.
7,650,190 B2 1/2010 Zhou et al.
7,651,489 B2 1/2010 Estes et al.
7,651,868 B2 1/2010 McDevitt et al.
7,653,425 B2 1/2010 Hayter et al.
7,653,639 B2 1/2010 Classen et al.
7,654,127 B2 2/2010 Krulevitch et al.
7,654,131 B2 2/2010 Ascheman
7,654,484 B2 2/2010 Mogensen et al.
7,654,976 B2 2/2010 Peterson et al.
7,654,982 B2 2/2010 Carlisle et al.
7,655,221 B2 2/2010 Rasmussen et al.
7,657,313 B2 2/2010 Rom
7,662,105 B2 2/2010 Hatlestad
7,662,140 B2 2/2010 Heruth et al.
7,662,558 B2 2/2010 Liew
7,668,731 B2 2/2010 Martucci et al.
7,674,243 B2 3/2010 Dacquay et al.
7,674,485 B2 3/2010 Bhaskaran et al.
7,676,263 B2 3/2010 Harris et al.
7,676,519 B2 3/2010 McBride et al.
7,678,071 B2 3/2010 Lebel et al.
7,678,084 B2 3/2010 Judson et al.
7,678,761 B2 3/2010 Coleman
7,678,762 B2 3/2010 Green et al.
7,678,763 B2 3/2010 Green et al.
7,678,772 B2 3/2010 Jia et al.
7,678,833 B2 3/2010 Ott
7,681,570 B2 3/2010 Vendrine et al.
7,682,338 B2 3/2010 Griffin
7,682,430 B2 3/2010 Kraemer et al.
7,682,563 B2 3/2010 Carpenter et al.
7,683,029 B2 3/2010 Hindle et al.
7,685,865 B2 3/2010 Norenberg
7,686,787 B2 3/2010 Moberg et al.
7,687,272 B1 3/2010 Buchwald et al.
RE41,288 E 4/2010 Coolidge et al.
D613,411 S 4/2010 Collins et al.
7,691,330 B1 4/2010 Winkler et al.
7,695,454 B2 4/2010 Barron et al.
7,695,627 B2 4/2010 Bosch et al.
7,697,967 B2 4/2010 Stafford
7,697,995 B2 4/2010 Cross et al.
7,699,767 B2 4/2010 Mueth et al.
7,699,775 B2 4/2010 Desai et al.
7,699,808 B2 4/2010 Marrs et al.
7,699,833 B2 4/2010 Moberg et al.
7,704,226 B2 4/2010 Mueller et al.
7,704,227 B2 4/2010 Moberg et al.
7,704,237 B2 4/2010 Fischer et al.
7,704,238 B2 4/2010 Atterbury et al.
7,708,717 B2 * 5/2010 Estes ................. A61M 5/14244
604/890.1
7,708,872 B2 5/2010 Eidsnes et al.
7,708,915 B2 5/2010 Castor
7,713,238 B2 5/2010 Mernoe
7,713,240 B2 5/2010 Istoc et al.
7,713,262 B2 5/2010 Adams et al.
7,713,574 B2 5/2010 Brister et al.
7,714,757 B2 5/2010 Denison et al.
7,714,889 B2 5/2010 Silverbrook
7,715,917 B2 5/2010 Chinchoy et al.
7,716,964 B2 5/2010 Kurtz et al.
7,717,856 B2 5/2010 Chen et al.
7,717,871 B2 5/2010 Odland
7,717,903 B2 5/2010 Estes et al.
7,722,536 B2 5/2010 Goodnow
7,726,955 B2 6/2010 Ryser et al.
7,727,148 B2 6/2010 Talbot et al.
7,727,181 B2 6/2010 Rush
7,734,323 B2 6/2010 Blomquist et al.
7,736,309 B2 6/2010 Miller et al.
7,736,338 B2 6/2010 Kavazov et al.
7,736,344 B2 6/2010 Moberg et al.
7,737,581 B2 6/2010 Spurlin et al.
7,740,708 B2 6/2010 Lofton et al.
7,743,007 B2 6/2010 Jung et al.
7,744,554 B2 6/2010 Howard
7,744,589 B2 6/2010 Mounce et al.
7,749,528 B2 7/2010 De Carvalho et al.
7,751,907 B2 7/2010 Blomquist
7,753,660 B2 7/2010 Gray
7,753,873 B2 7/2010 Rush et al.
7,753,879 B2 7/2010 Mernoe
7,753,885 B2 7/2010 Duchon et al.
7,756,722 B2 7/2010 Levine et al.
7,758,547 B2 7/2010 Tonelli et al.
7,758,568 B2 7/2010 Olsen et al.
7,760,601 B2 7/2010 Igi
7,762,793 B2 7/2010 Gray et al.
7,766,301 B2 8/2010 Gray et al.
7,766,829 B2 8/2010 Sloan et al.

(56) References Cited

U.S. PATENT DOCUMENTS

| | | | |
|---|---|---|---|
| 7,766,830 | B2 | 8/2010 | Fox et al. |
| 7,766,831 | B2 | 8/2010 | Essenpreis et al. |
| 7,766,863 | B2 | 8/2010 | Gillespie et al. |
| 7,766,873 | B2 | 8/2010 | Moberg et al. |
| 7,768,386 | B2 | 8/2010 | Hayter et al. |
| 7,768,408 | B2 | 8/2010 | Reggiardo et al. |
| 7,771,385 | B2 | 8/2010 | Eggers et al. |
| 7,771,386 | B2 | 8/2010 | Eggers et al. |
| 7,771,414 | B2 | 8/2010 | Trieu et al. |
| 7,774,145 | B2 | 8/2010 | Brauker et al. |
| 7,775,975 | B2 | 8/2010 | Brister et al. |
| 7,776,006 | B2 | 8/2010 | Childers et al. |
| 7,776,030 | B2 | 8/2010 | Estes et al. |
| 7,776,031 | B2 | 8/2010 | Hartlaub et al. |
| 7,778,680 | B2 | 8/2010 | Goode et al. |
| 7,780,981 | B2 | 8/2010 | Dipierro et al. |
| 7,782,192 | B2 | 8/2010 | Jeckelmann et al. |
| 7,785,288 | B2 | 8/2010 | Mernoee et al. |
| 7,785,293 | B2 | 8/2010 | Gray et al. |
| 7,785,313 | B2 | 8/2010 | Mastrototaro |
| 7,788,369 | B2 | 8/2010 | McAllen et al. |
| 7,789,849 | B2 | 9/2010 | Busby et al. |
| 7,789,857 | B2 | 9/2010 | Moberg et al. |
| 7,790,103 | B2 | 9/2010 | Shah et al. |
| 7,794,426 | B2 | 9/2010 | Briones et al. |
| 7,794,427 | B2 | 9/2010 | Estes et al. |
| 7,794,428 | B2 | 9/2010 | Estes et al. |
| 7,794,434 | B2 | 9/2010 | Mounce et al. |
| 7,797,028 | B2 | 9/2010 | Goode et al. |
| 7,801,582 | B2 | 9/2010 | Peyser |
| 7,806,853 | B2 | 10/2010 | Wittmann et al. |
| 7,806,854 | B2 | 10/2010 | Damiano et al. |
| 7,806,867 | B2 | 10/2010 | Willis et al. |
| 7,806,868 | B2 | 10/2010 | De Polo et al. |
| 7,811,231 | B2 | 10/2010 | Jin et al. |
| 7,811,246 | B2 | 10/2010 | Koops |
| 7,811,262 | B2 | 10/2010 | Moberg et al. |
| 7,811,279 | B2 | 10/2010 | John et al. |
| 7,815,595 | B2 | 10/2010 | Busby et al. |
| 7,815,602 | B2 | 10/2010 | Mann et al. |
| 7,815,609 | B2 | 10/2010 | Hines et al. |
| 7,815,622 | B2 | 10/2010 | Istoc et al. |
| 7,819,843 | B2 | 10/2010 | Mann et al. |
| 7,822,455 | B2 | 10/2010 | Hoss et al. |
| RE41,956 | E | 11/2010 | Klitgaard et al. |
| 7,826,382 | B2 | 11/2010 | Sicurello et al. |
| 7,826,879 | B2 | 11/2010 | Hoss et al. |
| 7,828,528 | B2 | 11/2010 | Estes et al. |
| 7,828,747 | B2 | 11/2010 | Heske et al. |
| 7,828,764 | B2 | 11/2010 | Moberg et al. |
| 7,828,771 | B2 | 11/2010 | Chiang et al. |
| 7,831,310 | B2 | 11/2010 | Lebel et al. |
| 7,833,196 | B2 | 11/2010 | Estes et al. |
| 7,835,927 | B2 | 11/2010 | Schlotterbeck et al. |
| 7,837,647 | B2 | 11/2010 | Estes et al. |
| 7,837,648 | B2 | 11/2010 | Blair et al. |
| 7,850,641 | B2 | 12/2010 | Lebel et al. |
| 7,850,658 | B2 | 12/2010 | Faust et al. |
| 7,850,674 | B2 | 12/2010 | Goodnow et al. |
| 7,851,509 | B2 | 12/2010 | Miller et al. |
| 7,857,756 | B2 | 12/2010 | Warren et al. |
| 7,857,791 | B2 | 12/2010 | Jacobs et al. |
| 7,860,544 | B2 | 12/2010 | Say et al. |
| 7,860,583 | B2 | 12/2010 | Condurso et al. |
| 7,867,189 | B2 | 1/2011 | Childers et al. |
| 7,869,853 | B1 | 1/2011 | Say et al. |
| 7,874,718 | B2 | 1/2011 | Demers et al. |
| 7,875,022 | B2 | 1/2011 | Wenger et al. |
| 7,877,489 | B2 | 1/2011 | Salesky et al. |
| 7,877,703 | B1 | 1/2011 | Fleming |
| 7,879,026 | B2 | 2/2011 | Estes et al. |
| 7,881,883 | B2 | 2/2011 | Remde |
| 7,882,611 | B2 | 2/2011 | Shah et al. |
| 7,883,464 | B2 | 2/2011 | Stafford et al. |
| 7,884,729 | B2 | 2/2011 | Reggiardo et al. |
| 7,885,699 | B2 | 2/2011 | Say et al. |
| 7,887,505 | B2 | 2/2011 | Flaherty |
| 7,887,511 | B2 | 2/2011 | Mernoee et al. |
| 7,887,512 | B2 | 2/2011 | Estes et al. |
| 7,890,295 | B2 | 2/2011 | Shin et al. |
| 7,892,199 | B2 | 2/2011 | Mhatre et al. |
| 7,892,206 | B2 | 2/2011 | Moberg et al. |
| 7,896,842 | B2 | 3/2011 | Palmroos et al. |
| 7,901,394 | B2 | 3/2011 | Ireland et al. |
| 7,905,710 | B2 | 3/2011 | Wang et al. |
| 7,905,859 | B2 | 3/2011 | Bynum et al. |
| 7,905,866 | B2 | 3/2011 | Haider et al. |
| 7,905,868 | B2 | 3/2011 | Moberg et al. |
| 7,909,267 | B2 | 3/2011 | Redl et al. |
| 7,912,674 | B2 | 3/2011 | Killoren et al. |
| 7,914,450 | B2 | 3/2011 | Goode et al. |
| 7,914,499 | B2 | 3/2011 | Gonnelli et al. |
| 7,914,500 | B2 | 3/2011 | Gafner-Geiser et al. |
| 7,914,742 | B2 | 3/2011 | Arbogast et al. |
| 7,917,186 | B2 | 3/2011 | Kamath et al. |
| 7,918,825 | B2 | 4/2011 | O'Connor et al. |
| 7,919,063 | B2 | 4/2011 | Sarofim |
| 7,920,907 | B2 | 4/2011 | McGarraugh et al. |
| 7,922,096 | B2 | 4/2011 | Eilersen |
| 7,922,458 | B2 | 4/2011 | Rush et al. |
| 7,922,462 | B2 | 4/2011 | Preuthun et al. |
| 7,922,899 | B2 | 4/2011 | Vasta et al. |
| 7,926,850 | B1 | 4/2011 | Hayter et al. |
| 7,931,592 | B2 | 4/2011 | Currie et al. |
| 7,931,613 | B2 | 4/2011 | Haueter et al. |
| 7,931,642 | B2 | 4/2011 | Tonnies |
| 7,931,864 | B2 | 4/2011 | Kloepfer et al. |
| 7,933,639 | B2 | 4/2011 | Goode et al. |
| 7,933,760 | B2 | 4/2011 | De |
| 7,935,074 | B2 | 5/2011 | Plahey et al. |
| 7,935,076 | B2 | 5/2011 | Estes et al. |
| 7,935,079 | B2 | 5/2011 | Ludin et al. |
| 7,935,104 | B2 | 5/2011 | Yodfat et al. |
| 7,935,105 | B2 | 5/2011 | Miller et al. |
| 7,935,499 | B2 | 5/2011 | Dunn et al. |
| 7,937,163 | B2 | 5/2011 | Sekiguchi |
| 7,938,792 | B2 | 5/2011 | Roger et al. |
| 7,938,797 | B2 | 5/2011 | Estes |
| 7,938,802 | B2 | 5/2011 | Bicknell et al. |
| 7,938,803 | B2 | 5/2011 | Mernoe et al. |
| 7,941,200 | B2 | 5/2011 | Weinert et al. |
| 7,942,069 | B2 | 5/2011 | Peterson |
| 7,942,844 | B2 | 5/2011 | Moberg et al. |
| 7,944,366 | B2 | 5/2011 | Krulevitch et al. |
| 7,945,452 | B2 | 5/2011 | Fathallah et al. |
| 7,946,985 | B2 | 5/2011 | Mastrototaro et al. |
| 7,948,370 | B2 | 5/2011 | Reggiardo et al. |
| 7,951,112 | B2 | 5/2011 | Patzer |
| 7,951,114 | B2 | 5/2011 | Rush et al. |
| 7,951,122 | B2 | 5/2011 | Shekalim |
| 7,955,261 | B2 | 6/2011 | Goode et al. |
| 7,955,295 | B2 | 6/2011 | Lee et al. |
| 7,955,305 | B2 | 6/2011 | Moberg et al. |
| 7,955,319 | B2 | 6/2011 | Miesel |
| 7,955,843 | B2 | 6/2011 | Barringer, Jr. et al. |
| 7,957,984 | B1 | 6/2011 | Vallone |
| 7,959,569 | B2 | 6/2011 | Goode et al. |
| 7,959,608 | B2 | 6/2011 | Nash et al. |
| 7,959,715 | B2 | 6/2011 | Kavazov et al. |
| 7,959,938 | B2 | 6/2011 | Rohloff et al. |
| 7,963,945 | B2 | 6/2011 | Miller et al. |
| 7,963,946 | B2 | 6/2011 | Moubayed et al. |
| 7,963,954 | B2 | 6/2011 | Kavazov |
| 7,964,555 | B2 | 6/2011 | Zhou |
| 7,967,010 | B2 | 6/2011 | Vedrine et al. |
| 7,967,022 | B2 | 6/2011 | Grant et al. |
| 7,967,740 | B2 | 6/2011 | Mertens et al. |
| 7,967,752 | B2 | 6/2011 | Ocvirk et al. |
| 7,967,773 | B2 | 6/2011 | Amborn et al. |
| 7,967,785 | B2 | 6/2011 | Morgan et al. |
| 7,967,806 | B2 | 6/2011 | Jasperson et al. |
| 7,967,810 | B2 | 6/2011 | Freedman et al. |
| 7,967,812 | B2 | 6/2011 | Jasperson et al. |
| 7,970,620 | B2 | 6/2011 | Brown |

(56) References Cited

U.S. PATENT DOCUMENTS 7,972,286 B2 7/2011 Prausnitz et al.
7,972,296 B2 7/2011 Braig et al.
7,972,302 B2 7/2011 Caizza et al.
7,972,303 B2 7/2011 Caizza et al.
7,972,304 B2 7/2011 Caizza et al.
7,973,667 B2 7/2011 Crnkovich et al.
7,976,478 B2 7/2011 Fujiwara et al.
7,976,492 B2 7/2011 Brauker et al.
7,976,493 B2 7/2011 Carter et al.
7,976,496 B2 7/2011 Kennedy, II et al.
7,976,499 B2 7/2011 Grunhut et al.
7,976,500 B2 7/2011 Adams et al.
7,976,505 B2 7/2011 Hines et al.
7,976,508 B2 7/2011 Hoag
7,976,514 B2 7/2011 Abry et al.
7,976,530 B2 7/2011 Johnson et al.
7,976,778 B2 7/2011 Drucker et al.
7,976,865 B2 7/2011 Kawamura et al.
7,976,870 B2 7/2011 Berner et al.
7,979,104 B2 7/2011 Kamath et al.
7,979,136 B2 7/2011 Young et al.
7,981,034 B2 7/2011 Jennewine et al.
7,981,042 B2 7/2011 Stahmann et al.
7,981,076 B2 7/2011 Sullivan et al.
7,981,081 B2 7/2011 Marsh et al.
7,981,084 B2 7/2011 Estes et al.
7,981,090 B2 7/2011 Plishka et al.
7,981,102 B2 7/2011 Patel et al.
7,981,105 B2 7/2011 Adair et al.
7,981,107 B2 7/2011 Olsen
7,983,745 B2 7/2011 Hatlestad et al.
7,985,057 B2 7/2011 Haar et al.
7,985,330 B2 7/2011 Wang et al.
7,986,986 B2 7/2011 Goode, Jr. et al.
7,988,630 B1 8/2011 Osorio et al.
7,988,660 B2 8/2011 Byland et al.
7,988,663 B2 8/2011 Schiller et al.
7,988,674 B2 8/2011 Adams et al.
7,988,687 B2 8/2011 Friedli et al.
7,988,849 B2 8/2011 Biewer et al.
7,988,850 B2 8/2011 Roncadi et al.
7,990,251 B1 * 8/2011 Ford, Jr. ................ G16H 40/67
715/767
7,993,108 B2 8/2011 Rush et al.
7,993,140 B2 8/2011 Sakezles
7,993,300 B2 8/2011 Nyholm et al.
7,993,306 B2 8/2011 Marrs et al.
7,996,158 B2 8/2011 Hayter et al.
7,998,110 B2 8/2011 Leung et al.
7,998,111 B2 8/2011 Moberg et al.
7,998,117 B2 8/2011 Gross et al.
7,999,674 B2 8/2011 Kamen
7,999,927 B2 8/2011 Braig et al.
8,000,763 B2 8/2011 Mazza et al.
8,002,700 B2 8/2011 Ferek-Petric et al.
8,002,747 B2 8/2011 Lord et al.
8,003,630 B2 8/2011 Zagon et al.
8,005,524 B2 8/2011 Brauker et al.
8,005,540 B2 8/2011 Zhang et al.
8,005,688 B2 8/2011 Coffman et al.
8,007,460 B2 8/2011 Gelfand et al.
8,007,724 B2 8/2011 Guzman
RE42,682 E 9/2011 Barreras et al.
8,011,039 B2 9/2011 Stryker et al.
8,012,104 B2 9/2011 Escutia et al.
8,012,114 B2 9/2011 Daniel et al.
8,012,119 B2 9/2011 Estes et al.
8,012,121 B2 9/2011 Goodson et al.
8,012,132 B2 9/2011 Lum et al.
8,014,857 B2 9/2011 Doerr
8,016,740 B2 9/2011 Connors et al.
8,016,772 B2 9/2011 Heske et al.
8,016,783 B2 9/2011 Pastore et al.
8,016,789 B2 9/2011 Grant et al.
8,016,812 B2 9/2011 Koh
8,016,859 B2 9/2011 Donofrio et al.
8,019,721 B2 9/2011 Baker et al.
8,020,564 B2 9/2011 Batch
8,021,299 B2 9/2011 Miesel et al.
8,021,334 B2 9/2011 Shekalim et al.
8,021,680 B2 9/2011 Anderson et al.
8,022,042 B2 9/2011 Ko
8,022,366 B2 9/2011 Hartley
8,025,634 B1 9/2011 Moubayed et al.
8,026,209 B2 9/2011 Gaillard et al.
8,026,215 B2 9/2011 Unemori
8,026,227 B2 9/2011 Hausheer
8,027,740 B2 9/2011 Altman et al.
8,029,245 B2 10/2011 Rush et al.
8,029,250 B2 10/2011 Rush et al.
8,029,454 B2 10/2011 Kelly et al.
8,029,459 B2 10/2011 Rush et al.
8,029,460 B2 10/2011 Rush et al.
8,030,058 B1 10/2011 Benedict et al.
8,030,802 B2 10/2011 Lindegger et al.
8,030,891 B2 10/2011 Welsch et al.
8,032,226 B2 10/2011 Miller et al.
8,034,015 B2 10/2011 Braig et al.
8,034,019 B2 10/2011 Nair et al.
8,034,026 B2 10/2011 Grant et al.
8,034,793 B2 10/2011 Heidenreich et al.
8,038,650 B2 10/2011 Shekalim et al.
8,038,709 B2 10/2011 Palasis et al.
8,043,074 B2 10/2011 Tada
8,043,258 B2 10/2011 Ostroot
8,043,277 B2 10/2011 Junker
8,043,281 B2 10/2011 Heruth et al.
8,043,744 B2 10/2011 Traulsen et al.
8,046,043 B2 10/2011 Asano et al.
8,047,202 B2 11/2011 Djupesland
8,047,811 B2 11/2011 Rush et al.
8,047,812 B2 11/2011 Rush et al.
8,047,819 B2 11/2011 Lawrence et al.
8,048,041 B2 11/2011 Cefai et al.
8,048,619 B2 11/2011 Chow
8,049,009 B2 11/2011 Vasireddy et al.
8,049,059 B2 11/2011 Bleyer et al.
8,050,729 B2 11/2011 Shekalim
8,052,614 B2 11/2011 Heske et al.
8,053,429 B2 11/2011 Cumming et al.
8,056,582 B2 11/2011 DiPerna et al.
8,057,156 B2 11/2011 List
8,057,426 B2 11/2011 Nayak et al.
8,057,679 B2 11/2011 Yu et al.
8,060,185 B2 11/2011 Hunter et al.
8,060,209 B2 11/2011 Jaax et al.
8,062,249 B2 11/2011 Wilinska et al.
8,062,256 B2 11/2011 Carter et al.
8,062,257 B2 11/2011 Moberg et al.
8,062,264 B2 11/2011 Godfrey et al.
8,062,513 B2 11/2011 Yu et al.
8,065,096 B2 11/2011 Moberg et al.
8,065,161 B2 11/2011 Howard et al.
8,066,197 B2 11/2011 Sheppard
8,066,198 B2 11/2011 Palachon et al.
8,066,629 B2 11/2011 Dlugos et al.
8,066,665 B2 11/2011 Rush et al.
8,066,668 B2 11/2011 Wayman et al.
8,066,671 B2 11/2011 Busby et al.
8,066,672 B2 11/2011 Mandro
8,066,680 B2 11/2011 Alchas et al.
8,066,940 B2 11/2011 Denkewicz, Jr. et al.
8,067,031 B2 11/2011 Daniloff et al.
8,067,173 B2 11/2011 Liew
8,070,723 B2 12/2011 Bazargan et al.
8,070,726 B2 12/2011 Gonnelli et al.
8,070,741 B2 12/2011 Barrelle et al.
8,070,742 B2 12/2011 Woo et al.
8,071,075 B2 12/2011 Reed et al.
8,071,722 B2 12/2011 Kaplan et al.
8,073,543 B2 12/2011 Pyles
8,073,549 B2 12/2011 Chen
8,075,503 B2 12/2011 Jaeb
8,075,522 B2 12/2011 Larsen et al.

(56) References Cited

U.S. PATENT DOCUMENTS

| | | | |
|---|---|---|---|
| 8,075,527 | B2 | 12/2011 | Rush et al. |
| 8,075,919 | B2 | 12/2011 | Brown et al. |
| 8,078,983 | B2 | 12/2011 | Davis et al. |
| 8,079,983 | B2 | 12/2011 | Rush et al. |
| 8,079,984 | B2 | 12/2011 | Rush et al. |
| 8,080,002 | B2 | 12/2011 | Stergiopulos et al. |
| 8,081,069 | B2 | 12/2011 | Haueter et al. |
| 8,082,041 | B1 | 12/2011 | Radziemski |
| 8,083,209 | B2 | 12/2011 | Kozdras et al. |
| 8,083,711 | B2 | 12/2011 | Enggaard |
| 8,083,718 | B2 | 12/2011 | Rush et al. |
| 8,083,720 | B2 | 12/2011 | Solar et al. |
| 8,083,722 | B2 | 12/2011 | McKay |
| 8,083,730 | B2 | 12/2011 | Miesel |
| 8,088,098 | B2 | 1/2012 | Yodfat et al. |
| 8,088,789 | B2 | 1/2012 | Yan et al. |
| 8,089,787 | B2 | 1/2012 | Melse |
| 8,090,430 | B2 | 1/2012 | Makower et al. |
| 8,090,435 | B2 | 1/2012 | Gill et al. |
| 8,092,005 | B2 | 1/2012 | Silverbrook et al. |
| 8,092,428 | B2 | 1/2012 | Ramey et al. |
| 8,093,038 | B2 | 1/2012 | Hatziavramidis |
| 8,093,212 | B2 | 1/2012 | Gardner et al. |
| 8,093,214 | B2 | 1/2012 | Crockford |
| 8,093,781 | B2 | 1/2012 | Chiang et al. |
| 8,094,009 | B2 | 1/2012 | Allen et al. |
| 8,095,123 | B2 | 1/2012 | Gray |
| 8,095,390 | B2 | 1/2012 | Bluemler et al. |
| 8,096,329 | B2 | 1/2012 | Thout et al. |
| 8,096,487 | B2 | 1/2012 | Hornsby |
| 8,096,972 | B2 | 1/2012 | Varner et al. |
| 8,096,983 | B2 | 1/2012 | Uchino et al. |
| 8,099,800 | B2 | 1/2012 | Swalski et al. |
| 8,100,842 | B2 | 1/2012 | Rousso et al. |
| 8,100,852 | B2 | 1/2012 | Moberg et al. |
| 8,100,871 | B2 | 1/2012 | Haase |
| 8,101,358 | B2 | 1/2012 | Liew |
| 8,101,402 | B2 | 1/2012 | Holmes et al. |
| 8,101,727 | B2 | 1/2012 | Stover et al. |
| 8,105,265 | B2 | 1/2012 | Demers et al. |
| 8,105,268 | B2 | 1/2012 | Lebel et al. |
| 8,105,269 | B2 | 1/2012 | Zhou |
| 8,105,279 | B2 | 1/2012 | Mernoe et al. |
| 8,105,280 | B2 | 1/2012 | Iddan et al. |
| 8,105,351 | B2 | 1/2012 | Lehman et al. |
| 8,106,534 | B2 | 1/2012 | Spurlin et al. |
| 8,108,051 | B2 | 1/2012 | Cross, Jr. et al. |
| 8,109,893 | B2 | 2/2012 | Lande |
| 8,109,912 | B2 | 2/2012 | Alferness et al. |
| 8,109,921 | B2 | 2/2012 | Estes et al. |
| 8,110,224 | B2 | 2/2012 | Ausborn et al. |
| 8,110,358 | B2 | 2/2012 | Liew |
| 8,110,555 | B2 | 2/2012 | Jia et al. |
| 8,112,287 | B1 | 2/2012 | Paul et al. |
| 8,112,288 | B1 | 2/2012 | Paul et al. |
| 8,114,023 | B2 | 2/2012 | Ward et al. |
| 8,114,056 | B2 | 2/2012 | Niklaus et al. |
| 8,114,064 | B2 | 2/2012 | Alferness et al. |
| 8,114,066 | B2 | 2/2012 | Naef et al. |
| 8,114,350 | B1 | 2/2012 | Silver et al. |
| 8,114,430 | B2 | 2/2012 | Rohlhoff et al. |
| 8,114,597 | B2 | 2/2012 | Liew |
| 8,115,600 | B2 | 2/2012 | Stevenson et al. |
| 8,116,862 | B2 | 2/2012 | Stevenson et al. |
| 8,118,571 | B2 | 2/2012 | Krisher et al. |
| 8,118,770 | B2 | 2/2012 | Galley et al. |
| 8,118,782 | B2 | 2/2012 | Remde et al. |
| 8,119,159 | B2 | 2/2012 | Cumming et al. |
| 8,119,593 | B2 | 2/2012 | Richardson et al. |
| 8,121,689 | B2 | 2/2012 | Kalgren et al. |
| 8,121,857 | B2 | 2/2012 | Galasso et al. |
| 8,123,717 | B2 | 2/2012 | Weinert et al. |
| 8,123,720 | B2 | 2/2012 | Solomon |
| 8,124,689 | B2 | 2/2012 | Loubert et al. |
| 8,126,728 | B2 | 2/2012 | Dicks et al. |
| 8,126,729 | B2 | 2/2012 | Dicks et al. |
| 8,126,730 | B2 | 2/2012 | Dicks et al. |
| 8,126,732 | B2 | 2/2012 | Dicks et al. |
| 8,126,733 | B2 | 2/2012 | Dicks et al. |
| 8,126,734 | B2 | 2/2012 | Dicks et al. |
| 8,127,046 | B2 | 2/2012 | Grant et al. |
| 8,128,589 | B2 | 3/2012 | Freedman et al. |
| 8,128,597 | B2 | 3/2012 | Cross et al. |
| 8,128,946 | B2 | 3/2012 | Kawamura et al. |
| 8,129,429 | B2 | 3/2012 | Sporn et al. |
| 8,130,095 | B2 | 3/2012 | Allen et al. |
| 8,133,197 | B2 | 3/2012 | Blomquist et al. |
| 8,140,275 | B2 | 3/2012 | Campbell et al. |
| 8,140,312 | B2 | 3/2012 | Hayter et al. |
| 8,140,356 | B2 | 3/2012 | Dicks et al. |
| 8,147,511 | B2 | 4/2012 | Perry et al. |
| 8,149,117 | B2 | 4/2012 | Fennell et al. |
| 8,149,131 | B2 | 4/2012 | Blomquist |
| 8,152,764 | B2 | 4/2012 | Istoc et al. |
| 8,155,982 | B2 | 4/2012 | Dicks et al. |
| 8,156,070 | B2 | 4/2012 | Buck et al. |
| 8,167,832 | B2 | 5/2012 | Bowman et al. |
| 8,172,082 | B2 | 5/2012 | Edwards et al. |
| 8,172,798 | B2 | 5/2012 | Hungerford et al. |
| 8,177,739 | B2 | 5/2012 | Cartledge et al. |
| 8,182,447 | B2 | 5/2012 | Moberg et al. |
| 8,182,461 | B2 | 5/2012 | Pope et al. |
| 8,182,462 | B2 | 5/2012 | Istoc et al. |
| 8,187,228 | B2 | 5/2012 | Bikovsky et al. |
| 8,192,394 | B2 | 6/2012 | Estes et al. |
| 8,202,267 | B2 | 6/2012 | Field et al. |
| 8,204,729 | B2 | 6/2012 | Sher |
| 8,206,296 | B2 | 6/2012 | Jennewine |
| 8,206,350 | B2 | 6/2012 | Mann et al. |
| 8,206,378 | B1 | 6/2012 | Kalpin et al. |
| 8,208,984 | B2 | 6/2012 | Blomquist et al. |
| 8,211,062 | B2 | 7/2012 | Estes et al. |
| 8,211,093 | B2 | 7/2012 | Miller et al. |
| 8,211,364 | B2 | 7/2012 | Drucker et al. |
| 8,219,222 | B2 | 7/2012 | Blomquist |
| 8,221,385 | B2 | 7/2012 | Estes |
| 8,231,562 | B2 | 7/2012 | Buck et al. |
| 8,231,578 | B2 | 7/2012 | Fathallah et al. |
| 8,234,126 | B1 | 7/2012 | Estes |
| 8,234,128 | B2 | 7/2012 | Martucci et al. |
| 8,235,938 | B2 | 8/2012 | Eggers et al. |
| 8,237,715 | B2 | 8/2012 | Buck et al. |
| 8,251,906 | B2 | 8/2012 | Brauker et al. |
| 8,257,259 | B2 | 9/2012 | Brauker et al. |
| 8,257,300 | B2 | 9/2012 | Budiman et al. |
| 8,257,652 | B2 | 9/2012 | Drucker et al. |
| 8,257,653 | B2 | 9/2012 | Drucker et al. |
| 8,267,893 | B2 | 9/2012 | Moberg et al. |
| 8,282,627 | B2 | 10/2012 | Shelton et al. |
| 8,285,328 | B2 | 10/2012 | Caffey et al. |
| 8,287,454 | B2 | 10/2012 | Wolpert et al. |
| 8,287,487 | B2 | 10/2012 | Estes |
| 8,287,495 | B2 | 10/2012 | Michaud et al. |
| 8,287,521 | B2 | 10/2012 | Kriesel et al. |
| 8,292,876 | B2 | 10/2012 | Kriesel et al. |
| 8,294,581 | B2 | 10/2012 | Kamen |
| 8,298,183 | B2 | 10/2012 | Menot et al. |
| 8,298,184 | B2 | 10/2012 | DiPerna et al. |
| 8,313,433 | B2 | 11/2012 | Cohen et al. |
| 8,317,752 | B2 | 11/2012 | Cozmi et al. |
| 8,328,754 | B2 | 12/2012 | Estes et al. |
| 8,328,793 | B2 | 12/2012 | Birkenbach et al. |
| 8,344,847 | B2 | 1/2013 | Moberg et al. |
| 8,348,886 | B2 | 1/2013 | Kanderian, Jr. et al. |
| 8,348,923 | B2 | 1/2013 | Kanderian, Jr. et al. |
| 8,361,030 | B2 | 1/2013 | Carter et al. |
| 8,376,943 | B2 | 2/2013 | Kovach et al. |
| 8,380,536 | B2 | 2/2013 | Howard et al. |
| 8,395,581 | B2 | 3/2013 | Graaskov et al. |
| 8,398,592 | B2 | 3/2013 | Leibner-Druska |
| 8,407,063 | B2 | 3/2013 | Brown |
| 8,408,421 | B2 | 4/2013 | DiPerna et al. |
| 8,414,563 | B2 | 4/2013 | Kamen et al. |
| 8,444,592 | B2 | 5/2013 | Williams et al. |

(56) References Cited

U.S. PATENT DOCUMENTS 8,449,524 B2 5/2013 Braig et al.
8,452,953 B2 5/2013 Buck et al.
8,454,562 B1 6/2013 Sims et al.
8,457,901 B2 6/2013 Beshan et al.
8,461,985 B2 6/2013 Fennell et al.
8,502,662 B2 8/2013 Pohlman et al.
8,512,276 B2 8/2013 Talbot et al.
8,517,991 B2 8/2013 Clemente
8,562,558 B2 10/2013 Kamath et al.
8,568,357 B2 10/2013 Ortega et al.
8,573,027 B2 11/2013 Rosinko et al.
8,579,853 B2 11/2013 Reggiardo et al.
8,601,465 B2 12/2013 Bernstein et al.
8,663,201 B2 3/2014 Hill et al.
8,726,266 B2 5/2014 Kiaie et al.
8,905,965 B2 12/2014 Mandro et al.
8,938,306 B2 1/2015 Lebel et al.
8,977,883 B2 3/2015 Imhof et al.
8,992,475 B2 3/2015 Mann et al.
9,114,210 B2 8/2015 Estes
9,132,227 B2 9/2015 Bryant, Jr. et al.
9,238,100 B2 1/2016 Kruse et al.
9,335,910 B2 5/2016 Farnan et al.
9,474,856 B2 10/2016 Blomquist
9,486,571 B2 11/2016 Rosinko
9,565,718 B2 2/2017 Swanson
9,675,756 B2 6/2017 Kamen
9,715,327 B2 7/2017 Rosinko et al.
9,737,656 B2 8/2017 Rosinko
9,814,835 B2 11/2017 Kruse et al.
10,213,547 B2 2/2019 Rosinko
10,434,253 B2 10/2019 DiPerna et al.
11,135,362 B2* 10/2021 DiPerna ................ F04B 53/143
12,042,627 B2* 7/2024 DiPerna ................ G16H 40/63
2001/0000262 A1 4/2001 Poleshuk et al.
2001/0027791 A1 10/2001 Wallace et al.
2001/0041869 A1 11/2001 Causey, III et al.
2002/0004015 A1 1/2002 Carlisle et al.
2002/0018720 A1 2/2002 Carlisle et al.
2002/0019714 A1 2/2002 Carliale et al.
2002/0029776 A1 3/2002 Blomquist
2002/0040208 A1 4/2002 Flaherty et al.
2002/0045265 A1 4/2002 Bergh et al.
2002/0048536 A1 4/2002 Bergh et al.
2002/0055787 A1 5/2002 Lennox et al.
2002/0059959 A1 5/2002 Qatu et al.
2002/0065484 A1 5/2002 Douglas et al.
2002/0072733 A1 6/2002 Flaherty
2002/0076679 A1 6/2002 Aman
2002/0117214 A1 8/2002 Tucker et al.
2002/0120234 A1 8/2002 Kong
2002/0154571 A1 10/2002 Cefai et al.
2002/0173769 A1 11/2002 Gray et al.
2002/0193679 A1 12/2002 Malave
2003/0014016 A1 1/2003 Purdy
2003/0032930 A1 2/2003 Branch
2003/0036725 A1 2/2003 Lavi et al.
2003/0055380 A1 3/2003 Flaherty et al.
2003/0060765 A1 3/2003 Campbell et al.
2003/0065287 A1 4/2003 Spohn et al.
2003/0065308 A1 4/2003 Lebel et al.
2003/0078547 A1 4/2003 Shekalim
2003/0093105 A1 5/2003 Huffmaster
2003/0097062 A1 5/2003 Purdy et al.
2003/0100863 A1 5/2003 Shekalim
2003/0109836 A1 6/2003 Shekalim
2003/0130577 A1 7/2003 Purdy et al.
2003/0161744 A1 8/2003 Vilks et al.
2003/0163088 A1 8/2003 Blomquist
2003/0163789 A1 8/2003 Blomquist
2003/0183289 A1 10/2003 Seuret et al.
2003/0199378 A1 10/2003 Saviano
2003/0212364 A1 11/2003 Mann et al.
2003/0216683 A1 11/2003 Shekalim
2004/0010207 A1 1/2004 Flaherty et al.
2004/0019325 A1 1/2004 Shekalim
2004/0051368 A1 3/2004 Caputo et al.
2004/0068230 A1 4/2004 Estes et al.
2004/0073095 A1 4/2004 Causey, III et al.
2004/0073161 A1 4/2004 Tachibana
2004/0074785 A1 4/2004 Holker et al.
2004/0078028 A1 4/2004 Flaherty et al.
2004/0092865 A1 5/2004 Flaherty et al.
2004/0116866 A1 6/2004 William et al.
2004/0116905 A1 6/2004 Pedersen et al.
2004/0122353 A1 6/2004 Shahmirian et al.
2004/0133220 A1 7/2004 Lashinski et al.
2004/0138744 A1 7/2004 Lashinski et al.
2004/0152622 A1 8/2004 Keith et al.
2004/0153146 A1 8/2004 Lashinski et al.
2004/0167478 A1 8/2004 Mooney et al.
2004/0171987 A1 9/2004 Bridle et al.
2004/0176727 A1 9/2004 Shekalim
2004/0193025 A1 9/2004 Steil
2004/0193090 A1 9/2004 Lebel et al.
2004/0204673 A1 10/2004 Flaherty
2004/0220551 A1 11/2004 Flaherty et al.
2004/0225252 A1 11/2004 Gillespie et al.
2004/0235446 A1 11/2004 Flaherty et al.
2004/0260233 A1 12/2004 Garibotto et al.
2005/0004514 A1 1/2005 Hochman et al.
2005/0020980 A1 1/2005 Inoue et al.
2005/0022274 A1 1/2005 Campbell et al.
2005/0027182 A1 2/2005 Siddiqui et al.
2005/0038379 A1 2/2005 Beebe et al.
2005/0043710 A1 2/2005 Hadzic et al.
2005/0054994 A1 3/2005 Cioanta et al.
2005/0060030 A1 3/2005 Lashinski et al.
2005/0065464 A1 3/2005 Talbot et al.
2005/0096593 A1 5/2005 Pope et al.
2005/0115622 A1 6/2005 Bennett et al.
2005/0137530 A1 6/2005 Campbell et al.
2005/0137578 A1 6/2005 Heruth et al.
2005/0143864 A1 6/2005 Blomquist
2005/0148832 A1 7/2005 Reghabi et al.
2005/0171512 A1 8/2005 Flaherty
2005/0171513 A1 8/2005 Mann et al.
2005/0171569 A1 8/2005 Girard et al.
2005/0177395 A1 8/2005 Blomquist
2005/0182366 A1 8/2005 Vogt et al.
2005/0203360 A1 9/2005 Brauker
2005/0211322 A1 9/2005 Lohbeck
2005/0238507 A1 10/2005 Dilanni et al.
2005/0240092 A1 10/2005 Shah et al.
2005/0240119 A1 10/2005 Draudt et al.
2005/0245867 A1 11/2005 Olsen et al.
2005/0246416 A1 11/2005 Blomquist
2005/0267550 A1 12/2005 Hess et al.
2005/0272989 A1 12/2005 Shah et al.
2006/0031094 A1 2/2006 Cohen et al.
2006/0033361 A1 2/2006 Frederick et al.
2006/0041229 A1 2/2006 Garibotto et al.
2006/0042695 A1 3/2006 Gonia
2006/0076236 A1 4/2006 Shah et al.
2006/0093785 A1 5/2006 Hickle
2006/0116757 A1 6/2006 Lashinski et al.
2006/0139354 A1 6/2006 Suma
2006/0147313 A1 7/2006 Zengerle et al.
2006/0149214 A1 7/2006 Breiter et al.
2006/0150747 A1 7/2006 Mallett
2006/0150748 A1 7/2006 Mallett
2006/0172026 A1 8/2006 Stutz
2006/0173444 A1 8/2006 Choy et al.
2006/0178633 A1 8/2006 Garibotto et al.
2006/0189895 A1 8/2006 Neel et al.
2006/0195064 A1 8/2006 Plahey et al.
2006/0202859 A1 9/2006 Mastrototaro et al.
2006/0206029 A1 9/2006 Yair et al.
2006/0206054 A1 9/2006 Shekalim et al.
2006/0224109 A1 10/2006 Steil
2006/0229557 A1 10/2006 Fathallah et al.
2006/0243604 A1 11/2006 Christoffersen et al.
2006/0253086 A1 11/2006 Moberg et al.
2006/0253296 A1 11/2006 Liisberg et al.

(56) References Cited

U.S. PATENT DOCUMENTS

2006/0264835 A1 11/2006 Nielsen et al.
2006/0271022 A1 11/2006 Steinbach et al.
2006/0272652 A1 12/2006 Stocker et al.
2006/0281980 A1 12/2006 Randlov et al.
2006/0282290 A1 12/2006 Flaherty et al.
2006/0293576 A1 12/2006 Van et al.
2006/0293577 A1 12/2006 Morrison et al.
2007/0000337 A1 1/2007 Gross et al.
2007/0003434 A1 1/2007 Padmanabhan et al.
2007/0016170 A1 1/2007 Kovelman
2007/0016449 A1 1/2007 Cohen et al.
2007/0033074 A1 2/2007 Nitzan et al.
2007/0060869 A1 3/2007 Tolle et al.
2007/0060870 A1 3/2007 Tolle et al.
2007/0061735 A1 3/2007 Hoffberg
2007/0066956 A1 3/2007 Finkel
2007/0073129 A1 3/2007 Shah et al.
2007/0073236 A1 3/2007 Mernoe et al.
2007/0088267 A1 4/2007 Shekalim et al.
2007/0093786 A1 4/2007 Goldsmith et al.
2007/0100222 A1 5/2007 Mastrototaro et al.
2007/0100235 A1 5/2007 Kennedy, II
2007/0112261 A1 5/2007 Enegren et al.
2007/0112301 A1 5/2007 Preuthun et al.
2007/0118405 A1 5/2007 Campbell et al.
2007/0123819 A1 5/2007 Mernoe et al.
2007/0124002 A1 5/2007 Estes et al.
2007/0142822 A1 6/2007 Rembe
2007/0149926 A1 6/2007 Moberg et al.
2007/0150019 A1 6/2007 Youker et al.
2007/0156033 A1 7/2007 Causey, III et al.
2007/0156092 A1 7/2007 Estes et al.
2007/0161955 A1 7/2007 Bynum et al.
2007/0167905 A1 7/2007 Estes et al.
2007/0167912 A1 7/2007 Shah et al.
2007/0173712 A1 7/2007 Shah et al.
2007/0173762 A1 7/2007 Estes et al.
2007/0179444 A1 8/2007 Causey et al.
2007/0201992 A1 8/2007 Mernoe et al.
2007/0203459 A1 8/2007 Mernoe
2007/0219480 A1 9/2007 Kamen et al.
2007/0219496 A1 9/2007 Kamen et al.
2007/0219597 A1 9/2007 Kamen et al.
2007/0227907 A1 10/2007 Shah et al.
2007/0228071 A1 10/2007 Kamen et al.
2007/0250007 A1 10/2007 Shekalim
2007/0251835 A1 11/2007 Mehta et al.
2007/0253021 A1 11/2007 Mehta et al.
2007/0253380 A1 11/2007 Jollota et al.
2007/0254593 A1 11/2007 Jollota et al.
2007/0255116 A1 11/2007 Mehta et al.
2007/0255125 A1 11/2007 Moberg et al.
2007/0255126 A1 11/2007 Moberg et al.
2007/0255348 A1 11/2007 Holtzclaw
2007/0258395 A1 11/2007 Jollota et al.
2007/0264130 A1 11/2007 Mallett et al.
2007/0287985 A1 12/2007 Estes et al.
2007/0288176 A1 12/2007 Carlisle et al.
2007/0293843 A1 12/2007 Ireland et al.
2008/0004601 A1 1/2008 Jennewine et al.
2008/0015510 A1 1/2008 Sandoz et al.
2008/0026473 A1 1/2008 Wang et al.
2008/0029173 A1 2/2008 Diperna et al.
2008/0033350 A1 2/2008 Wilson et al.
2008/0033357 A1 2/2008 Mann et al.
2008/0033360 A1 2/2008 Evans et al.
2008/0033402 A1 2/2008 Blomquist
2008/0033749 A1 2/2008 Blomquist
2008/0034323 A1 2/2008 Blomquist
2008/0045891 A1 2/2008 Maule et al.
2008/0045902 A1 2/2008 Estes et al.
2008/0045903 A1 2/2008 Estes et al.
2008/0045904 A1 2/2008 Estes et al.
2008/0045931 A1 2/2008 Estes et al.
2008/0051697 A1 2/2008 Mounce et al.
2008/0051698 A1 2/2008 Mounce et al.
2008/0051709 A1 2/2008 Mounce et al.
2008/0051711 A1 2/2008 Mounce et al.
2008/0051716 A1 2/2008 Stutz
2008/0051727 A1 2/2008 Moberg et al.
2008/0051765 A1 2/2008 Mounce et al.
2008/0058697 A1 3/2008 Kamen et al.
2008/0065007 A1 3/2008 Peterson et al.
2008/0065016 A1 3/2008 Peterson et al.
2008/0071220 A1 3/2008 Rhinehart et al.
2008/0071580 A1 3/2008 Marcus et al.
2008/0082040 A1 4/2008 Kubler et al.
2008/0082363 A1 4/2008 Habashi
2008/0092989 A1 4/2008 Diperna et al.
2008/0097289 A1 4/2008 Steil et al.
2008/0097291 A1 4/2008 Hanson et al.
2008/0097309 A1 4/2008 Enegren et al.
2008/0097327 A1 4/2008 Bente et al.
2008/0097375 A1 4/2008 Bikovsky et al.
2008/0103554 A1 5/2008 Dicks et al.
2008/0114228 A1 5/2008 McCluskey et al.
2008/0116647 A1 5/2008 Anderson et al.
2008/0119705 A1 5/2008 Patel et al.
2008/0125700 A1 5/2008 Moberg et al.
2008/0126969 A1 5/2008 Blomquist
2008/0139910 A1 6/2008 Blomquist
2008/0147004 A1 6/2008 Mann et al.
2008/0147050 A1 6/2008 Mann et al.
2008/0148235 A1 6/2008 Foresti et al.
2008/0154513 A1 6/2008 Kovatchev
2008/0156661 A1 7/2008 Cooper et al.
2008/0160492 A1 7/2008 Campbell et al.
2008/0171967 A1 7/2008 Blomquist et al.
2008/0172027 A1 7/2008 Blomquist
2008/0172028 A1 7/2008 Blomquist
2008/0172029 A1 7/2008 Blomquist
2008/0172030 A1 7/2008 Blomquist
2008/0172031 A1 7/2008 Blomquist
2008/0177154 A1 7/2008 Hansen et al.
2008/0177155 A1 7/2008 Hansen et al.
2008/0183060 A1 7/2008 Steil et al.
2008/0188723 A1 8/2008 Kristensen et al.
2008/0196762 A1 8/2008 Mallett et al.
2008/0197801 A1 8/2008 Manor et al.
2008/0200868 A1 8/2008 Alberti et al.
2008/0200869 A1 8/2008 Bedingfield
2008/0206799 A1 8/2008 Blomquist
2008/0221523 A1 9/2008 Moberg et al.
2008/0228056 A1 9/2008 Blomquist et al.
2008/0234637 A1 9/2008 McConnell et al.
2008/0243062 A1 10/2008 Destefano et al.
2008/0249470 A1 10/2008 Malave et al.
2008/0269584 A1 10/2008 Shekalim
2008/0269680 A1 10/2008 Ibranyan et al.
2008/0269681 A1 10/2008 Kavazov et al.
2008/0269682 A1 10/2008 Kavazov et al.
2008/0269714 A1 10/2008 Mastrototaro et al.
2008/0269723 A1 10/2008 Mastrototaro et al.
2008/0281276 A1 11/2008 Shekalim
2008/0287887 A1 11/2008 Mack et al.
2008/0287922 A1 11/2008 Panduro
2008/0294094 A1 11/2008 Mhatre et al.
2008/0294108 A1 11/2008 Briones et al.
2008/0294109 A1 11/2008 Estes et al.
2008/0294142 A1 11/2008 Patel et al.
2008/0300534 A1 12/2008 Blomquist
2008/0300572 A1 12/2008 Rankers et al.
2008/0300651 A1 12/2008 Gerber et al.
2008/0304366 A1 12/2008 Jarvis et al.
2008/0306434 A1 12/2008 Dobbles et al.
2008/0306444 A1 12/2008 Brister et al.
2008/0312584 A1* 12/2008 Montgomery ......... G16H 40/67
600/300
2008/0317605 A1 12/2008 Amley et al.
2009/0006129 A1 1/2009 Thukral et al.
2009/0014458 A1 1/2009 Heffron
2009/0018495 A1 1/2009 Panduro
2009/0018779 A1 1/2009 Cohen et al.
2009/0026146 A1 1/2009 Carlisle et al.

(56) References Cited

U.S. PATENT DOCUMENTS

| | | | |
|---|---|---|---|
| 2009/0030733 | A1 | 1/2009 | Cohen et al. |
| 2009/0036870 | A1 | 2/2009 | Mounce et al. |
| 2009/0037020 | A1 | 2/2009 | Brown |
| 2009/0043290 | A1 | 2/2009 | Villegas et al. |
| 2009/0062767 | A1 | 3/2009 | Van Antwerp et al. |
| 2009/0062887 | A1 | 3/2009 | Mass et al. |
| 2009/0063187 | A1 | 3/2009 | Johnson et al. |
| 2009/0067989 | A1 | 3/2009 | Estes et al. |
| 2009/0069745 | A1 | 3/2009 | Estes et al. |
| 2009/0069746 | A1 | 3/2009 | Miller et al. |
| 2009/0069749 | A1 | 3/2009 | Miller et al. |
| 2009/0069784 | A1 | 3/2009 | Estes et al. |
| 2009/0069785 | A1 | 3/2009 | Miller et al. |
| 2009/0069787 | A1 | 3/2009 | Estes et al. |
| 2009/0077179 | A1 | 3/2009 | Bi et al. |
| 2009/0082728 | A1 | 3/2009 | Bikovsky |
| 2009/0085768 | A1 | 4/2009 | Patel et al. |
| 2009/0088701 | A1 | 4/2009 | Larsen et al. |
| 2009/0088731 | A1 | 4/2009 | Campbell et al. |
| 2009/0099866 | A1 | 4/2009 | Newman |
| 2009/0099867 | A1 | 4/2009 | Newman |
| 2009/0101549 | A1 | 4/2009 | Kamen et al. |
| 2009/0107335 | A1 | 4/2009 | Wilt et al. |
| 2009/0108016 | A1 | 4/2009 | Brown et al. |
| 2009/0112626 | A1 | 4/2009 | Talbot et al. |
| 2009/0113295 | A1 | 4/2009 | Halpern et al. |
| 2009/0131663 | A1 | 5/2009 | Carlisle et al. |
| 2009/0137987 | A1 | 5/2009 | Ali |
| 2009/0143661 | A1 | 6/2009 | Taub et al. |
| 2009/0143732 | A1 | 6/2009 | O'Connor et al. |
| 2009/0144089 | A1 | 6/2009 | Heywood et al. |
| 2009/0150186 | A1 | 6/2009 | Cohen et al. |
| 2009/0150484 | A1 | 6/2009 | Roberts |
| 2009/0150865 | A1 | 6/2009 | Young et al. |
| 2009/0156990 | A1 | 6/2009 | Wenger et al. |
| 2009/0156991 | A1 | 6/2009 | Roberts et al. |
| 2009/0157202 | A1 | 6/2009 | Roberts et al. |
| 2009/0157622 | A1 | 6/2009 | Roberts et al. |
| 2009/0157695 | A1 | 6/2009 | Roberts |
| 2009/0158274 | A1 | 6/2009 | Roberts |
| 2009/0163855 | A1 | 6/2009 | Shin et al. |
| 2009/0170056 | A1 | 7/2009 | Nam et al. |
| 2009/0171269 | A1 | 7/2009 | Jennewine et al. |
| 2009/0171324 | A1 | 7/2009 | Chong et al. |
| 2009/0177142 | A1 | 7/2009 | Blomquist et al. |
| 2009/0177147 | A1 | 7/2009 | Blomquist et al. |
| 2009/0177154 | A1 | 7/2009 | Blomquist |
| 2009/0177248 | A1 | 7/2009 | Roberts |
| 2009/0177249 | A1 | 7/2009 | Roberts et al. |
| 2009/0177769 | A1 | 7/2009 | Roberts |
| 2009/0177991 | A1 | 7/2009 | Davis et al. |
| 2009/0191067 | A1 | 7/2009 | DiPerna et al. |
| 2009/0192366 | A1 | 7/2009 | Mensinger et al. |
| 2009/0192724 | A1 | 7/2009 | Brauker et al. |
| 2009/0192745 | A1 | 7/2009 | Kamath et al. |
| 2009/0204113 | A1 | 8/2009 | Macadam et al. |
| 2009/0212966 | A1 | 8/2009 | Panduro |
| 2009/0217982 | A1 | 9/2009 | DiPerna et al. |
| 2009/0221890 | A1 | 9/2009 | Saffer et al. |
| 2009/0221891 | A1 | 9/2009 | Yu et al. |
| 2009/0227855 | A1 | 9/2009 | Hill et al. |
| 2009/0227888 | A1 | 9/2009 | Salmi et al. |
| 2009/0229374 | A1 | 9/2009 | Carlisle et al. |
| 2009/0234594 | A1 | 9/2009 | Carlisle et al. |
| 2009/0240193 | A1 | 9/2009 | Mensinger et al. |
| 2009/0246035 | A1 | 10/2009 | Patzer |
| 2009/0247931 | A1 | 10/2009 | Damgaard-Sorensen |
| 2009/0247982 | A1 | 10/2009 | Krulevitch et al. |
| 2009/0254037 | A1 | 10/2009 | Bryant et al. |
| 2009/0256527 | A1 | 10/2009 | Welsch et al. |
| 2009/0259183 | A1 | 10/2009 | Chong et al. |
| 2009/0259198 | A1 | 10/2009 | Chong et al. |
| 2009/0259209 | A1 | 10/2009 | Chong et al. |
| 2009/0264825 | A1 | 10/2009 | Cote et al. |
| 2009/0267774 | A1 | 10/2009 | Enegren et al. |
| 2009/0267775 | A1 | 10/2009 | Enegren et al. |
| 2009/0270705 | A1 | 10/2009 | Enegren et al. |
| 2009/0270810 | A1 | 10/2009 | Debelser et al. |
| 2009/0270811 | A1 | 10/2009 | Mounce et al. |
| 2009/0270833 | A1 | 10/2009 | Debelser et al. |
| 2009/0272928 | A1 | 11/2009 | Alvarez et al. |
| 2009/0275886 | A1 | 11/2009 | Blomquist et al. |
| 2009/0275887 | A1 | 11/2009 | Estes |
| 2009/0275896 | A1 | 11/2009 | Kamen et al. |
| 2009/0281393 | A1 | 11/2009 | Smith |
| 2009/0287153 | A1 | 11/2009 | Bresina et al. |
| 2009/0287180 | A1 | 11/2009 | DiPerna et al. |
| 2009/0289916 | A1 | 11/2009 | Dai |
| 2009/0292245 | A1 | 11/2009 | Basso et al. |
| 2009/0299438 | A1 | 12/2009 | Nolan et al. |
| 2009/0321675 | A1 | 12/2009 | Alvarez et al. |
| 2009/0326458 | A1 | 12/2009 | Chong et al. |
| 2010/0008795 | A1 | 1/2010 | DiPerna |
| 2010/0010330 | A1 | 1/2010 | Rankers et al. |
| 2010/0010647 | A1 | 1/2010 | Schroeder et al. |
| 2010/0016791 | A1 | 1/2010 | Chong et al. |
| 2010/0022937 | A1 | 1/2010 | Bedingfield et al. |
| 2010/0028208 | A1 | 2/2010 | Shekalim et al. |
| 2010/0030045 | A1 | 2/2010 | Gottlieb et al. |
| 2010/0030092 | A1 | 2/2010 | Kristensen et al. |
| 2010/0032041 | A1 | 2/2010 | DiPerna |
| 2010/0036327 | A1 | 2/2010 | DiPerna et al. |
| 2010/0037680 | A1 | 2/2010 | Moberg et al. |
| 2010/0038572 | A1 | 2/2010 | Alvarez et al. |
| 2010/0043738 | A1 | 2/2010 | Grandvallet et al. |
| 2010/0049126 | A1 | 2/2010 | Bronfeld et al. |
| 2010/0049164 | A1 | 2/2010 | Estes |
| 2010/0050236 | A1 | 2/2010 | Miller |
| 2010/0063765 | A1 | 3/2010 | Carlisle et al. |
| 2010/0064257 | A1 | 3/2010 | Buck et al. |
| 2010/0065578 | A1 | 3/2010 | DiPerna |
| 2010/0065579 | A1 | 3/2010 | DiPerna et al. |
| 2010/0069890 | A1 | 3/2010 | Graeskov et al. |
| 2010/0071446 | A1 | 3/2010 | Brown |
| 2010/0081993 | A1 | 4/2010 | O'Connor |
| 2010/0087777 | A1 | 4/2010 | Hopping et al. |
| 2010/0094114 | A1 | 4/2010 | Robinson et al. |
| 2010/0094251 | A1 | 4/2010 | Estes |
| 2010/0095229 | A1 | 4/2010 | Dixon et al. |
| 2010/0096019 | A1 | 4/2010 | DiPerna et al. |
| 2010/0100026 | A1 | 4/2010 | Morris |
| 2010/0100037 | A1 | 4/2010 | Cozmi et al. |
| 2010/0105999 | A1 | 4/2010 | Dixon et al. |
| 2010/0106100 | A1 | 4/2010 | Petersen |
| 2010/0114015 | A1 | 5/2010 | Kanderian, Jr. et al. |
| 2010/0114027 | A1 | 5/2010 | Jacobson et al. |
| 2010/0119414 | A1 | 5/2010 | Eisenhardt et al. |
| 2010/0121169 | A1 | 5/2010 | Petisce et al. |
| 2010/0121170 | A1 | 5/2010 | Rule |
| 2010/0121306 | A1 | 5/2010 | Yodfat et al. |
| 2010/0121415 | A1 | 5/2010 | Skelton et al. |
| 2010/0125241 | A1 | 5/2010 | Prud et al. |
| 2010/0130933 | A1 | 5/2010 | Holland et al. |
| 2010/0134305 | A1 | 6/2010 | Lu et al. |
| 2010/0137833 | A1 | 6/2010 | Glynn |
| 2010/0138197 | A1 | 6/2010 | Sher |
| 2010/0145262 | A1 | 6/2010 | Bengtsson et al. |
| 2010/0145303 | A1 | 6/2010 | Yodfat et al. |
| 2010/0152658 | A1 | 6/2010 | Hanson et al. |
| 2010/0152674 | A1 | 6/2010 | Kavazov et al. |
| 2010/0160740 | A1 | 6/2010 | Cohen et al. |
| 2010/0161236 | A1 | 6/2010 | Cohen et al. |
| 2010/0161346 | A1 | 6/2010 | Getschmann et al. |
| 2010/0162786 | A1 | 7/2010 | Keenan et al. |
| 2010/0164727 | A1 | 7/2010 | Bazargan et al. |
| 2010/0165795 | A1 | 7/2010 | Elder et al. |
| 2010/0168538 | A1 | 7/2010 | Keenan et al. |
| 2010/0168539 | A1 | 7/2010 | Palerm et al. |
| 2010/0168543 | A1 | 7/2010 | Kamath et al. |
| 2010/0168670 | A1 | 7/2010 | Srisathapat et al. |
| 2010/0168711 | A1 | 7/2010 | Bazargan et al. |
| 2010/0174230 | A1 | 7/2010 | Istoc et al. |
| 2010/0174266 | A1 | 7/2010 | Estes |
| 2010/0174553 | A1 | 7/2010 | Kaufman et al. |

(56) References Cited

U.S. PATENT DOCUMENTS

2010/0179402 A1 7/2010 Goode et al.
2010/0185142 A1 7/2010 Kamen et al.
2010/0185175 A1 7/2010 Kamen et al.
2010/0191084 A1 7/2010 Shah et al.
2010/0191165 A1 7/2010 Appling et al.
2010/0192686 A1 8/2010 Kamen et al.
2010/0198034 A1 8/2010 Thomas et al.
2010/0198107 A1 8/2010 Groll et al.
2010/0198142 A1 8/2010 Sloan et al.
2010/0198143 A1 8/2010 Estes et al.
2010/0198183 A1 8/2010 Lanigan et al.
2010/0198520 A1 8/2010 Breton et al.
2010/0205001 A1 8/2010 Knudsen et al.
2010/0217192 A1 8/2010 Moberg et al.
2010/0217193 A1 8/2010 Moberg et al.
2010/0218132 A1 8/2010 Soni et al.
2010/0218586 A1 9/2010 Rosinko et al.
2010/0222735 A1 9/2010 Plahey et al.
2010/0222765 A1 9/2010 Blomquist et al.
2010/0224192 A1 9/2010 Dixon et al.
2010/0228186 A1 9/2010 Estes et al.
2010/0234709 A1 9/2010 Say et al.
2010/0235439 A1 9/2010 Goodnow
2010/0241065 A1 9/2010 Moberg et al.
2010/0249530 A1 9/2010 Rankers et al.
2010/0249566 A1 9/2010 Suess et al.
2010/0249706 A1 9/2010 Clemente
2010/0250697 A1 9/2010 Hansen et al.
2010/0251114 A1 9/2010 Wehba et al.
2010/0253768 A1 10/2010 El-Maraghi et al.
2010/0256466 A1 10/2010 Shekalim et al.
2010/0256561 A1 10/2010 Gillespie et al.
2010/0256565 A1 10/2010 Mernoe et al.
2010/0256598 A1 10/2010 Mernoe et al.
2010/0261987 A1 10/2010 Kamath et al.
2010/0262078 A1 10/2010 Blomquist
2010/0262434 A1 10/2010 Shaya
2010/0274192 A1 10/2010 Mernoe
2010/0274515 A1 10/2010 Hoss et al.
2010/0274592 A1 10/2010 Nitzan et al.
2010/0277119 A1 11/2010 Montague et al.
2010/0280329 A1 11/2010 Randloev et al.
2010/0280442 A1 11/2010 Shahmirian et al.
2010/0280486 A1 11/2010 Khair et al.
2010/0286563 A1 11/2010 Bryer et al.
2010/0292556 A1 11/2010 Golden
2010/0298662 A1 11/2010 Yu et al.
2010/0298681 A1 11/2010 Say et al.
2010/0298685 A1 11/2010 Hayter et al.
2010/0299156 A1 11/2010 Jorgensen
2010/0305421 A1 12/2010 Ow-Wing
2010/0305545 A1 12/2010 Kanderian et al.
2010/0312082 A1 12/2010 Batman et al.
2010/0317950 A1 12/2010 Galley et al.
2010/0317951 A1 12/2010 Rutkowski et al.
2010/0323431 A1 12/2010 Rutkowski et al.
2010/0324382 A1 12/2010 Cantwell et al.
2010/0324394 A1 12/2010 Say et al.
2010/0324853 A1 12/2010 Wang et al.
2010/0324932 A1 12/2010 Galley et al.
2010/0331651 A1 12/2010 Groll
2010/0331652 A1 12/2010 Groll et al.
2010/0331854 A1 12/2010 Moberg et al.
2011/0004188 A1 1/2011 Shekalim
2011/0006876 A1 1/2011 Moberg et al.
2011/0009725 A1 1/2011 Hill et al.
2011/0009798 A1 1/2011 Kelly et al.
2011/0009813 A1 1/2011 Rankers
2011/0009823 A1 1/2011 Chong et al.
2011/0009825 A1 1/2011 Chong et al.
2011/0009846 A1 1/2011 Istoc et al.
2011/0010105 A1 1/2011 Shah et al.
2011/0015509 A1 1/2011 Peyser
2011/0021898 A1 1/2011 Wei et al.
2011/0022025 A1 1/2011 Savoie et al.
2011/0028937 A1 2/2011 Powers et al.
2011/0030845 A1 2/2011 Chong et al.
2011/0033833 A1 2/2011 Blomquist et al.
2011/0034786 A1 2/2011 Cadio et al.
2011/0040247 A1 2/2011 Mandro et al.
2011/0040251 A1 2/2011 Blomquist et al.
2011/0044333 A1 2/2011 Sicurello et al.
2011/0046051 A1 2/2011 Moerman
2011/0046454 A1 2/2011 Ejlersen et al.
2011/0046469 A1 2/2011 Nelson et al.
2011/0046697 A1 2/2011 Gerber et al.
2011/0046892 A1 2/2011 Moerman
2011/0047499 A1 2/2011 Mandro et al.
2011/0048938 A1 3/2011 Shah et al.
2011/0048941 A1 3/2011 Shah et al.
2011/0050428 A1 3/2011 Istoc
2011/0053121 A1 3/2011 Heaton
2011/0054281 A1 3/2011 Shah et al.
2011/0054390 A1 3/2011 Searle et al.
2011/0054391 A1 3/2011 Ward et al.
2011/0054397 A1 3/2011 Menot et al.
2011/0056264 A1 3/2011 Kaplan et al.
2011/0058485 A1 3/2011 Sloan
2011/0060280 A1 3/2011 Caffey et al.
2011/0060281 A1 3/2011 Aeschlimann et al.
2011/0060328 A1 3/2011 Skwarek et al.
2011/0066108 A1 3/2011 Geipel et al.
2011/0066555 A1 3/2011 Dicks et al.
2011/0071372 A1 3/2011 Sloan et al.
2011/0071464 A1 3/2011 Palerm
2011/0071465 A1 3/2011 Wang et al.
2011/0071765 A1 3/2011 Yodfat et al.
2011/0077481 A1 3/2011 Say et al.
2011/0077493 A1 3/2011 Shadforth et al.
2011/0077554 A1 3/2011 Roe et al.
2011/0077963 A1 3/2011 Knudsen et al.
2011/0078441 A1 3/2011 Dicks et al.
2011/0082439 A1 4/2011 Wenger et al.
2011/0087195 A1 4/2011 Uhland et al.
2011/0092788 A1 4/2011 Long et al.
2011/0092894 A1 4/2011 McGill et al.
2011/0092907 A1 4/2011 Krogh et al.
2011/0092921 A1 4/2011 Beling et al.
2011/0093285 A1 4/2011 Dicks et al.
2011/0093286 A1 4/2011 Dicks et al.
2011/0097480 A1 4/2011 Shah et al.
2011/0098548 A1 4/2011 Budiman et al.
2011/0098637 A1 4/2011 Hill
2011/0098638 A1 4/2011 Chawla et al.
2011/0098674 A1 4/2011 Vicente et al.
2011/0098676 A1 4/2011 Chiang et al.
2011/0101995 A1 5/2011 Shah et al.
2011/0105873 A1 5/2011 Feldman et al.
2011/0105877 A1 5/2011 Wilt et al.
2011/0105955 A1 5/2011 Yudovsky et al.
2011/0105979 A1 5/2011 Schlaeper et al.
2011/0106011 A1 5/2011 Cinar et al.
2011/0106049 A1 5/2011 Damiano et al.
2011/0106050 A1 5/2011 Yodfat et al.
2011/0106318 A1 5/2011 Ledford
2011/0106480 A1 5/2011 Shah et al.
2011/0107853 A1 5/2011 Studer
2011/0108158 A1 5/2011 Huwiler et al.
2011/0111794 A1 5/2011 Bochenko et al.
2011/0112478 A1 5/2011 Gregor et al.
2011/0112504 A1 5/2011 Causey et al.
2011/0112505 A1 5/2011 Starkweather et al.
2011/0112506 A1 5/2011 Starkweather et al.
2011/0118578 A1 5/2011 Timmerman
2011/0118662 A1 5/2011 Mhatre et al.
2011/0118699 A1 5/2011 Yodfat et al.
2011/0118700 A1 5/2011 Remde
2011/0119087 A1 5/2011 Drucker et al.
2011/0120206 A1 5/2011 Troughton et al.
2011/0124996 A1 5/2011 Reinke et al.
2011/0124999 A1 5/2011 Reggiardo et al.
2011/0125085 A1 5/2011 McGill et al.
2011/0125095 A1 5/2011 Lebel et al.
2011/0125530 A1 5/2011 Drucker et al.

(56) References Cited

U.S. PATENT DOCUMENTS

| | | | |
|---|---|---|---|
| 2011/0126188 | A1 | 5/2011 | Bernstein et al. |
| 2011/0130746 | A1 | 6/2011 | Budiman |
| 2011/0133946 | A1 | 6/2011 | Kopp et al. |
| 2011/0137239 | A1 | 6/2011 | Debelser et al. |
| 2011/0144569 | A1 | 6/2011 | Britton et al. |
| 2011/0144586 | A1 | 6/2011 | Michaud et al. |
| 2011/0144616 | A1 | 6/2011 | Michaud et al. |
| 2011/0149759 | A1 | 6/2011 | Jollota |
| 2011/0151571 | A1 | 6/2011 | Wooldridge |
| 2011/0152653 | A1 | 6/2011 | Shekalim et al. |
| 2011/0152654 | A1 | 6/2011 | Wang et al. |
| 2011/0152757 | A1 | 6/2011 | Beck et al. |
| 2011/0152769 | A1 | 6/2011 | Ramey et al. |
| 2011/0152770 | A1 | 6/2011 | DiPerna et al. |
| 2011/0152824 | A1 | 6/2011 | DiPerna et al. |
| 2011/0152970 | A1 | 6/2011 | Jollota et al. |
| 2011/0154237 | A1 | 6/2011 | Bush et al. |
| 2011/0160650 | A1 | 6/2011 | Chong et al. |
| 2011/0160654 | A1 | 6/2011 | Hanson et al. |
| 2011/0160666 | A1 | 6/2011 | Hanson et al. |
| 2011/0160667 | A1 | 6/2011 | Bazargan et al. |
| 2011/0160678 | A1 | 6/2011 | Chong et al. |
| 2011/0160695 | A1 | 6/2011 | Sigrist et al. |
| 2011/0163125 | A1 | 7/2011 | Beavis et al. |
| 2011/0166544 | A1 | 7/2011 | Verhoef et al. |
| 2011/0166875 | A1 | 7/2011 | Hayter et al. |
| 2011/0172744 | A1 | 7/2011 | Davis et al. |
| 2011/0178461 | A1 | 7/2011 | Chong et al. |
| 2011/0178462 | A1 | 7/2011 | Moberg et al. |
| 2011/0184264 | A1 | 7/2011 | Galasso et al. |
| 2011/0190614 | A1 | 8/2011 | Brister et al. |
| 2011/0190694 | A1 | 8/2011 | Lanier et al. |
| 2011/0190700 | A1 | 8/2011 | Kavazov et al. |
| 2011/0190701 | A1 | 8/2011 | Remde et al. |
| 2011/0192478 | A1 | 8/2011 | Chong et al. |
| 2011/0193704 | A1 | 8/2011 | Harper et al. |
| 2011/0196213 | A1 | 8/2011 | Thukral et al. |
| 2011/0196248 | A1 | 8/2011 | Grunwald |
| 2011/0196289 | A1 | 8/2011 | Plahey et al. |
| 2011/0205065 | A1 | 8/2011 | Strachan et al. |
| 2011/0208122 | A1 | 8/2011 | Shekalim et al. |
| 2011/0208123 | A1 | 8/2011 | Gray et al. |
| 2011/0208155 | A1 | 8/2011 | Palerm et al. |
| 2011/0213225 | A1 | 9/2011 | Bernstein et al. |
| 2011/0213306 | A1 | 9/2011 | Hanson et al. |
| 2011/0224522 | A1 | 9/2011 | Fennell |
| 2011/0224601 | A1 | 9/2011 | Shekalim |
| 2011/0230821 | A1 | 9/2011 | Babic |
| 2011/0230825 | A1 | 9/2011 | Kamen et al. |
| 2011/0238033 | A1 | 9/2011 | Prod et al. |
| 2011/0247397 | A1 | 10/2011 | Friedli et al. |
| 2011/0251557 | A1 | 10/2011 | Powers |
| 2011/0251579 | A1 | 10/2011 | Aklog et al. |
| 2011/0256024 | A1 | 10/2011 | Cole et al. |
| 2011/0257895 | A1 | 10/2011 | Brauker et al. |
| 2011/0309107 | A1 | 12/2011 | Shekalim et al. |
| 2011/0319862 | A1 | 12/2011 | Friedman et al. |
| 2012/0013625 | A1 | 1/2012 | Blomquist et al. |
| 2012/0013802 | A1 | 1/2012 | Blomquist et al. |
| 2012/0017688 | A1 | 1/2012 | Shekalim et al. |
| 2012/0022452 | A1 | 1/2012 | Welsch et al. |
| 2012/0029433 | A1 | 2/2012 | Michaud et al. |
| 2012/0029468 | A1 | 2/2012 | DiPerna et al. |
| 2012/0029486 | A1 | 2/2012 | Laerdal et al. |
| 2012/0029708 | A1 | 2/2012 | Miller et al. |
| 2012/0029941 | A1 | 2/2012 | Malave et al. |
| 2012/0030610 | A1 | 2/2012 | DiPerna et al. |
| 2012/0041415 | A1 | 2/2012 | Estes et al. |
| 2012/0059353 | A1 | 3/2012 | Kovatchev et al. |
| 2012/0059673 | A1 | 3/2012 | Cohen et al. |
| 2012/0232520 | A1 | 9/2012 | Sloan et al. |
| 2012/0330227 | A1 | 12/2012 | Budiman et al. |
| 2013/0053816 | A1 | 2/2013 | DiPerna et al. |
| 2013/0150766 | A1 | 6/2013 | Olde et al. |
| 2013/0204542 | A1 | 8/2013 | Olde et al. |
| 2013/0283196 | A1 | 10/2013 | Farnan et al. |
| 2013/0298024 | A1 | 11/2013 | Rhee et al. |
| 2013/0306191 | A1 | 11/2013 | Metzmaker et al. |
| 2013/0324928 | A1 | 12/2013 | Kruse |
| 2013/0332874 | A1 | 12/2013 | Rosinko et al. |
| 2013/0345625 | A1 | 12/2013 | Causey, III et al. |
| 2014/0012511 | A1 | 1/2014 | Mensinger et al. |
| 2014/0039805 | A1 | 2/2014 | Sharpe et al. |
| 2014/0200426 | A1 | 7/2014 | Taub |
| 2014/0323961 | A1 | 10/2014 | Blomquist et al. |
| 2015/0052511 | A1 | 2/2015 | Kiaie et al. |
| 2015/0174320 | A1 | 6/2015 | Grant |
| 2016/0121047 | A1 | 5/2016 | Kruse et al. |
| 2016/0199571 | A1 | 7/2016 | Rosinko et al. |
| 2016/0271325 | A1 | 9/2016 | Farnan et al. |
| 2017/0056590 | A1 | 3/2017 | DiPerna et al. |
| 2017/0300206 | A1 | 10/2017 | Rosinko et al. |
| 2017/0312423 | A1 | 11/2017 | Rosinko |
| 2018/0064873 | A1 | 3/2018 | Kruse et al. |
| 2018/0361060 | A9 | 12/2018 | Rosinko |
| 2019/0175823 | A1 | 6/2019 | Rosinko |

FOREIGN PATENT DOCUMENTS

| | | |
|---|---|---|
| CN | 2668847 | 1/2005 |
| DE | 399065 | 7/1924 |
| DE | 19819407 | 11/1999 |
| EP | 0055836 | 7/1982 |
| EP | 0272530 | 6/1988 |
| EP | 0376894 | 7/1990 |
| EP | 0385916 | 9/1990 |
| EP | 0494042 | 7/1992 |
| EP | 0560571 | 9/1993 |
| EP | 1217275 | 6/2002 |
| EP | 1938750 | 7/2008 |
| EP | 2416826 | 2/2012 |
| GB | 2159496 | 12/1985 |
| JP | H0616165 | 4/1994 |
| JP | H08312820 | 11/1996 |
| JP | 2952037 | 9/1999 |
| JP | 2002143293 | 5/2002 |
| JP | 2006009944 | 1/2006 |
| JP | 2006101985 | 4/2006 |
| JP | 2009148591 | 7/2009 |
| JP | 2010075736 | 4/2010 |
| KR | 1020010080519 | 8/2001 |
| WO | 9013795 | 11/1990 |
| WO | 9100753 | 1/1991 |
| WO | 9426329 | 11/1994 |
| WO | 9532013 | 11/1995 |
| WO | 9608049 | 3/1996 |
| WO | 9625189 | 8/1996 |
| WO | 9819627 | 5/1998 |
| WO | 9857683 | 12/1998 |
| WO | 9901088 | 1/1999 |
| WO | 0010628 | 3/2000 |
| WO | 0035527 | 6/2000 |
| WO | 0040346 | 7/2000 |
| WO | 0072900 | 12/2000 |
| WO | 0130422 | 5/2001 |
| WO | 0211049 | 2/2002 |
| WO | 0211791 | 2/2002 |
| WO | 0226102 | 4/2002 |
| WO | 0228532 | 4/2002 |
| WO | 03081052 | 10/2003 |
| WO | 03082091 | 10/2003 |
| WO | 03102737 | 12/2003 |
| WO | 2004009152 | 1/2004 |
| WO | 2004009160 | 1/2004 |
| WO | 2004036150 | 4/2004 |
| WO | 2004047677 | 6/2004 |
| WO | 2004056412 | 7/2004 |
| WO | 2004060464 | 7/2004 |
| WO | 2004088148 | 10/2004 |
| WO | 2004093648 | 11/2004 |
| WO | 2004105827 | 12/2004 |
| WO | 2005018507 | 3/2005 |
| WO | 2005082450 | 9/2005 |
| WO | 2006001024 | 1/2006 |

(56) References Cited

FOREIGN PATENT DOCUMENTS

| | | |
|---|---|---|
| WO | 2006108219 | 10/2006 |
| WO | 2006127841 | 11/2006 |
| WO | 2007038059 | 4/2007 |
| WO | 2007038060 | 4/2007 |
| WO | 2007038091 | 4/2007 |
| WO | 2007056504 | 5/2007 |
| WO | 2007056592 | 5/2007 |
| WO | 2007065944 | 6/2007 |
| WO | 2007089983 | 8/2007 |
| WO | 2007098265 | 8/2007 |
| WO | 2007098287 | 8/2007 |
| WO | 2007106232 | 9/2007 |
| WO | 2007119149 | 10/2007 |
| WO | 2008024812 | 2/2008 |
| WO | 2008028509 | 3/2008 |
| WO | 2008037270 | 4/2008 |
| WO | 2008037271 | 4/2008 |
| WO | 2008037272 | 4/2008 |
| WO | 2008037273 | 4/2008 |
| WO | 2008043381 | 4/2008 |
| WO | 2008050126 | 5/2008 |
| WO | 2008050128 | 5/2008 |
| WO | 2008056363 | 5/2008 |
| WO | 2008071220 | 6/2008 |
| WO | 2008103175 | 8/2008 |
| WO | 2008121599 | 10/2008 |
| WO | 2008144693 | 11/2008 |
| WO | 2008144695 | 11/2008 |
| WO | 2008144697 | 11/2008 |
| WO | 2008144698 | 11/2008 |
| WO | 2009016636 | 2/2009 |
| WO | 2009032399 | 3/2009 |
| WO | 2009032400 | 3/2009 |
| WO | 2009032402 | 3/2009 |
| WO | 2009035753 | 3/2009 |
| WO | 2009035759 | 3/2009 |
| WO | 2009035761 | 3/2009 |
| WO | 2009035762 | 3/2009 |
| WO | 2009044221 | 4/2009 |
| WO | 2009094590 | 7/2009 |
| WO | 2009098648 | 8/2009 |
| WO | 2009106233 | 9/2009 |
| WO | 2009108639 | 9/2009 |
| WO | 2009124133 | 10/2009 |
| WO | 2009143188 | 11/2009 |
| WO | 2009147680 | 12/2009 |
| WO | 2010016977 | 2/2010 |
| WO | 2010016978 | 2/2010 |
| WO | 2010033634 | 3/2010 |
| WO | 2010033878 | 3/2010 |
| WO | 2010038031 | 4/2010 |
| WO | 2010096449 | 8/2010 |
| WO | 2010097774 | 9/2010 |
| WO | 2010099490 | 9/2010 |
| WO | 2010113162 | 10/2010 |
| WO | 2011014704 | 2/2011 |
| WO | 2011017667 | 2/2011 |
| WO | 2012019726 | 2/2012 |
| WO | 2012034084 | 3/2012 |
| WO | 2016086033 | 6/2017 |

OTHER PUBLICATIONS

Arrow, "Intemational Europe Web Page for: Multiple Lumen Peripheral Catheter," Product No. IV-01150, retrieved from internet on Nov. 15, 2011, 3 pages.
Canadlan Examiner's Report for Canadian Application No. 2,769,030 dated Aug. 27, 2014, 2 pages.
Angiodynamics, "Smart Port, Power-Injectable Ports," Product Brochure, 2010, 4 pages.
Arrow, "International Europe Web Page for: Multiple Lumen Peripheral Catheter," Product No. IV-01150, retrieved from internet on Nov. 15, 2011, 3 pages.
Canadian Examiner's Report for Canadian Application No. 2,769,030 dated Aug. 27, 2014, 2 pages.
Examination Report No. 1 for Australian Patent Application No. 2009249132 dated Jan. 23, 2014, 4 pages.
I-Port, "Advance Product Brochure," Patton Medical Devices and Manufactured by Unomedical, a Cardiovascular Company, 2010, 2 pages.
Miller E.J., "The Reciprocating Pump, Theory, Design and Use," Second Edition, Krieger Publishing Company, Malabar, Florida 1995, 47 pages.
Spring, "Zone Insulin Pump," Spring Zone Insulin Delivery System Product Brochure, a D-Medical company, Copyright 2011, 4 pages.
U.S. Appl. No. 60/789,243, filed Apr. 5, 2006, Beavis, 22 pages.
Written Opinion for Application No. PCT/US2008/058044, mailed on Aug. 11, 2008, 4 pages.

* cited by examiner

INFUSION PUMP SYSTEMS WITH DISPOSABLE CARTRIDGE HAVING PRESSURE VENTING AND PRESSURE FEEDBACK

RELATED APPLICATIONS

This application is a continuation of U.S. application Ser. No. 16/502,248 filed Jul. 3, 2019, which in turn is a continuation of U.S. application Ser. No. 15/340,417 filed Nov. 1, 2016, now U.S. Pat. No. 10,434,253, which in turn is a continuation of U.S. application Ser. No. 12/846,688 filed Jul. 29, 2010, now abandoned, which claims the benefit of U.S. Provisional Patent Application No. 61/230,061, titled Infusion System and Methods for Using Same, filed Jul. 30, 2009, by P. DiPerna et al., each of which is hereby incorporated herein by reference in its entirety. This application is also related to U.S. patent application Ser. No. 12/846,706, titled Infusion Pump System with Disposable Cartridge Having Pressure Venting and Pressure Feedback, filed Jul. 29, 2010, by G. Kruse, et al., U.S. patent application Ser. No. 12/846,720, titled Infusion Pump System with Disposable Cartridge Having Pressure Venting and Pressure Feedback, filed Jul. 29, 2010, by D. Brown, et al., U.S. patent application Ser. No. 12/846,733, titled Infusion Pump System with Disposable Cartridge Having Pressure Venting and Pressure Feedback, filed Jul. 29, 2010, by M. Michaud, et al., U.S. patent application Ser. No. 12/846,734, titled Infusion Pump System with Disposable Cartridge Having Pressure Venting and Pressure Feedback, filed Jul. 29, 2010, by P. DiPerna, et al., and PCT Patent Application No. PCT/US2010/043789, titled Infusion Pump System with Disposable Cartridge Having Pressure Venting and Pressure Feedback, filed Jul. 29, 2010, by P. DiPerna, et al., all of which are incorporated by reference herein in their entirety.

FIELD OF THE INVENTION

This disclosure is directed to portable infusion devices, systems, and methods of using the same for dispensing materials. In some cases, the devices, systems and methods may be used for infusing a material such as medicament, e.g., insulin, into a body in need thereof.

BACKGROUND

There are many applications in academic, industrial, and medical fields, as well as others, that may benefit from devices and methods that are capable of accurately and controllably delivering fluids, including liquids and gases that have a beneficial effect when administered in known and controlled quantities. This may be particularly true in the medical field where much of the treatment for a large percentage of patients includes the administration of a known amount of a substance at predetermined intervals. The treatment of diabetes often involves just such a regimented dosage of materials, in particular, the administration of insulin. In addition, the administration of insulin for a diabetic patient is one of a few medical indications wherein the patient routinely administers the medicament to themselves by a subcutaneous modality, such as a hypodermic syringe injection. As such, providing a patient with the means to safely, reliably and comfortably administer required doses of medication may be particularly important in order to facilitate patient compliance and accurate treatment of the condition.

Blood glucose is an important factor for metabolism and the provision of energy and proper organ functioning in mammals. The accurate regulation of blood glucose is, therefore, an essential task necessary for the well being of the mammal. For instance, the neurons of the brain of an organism depend on glucose for fueling their functioning. Hence, blood glucose levels are typically regulated by feedback loops between the brain and the pancreas. The pancreas functions in response to various hormones released by the brain by itself releasing hormones that regulate the uptake, e.g., storage, of blood sugar, or the release of stored blood sugar. For instance, two essential hormones in the regulation of blood sugar levels are insulin and glucagon, both of which are synthesized by specialized cells in the pancreas. Specifically, the 3 cells of the islets of Langerhans function to synthesize insulin, while the a cells of the islets of Langerhans function to synthesize glucagon.

Maintaining appropriate blood glucose homeostasis is an important factor for promoting the length and quality of life. However, there are many factors that affect the body's ability to maintain such homeostasis. For instance, factors such as the body's ability to produce or respond to insulin, one's physiological condition and/or health, the quantity and type of food one eats, one's metabolic rate, activity level, the types of activities and the exertion level in which one engages, as well as other such factors that make up a person's daily life and/or routine, all play important roles in effecting the body's ability to maintain homeostasis.

Continuous subcutaneous insulin injection and/or infusion therapy is initiated for the replacement of insulin and thereby the treatment of diabetes. Such therapy may include the regular and/or continuous injection or infusion of insulin into the skin of a person suffering from diabetes. Injection is the traditional and most common method for administering insulin. Typically the diabetic will measure his or her blood glucose level, and depending on the level thereof may prepare a syringe or injection pen with insulin to be injected transdermally into the body. However, recently, insulin injecting pumps have been developed for the administration of insulin for those suffering from both type I and II diabetes. Insulin pumps are medical devices used for the administration of insulin in the treatment of diabetes and offer an alternative to multiple daily injections of insulin by an insulin syringe or an insulin pen. They also allow for continuous insulin therapy.

There are, however, several drawbacks associated with the use of subcutaneous injection syringes and/or some currently available infusion pumps for the delivery of insulin. Patient compliance, for instance, is a major problem with respect to the use of insulin syringes. A high percent of subjects suffering from diabetes experience dread when it comes to insulin injections due to the anxiety and discomfort associated with regular use of a the needle therefore. Further complications involve the cost of the syringes, which cost may lead to the spread of infections and diseases, such as human immunodeficiency virus (HIV) and hepatitis, through the sharing and/or reusing of needles. In addition, diabetes patients who choose to use commercially available pumps to avoid the disadvantages of syringe delivery often find that wearing them together with their required infusion set tubing is uncomfortable or unwieldy, particularly while participating in sporting activities or while sleeping.

Some commercially available pumps are designed to be smaller than others, but typically include a patch type element that may be adhered directly to the skin. Such a pump may contain the insulin reservoir, pumping mechanism, power supply as well as an infusion set and automated insert. The patch may be quite a bit heavier than typical infusion set patches. This may pose the problem of the infusion set slowly being pulled out of the patient due to the weight of the patch itself resulting in waste and inaccuracies in treatment. Once the patch is inadvertently knocked off the skin or loosened there may be no means to reinsert the infusion set also resulting in waste and added expense.

Furthermore, the smaller the size of an infusion pump, the more difficult it is for a patient to interface with the device. Commercially available pumps typically have a single screen and one or more hard buttons for enabling a user to navigate through multiple menus and screens. A drawback of requiring a user to navigate through multiple menus and pages to set up a delivery of insulin may be that the user finds the process too complex and time consuming to properly use the infusion device to its fullest potential. As a result, some users tend to “set-it and forget-it”.

Generally a patient’s insulin requirements vary greatly, as mentioned above, and may be influenced by a variety of factors (e.g., caloric intake, physiological conditions). Therefore, there is a need for a user friendly portable infusion device that has the ability to tailor appropriate insulin delivery profiles to a user. There is also a need for an infusion device providing an interface that facilitates its use.

SUMMARY

Some embodiments are directed to an infusion pump kit configured for delivering a therapeutic fluid to a patient. The device may include a first pump device including a first housing and a first drive mechanism, a second pump device comprising a second housing and a second drive mechanism, and an infusion cartridge. The infusion cartridge may further include a fluid reservoir configured to be filled with a volume of the therapeutic fluid sufficient for a prolonged single infusion protocol. The infusion cartridge may additionally include a delivery mechanism having a distal end in fluid communication with an interior volume of the fluid reservoir and a proximal end configured to couple to either the first drive mechanism or the second drive mechanism and be translated between a plurality of linear positions to deliver the therapeutic fluid to the patient. In addition, the infusion cartridge may be configured to be interchangeably coupled to, and alternated between, the first pump device and the second pump device during the single infusion protocol of the therapeutic fluid to the patient.

Some embodiments are directed to a method of delivering a therapeutic fluid to a patient. The method may include providing a first pump device having a full featured user interface, installing a disposable infusion cartridge on the first pump device, and removing the disposable infusion cartridge from the first pump device. In addition, the method may include installing the disposable infusion cartridge onto a second pump device while maintaining the sterility of the fluid disposed within a reservoir of the disposable infusion cartridge.

Some embodiments of the device may additionally include a fluid delivery system for delivering a therapeutic fluid to a patient. The system may include a pump housing comprising a drive mechanism translatable between a plurality of linear positions to deliver the therapeutic fluid to the patient and an infusion cartridge removably coupled to the pump housing. The infusion cartridge may include a fillable fluid reservoir and a delivery mechanism comprising a distal end in fluid communication with an interior volume of the fluid reservoir and a drive coupling disposed at a proximal end. The drive coupling may be further configured to receive and couple to a drive portion of the drive mechanism independent of the linear position of the drive mechanism.

Some embodiments of the device are directed at a method of coupling a disposable fluid reservoir cartridge to an infusion pump device. The method may include providing an infusion pump device including a drive portion of a drive mechanism that includes a ball or capturable feature at an end of a drive shaft. The method may further include providing a disposable fluid reservoir cartridge including a drive coupling of a delivery mechanism that comprises a flexible female receptacle configured to snap fit over the ball of the drive shaft with the ball introduce from either a lateral direction or axial direction. The method may additionally include returning the ball of the drive mechanism to a home position at a proximal position of a drive stroke, inserting the disposable fluid reservoir cartridge onto the infusion pump device, and advancing the ball of the drive shaft of the drive mechanism from the proximal position to engage and snap fit with the flexible female receptacle of the delivery mechanism of the cartridge.

Some embodiments are directed to a method of switching a fluid reservoir cartridge from a first pump device to a second pump device. The method may include providing a first infusion pump device including a drive portion of a drive mechanism that includes a ball or capturable feature at an end of a drive shaft. The method may further include providing a disposable fluid reservoir cartridge including a drive coupling of a delivery mechanism that comprises a flexible female receptacle which is snap fit over the ball of the drive shaft and which is configured to release the ball from either a lateral direction or axial direction. The method may additionally include returning the ball of the drive mechanism to a home position at a proximal position of a drive stroke, inserting the disposable fluid reservoir cartridge onto the infusion pump device, and advancing the drive shaft of the drive mechanism from the proximal position to engage and snap fit with the flexible female receptacle of the delivery mechanism of the cartridge.

Some embodiments of the infusion pump system may include a housing and a disposable cartridge. The disposable cartridge may further include a collapsible reservoir surrounded by a flexible material and a substantially rigid container sealed around the flexible material of the collapsible reservoir. Furthermore, the cartridge may be releasably secured to the housing. The infusion pump may further include a disposable delivery mechanism disposed within the disposable cartridge and having a reservoir inlet port in fluid communication with an interior volume of the reservoir. The infusion pump may additionally include a drive mechanism including a motor disposed in the housing and detachably coupled to a spool member of the delivery mechanism with the drive mechanism being operatively coupled to the spool member. The infusion pump may further include at least one pressure sensor disposed in a volume disposed between the outside surface of the flexible material of the reservoir and an inside surface of the substantially rigid container/case, a graphic user interface operatively coupled to a controller, and a power storage cell. Additionally, the infusion pump may include a vent inlet port disposed on the delivery mechanism in fluid communication with the volume disposed between the outside surface of the flexible material of the reservoir and an inside surface of the substantially rigid container/case and a controller including at least one processor and a memory device. The controller may be operatively coupled to the drive mechanism, GUI, and at least one pressure sensor and configured to generate a signal to the drive mechanism to displace the spool of the delivery mechanism.

Some embodiments of the infusion pump system may include a pump device including a housing, a drive mechanism with a motor, a controller operatively coupled to the drive mechanism and a slot configured to accept a disposable fluid cartridge. The infusion pump system may further include a disposable fluid cartridge which may be operatively coupled to the housing. The disposable fluid cartridge may further include a delivery mechanism, a collapsible reservoir having an interior volume surrounded by a flexible fluid tight membrane, and the interior volume being in fluid communication with a reservoir inlet port. The cartridge may also include a substantially rigid shell disposed over the reservoir and forming a second interior volume between an outside surface of the reservoir and an inside surface of the rigid shell with a vent inlet port in communication with the second interior volume. Additionally, the infusion pump system may include a pressure sensor disposed between an interior surface of the rigid case and an exterior surface of the collapsible reservoir shell, a bore within a pump body of the delivery mechanism, and a spool. In addition, the spool may be slidingly disposed in the bore having a collapsible first volume which is configured to communicate with the reservoir inlet port and outlet/dispense port of the bore independently of each other, and a second volume isolated from the first collapsible volume, the second volume configured to be moveable between a position that allows a vent inlet port to communicate with a vent outlet port and a position where the vent inlet and outlet ports are isolated from each other.

Some embodiments are directed to an infusion pump for dispensing fluid to a patient. The device may include a disposable fluid cartridge. The cartridge may include a delivery mechanism, which may include a delivery mechanism body. Additionally, a bore may be disposed in the delivery mechanism body, which may further include a distal end, a proximal end disposed towards a drive mechanism of the infusion pump, an interior volume, a reservoir inlet port, a fluid dispense port, a vent inlet port, and a vent outlet port. The infusion pump may further include a spool slidingly disposed within the bore. The spool may further include a collapsible first volume which is positionable to overlap the reservoir inlet port independent of an overlap of the fluid dispense port and which is formed between a first seal around the spool, a second seal around the spool, an outer surface of the spool body between the first and second seal and an interior surface of the bore between the first and second seal. Furthermore, the first and second seals may be axially moveable relative to each other. The spool may additionally include a vent second volume, which is positionable to overlap the vent inlet port and vent outlet port simultaneously and which is formed by a third seal around the spool, a fourth seal around the spool, an outside surface of the spool between the third and fourth seal, and an inside surface of the bore between the third and fourth seal. The infusion pump may further include a collapsible fluid reservoir bounded by a flexible membrane and including an interior volume in fluid communication with the reservoir inlet port. The infusion pump may further include a substantially rigid shell disposed about the collapsible fluid reservoir with an interior volume that contains the collapsible fluid reservoir and a vented volume disposed between an outer surface of the flexible membrane and an interior surface of the rigid shell, the vent inlet port being in fluid communication with the vented volume. Additionally, the infusion pump may include a drive mechanism operatively coupled to the spool of the delivery mechanism, a user interface configured to accommodate user data input regarding fluid delivery, a controller having a processor and memory device operatively coupled to the drive mechanism, and a power cell. The power cell may further be operatively coupled to the controller, the GUI, and the drive mechanism.

Some embodiments of the device are directed at a method of venting a cartridge of an infusion pump system. The method may include providing an infusion pump system, which may further include a disposable fluid reservoir cartridge. The cartridge may include a delivery mechanism, which may further include a delivery mechanism body. The device may further include a bore disposed in the delivery mechanism body including a distal end, a proximal end disposed towards a drive mechanism of the infusion pump, an interior volume, a reservoir inlet port, a fluid dispense port, a vent inlet port and a vent outlet port. The device may further include a spool slidingly disposed within the bore, which may further include a collapsible first volume. The collapsible first volume may be positionable to overlap the reservoir inlet port independent of an overlap of the fluid dispense port and which is formed between a first seal around the spool, a second seal around the spool, an outer surface of the spool body between the first and second seal and an interior surface of the bore between the first and second seal, the first and second seals being axially moveable relative to each other. The spool may also include a vent second volume which is positionable to overlap the vent inlet port and vent outlet port simultaneously and which is formed by a third seal around the spool, a fourth seal around the spool, an outside surface of the spool between the third and fourth seal and an inside surface of the bore between the third and fourth seal. The device may further include a collapsible fluid reservoir bounded by a flexible membrane and including an interior volume in fluid communication with the reservoir inlet port. The device may additionally include a substantially rigid shell disposed about the collapsible fluid reservoir with an interior volume that contains the collapsible fluid reservoir and a vented volume disposed between an outer surface of the flexible membrane and an interior surface of the rigid shell, with the vent inlet port being in fluid communication with the vented volume. The device may further include a drive mechanism operatively coupled to the spool of the delivery mechanism. The method of venting a cartridge of an infusion pump system may further include initiating a dispense cycle by driving the spool with the drive mechanism to a position with the collapsible first volume in communication with the reservoir inlet port. The method may further include driving the spool so as to separate the first and second seals of the collapsible first volume and draw fluid into the first volume through the reservoir inlet port from the reservoir and decrease the pressure within the vented volume. The method may additionally include driving the spool with the drive mechanism to a position with the collapsible first volume in communication with the fluid dispense port, driving the spool so as to at least partially collapse the collapsible first volume and dispense fluid from the collapsible first volume through the fluid dispense port, and driving the spool to a position with the vent second volume in simultaneous communication with the inlet vent port and vent outlet port to allow the vent second volume to arrive at the same pressure as the vent outlet port.

Some embodiments are directed to a delivery mechanism for an infusion pump. The delivery mechanism of an infusion pump may include a bore disposed in a delivery mechanism body, a spool disposed in the bore which is axially displaceable within the bore, and a collapsible volume. The collapsible volume may be bounded by an outside surface of the spool, an inside surface of the bore, a first seal between the spool and the bore that is axially fixed relative to the spool but displaceable relative to an inside surface of the bore and a second seal between the spool and inside surface of the bore which is configured to slide over a slide portion of the spool disposed in an aperture of the second seal, which forms a substantially fluid tight but displaceable seal between an outside surface of the second seal and the inside surface of the bore and which forms a fluid tight but displaceable seal between an outside surface of the slide portion and the second seal.

Some embodiments may be directed to an infusion pump for dispensing fluid to a patient. The device may further include a disposable fluid cartridge, which may include a delivery mechanism. The delivery mechanism may further include a delivery mechanism body. The device may additionally include a bore disposed in the delivery mechanism body including a distal end, a proximal end disposed towards a drive mechanism of the infusion pump, an interior volume, a reservoir inlet port, a fluid dispense port, a vent inlet port and a vent outlet port. The device may further include a spool slidingly disposed within the bore, which may further include a collapsible first volume. The collapsible first volume may be bounded by an outside surface of the spool, an inside surface of the bore, a first seal between the spool and the bore that is axially fixed relative to the spool but displaceable relative to an inside surface of the bore and a second seal between the spool and inside surface of the bore which is configured to slide over a slide portion of the spool disposed in an aperture of the second seal, which forms a substantially fluid tight but displaceable seal between an outside surface of the second seal and the inside surface of the bore and which forms a fluid tight but displaceable seal between an outside surface of the slide portion and the second seal. The spool may further include a vent second volume which may be positionable to overlap the vent inlet port and vent outlet port simultaneously and which may be formed by a third seal around the spool, a fourth seal around the spool, an outside surface of the spool between the third and fourth seal and an inside surface of the bore between the third and fourth seal. The device may further include a collapsible fluid reservoir bounded by a flexible membrane and including an interior volume in fluid communication with the reservoir inlet port, a substantially rigid shell disposed about the collapsible fluid reservoir with an interior volume that contains the collapsible fluid reservoir, and a vented volume disposed between an outer surface of the flexible membrane and an interior surface of the rigid shell, the vent inlet port being in fluid communication with the vented volume.

Some embodiments of the device may include an o-ring seal, which may have a gland for seating an o-ring. The seating may further include an outer circumferential groove extending circumferentially around a longitudinal axis of a cylindrical body, with the circumferential groove including an angled first edge and an angled second edge opposite the angled first edge and an inner overflow channel disposed below the angled first and second edges. The o-ring seal may further include an o-ring disposed in the gland with a first circumferential band of the o-ring resting on the first angled edge and a second circumferential band of the o-ring resting on the second angled edge above the overflow channel with the o-ring in a substantially uncompressed state.

Some embodiments of the device may include a delivery mechanism of an infusion pump for dispensing fluid to a patient. The delivery mechanism may include a spool slidingly disposed in a bore of a delivery mechanism housing, and an o-ring seal disposed on the spool. The o-ring seal may further include a gland for seating an o-ring, which may include an outer circumferential groove extending circumferentially around a longitudinal axis of a cylindrical body of the spool. The circumferential groove may further include an angled first edge and an angled second edge opposite the angled first edge and an inner overflow channel disposed below the angled first and second edges. The delivery mechanism may further include an o-ring disposed in the gland with a first circumferential band of the o-ring resting on the first angled edge and a second circumferential band of the o-ring resting on the second angled edge above the overflow channel with the o-ring in a substantially uncompressed state.

Some embodiments of the portable infusion device may be configured for generating an estimate of an amount of a fluid to be delivered to a body of a user. The device may further include a processor that may be coupled to a memory and configured for receiving user input data from the memory and using the input data for generating an estimate of an amount of fluid to be delivered to the body. The memory may be configured for receiving and storing user input data coupled to the processor and may be further configured for communicating that data to the processor. The device may further include a touch sensitive screen configured for displaying at least one request for user input, where said display is further configured for receiving user input in response to the request and communicating the input to the memory.

Some embodiments of the portable infusion device may be configured for generating an estimate of an amount of a fluid to be delivered to a body of a user. The device may further include a reservoir for storing the fluid, a delivery mechanism for effecting the delivery of the fluid, and a processor coupled to a memory and configured for receiving user input data from the memory and using the input data for generating an estimate of an amount of fluid to be delivered to the body. The device may further include a memory for receiving and storing user input data coupled to the processor and configured for communicating that data to the processor. The device may additionally include a display configured for displaying a request for a user to input data, wherein the display is further configured for receiving user input data in response to the request and communicating that data to the memory.

Some embodiments of the portable infusion device may be directed at a method for delivering an amount of a fluid to a body of a user. The method may include providing a portable infusion device, which may further include a reservoir for storing the fluid, a delivery mechanism for delivering the fluid, and a processor for generating an estimate of an amount of fluid to be delivered to the body in response to user input data and for controlling the delivery mechanism. The device may further include a data input interface for communicating with the processor the data input interface is configured for receiving user input data. The device may additionally include a display for displaying the estimate of an amount of a fluid to be delivered and inputting externally supplied values into the data input interface. The input may include data that the input interface receives and the user input data may be communicated to the processor. The processor may further receive the user input data, generate an estimate of an amount of a fluid to be delivered to the body of the user, and communicate the estimate to the display. The device may be further configured for receiving the generated estimate of an amount of fluid to be delivered on the display of the portable infusion device and receiving a request for a user input on the display of the portable infusion device. Furthermore, the request may require the user to make a selection before delivering the amount of fluid to the body of the user or making a selection based on the estimate such that once the selection is made the portable infusion device delivers the quantity of fluid to the body in response to the selection.

Some embodiments of the portable infusion device may be configured for generating an estimate of an amount of fluid to be delivered to a body and delivering the amount of fluid to the body of a user in accordance with the generated estimate. The system may further include a remote commander that includes a processor, for generating an estimate of an amount of fluid to be delivered to a body in response to user input data. The system may further include a data input interface for communicating with the processor such that the data input interface is configured for receiving user input data. The system may further include a memory coupled to the processor for receiving and storing user input data. The system may further include a display for displaying the estimate of an amount of a fluid to be delivered and a transmitter for transmitting a command to an infuser device such that the command instructs the infuser device to deliver an amount of fluid in accordance with the generated and confirmed estimate. The system may further include a portable infusion device configured for delivering an amount of a fluid to be delivered to a body of a user in accordance with a generated estimate. The portable infusion device may include a reservoir for storing the fluid, a delivery mechanism for effectuating the delivery of the fluid, a receiver for receiving the command from the transmitter of the remote commander; and a processor for instructing the reservoir and delivery mechanism to deliver the amount of fluid to the body of a user in accordance with the generated estimate.

Some embodiments may be directed at a kit. The kit may include an infusion device and instructions for using the system. Some embodiments of the portable infusion device may be configured for facilitating instructing a user on how to operate a portable infusion device, which may include a portable infusion device, a processor functionally linked to the portable infusion device, and a user-interactive touch screen display functionally linked to the processor. The portable infusion device may further include processor instructions that are accessible by the processor and configured to instruct the processor to load a program. Furthermore, the program file may include data corresponding to an arrangement of at least one of a text and graphic, that when displayed on the user-interactive touch screen display, provides information to the user. In addition, at least one of the text and graphic may be displayed on the user-interactive touch screen that is animated.

Some embodiments may be directed to a method of using a portable infusion device to provide information to a user. The method of using the device may include providing a user with a portable infusion device that has a user-interactive touch screen display that displays a graphical user interface. Furthermore, the user-interactive touch screen may display at least one object relating to at least one of a text and a graphic that may provide information to a user. In addition, at least one object displayed on said user-interactive touch screen display may be animated.

Some embodiments may be directed to a system for facilitating user error prevention of a portable infusion device. The user error prevention feature may include a portable infusion device having a processor functionally linked to the portable infusion device. In addition, the portable infusion device may include a user-interactive touch screen display functionally linked to the processor and processor instructions that are accessible by the processor and are configured to instruct the processor to display a plurality of objects on the user-interactive touch screen display. Furthermore, at least two objects representing different user input may be displayed to allow a user to select at least one displayed object as user input and prevent a user from selecting at least one displayed object as user input.

Some embodiments are directed to a method of using a portable infusion device for facilitating user error prevention. The method may include displaying a graphical user interface on a user-interactive touch screen display, which displays a plurality of objects with at least two objects representing a different user input. The method may further include allowing a user to select at least one object as a user input and preventing a user from selecting at least one object as user input.

Some embodiments are directed to a portable infusion device including a processor functionally linked to the portable infusion device and a user-interactive touch screen display functionally linked to the processor. The touch screen display may further include a display area that also operates as a touch input area, which may simultaneously display a plurality of touch sensitive modifiable objects representing various information. Furthermore, the user-interactive touch screen display and processor may allow a user to touch any one of the touch sensitive modifiable objects for at least one of viewing, inputting, and modifying information associated with the object touched by the user.

Some embodiments are directed to a device configured for generating an estimate of an amount of a fluid to be delivered to a body of a user. The device may include a processor coupled to a memory, wherein the processor is configured for receiving user input data from the memory and using the input data for generating an estimate of an amount of fluid to be delivered to the body. The user input data may include one or more of a blood glucose level, a stress level, a physiological condition, a complexity of a meal to be ingested, an activity level, user history, and the like. The processor may also be configured for receiving non-user entered data and using the non-user entered data in generating the estimate of the amount of fluid to be delivered. The non-user entered data may include sensor data, data received from a wireless communication device, and the like.

Some embodiments of the portable infusion device may include a processor that executes instructions for generating an estimate of an amount of fluid for delivery to a body of a user. The infusion device may also include a touch sensitive display configured for displaying at least one display object, so that user interaction with the display object generates a user input value. In addition, the infusion device may include a data interface configured for receiving the user input value from the display in response to user interaction with the display object such that the user input value is communicated from the data interface to the processor for generating the estimate.

Some embodiments of the portable infusion device may be configured for delivery of a fluid to a body of a user and may include a fluid interface for receiving the fluid and a delivery mechanism for effectuating the delivery of the fluid. In addition, the infusion device may include a processor that executes instructions for generating an estimate of an amount of the fluid for delivery. The infusion device may further include a touch sensitive display configured for displaying at least one display object such that user interaction with the display object generates a user input value. The infusion device may further include a data interface configured for receiving the user input value from the touch sensitive display in response to user interaction with the display object such that the received user input value is communicated from the data interface to the processor for generating the estimate.

Some embodiments of the portable infusion device are directed at a method for delivering an amount of a fluid to a body of a user. The method may include receiving user interaction from a touch sensitive display configured for displaying at least one display object, such that user interaction with the display object generates a user input value. The method may further include generating an estimate of an amount of fluid to be delivered to the body in response to the user input value, and displaying a confirmation display object on the touch sensitive display, such that the confirmation display object requests a confirmation input from the user for confirmation before delivery of the amount of fluid to the body of the user. The method may further include initiating delivery of the fluid in response to receiving the confirmation input.

Some embodiments of the system for generating an estimate of an amount of fluid to be delivered to a body and delivering the amount of fluid to the body of a user in accordance with the generated estimate may include a remote commander. The remote commander may include a display configured for displaying at least one display object, such that the display object indicates a value such that user interaction with the display object generates a user input value. The remote commander may further include a data interface configured for receiving the user input value from the display in response to user interaction with the display, and a processor that receives the user input value from the data interface and generates an estimate of the amount of fluid to be delivered to the body. Furthermore, the processor may provide the estimate to the data interface for display of the estimate on the display. The processor may further generate an infusion command in response to receiving a confirmation input from the data interface. In addition, the confirmation input may include a user interaction with the display in response to display of a confirmation display object on the display, such that the confirmation display object requests a confirmation input from the user for confirmation before delivery of the amount of fluid to the body of the user. The remote commander may further include a transmitter that transmits the infusion command, with the infusion command comprising an instruction for delivery of the amount of the fluid in accordance with the generated estimate and confirmation input. The system may further include an infusion device. The infusion device may include a fluid interface configured for receiving the fluid, a delivery mechanism configured for effectuating the delivery of the fluid, and a receiver configured for receiving the infusion command from the transmitter of the remote commander. In addition, the system may include a processor that receives the infusion command from the receiver and initiates delivery of the amount of the fluid from the fluid interface to the body of the user in accordance with the generated estimate.

Some embodiments of the system may facilitate instructing a user on how to operate a portable infusion device. The system may include a touch sensitive display configured for displaying at least one display object, such that user interaction with the touch sensitive display generates a user input value. In addition, the system may include a processor functionally linked to the touch sensitive display and configured for receiving the user input value. The system may further include a program file for execution by the processor, which may include data corresponding to an arrangement of at least one of a text and a graphic, such that when the program file is executed by the processor the at least one of the text and graphic is displayed on the touch sensitive display and provides information to the user about operation of the portable infusion device. In addition, at least one of the text and graphic displayed on the touch sensitive display may be animated. Furthermore, the processor may execute the program file in response to the user input value corresponding to a request for the information.

Some embodiments of the device may be directed at a method of providing information to a user of a portable infusion device. The method may include displaying at least one display object on a touch sensitive display of the portable infusion device. In addition, the at least one display object may relate to at least one of a text and a graphic providing information to the user about the portable infusion device. The method may also include the portable infusion device detecting user interaction with the touch sensitive display and being responsive to the detected user interaction. In addition, the method may include animating at least one display object displayed on the touch sensitive display.

Some embodiments of the system for facilitating user error prevention of a portable infusion device may include a touch sensitive display configured for displaying at least one display object. In addition, the touch sensitive display may be configured such that user interaction with the display generates a user input value. The system may further include a processor functionally linked to the display and configured for receiving the user input value and processor instructions that are accessible by the processor and are configured to instruct the processor to execute a number of tasks. In addition, some tasks may include displaying a plurality of objects on the touch sensitive display such that the plurality of objects include at least two objects, each of which represents a different user input value. Furthermore, processor tasks may include receiving a user selection of one displayed object and corresponding it to a represented user input value. Additionally, processor tasks may include ignoring the received user selection if the represented user input value is not an acceptable value for operation of the portable infusion device, and otherwise accept the received user selection as a user input value for operation of the portable infusion device.

Some embodiments may be directed at a method of using a portable infusion device for facilitating user error prevention. The method may include displaying a plurality of objects on a touch sensitive display of the portable infusion device, such that the plurality of objects including at least two objects where each of which represents a different user input value. Additionally, the method may include receiving a user selection of one displayed object on the touch sensitive display, such that the user selection corresponding to a represented user input value. Furthermore, the method may include ignoring the received user selection if the represented user input value is not an acceptable value for operation of the portable infusion device, and otherwise accepting the received user selection as a user input value for operation of the portable infusion device.

Some embodiments may include a portable infusion device, which may include a processor and a touch screen display functionally linked to the processor and having a display area that operates as a touch input area that detects user interaction therewith. In addition, the portable infusion device may include a plurality of modifiable objects displayed on the touch screen display, such that the plurality of modifiable objects representing various information may be simultaneously displayed in the touch input area of said touch screen display. Additionally, the touch screen display and processor may respond to a user touch to any one of said modifiable objects on the touch screen display for at least one of viewing, inputting, and modifying information associated with the object touched by said user.

Some embodiments of the device may further include a memory for receiving and storing user input data which memory is coupled to the processor and is configured for communicating that data to the processor.

Some embodiments of the device may additionally include a display such as a display that is configured for displaying a request for a user to input data. The display may further be configured for receiving user input data in response to the request and communicating that data to the memory. The display may additionally be configured for displaying a request for additional user interaction prior to delivering the fluid to the body. The request for additional user interaction includes one or more of an acceptance of delivery, a rejection of delivery, or a request for more information.

In certain instances, device embodiments may include a reservoir for storing a fluid such as insulin to be delivered to a body of a user and a delivery mechanism, for effecting the delivery of the fluid. In such an embodiment, the processor may further be configured for controlling one or both of the delivery mechanism and reservoir in accordance with the generated estimate of the amount of fluid to be delivered to the body.

Some embodiments are directed to a method for delivering an amount of a fluid to a body of a user. The method may include providing an infusion device such as a device described above having at least a data input interface, a processor, and a display. The method may further include inputting externally supplied values into the data input interface, wherein the data input interface receives the user input data and communicates that data to the processor, the processor receives the user input data, generates an estimate of an amount of a fluid to be delivered to the body of the user, and communicates the estimate to the display. The method may additionally include receiving the generated estimate of an amount of fluid to be delivered on the display of the device and receiving a request for a user input on the display of the device. Furthermore, the request may require the user to make a selection before delivering the amount of fluid to the body of the user and making a selection based on the estimate so that once the selection is made, the device delivers the quantity of fluid to the body in response to the selection. The user input data includes one or more of a blood glucose level, a stress level, a physiological condition, a complexity of a meal to be ingested, an activity level, user history, and the like.

Some embodiments are directed to a system for generating an estimate of an amount of fluid to be delivered to a body and delivering the amount of fluid to the body of a user in accordance with the generated estimate. The system may include a remote commander, which may include one or more of a processor for generating an estimate of an amount of fluid to be delivered to a body in response to user input data, and a data input interface for communicating with the processor. Furthermore, the data input interface may be configured for receiving user input data. The system may further include a memory coupled to the processor for receiving and storing user input data, a display for displaying the estimate of an amount of a fluid to be delivered, and/or a transmitter for transmitting a command to an infuser device. In addition, the command may instruct the infuser device to deliver an amount of fluid in accordance with the generated and confirmed estimate. The system may further include an infuser device, such as one described above, configured for delivering an amount of a fluid to be delivered to a body of a user in accordance with a generated estimate. For instance, the device may include a reservoir, for storing the fluid, a delivery mechanism for effectuating the delivery of the fluid, a receiver for receiving the command from the transmitter of the remote commander, and a processor for instructing the reservoir and delivery mechanism to deliver the amount of fluid to the body of a user in accordance with the generated estimate. In an additional aspect, the disclosure is directed to a kit including one or more of an infusion device and/or a remote commander, as described above, and instructions for using the same.

Certain embodiments are described further in the following description, examples, claims and drawings. These features of embodiments will become more apparent from the following detailed description when taken in conjunction with the accompanying exemplary drawings.

Figure 1:
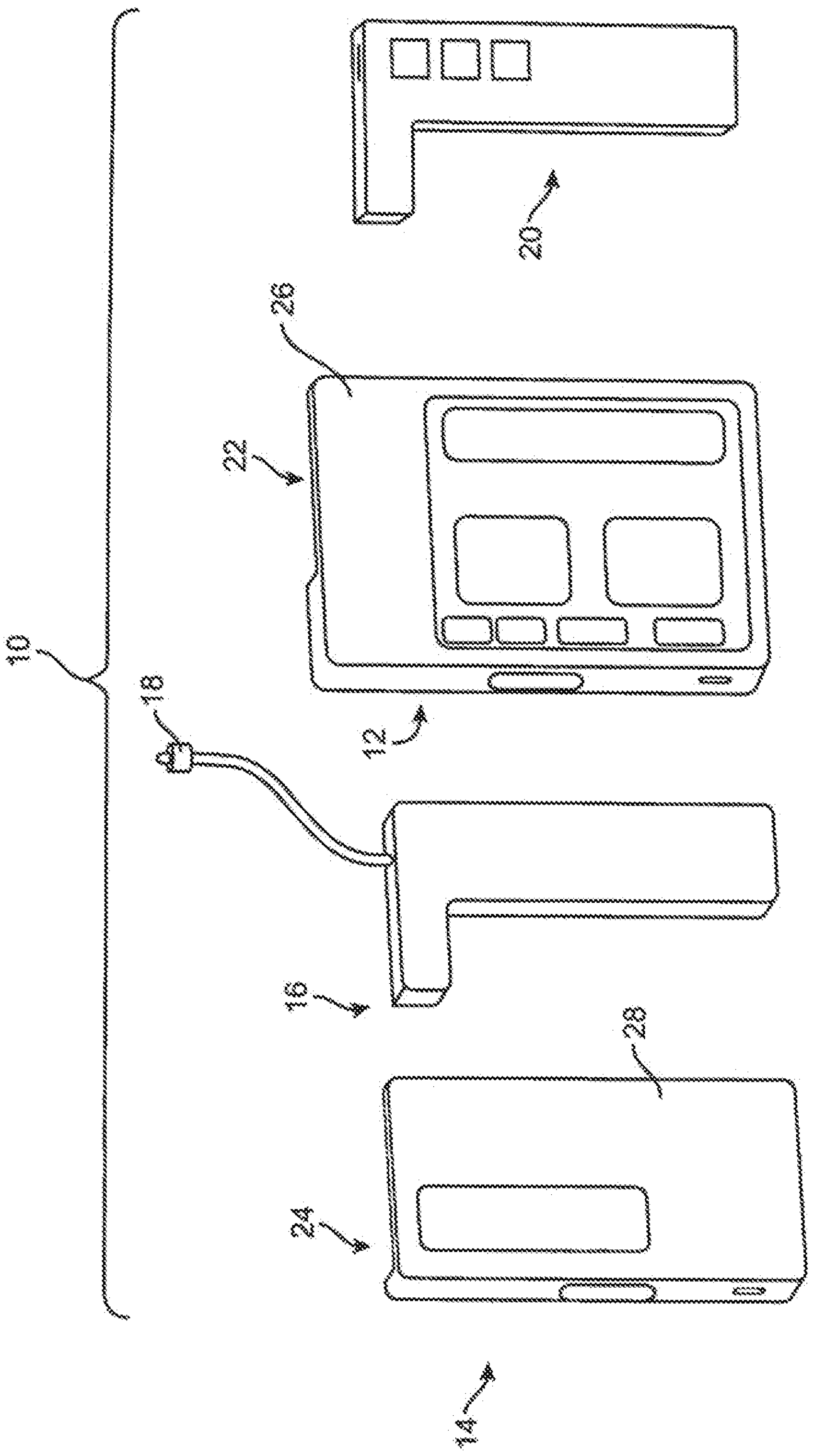
FIG. 1 illustrates an embodiment of an interchangeable pump assembly.

The drawings illustrate embodiments of the technology and are not limiting. For clarity and ease of illustration, the drawings may not be made to scale and, in some instances, various aspects may be shown exaggerated or enlarged to facilitate an understanding of particular embodiments.

DETAILED DESCRIPTION

As discussed above generally, there is a need for an infusion device that is capable of taking into account factors in determining an appropriate amount of medicament (e.g., insulin) to be delivered to the body so as to achieve blood glucose homeostasis. Medicament infuser embodiments are discussed herein that are configured in hardware, software, and/or user interface so as to receive user input and/or other data, which may be input by the users interaction with an intuitive user interface, processed to determine an estimate of an amount and/or rate of medicament delivery, which estimate may then be accepted, rejected, or manipulated by the user, so as to effectuate the delivery of the appropriate amount of medicament and thereby maintain homeostasis.

Some infusion device, system, and the method embodiments discussed herein may account for a wide range of variables in determining an amount of medicament, e.g., insulin, to be infused into a patient over a given period of time. Further, some embodiments discussed herein may allow for fine regulation of the amount of medicament delivered as well as the time during which the medicament is delivered. Some embodiments may include advances both in the internal components and the control circuitry as well as improvements in a user interface. The advances may allow for a more fine tuned regulation of blood glucose levels than is currently attainable by the devices, systems, and methods that are available at this time. Although embodiments described herein may be discussed in the context of the controlled delivery of medicaments such as insulin, other indications and applications are also contemplated. Device and method embodiments discussed herein may be used for pain medication, chemotherapy, iron cleation, immunoglobulin treatment, dextrose or saline IV delivery, or any other suitable indication or application. Non-medical applications are also contemplated.

Maintaining appropriate blood glucose homeostasis is an important factor for promoting the length and quality of life of a diabetic patient. Different types of pumps provide a user with various advantages, some of which can be mutually exclusive. For example, a pump device having a large output display can be easier to read and use compared to a pump device with a smaller output display. But that pump may also have a housing that is generally larger and may require a greater power usage. Large and bulky pump devices can be uncomfortable or unwieldy which can contribute to problems with user compliance. For example, a user may be less likely to wear a larger pump device while sleeping or when involved in certain activities. Smaller and more discreet pump systems known in the art can be more easily worn at night, but do not provide all the features patients have come to rely upon for safety and convenience. And once removed from the skin, known pump devices and their associated insulin cartridges cannot be used again.

A single insulin infusion cartridge can be used with a pump device to supply a user with insulin over an extended period of days, such as 3 days. During this time period a user's needs with respect to pump features can change. As mentioned above, full-featured pumps offer certain advantages that a user may not desire at other times such as during sleep or busy weekend activities. Because known insulin cartridges and infusion sets are not interchangeable they cannot be used again once the sterile field is broken and the infusion set and cartridge is used with one pump device. Known infusion sets and insulin cartridges must be thrown out once they are disconnected from a patient.

Provided herein is an interchangeable pump assembly that provides a user with the flexibility and convenience to alternate between pump devices having various features and advantages at any given moment during a single treatment protocol. In some cases a single insulin cartridge can be alternated between pump devices, such as a smaller, more discreet pumping device having fewer features and a larger, full-featured pumping device, during a single treatment without compromising the sterility, and thus wasting the cartridge.

Turning now to the figures, FIG. 1 shows an embodiment of interchangeable infusion assembly 10. The assembly 10 can include a first pump device 12, a second pump device 14, an infusion cartridge 16 having an infusion set connector 18, and optionally a glucose meter 20. Either the infusion cartridge 16 or the glucose meter 20 can be functionally and interchangeably inserted in a receiving slot 22 located in the first pump 12 and a receiving slot 24 located in the second pump 14, as will be discussed in more detail below. The first pump 12 can have a housing 26 that is generally larger than the housing 28 of the second pump 14 (see also FIGS. 2 and 4). Similarly, the first pump 12 generally includes more features than the second pump 14, as will be discussed in more detail below. It should be noted that some or all of the suitable features, dimensions, materials and methods of use of the infusion assembly 10 may be used or incorporated into any other infusion system, or components thereof, discussed herein. It should also be noted that the interchangeability of infusion cartridge embodiments is discussed herein generally in the context of transferring an infusion cartridge from a first pump to a second pump having features different from those of the first pump. However, all of the interchangeability features and methods associated with this type of transfer may also be applied to the transfer of an infusion cartridge from a first pump to a second pump having the same features as the first pump.

Figure 3:
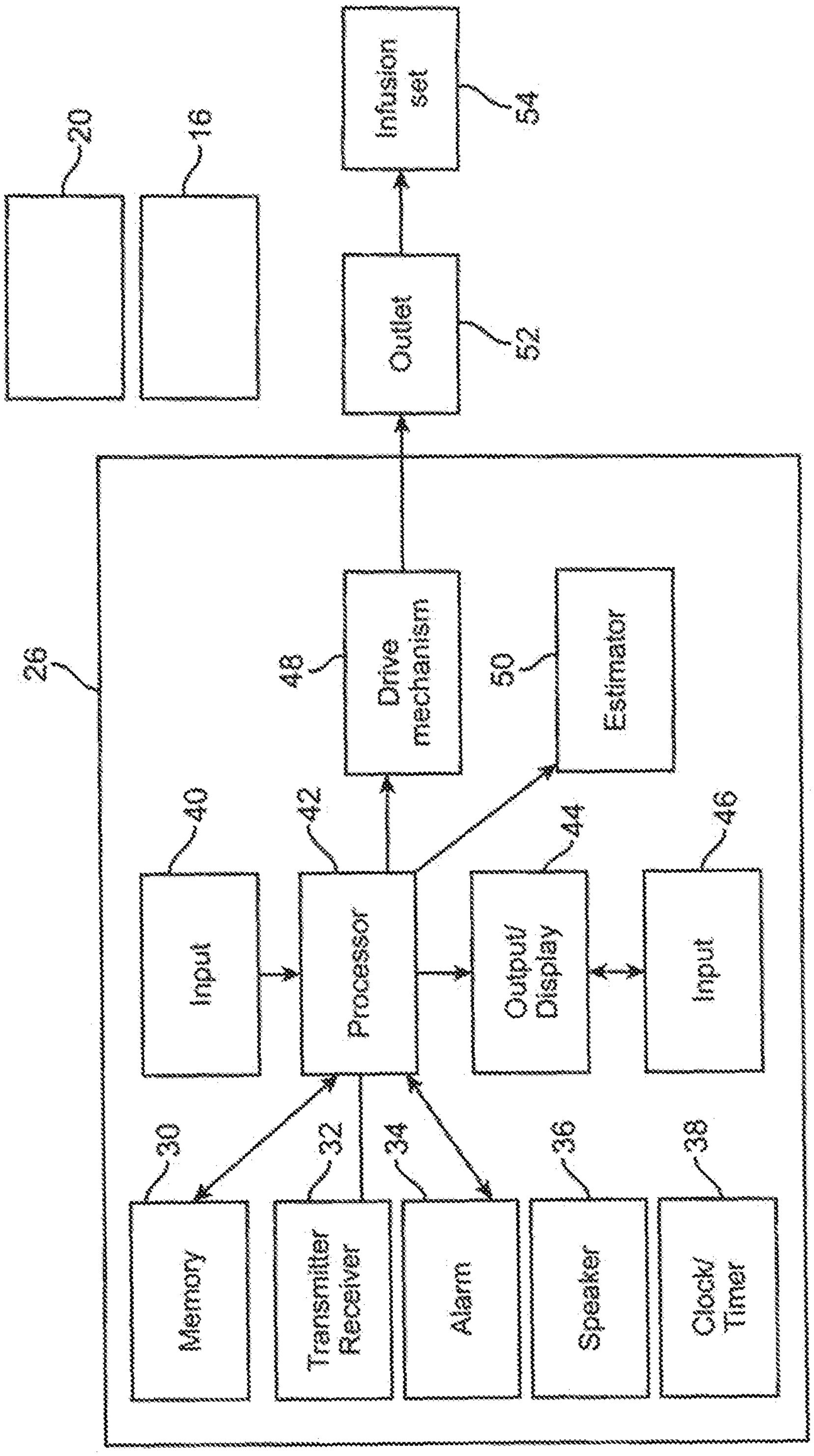
FIG. 3 illustrates a block diagram representing an example of a full-featured pump device.

FIG. 3 illustrates a block diagram of some of the features that can be incorporated within the housing 26 of the first pump 12. The first pump 12 can include a memory device 30, a transmitter/receiver 32, an alarm 34, a speaker 36, a clock/timer 38, an input device 40, a processor 42, an output/display 44 such as a graphic user interface or GUI having an input 46, a drive mechanism 48, and an estimator device 50. As mentioned, the housing 26 of the first pump 12 may be functionally associated with an interchangeable and removable glucose meter 20 or infusion cartridge 16. The infusion cartridge 16 may have an outlet port 52 that may be connected to an infusion set connector 18 and an infusion set 54.

Figure 5:
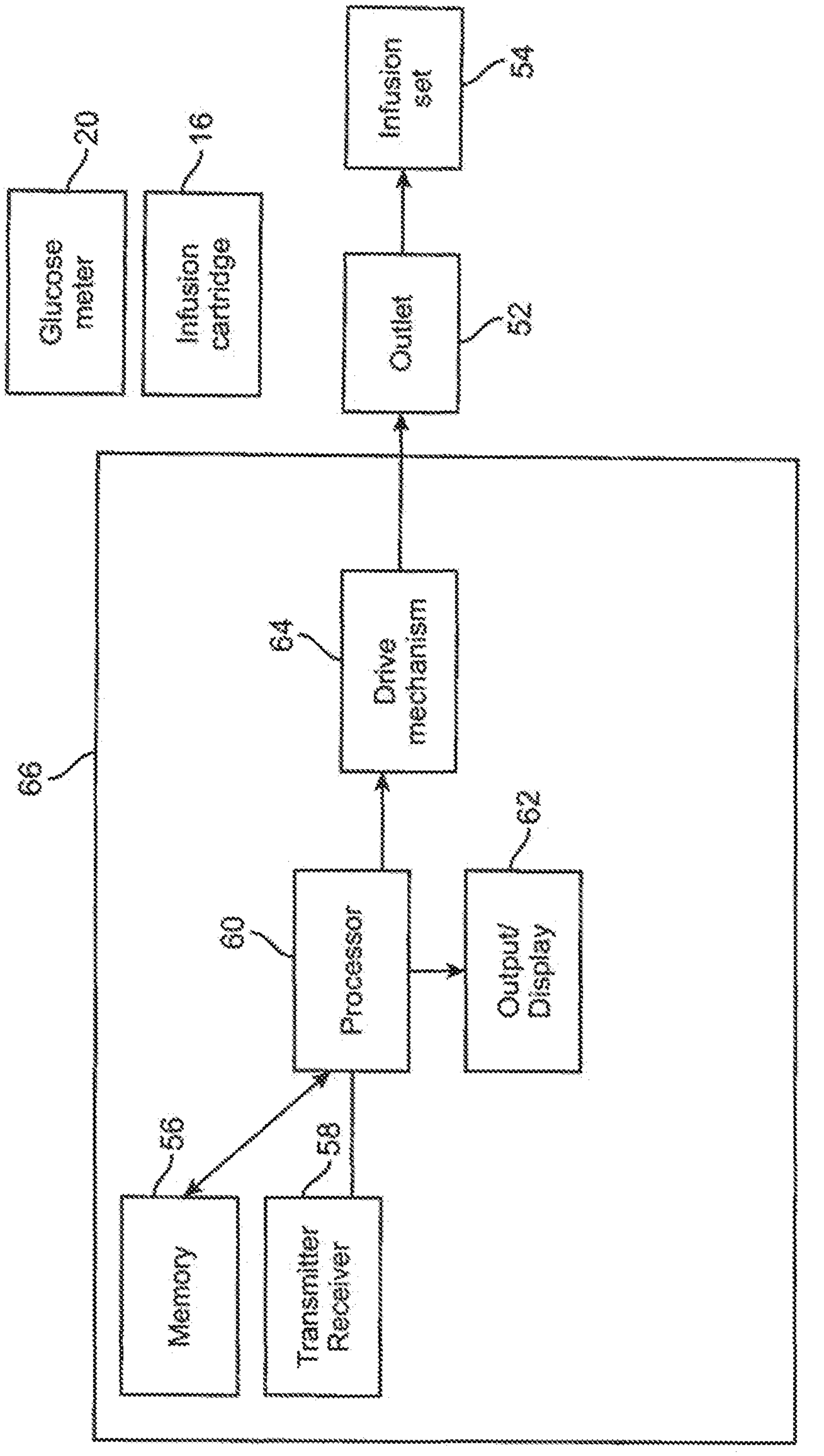
FIG. 5 illustrates a block diagram representing an example of a pump device incorporating basic features.

FIG. 5 illustrates a block diagram of features that can be incorporated within the more basic, second pump device 14. The second pump device 14 can include memory 56, transmitter/receiver 58, processor 60, output/display 62, and drive mechanism 64. The housing 66 of the second pump device 14 can be functionally associated with interchangeable and removable glucose meter 20 or infusion cartridge 16. The infusion cartridge 16 can have an outlet 52 that can be connected to an infusion set connector 18 and an infusion set 54.

Variations of the pump devices and features described herein may exist. For example, the full-featured pump device 12 may include a number of features that may or may not be included in the basic pump device 14. The features of each of the pump devices may vary and one or both pump devices may include certain features that are described herein. For example, although the full-featured pump device 12 may be described in an embodiment as having a metal housing 26, the full featured pump 12 may also have a plastic housing 26. Conversely, although the more basic pump device 14 may be described in an embodiment as having a plastic housing 28 it should be appreciated that it can also have a metal housing 28. In general, the full-featured pump device embodiments 12 described herein may include features that ultimately account for the difference in size and weight compared to the basic pumping device 14. It should be appreciated that because a feature or characteristic is described herein as being present on the full-featured pump device 12, that same feature or characteristic is not necessarily missing or different on the more basic pump device 14. The description below provides examples of some of the features that may be incorporated into one or both of the full-featured pump device 12 and the basic pump device 14.

The housing 26 of the first pump device 12 (see FIG. 2) and the housing 28 of the second pump device 14 (see FIG. 4) can each be of any suitable shape and size. For instance, the housings 26 and 28 may be extended and tubular, or in the shape of a square, rectangle, circle, cylinder or the like. The housings 26 and 28 may be dimensioned so as to be comfortably associated with a user and/or hidden from view, for instance, within the clothes of a user. The housing 26 of the first pump device 12 may generally be larger than the housing 28 of the second pump device 14. In some embodiments, the housing 26 of the full-featured pump device 12 may have a width of about 2 inches to about 5 inches, a height of about 1 inch to about 3 inches and a thickness of about 0.25 inch to about 0.75 inch, more specifically, the housing 26 may have a width of about 2.5 inches to about 3.5 inches, a height of about 1.5 inches to about 2.5 inches and a thickness of about 0.4 inches to about 0.8 inches. For some embodiments, the housing 28 of the basic pump device 14 may have a width of about 2.5 inches to about 3.5 inches, a height of about 1 inch to about 2 inches and a thickness of about 0.2 inches to about 0.6 inches. The materials of the housings 26 and 28 may vary as well. In some embodiments, housing of the full-featured pump device 12 may be a water-tight, metal housing that may be taken apart for repairs. In some embodiments, housing 28 of the basic pump device 14 may be a very water-tight, plastic housing that is glued together permanently.

Figure 2:
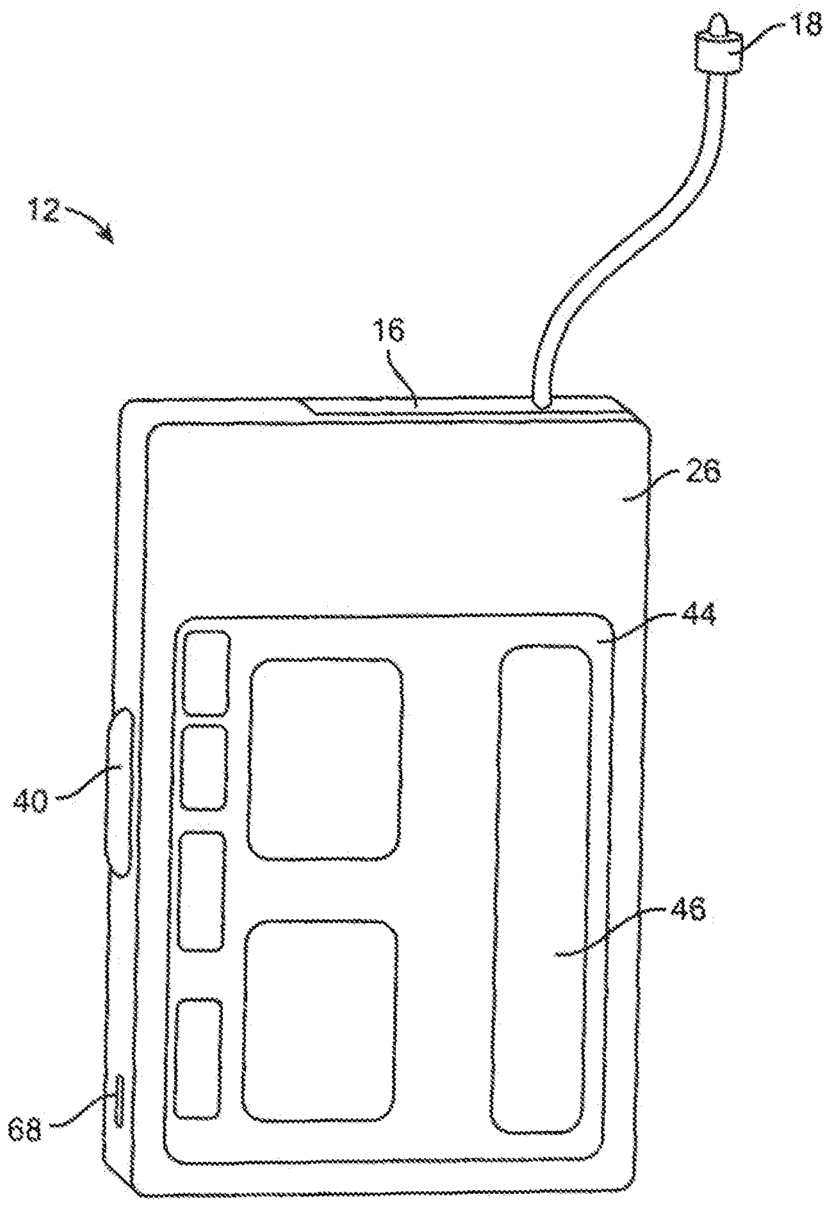
FIG. 2 illustrates an embodiment of a full-featured pump device having an infusion cartridge coupled thereto.
Figure 4:
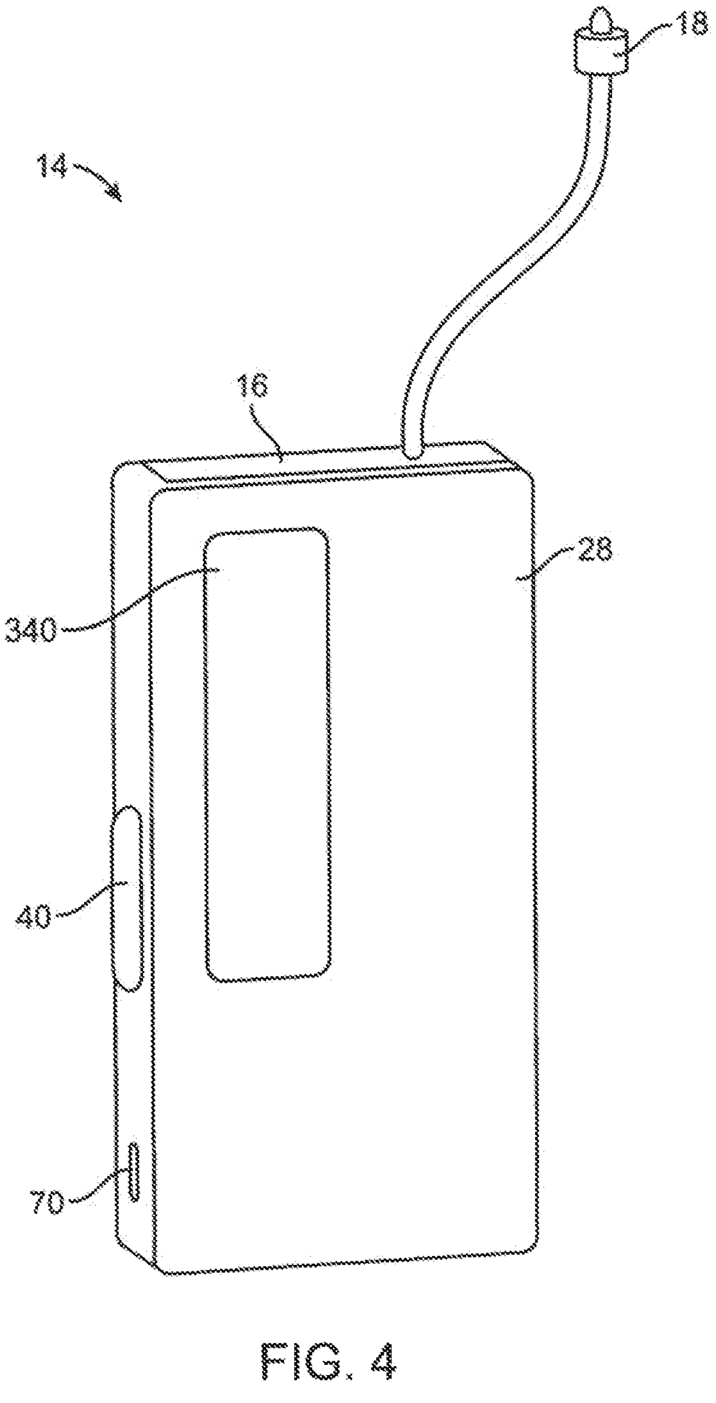
FIG. 4 illustrates an embodiment of a basic pump device having an infusion cartridge coupled thereto.

Still with respect to FIGS. 2 and 4, the pump devices 12 and 14 may include an output/display 44 or 62. The type of output/display 44 or 62 may vary as may be useful for particular application. The type of visual output/display may include LCD displays, LED displays, plasma displays, OLED displays and the like. The output/display 44 or 62 may also be an interactive or touch sensitive screen having an input device such as a touch screen, a capacitance screen, a resistive screen or the like. The output/display 44 of the first pump device 12 may be generally larger than the output/display 62 of the second pump device 14. In some embodiments, the output/display 44 of the full-featured pump device 12 may be an OLED screen and the input 40 may be a capacitance touch screen. In some embodiments, the output/display 62 of the basic pump device 14 may be an LCD screen. The pump devices 12 and 14 may additionally include a keyboard or other input device known in the art for data entry, which may be separate from the display. The output/display 44 or 62 of the pump devices 12 or 14 may also include a capability to operatively couple to a secondary display device such as a laptop computer, mobile communication device such as a smartphone or personal digital assistant (PDA) or the like.

The pump devices 12 or 14 may have wired or wireless communication capability such as for the sending and receiving of data as is known in the art. The wireless capability may be used for a variety purposes, including updating of any software or firmware for the processor of the device. The wireless communication capability may vary including, e.g., a transmitter and/or receiver, radiofrequency (RF) transceiver, WIFI connection, infrared or Bluetooth® communication device. The wired communication capability may also vary including, e.g., USB or SD port, flash drive port, or the like. In some embodiments, the first pump device 12 and the second pump device 14 each has a transmitter/receiver 32, such as a radiofrequency (RF) transceiver, that allows the first and second pump devices 12 and 14 to communicate with one another and be used interchangeably without loss of data or information during an infusion protocol with a single infusion cartridge 16. A user can alternate between the full-featured first pump device 12 and the more basic, second pump device 14 during a single infusion protocol and the transfer of data between the two can be automatic. The first pump device 12 may also act as a PDA or controller to wirelessly control the second pump device 14. For such an embodiment, data may be transferred between the controller of the first pump device and second pump device by radio signal, optical transmission or any other suitable means. Both the first and second pump devices 12 and 14 may be used as stand-alone devices as well.

One or more of the pump devices 12 or 14 may also include GPS functionality, phone functionality, warning and/or alarm programming; music storage and replay functionality, e.g., an MP3 player; a camera or video mechanism; auto scaling capabilities, and/or one or more video type games or other applications developed by third parties for use thereon. One or more of the pump devices 12 or 14 may also include an accelerometer, for instance, which may be used for changing presented estimates, wherein instead of scrolling through a menu of options or using a numerical keypad, values can be input or changed via the accelerometer, such as by gesturing with or otherwise shaking the device.

As shown in FIGS. 3 and 5 the first and second pump devices 12 and 14 each has a processor 42 and 60 that functions to control the overall functions of the device. The processors 42 and 60 may include programming that functions to control the respective device and its components. The processors 42 and 60 may communicate with and/or otherwise control the drive mechanism, output/display, memory, transmitter/receiver and the like. The processor of one of the pump devices may communicate with the processor of the other pump device, for example, through the transmitter/receiver. The processors may include programming that can be run to control the infusion of insulin or other medicament from the cartridge, the data to be displayed by the display, the data to be transmitted via the transmitter, etc. The processors may also include programming that allows the processors to receive signals and/or other data from an input device, such as a sensor that senses pressure, temperature, and the like, that may be included as a part of the device or used in conjunction therewith. The processors 42 and 60 may receive signals, for instance, from a transmitter/receiver on the blood glucose monitor (see FIG. 8) and store the signals in the memory, as will be discussed in more detail below.

The processors 42 and 60 may also include additional programming to allow the processor to learn user preferences and/or user characteristics and/or user history data, for instance, to implement changes in use suggestions based on detected trends, such as weight gain or loss; and may include programming that allows the device to generate reports, such as reports based upon user history, compliance, trending, and/or other such data. Additionally, pump device embodiments of the disclosure may include a "power off" or "suspend" function for suspending one or more functions of the device, such as suspending a delivery protocol, and/or for powering off the device or the delivery mechanism thereof. For some embodiments, two or more processors may be used for controller function of the pumps, including a high power controller and a low power controller used to maintain programming and pump functions in low power mode in order to save battery life.

The first pump device 12 and the second pump device 14 may each include a memory device 30 and 56. The memory devices 30 and 56 may be any type of memory capable of storing data and communicating that data to one or more other components of the device, such as the processor. The memory may be one or more of a Flash memory, SRAM, ROM, DRAM, RAM, EPROM, dynamic storage, and the like. For instance, the memory may be coupled to the processor and configured to receive and store input data and/or store one or more template or generated delivery patterns. For example, the memory can be configured to store one or more personalized (e.g., user defined) delivery profiles, such as a profile based on a user's selection and/or grouping of various input factors (as described below); past generated delivery profiles; recommended delivery profiles; one or more traditional delivery profiles, e.g., square wave, dual square wave, basal and bolus rate profiles; and/or the like. The memory can also store user information, history of use, glucose measurements, compliance, an accessible calendar of events, and the like. The first pump device 12 may have a relatively large memory compared to the memory of the second pump device 14. In some embodiments, the memory 30 of the first pump device 12 may be up to about 10 GB, more specifically, up to about 3 GB, even more specifically, about 1 MB to about 200 MB. In some embodiments, the memory 56 of the second pump 14 may be up to about 3 GB, more specifically, up to about 500 MB, and even more specifically, about 200 kB to about 200 MB.

The first and second pump devices 12 and 14 may include a power charging mechanism in some cases, such as a USB port, induction charger, or the like. The power charging system may be used to charge a power storage cell such as a rechargable battery of the pump device. Some embodiments may use a rechargable battery such as a NiCad battery, LiPo battery, NiMH battery or the like. In some embodiments, the power charging mechanism 68 of the first pump 12 may be a USB port. As such, all data may be kept in the first pump device 12 for quick and easy downloading of data to a computer, other pump device, network etc. using the USB port. The USB port 68 of the first pump device 12 may also provide the first pump device 12 with power charging. In some instances, the power charging mechanism 70 of the second pump device 14 may be an induction charging device. In some cases, an advantage of having interchangeable pumping devices 12 and 14 may be that while one pump device is being used for infusion, the other pump device can be charging. Further, the use of dual pump devices may provide a user of the pumps with a back-up in case of failure of one pump device.

The first pump 12 may also include programming to allow processor 42 to make a recommendation regarding a variety of treatment parameters. For instance, the processor 42 may include one or more estimator functionalities 50, which may allow the processor 42 to receive data from various sources, parse the data, collate the same, and generate an estimate based on the same. For instance, the processor 42 may receive user input data and/or data from one or more sensors or other external sources, which the processor 42 can process and thereby use to generate an estimate, such as an estimate of an amount of fluid to deliver to a body, a rate of fluid delivery, and/or a specific fluid delivery profile. For example, the processor 42 may be configured to process data pertinent to a current or predicted condition and to generate an estimate, represented as an amount, rate, profile, etc. of fluid to be delivered based on that data, which estimate may then be displayed to a user, thereby allowing the user to interact with the estimate to accept, decline, and/or otherwise modify the estimate.

Figure 6:
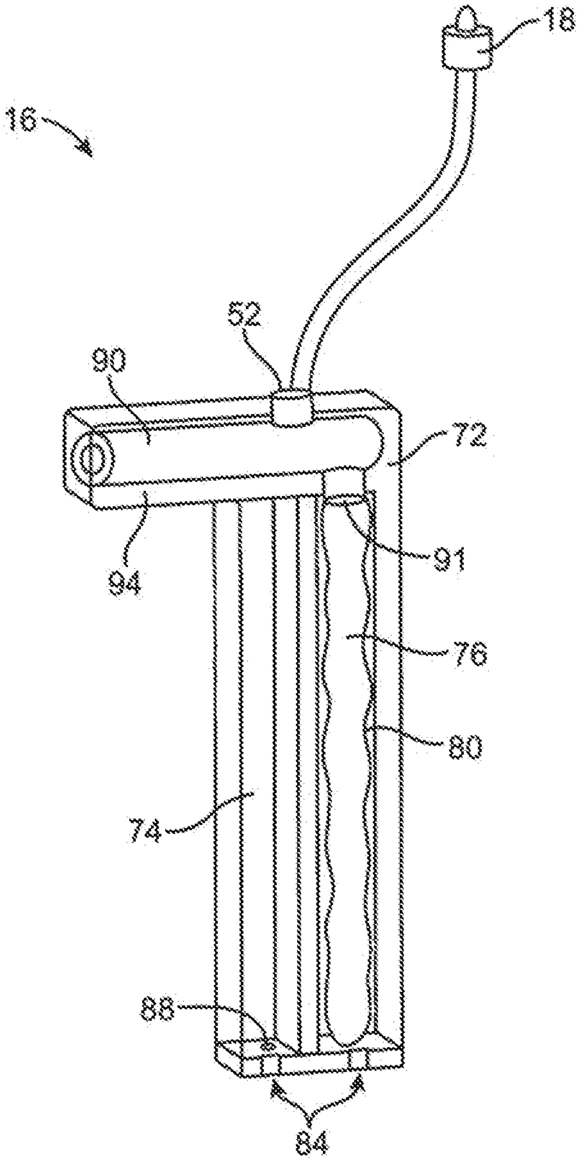
FIG. 6 illustrates an embodiment of an interchangeable infusion cartridge.

FIG. 6 shows an embodiment of the infusion cartridge 16. The infusion cartridge 16 may include a housing 72 having an inner chamber 74 containing a fluid reservoir that can store, for example liquid insulin or other suitable medicament. The fluid reservoir 76 may have any suitable shape and size configured for receiving fluid through a fill port 134 (see FIG. 10), storing the fluid and releasing the fluid. The fluid reservoir 76 may be an expandable bag. In some embodiments, the fluid reservoir 76 may be a bag or container surrounded or formed by a flexible material 80 that may be expandable, but not elastic or stretchy. In some embodiments, the fluid reservoir 76 may be filled such that the fluid reservoir occupies approximately ¾ of the volume of an inner chamber 74 of the housing 72. In these embodiments, the remaining ¼ of the inner chamber 74 of the housing 72 may hold or store a gas such as air, carbon dioxide or the like. The fluid reservoir 76 and the inner chamber 74 may store their respective fluids under pressure, such as atmospheric, a pressure higher than atmospheric pressure or a pressure lower than atmospheric or ambient pressure.

Still with respect to FIG. 6, the infusion cartridge 16 may be a reversibly removable and interchangeable element that can be inserted in either the receiving slot 22 of the first pump device 12 or the receiving slot 24 of the second pump device 14. Each of the pump housings 26 and 28 may include an alignment and attachment mechanism (see FIGS. 7A and 7B) corresponding to a receiving mechanism 84 on the cartridge 16. The receiving mechanism 84 may couple with the attachment mechanism 82 such that the infusion cartridge 16 may be reversibly attached and detached from the housings 26 and 28 of the pump devices 12 and 14 for fluid delivery as will be discussed in more detail below. The alignment and attachment mechanism 82 may also include a needle 86 that penetrates a septum 88 on the end of the infusion cartridge 16.

Figure 7B:
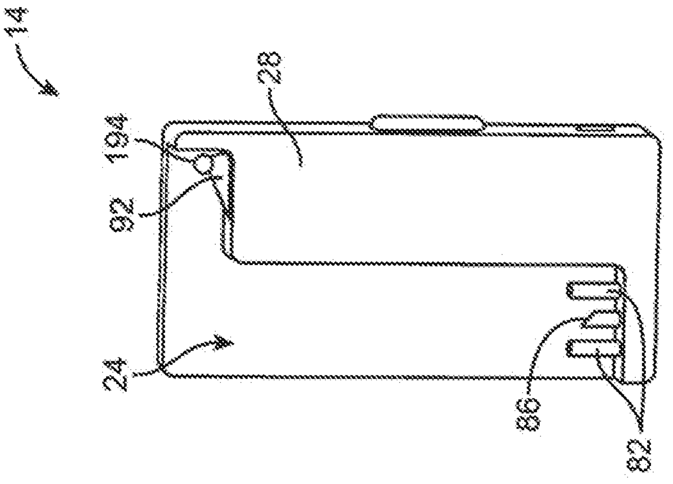
FIG. 7B shows a rear view of a basic infusion pump having a slot configured to receive an infusion cartridge or glucose meter.
Figure 7A:
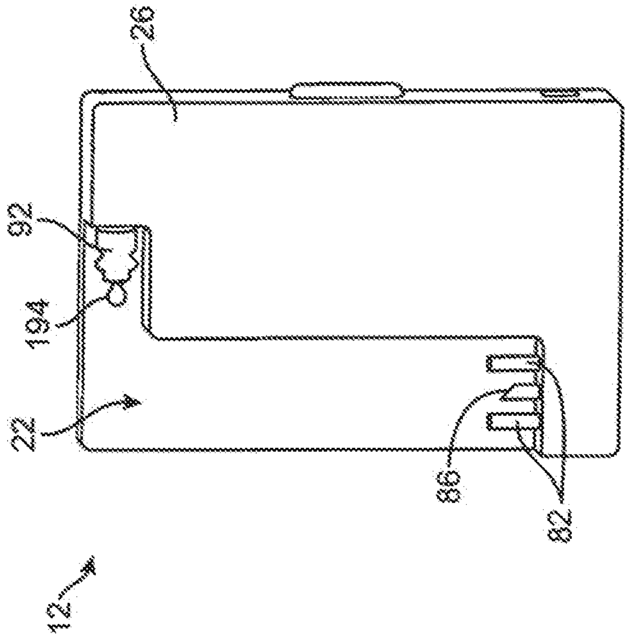
FIG. 7A shows a rear view of a full featured infusion pump having a slot configured to receive an infusion cartridge or glucose meter.

As shown in FIGS. 7A and 7B, the needle 86 may be positioned between pins of the attachment mechanism 82 such that the pins of the attachment mechanism 82 act to align the cartridge 16 to ensure proper insertion of the needle 86 through the septum 88 (shown in FIG. 6). The needle 86 can penetrate the septum 88 upon installation of the infusion cartridge 16 in the slot 22 such that the inner chamber 74 of the infusion cartridge 16 may be in sealed communication with the pump device 12. In some instances, the septum 88 may be a self-sealing septum such that upon removal of the cartridge 16 from the slot 22 and the needle 86 through the septum 88, the septum re-seals. The configuration of the receiving mechanism and corresponding attachment mechanism 82 may vary in some instances. For example, the mechanisms may be a pin and receiver port type of mechanism as shown in FIGS. 7A and 7B or a pneumatic tap system as will be described in more detail below.

Figure 7D:
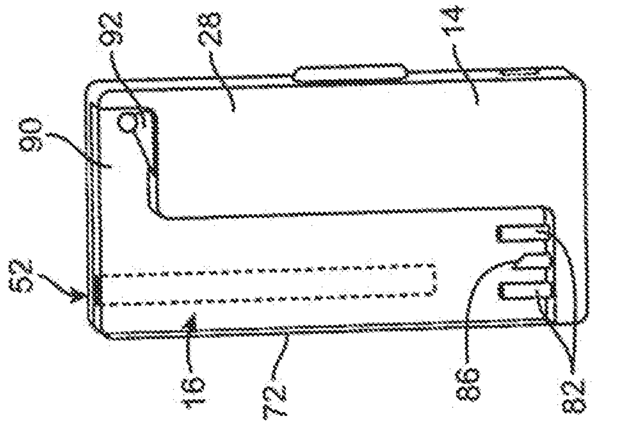
FIG. 7D shows the basic infusion pump of FIG. 7B with a glucose meter disposed in the slot of the basic infusion pump.
Figure 7C:
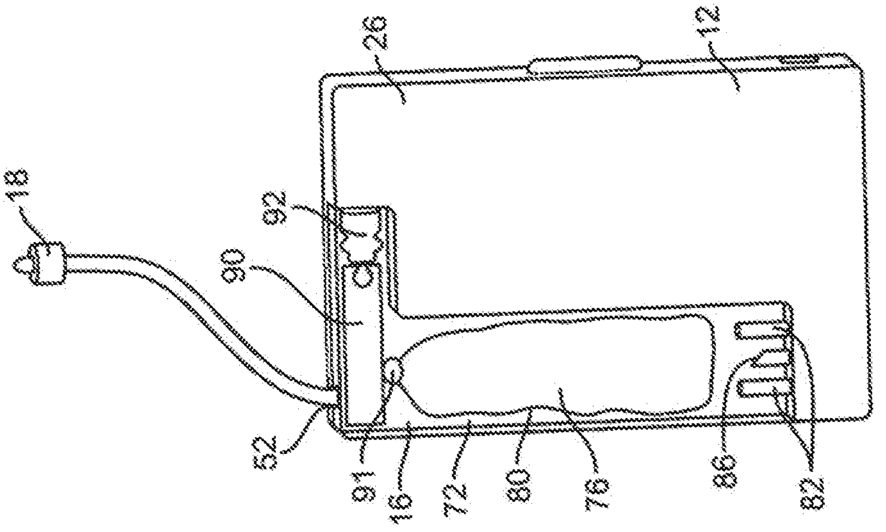
FIG. 7C shows a rear view of the full featured infusion pump of FIG. 7A with an infusion cartridge disposed in the slot.

Now with respect to FIGS. 7C and 7D, the infusion cartridge 16 may also include a delivery mechanism 90 that functionally and operably interfaces with the drive mechanism 92 of the pump devices 12 and 14. The infusion cartridge 16 and the pump devices 12 and 14 may be reversibly attached and detached to each other regardless of the stage of treatment or the position of the drive mechanism 92. The drive mechanism 92 regulates the flow of fluid from the reservoir outwards through the outlet 52. In some embodiments, the inner chamber 74 may include an opening 52 that fluidly communicates with the delivery mechanism 90 and may allow the fluid stored within the reservoir 76 to be expelled from the reservoir 76 through the opening 52 into the delivery mechanism 90 upon control of a valve or other mechanism. Ultimately the fluid can be expelled through outlet 52 towards the infusion set connector 18 and to the user. The drive mechanism 92 may be an electrically powered drive mechanism 92 as translated by a gear or reduction system. For some embodiments, the drive mechanism 92 may include a hydraulic mechanism, pneumatic mechanism, piezoelectric mechanism, stepper motor, continuous motor, or the like. In some embodiments, the drive mechanism 92 may include a rack and pinion system in which the rack upon rotation of the pinion moves laterally within a translation chamber of the delivery mechanism.

As mentioned above, the attachment mechanism 82 may act as an alignment device to ensure proper insertion of the needle 86 through the septum 88 and proper coupling of the delivery mechanism 90 with the drive mechanism 92. The infusion cartridge 16 and pump devices 12 and 14 may include additional alignment mechanisms that ensure proper coupling occurs to prevent inadvertent lateral translation and delivery of insulin or other medicament to the patient. For example, the pump device 12 or 14 may also include a horse collar type device or other feature positioned near a location where the delivery mechanism 90 couples to the drive mechanism 92. Such a feature may prevent lateral movement of the infusion cartridge 16 (and in turn the delivery mechanism 90) for some configurations as it couples with the pump device 12 and 14 such that inadvertent delivery of insulin to the patient upon insertion of the cartridge into the pump device is prevented. The head 94 of the cartridge 16 which contains the delivery mechanism 90 may also be held using a rail system as will be described in more detail below. A snap system including corresponding male and female parts that allow the infusion cartridge 16 to snap into place in operable contact with the pump devices 12 and 14 may also be used.

Figure 8:
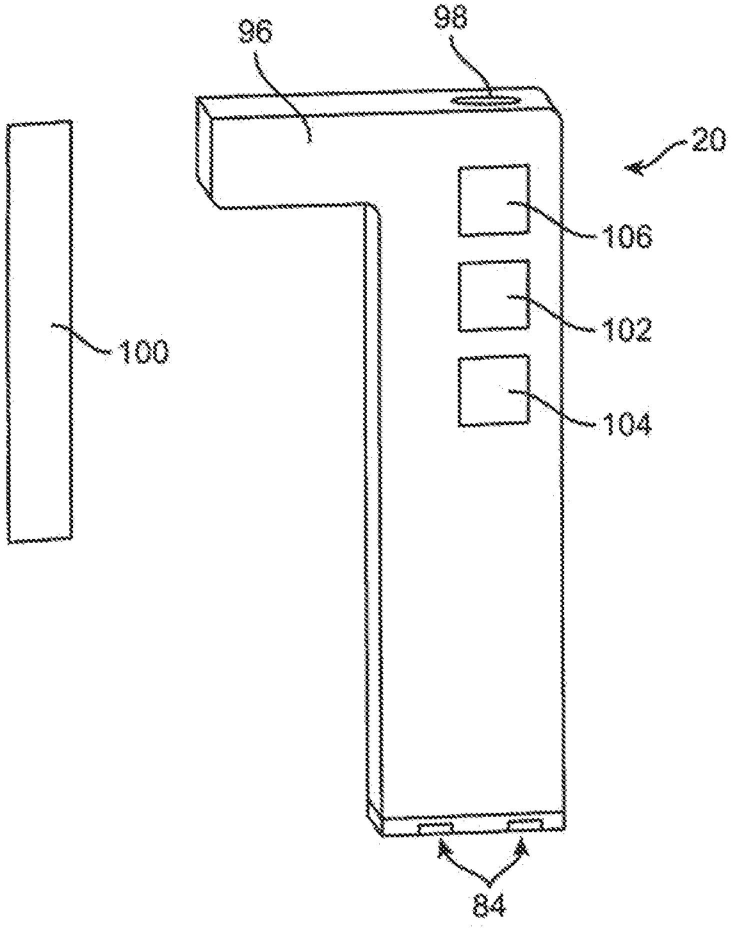
FIG. 8 illustrates an embodiment of a removable glucose meter and associated glucose test strip.

Some embodiments of the pump assembly 12 or 14 may also include a removable glucose meter 20 (FIG. 8). The glucose meter 20 may include a housing 96 having an insert hole 98. A measuring probe or glucose test strip 100 may be inserted into the insert hole 98. The glucose meter 20 may include a control panel 102 configured to control and a measuring lamp 104. Alternatively, the glucose meter 20 may be controlled by the input on the pump devices 12 or 14. The control panel 102 may also convert a measured value from the measuring lamp 104 into a signal that may be transmitted and recognized by the processor 42 or 60 of the pump device 12 or 14. The data may be transmitted wirelessly such as by a transmitter/receiver or may be a wired connection between the pump device and the glucose meter 20 upon insertion into the receiving slot 22 or 24. In some embodiments, the communication between the glucose meter 20 and the pump device 12 or 14 occurs wirelessly by RF or the like. Although the glucose meter discussed above utilizes a test strip for testing, any other suitable glucose testing method or device may be used such as the use of optical methods or electrical methods.

As described above, each of the pump devices 12 and 14 may have a receiving slot 22 or 24 into which the infusion cartridge 16 or the glucose meter 20 may be inserted. Like the infusion cartridge 16, the glucose meter 20 may be a reversibly removable and interchangeable element that can be inserted in either the receiving slot 22 of the first pump device 12 or the receiving slot 24 of the second pump device 14. The housing 96 of the glucose meter 20 may have the same or similar dimensions as the housing 72 of the infusion or reservoir cartridge 16 and include the same attachment mechanism 84 as that of the cartridge 16. As described above, each of the pump housings 26 and 28 may include an attachment mechanism 82 (see FIGS. 7A and 7B). The attachment mechanism 84 of the glucose meter 20 may corresponding to the attachment mechanism on the pump devices 12 or 14 such that the glucose meter 20 may be removably coupled to the housings 26 or 28 of the pumps 12 or 14. The configuration of the attachment mechanisms may vary as described above. Embodiments of the glucose meter 20, once inserted into the receiving slot 22 or 24, may communicate with the pump devices 12 and 14 such that the results of the glucose meter, such as a glucose monitoring test strip 100, may automatically be entered into the data log.

The glucose meter 20 may be inserted into the same receiving slot 22 or 24 as the infusion cartridge 16. The assembly therefore may have the added advantage of fewer devices for which the user must mind. For example, while the infusion cartridge 16 is inserted into the receiving slot 22 of the first pump device 12 and being used for a treatment infusion protocol, the glucose meter 20 may be inserted within the receiving slot 24 of the second pump device 14 while that pump device 14 is not being used or is charging. Thus, the receiving slot 22 or 24 of the pump device 12 or 14 not being actively used provides a storage location for the glucose meter 20 (see FIGS. 7C and 7D). Further, the assembly may have an advantage that the glucose meter 20 may be any number of different glucose meters made by a number of different companies such that the user has the added flexibility to decide which company's glucose meter and glucose test strips 100 they prefer to use.

Figure 9A:
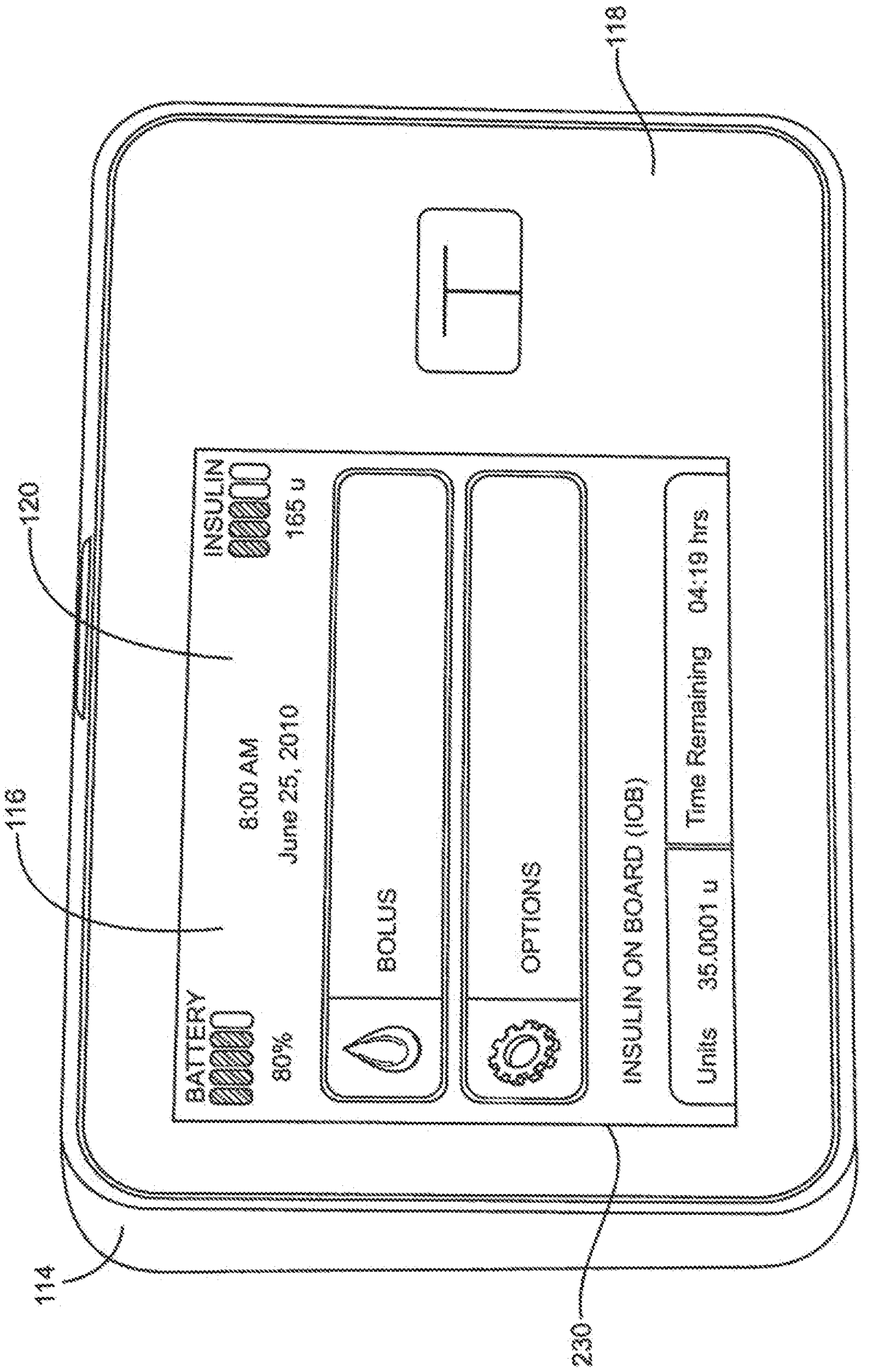
FIG. 9A is a front view in perspective of an embodiment of a full featured infusion pump system.
Figure 9B:
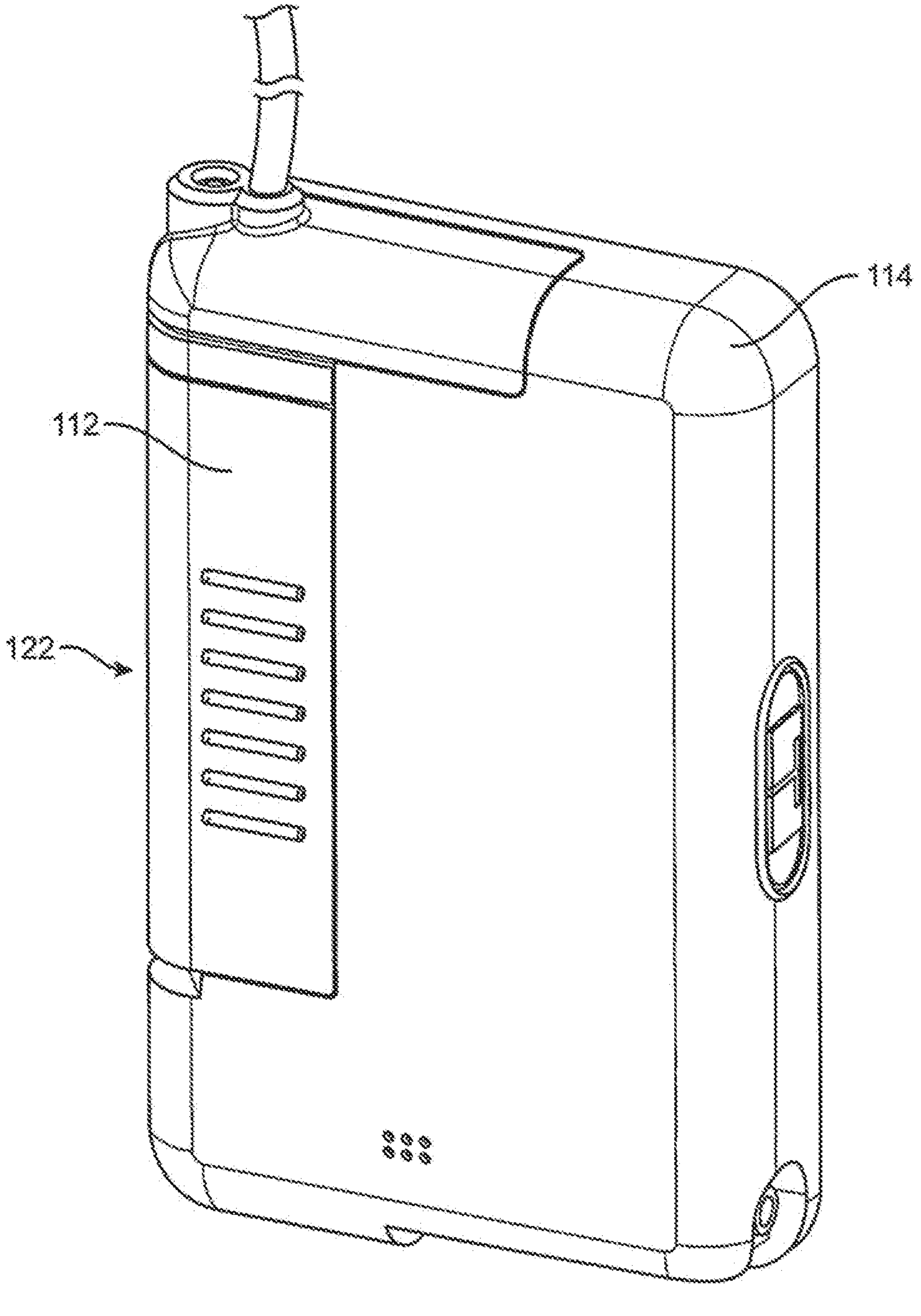
FIG. 9B is a rear view of an infusion cartridge coupled to the infusion pump device of FIG. 9A.

FIGS. 9A-14 show another embodiment of an infusion pump system 110 including an infusion cartridge 112 and pump device 114. As with previously described embodiments, the infusion cartridge 112 is a reversibly removable and interchangeable element that may be inserted into different pump devices. The pump device embodiment 114 may have some or all of the same or similar features, dimensions or materials as those of the pump devices 12 and 14 illustrated in FIG. 2. Referring to FIG. 9A, a front view of the pump device 114 is shown and includes a user friendly user interface 116 on a front surface 118 of the pump device 114. The user interface 116 includes a touch sensitive screen 120 that may be configured to display a variety of screens used for displaying data, facilitating data entry by a patient, providing visual tutorials, as well as other interface features that may be useful to a patient operating the pump device 114. FIG. 9B is a rear view of the pump device 114 and illustrates the detachable installment of the infusion cartridge 112 in a slot 122 of the pump device 114 which is configured to accept the cartridge 112. FIG. 9C is a schematic view of an open housing 124 of the pump device 114 which shows schematically some components that may be included in embodiments of the pump device 114. FIG. 9D shows the pump system 110 operatively coupled to a patient 127. FIG. 9E shows an outlet 123 of an infusion set 125 disposed beneath the skin of a patient 127. The infusion set is in fluid communication with a dispense part at the pump system 110 and a fluid 121, such as insulin or other suitable medicament, is shown being disposed form the outlet 123 into the body of the patient 127. It should be noted that some or all of the suitable features, dimensions, materials and methods of use of the infusion pump system 110 may be used or incorporated into any other infusion system, or components thereof, discussed herein.

For some embodiments, the pump system 110 may include a disposable fluid reservoir cartridge 112. The disposable cartridge 112 may include a fluid interface configured to receive a fluid such as collapsible reservoir 126. The collapsible reservoir 126 may be formed from a flexible material or membrane 128 that is disposed about an interior volume of the reservoir 126. The cartridge 112 also includes a substantially rigid container 130 sealed around the flexible material of the collapsible reservoir 126. A disposable delivery mechanism 132 is disposed within the disposable cartridge 112 and may have a fill port 134 with a re-sealable septum 136 sealed over the fill port 134, a reservoir inlet port 138 in fluid communication with an interior volume 140 of the collapsible reservoir 126, a fluid dispense port 142 in fluid communication with a bore 144 of the delivery mechanism 132, a vent inlet port 146 and a vent outlet port 148 both in fluid communication with the bore 144. The collapsible reservoir 126 may have a bag-like structure with flexible walls that can collapse and expand depending upon the amount of material in the volume of the reservoir. The interior volume of the reservoir may be in fluid isolation from the remaining interior volume of the rigid container 130.

For some embodiments, the reservoir may be formed from a membrane having a thickness of about 0.001 inches to about 0.005 inches, more specifically, about 0.002 inches to about 0.004 inches. In some cases, the membrane of the reservoir may be made from polymers such as PET, SiO, linear low density polyethylene or the like. Some embodiments of the reservoir may have an interior volume in a fully expanded state of about 1 ml to about 10 ml, more specifically, about 3 ml to about 5 ml. The membrane of the reservoir 126 may have a generally enclosed configuration with a top portion in sealed relation to the housing of the delivery mechanism. The membrane may be sealed and bonded to the housing of the delivery mechanism by heat welding, adhesive bonding or any other suitable method. The rigid container 130 of the cartridge may have an interior volume of about 2 to about 15 ml, more specifically, about 3 ml to about 5 ml. The shell 130 may be made from any suitable material, and particularly moldable materials, including polymers and specific materials such as polycarbonate or the like. The shell may have a nominal wall thickness of about 0.03 inches to about 0.08 inches, more specifically, about 0.04 inches to about 0.06 inches.

Figure 9C:
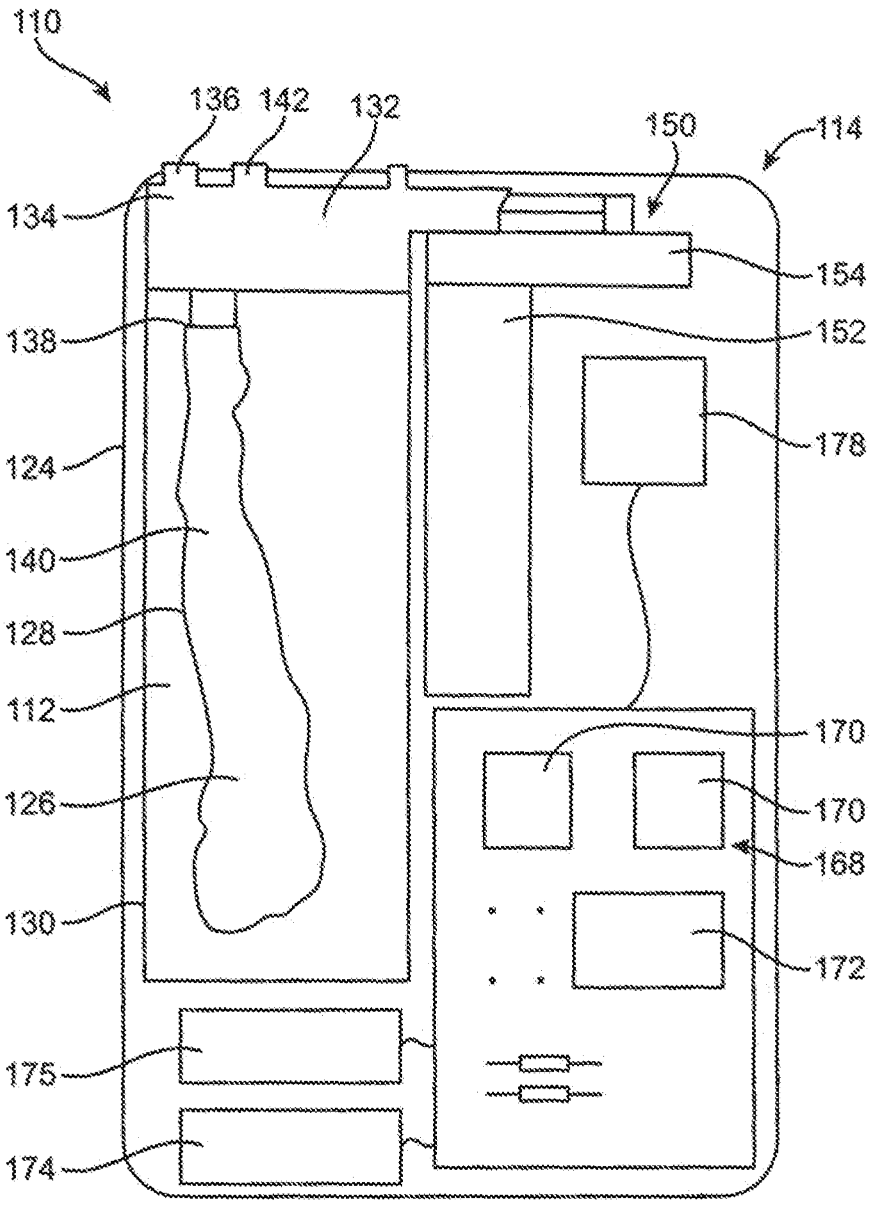
FIG. 9C is a rear schematic view of an interior of the infusion pump and cartridge embodiments of FIG. 9A.

The cartridge 112 may be releasably and operatively secured to a housing 124 of the pump device 114. The housing 124 may be configured to house a drive mechanism 150 including a motor 152 and gear box 154 disposed in the housing 124 and detachably coupled to a spool member 156 of the delivery mechanism 132. The drive mechanism 150 may be detachably and operatively coupled to the spool 156 member of the delivery mechanism 132. At least one pressure sensor 158 may be disposed in a volume 160 between an outside surface 162 of the flexible material or membrane 128 of the collapsible reservoir 126 and an inside surface 164 of the substantially rigid shell or case 130. As shown in FIG. 9C, a graphic user interface 166 may be operatively coupled to a controller 168, which may include at least one processor 170, a memory device 172 and connective circuitry or other data conduits that couple the data generating or data managing components of the device. A power storage cell in the form of a battery 174 that may be rechargable may also be disposed within the housing 124. Data generating or managing components of the device may include the processor(s) 170, the memory device 172, sensors 158, including any pressure or temperature sensors, the GUI 166 and the like.

Other components such as the vibratory motor 175, speaker 178, battery 174 and motor 152 of the drive mechanism 150 may also be operatively coupled to the controller 168. Connective circuitry may include conductive wiring such as copper wiring, fiber optic conduits, RF conduits and the like. For some embodiments, the fluid reservoir cartridge 112, and any of the fluid reservoir cartridges discussed herein, may include an encoder or bar code type strip (not shown). The encoder strip or device may be configured to be scanned and read by a reader device of the pump 114 with the reader device in operative communication with the controller 168 or processor 170 thereof. The encoder device may alternatively be an RFID chip or the like that transmits data to a reader such as a data receiving processor or the like. Such encoder device embodiments may include the ability to securely transmit and store data, such as, via, encryption, to prevent unauthorized access or tampering with such data. The identification of the fluid reservoir cartridge 112 may be used by the controller 168 to set or to adjust certain dispense parameters or any other suitable parameters.

For the embodiment shown, the vent inlet port 146 may be disposed on the delivery mechanism 132 in fluid communication with the volume 160 disposed between the outside surface 162 of the flexible material or membrane 128 of the collapsible reservoir 126 and an inside surface 164 of the substantially rigid shell or case 130 of the infusion cartridge. The controller 168 may include at least one processor 170 and a memory device 172, the controller 168 being operatively coupled to the drive mechanism 150, GUI 166, and at least one pressure sensor 158. The controller may be configured to generate a signal to the drive mechanism 150 to displace the spool 156 of the delivery mechanism 132.

Figure 10:
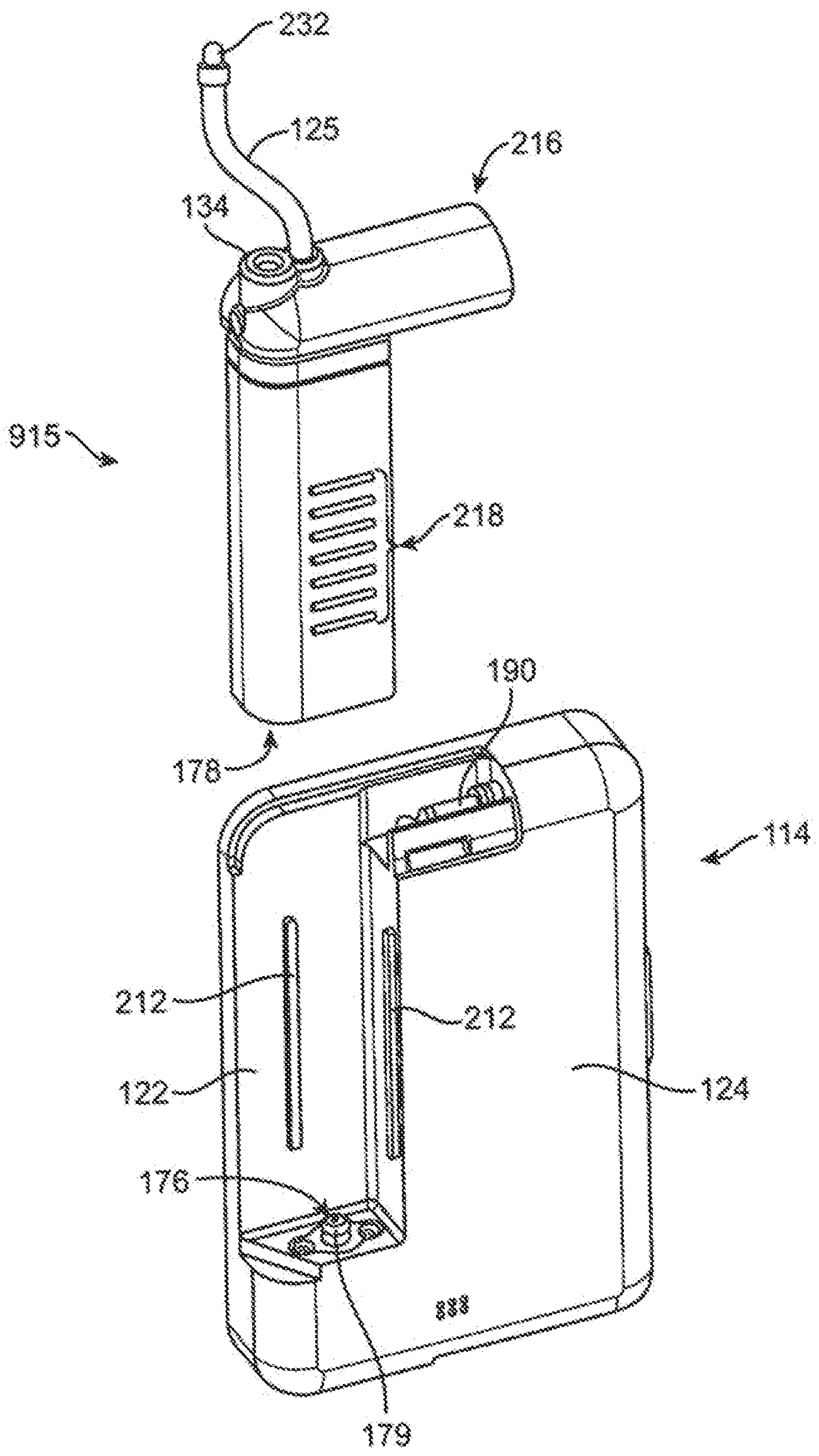
FIG. 10 illustrates an exploded view of the infusion cartridge and pump device of FIG. 9.
Figure 11:
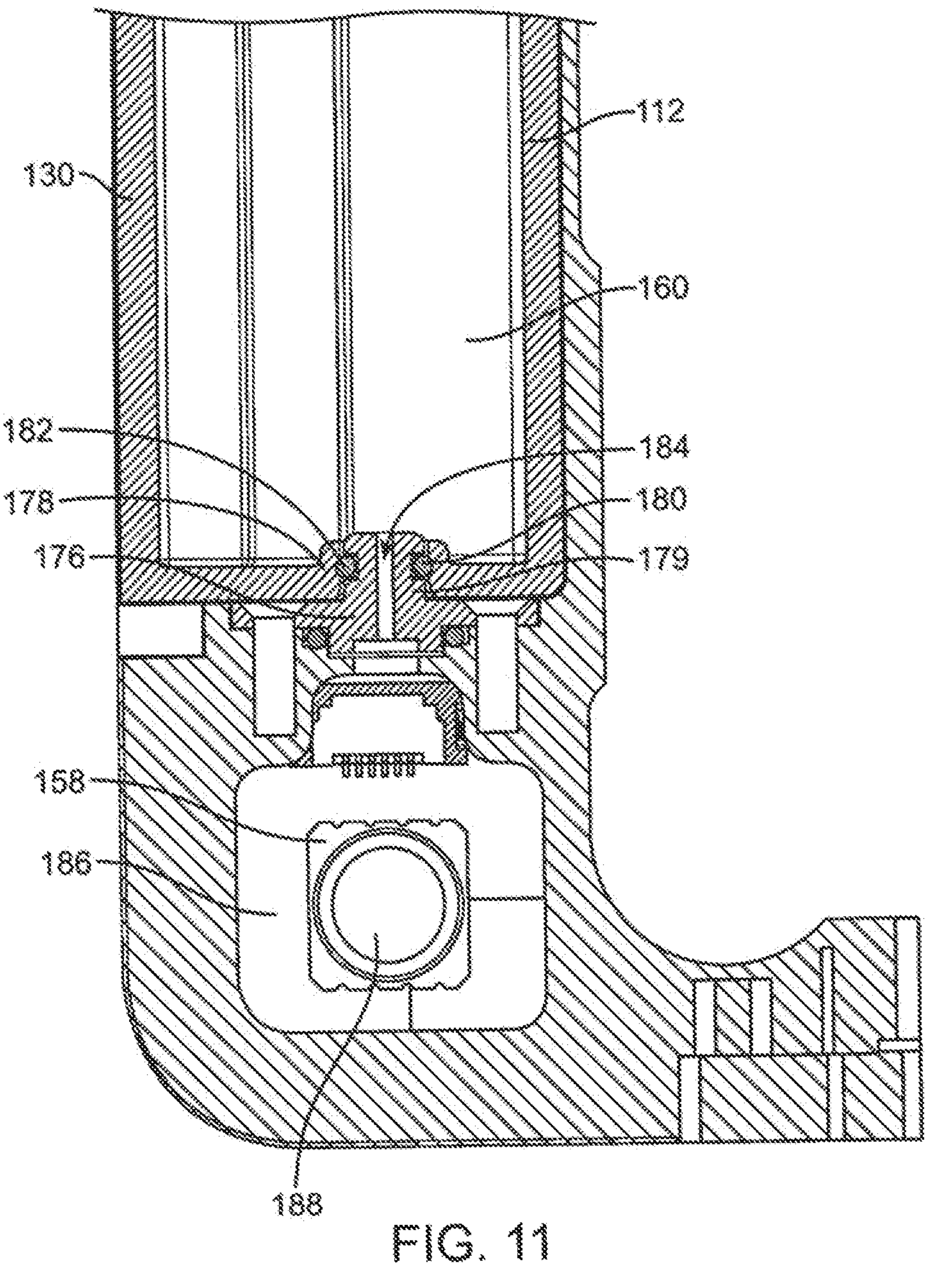
FIG. 11 illustrates a section view of an attachment mechanism of the infusion cartridge and pump device of FIG. 9.

As shown in FIGS. 10-11, the pump device 114 may include an attachment mechanism 176 positioned within the slot 122 near its terminus that corresponds to a receiving mechanism 178 at an end of the infusion cartridge 112. The attachment and receiving mechanisms may be configured to removably couple an interior volume of the cartridge with a volume of the pump that is sealed from the surrounding environment with the coupling able to retain a fluid within the volumes even under significant pressure. The o-ring based tap attachment embodiment discussed below may be so configured and suitable for producing a leak free detachable coupling that can withstand significant pressure. The receiving mechanism 178 may be configured to detachably couple with the attachment mechanism 176 such that the infusion cartridge 112. The infusion cartridge may be reversibly attached to the housing 124 of the pump device 114 for fluid delivery. In these embodiments, the attachment mechanism 176 may include a pneumatic tap 179 having an O-ring 180 or other sealing device. The corresponding receiving mechanism 178 positioned on an end of the infusion cartridge 112 may include a port 182 through which the pneumatic tap 179 may be inserted.

The pneumatic tap 179 may include an inner channel 184 running therethrough. The channel 184 may allow the tap 179 to fluidly connect the inner chamber volume 160 of the infusion cartridge 112 to the pump device 114 once the tap 179 is inserted through the port. The inner channel 184 of the tap 179 may connect to a pocket 186 of the pump device 114 that may be filled with a fluid such as air. In some embodiments, the pocket 186 in the pump may hold approximately 1 mL of the air. When the fluid reservoir of the infusion cartridge may be filled with 3 mL insulin or other medicament a residual volume of the inner chamber may exist. This residual volume may be, for example, 1 mL of air. Upon connection between the infusion cartridge 112 and the pump device 114, the residual volume of air within the inner chamber on volume 160 and the air within the pocket 186 may equalize and equilibrate in both temperature and pressure. The volume of the pocket 186 and volume 160 of the cartridge may also be in sealed relation with respect to each other and with respect to the surrounding environment. Thus, the pressure within volume 160 will equalize with the pressure in the pocket 186, thus, the pressure or pressure changes within volume 160 may be measured by the pressure sensor 158 in the pocket 186.

The pump devices 114 and others described herein may include a thermistor or other temperature sensor 188 including an optical or infrared sensor that measures the temperature of the insulin or other medicament within the reservoir 126 upon coupling the infusion cartridge 112 with the pump device 114. Taking the temperature of the air may be important in measuring how much insulin or other medicament is in the fluid reservoir. In some embodiments, the sensor 188 can be integrated with the attachment mechanism 176. For example, in the embodiment shown in FIGS. 7A-7B one or more of the pins of the attachment mechanism may include a thermistor. In some embodiments shown in FIGS. 9A-14, the pocket 186 may have a thermistor or other temperature sensor 188 positioned therein such that it can measure the temperature of the air in the pocket 186 as shown in FIG. 11. The pocket 186 may also include a pressure sensor 158 coupled to the controller 168 for measuring pressure within the pocket 186 and volume 160 Because the air in the pocket 186 is in fluid communication with the residual air within the chamber 160, the temperature and pressure of the air in the infusion cartridge 112 surrounding the fluid reservoir 126 may be equal or approximately equal to the temperature and pressure of the air in contact with the temperature sensor 188 and pressure sensor 158. In turn, the temperature sensor 188 may provide a relatively accurate measurement of the temperature of the insulin or other medicament within the reservoir 126.

Figure 12A:
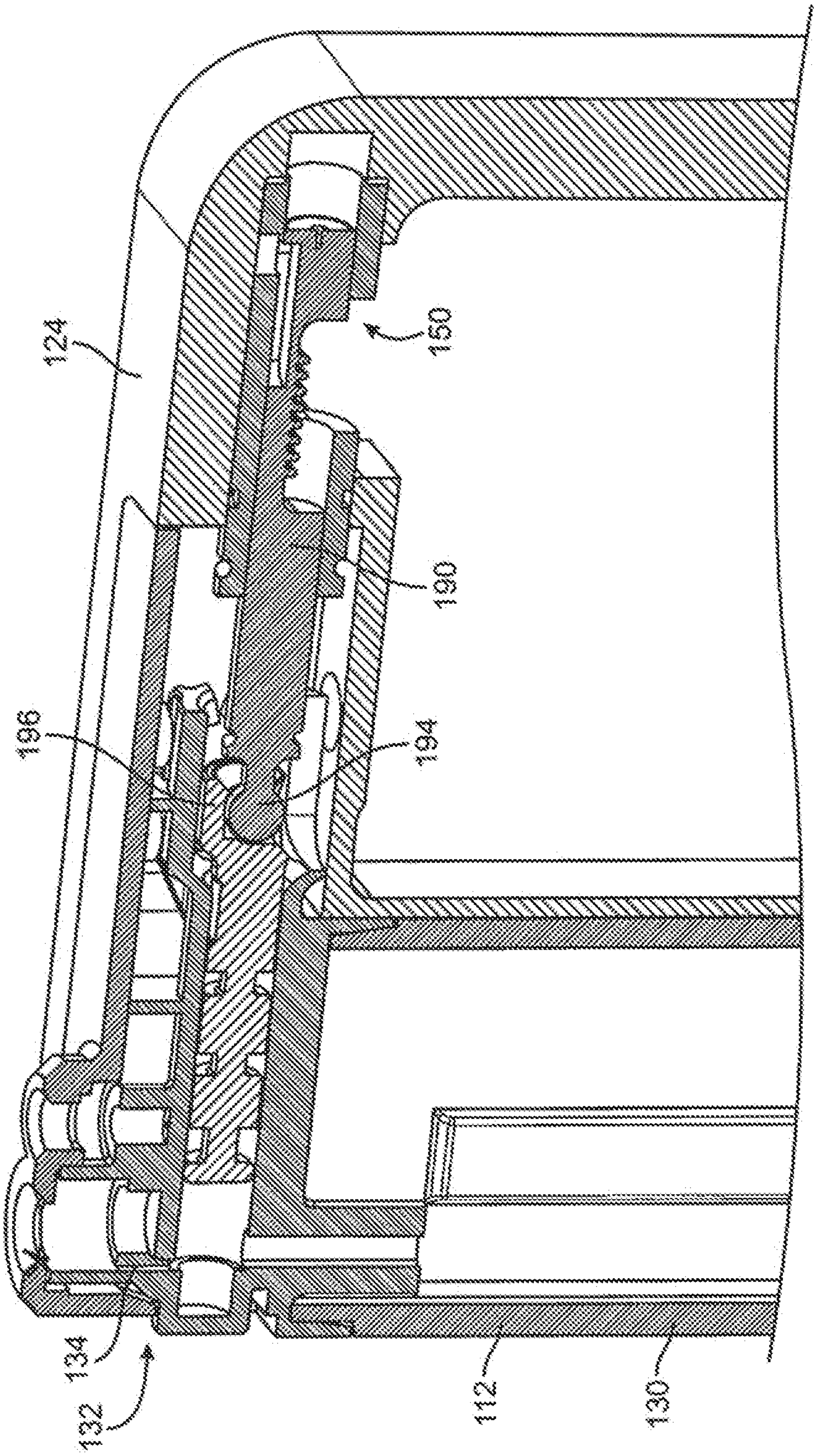
FIG. 12A illustrates in section an interface between embodiments of a spool of the delivery mechanism and drive mechanism of the infusion pump of FIG. 9.
Figure 12B:
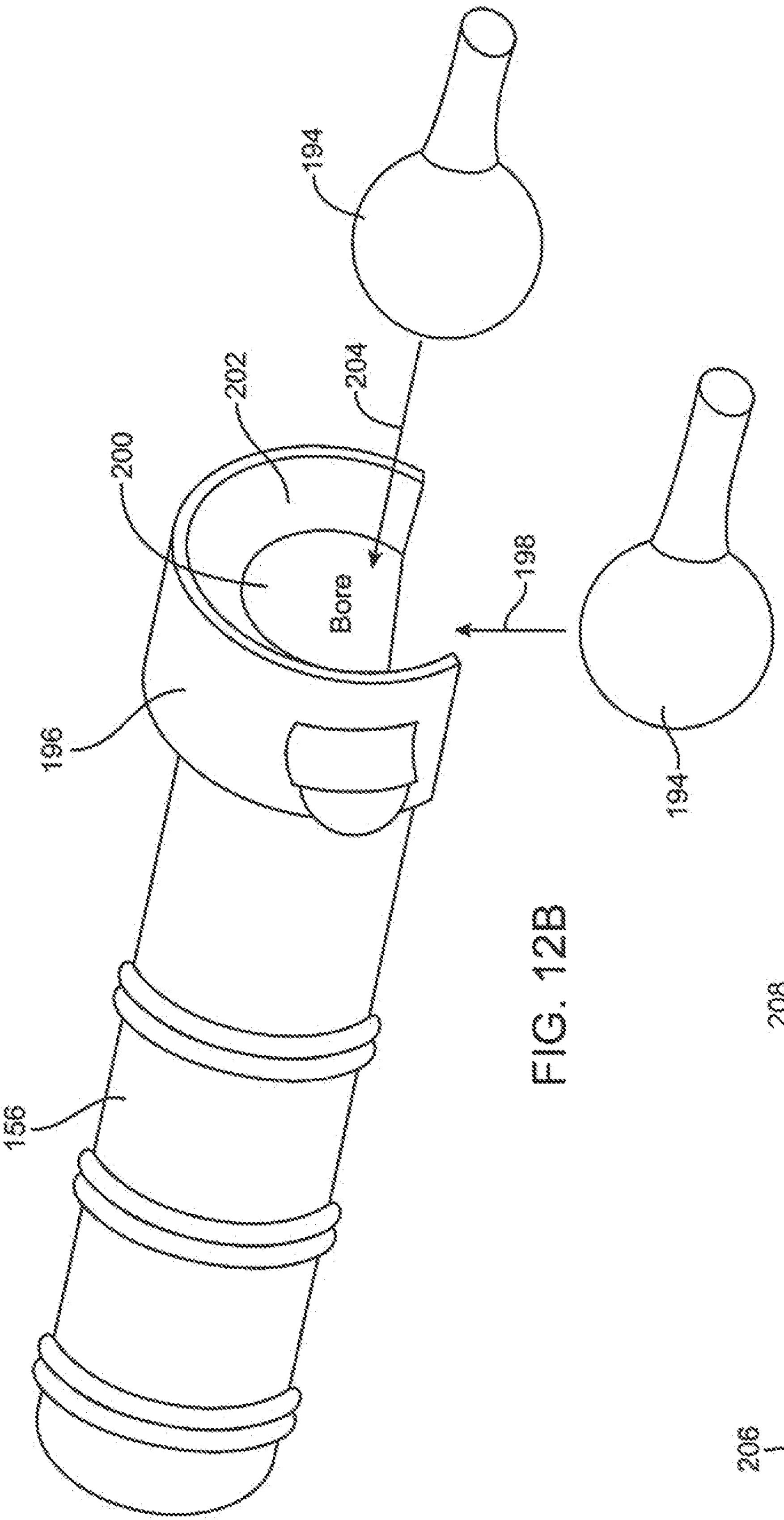
FIGS. 12B-12D illustrate interface embodiments of the bore of the spool and ball feature embodiments.
Figure 12D:
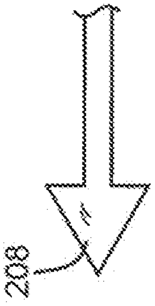
Figure 12C:
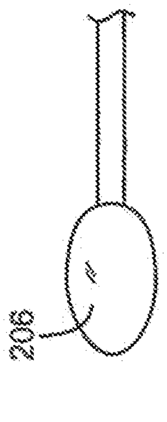

In some cases, the infusion cartridge 112 and the pump device 114 may be reversibly attached to and detached from each other regardless of the stage of treatment of a particular infusion cartridge 112 or position of the drive mechanism 150. As best shown in FIGS. 12A-12B, the delivery mechanism 132 of the cartridge may be configured to couple to a portion of the drive mechanism 150 of the pump device 114. As described above, the drive mechanism 150 may include a rack and pinion system. The rack or drive shaft 190 may couple to the delivery mechanism 132 at one end and the pinion 192, shown in FIG. 14, at an opposite end. The portion of the rack 190 that couples to the delivery mechanism 132 may include a ball or capturable feature 194 that inserts into a coupling element 196 on the delivery mechanism 132. As the pinion 192 rotates it causes linear motion of the rack 190 towards the delivery mechanism 132. The coupling element 196 of the delivery mechanism 132 may accept the ball feature 194 from a lateral side as shown by the arrow 198 in FIG. 12B. The drive mechanism 150 inserts the ball feature 194 in this manner, for example, upon insertion of a new infusion cartridge 112 into the pump device 114. In this process, the rack 190 and ball feature 194 may be in a position that is rotated back away from the delivery mechanism 132. After coupling the infusion cartridge 112 within the slot 122, the pinion 192 rotates such that the rack 190 translates horizontally (laterally) towards the coupling element 196 of the delivery mechanism 132 and the ball feature 194 inserts through a bore 200 of the coupling element 196. A flange 202 surrounding at least a portion of the bore 200 snaps in place around the ball feature 194 on the rack 190.

In some embodiments, the ball feature 194 of the rack 190 or drive shaft may attach to the coupling element 196 in at least two general directions. The coupling element 196 may be snapped down over the ball feature 194 of the rack 190 in a lateral direction as shown by the arrow 198 in FIG. 12B as well as being engaged by the ball feature 194 of the rack 190 in an axial direction or approach as shown by the arrow 204. The coupling element 196 including the bore or socket 200 of the spool 156 in addition to having an axially oriented opening to bore 200 also may have a lateral opening to the bore 200. This dual-directional insertion capability may allow for the infusion cartridge 112 to be removed and re-installed between pump devices 114, or any other suitable pump device embodiment such as pump devices 12 and 14, discussed herein, during a single infusion protocol and without unnecessary waste or inaccuracies. For example, when an infusion cartridge 112 is being used for the first time, the cartridge 112 may be inserted into the pump device 114 by translating it in a vertical direction down through the slot 122. The rack 190 may be generally in a withdrawn configuration, axially displaced away from the spool 156 of the delivery mechanism 132. Once the cartridge 112 is filled and primed, the rack 190 may be wound or axially advanced by the pinion 192 such that it translates in an axial direction and the ball feature 194 inserts through the axial opening into the bore 200 as shown by the arrow in FIG. 12B.

The ball or capturable feature 194 may be axially advanced until the flange of the coupling element 196 of the spool 156 snaps around the ball feature 194. At any stage during the infusion protocol, the infusion cartridge 112 may be removed from the pump device 114. The infusion cartridge 112 may be slid vertically upwards with respect to the pump housing 124 of the infusion device 110 such that the ball feature 194 exits the coupling element 196 of the spool 156 of the delivery mechanism 132 through the lateral opening 198 of the socket 200. The infusion cartridge 112 may then be re-inserted into another pump device by sliding it in a vertical direction downward through a slot of another housing until the ball feature 194 inserts through a lateral opening of a coupling element of the other pump device. The cartridge 112 may be advanced into the second pump device once again until the flange of the coupling element 196 snaps down from the top around a ball feature on the rack of the drive mechanism 150 of the second pump device.

The delivery mechanism 132 of the infusion cartridge 112 may remain in position providing a patient with the flexibility of changing pump devices during a single treatment protocol with a single infusion cartridge 112 regardless of the position of the drive mechanism 150. The method of switching between pump devices is described in more detail below. Although a ball-hitch type of configuration is shown in the figures, the configuration of the attachment between the rack 190 and the delivery or spool element 156 can vary. For example, the ball 194 and socket 196 of the embodiment shown may be reversed with the socket 196 on the drive shaft 190 and the ball element 194 on the spool or delivery element 156 of the delivery mechanism 132. In addition, the capturable element 194 of the detachable coupling may also include a different shape such as the oval capturable feature 206 shown in FIG. 12C or the triangular capturable feature 208 shown in FIG. 12D.

In some cases, it may be desirable for the ball feature 194 and socket 196 of the coupling element to be configured to snap or otherwise detachably couple together such that there is little or no appreciable axial play between the drive shaft 190 of the drive mechanism 150 and the spool 156 of the delivery mechanism 132. Any of these embodiments or similar embodiments of capturable features 194 may be used and detachably captured by a resilient socket or bore 200 in an axial or lateral direction as discussed above with regard to the spool embodiment 156. In addition, the pump devices 114 between which the patient is switching may be configured to communicate and prepare themselves to receive an infusion cartridge 112 such that the drive mechanism 150 translates to the appropriate position to maintain consistency in infusion protocols as will be described in more detail below.

As discussed above, FIGS. 10 and 13 illustrate an embodiment of an alignment mechanism 210 between the pump device 114 and the infusion cartridge 112. The pump device 114 may have a rail system that includes rails 212 positioned within the slot 122 that may be received within corresponding grooves 214 in the infusion cartridge 112. In some embodiments, the rails 212 may be positioned about 90 degrees apart around the receiving slot 122 that dove-tail or otherwise insert and capture the grooves 124 on the outer housing or shell 130 of the cartridge 112 such that the cartridge 112 slidably couples to the pump device 114 such as in a vertical plane or other plane. The rails 212 and grooves 214 of the rail system may prevent lateral movement as the delivery mechanism 132 couples with the drive mechanism 150.

Figure 13:
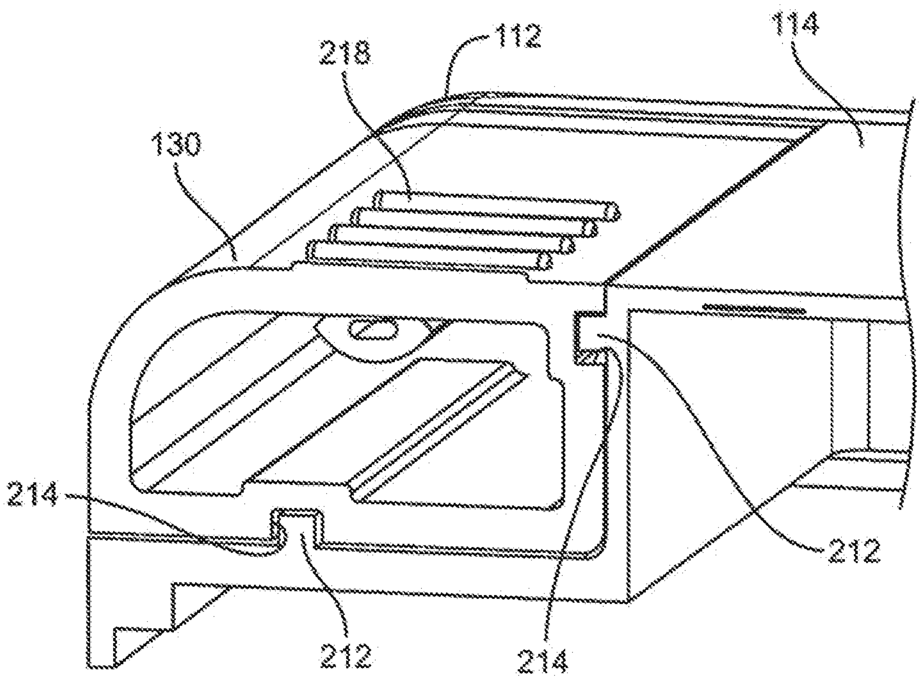
FIG. 13 illustrates an alignment mechanism embodiment of the infusion pump embodiment of FIG. 9.
Figure 13A:
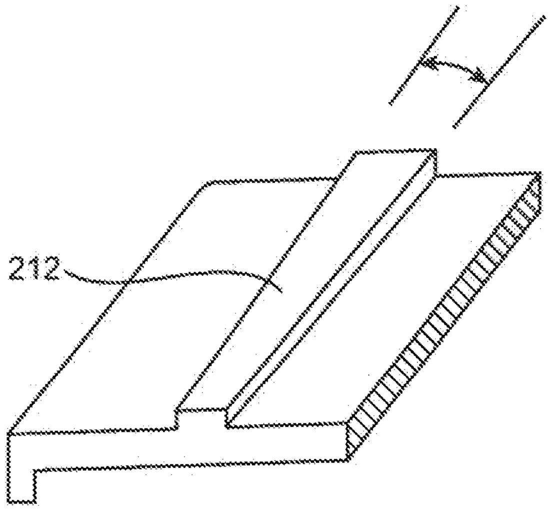
FIG. 13A illustrates a flared rail embodiment of the pump housing and reservoir cartridge.

For some embodiments, inadvertent lateral movement of the infusion cartridge 112 and, in turn, lateral movement of the delivery mechanism 132 relative to the ball feature 194 may result in inadvertent delivery of fluid to the patient 127 upon insertion of the cartridge 112. The rail system shown is configured to hold the head 216 of the infusion cartridge 112 in a proper and stable position once the delivery mechanism 132 inserts over the ball feature 194. The rails 212 of the rail system for some embodiments may also have a tapered configuration as shown in cut away illustration of FIG. 13A. As shown, either or both rails of the rail system 212 shown in FIG. 13 may have a transverse dimension that flares to a larger dimension in a direction of engagement so as to provide a taper locking type arrangement between the rails 212 and slots 214 of the rail system when fully engaged. The mating slots 214 of the tapered rails 212 may have a matching tapered configuration.

For some embodiments, the taper or flare angle of the rails 212 and slots 214 may be about 0.5 degrees to about 3 degrees. The outer housing 130 of the infusion cartridge 112 may also have three-dimensional features such as slots, knurling or any other suitable type of finger grips 218 that may aid a user during the installation and removal of the cartridge from the pump device. Some embodiments may also include a slot (not shown) that bridges the structure of the cartridge 112 and pump housing that is configured to allow a coin to be inserted into the slot and twisted to leverage the disengagement of the cartridge 112 from the pump housing. Typically, both halves of the slot would be aligned when the cartridge is fully engaged with the pump 114. In some cases, the rail system or slot of the pump housing generally may be configured to couple the cartridge to the pump with the top or head of the cartridge in a transversely fixed or secured arrangement to prevent any unwanted displacement between the delivery mechanism 132 and the drive mechanism 150. The coupling between the cartridge 112 and pump 114 at the attachment mechanism end may be configured to allow for some transverse play between the cartridge and the pump housing. The play between the cartridge and the pump may allow the attachment mechanism and receiving mechanism to be self-aligning.

A possible advantage of some system embodiments discussed herein may be that the infusion cartridge 112 even after being inserted within a receiving slot 122 of a first pump device 114 can be removed and re-inserted into the receiving slot of a second pump device without resetting the second pump device. In some cases, the spool 156 of the delivery mechanism 132 of the infusion cartridge 112 maintains its axial position and air is not pulled into the pump chamber 220 or fluid dispensed during the change. Further, in some cases, the first and second pump devices 114 involved in the transfer for switch of the cartridge 112 from one pump 114 to another may be configured to communicate either directly or wirelessly with each other. Such communication between pumps 114 or controllers 168 thereof may allow the position of the drive mechanism 150 of the second pump to be set to the position of the first pump 114 at the time the infusion cartridge 112 was removed thus, providing seamless interchangeability during a single infusion protocol. In addition, after being inserted within a receiving slot of a given pump device, the infusion cartridge 112 can be removed and re-inserted into the same receiving slot of that pump device without resetting the pump device. In this way, system embodiments are contemplated wherein the infusion cartridge 112 (*a*) is interchangeable between and/or among one or more different pump devices without those pump devices having to be reset, and which pump devices may be identical or different in any of their features, sizes, and functionalities, and (b) may be removed from and re-inserted into a receiving slot on a single given pump device without resetting the given pump. Such a transfer with communication between pumps 114, and other pump embodiments, allows the transfer to be made without changing the axial position of the spool 156 of the delivery mechanism 132 relative to the various ports of the delivery mechanism 132. For some embodiments, the socket or bore 200 of the coupling element 196 of the spool 156 may be configured to be self-centering such that the ball or capturable element 194 of the drive shaft 190 will be engaged and snapped into place even if the axial alignment of the ball element 194 and socket 196 are not perfectly aligned at the time of insertion or engagement.

In some cases, a new infusion cartridge 112 may be removed from its sterile packaging and inserted into the receiving slot of a first pump device 114. The attachment mechanism 176 of the first pump device 114 may couple with the receiving mechanism 178 of the infusion cartridge 112. The drive mechanism 150 at this stage may remain physically unconnected to the delivery mechanism 132. Once the cartridge 112 is secured to the pump 114, a patient 127 can fill the infusion cartridge 112 with insulin or other suitable medicament using a syringe having a hypodermic needle 222 inserted through a septum 136 of the fill port 134 (see, for example, FIG. 14). The pressure inside a vented volume 160 of the infusion cartridge 112 increases and is directly related to how much fluid was added to the fluid reservoir 126. For one example, if 3 ml of fluid is added to a fluid reservoir embodiment 126, the pressure inside the vented volume 160 of the infusion cartridge 112 may increase from about 0 psi to approximately 22 psi, depending on the volume of the vented volume 160. The septum 136 is configured to conform around the needle 222 and provide a resilient seal around an outer surface of the needle 222. The septum may have a thickness of about 0.05 inches to about 0.15 inches, more specifically, about 0.08 inches to about 0.1 inches, and may be made from an elastic resilient material such as silicone rubber having a shore hardness of about 45 A to about 55 A.

The pressure increase of 22 psi may then be used by the controller to determine the amount of insulin or other medicament or fluid that has been put into the reservoir 126. Pressure change measurements may also be used to measure an amount or amounts of fluid dispensed from the reservoir 126. Other means of measuring fluid volumes or changes of fluid volumes may also be useful in some embodiments. In some cases, methods and devices for determination of a fluid volume as used in any suitable application discussed herein may include acoustic sensors, including a loud speaker and one or more microphones which may be used for acoustic volume determination, optical devices, capacitive measurement devices, deflection measurement methods, thermal time of flight methods or any other suitable methods. The change in pressure in the system may be used to determine the volume of fluid added or dispensed from the reservoir by means of a ideal gas law calculation. If the volume of the system is known, i.e., the volume of the pocket 186 and volume of the shell 130 are known, then the ideal gas law equation $PV=nRT$ where P is pressure, V is volume, T is temperature and n and R are constants, may be used to calculate changes in volume based on changes in pressure assuming the temperature is also known. The temperature of the gas within the cartridge may be measured by a temperature sensor within the pocket 186 such that when fluid is added or dispensed from the reservoir, the pressure sensor will measure a change in pressure. The change in pressure is then used to calculate the change in volume that caused the pressure change. This method of volume measurement, as well as the other methods discussed above, may be used a redundancy check on electrical volume measurements, error detection within the pump system 110 or components thereof, or any other suitable purpose. The use of the ideal gas law for volume measurement may also be useful for dispensing fluids, including medicaments such as insulin or any other suitable medicament or material, without directly contacting the fluid.

The pressure inside the infusion cartridge 112, and particularly the vented volume 160 of the infusion cartridge 112, may be measured by a pressure sensor 158 disposed in the infusion cartridge 112 or in the pump device 114 in a volume, such as pocket 186. Pocket 186 is an interior volume disposed within the pump device 114 and in fluid communication with an interior volume of the fluid cartridge 112. The pocket 186 is in sealed relation with the interior volume 160 of the cartridge. As such, a pressure sensor 158 disposed within the volume of the pocket 186 will read the pressure of the volume 160 in the cartridge, but can remain with the pump device 114 after disposal of the disposable cartridge 112. This configuration lowers the cost of the cartridge while providing the means of pressure measurement within the cartridge 112. In some embodiments, data from the pressure sensor 158 may be used to provide a measurement of how much insulin or other medicament is being delivered by the first pump device 114.

Once the infusion cartridge 112 is filled, the drive mechanism 150 of the first pump device 114 may then connect to the delivery element or spool 156 of the infusion cartridge 112. For example as in FIGS. 12A-12B, the pinion 192 (not shown) can drive the rack or drive shaft 190 in an axial direction until the ball feature 194 applies an axial force against the coupling element 196 and moves the spool 156 in a distal direction until reaching a hard stop 226. The drive shaft 190 may then be advanced further distally in an axial direction until the ball element 194 enters the axial socket or coupling element 196 of the spool 156 and snaps into the bore 200 of the delivery element or spool 156. The controller 168 of the first pump device 114 may then transmit instructions to the motor 152 of the delivery mechanism 132 which may be configured to perform a priming protocol.

The priming protocol may be used to prepare the infusion cartridge 112 and the first pump device 114 for delivery of a desired fluid to a patient 127. The patient 127 can input externally supplied values into the data input interface 228 of the first pump device 114. The data input interface 228 may receive the user input data and communicate that data to the processor 170 of the controller 168. For some embodiments, the controller 168 may be programmed or otherwise configured to generate an estimate of an amount of the insulin or other medicament to be delivered to the patient 127 as either a baseline, bolus or any other suitable type of fluid delivery regimen. The controller 168 may then communicate the estimate to the display 230 for patient evaluation. The first pump device 114 may then deliver an approved quantity of medicament to the patient 127 according to the selected protocol. The user input data may include one or more of a blood glucose level, a stress level, a physiological condition, a complexity of a meal to be ingested, an activity level, user history, and the like.

At any stage during an infusion protocol, the patient 127 may slide the infusion cartridge 112 vertically through the slot 122 up away from the attachment mechanism 176 of the first pump device 114. In some cases it may be desirable for the patient 127 to enter data into the interface of the first pump 114 which is indicative that the cartridge 112 is going to be removed from the pump 114. As discussed above, the controller 168 of the first pump 114 may use this data to configure the position of the spool 156 of the delivery mechanism 132 of the first pump 114 or communicate information regarding the position of the spool 156 of the first pump 114 to the controller 168 of the second pump. In this way, the controller 168 of the second pump may use this information to configure the drive shaft 190 of the drive mechanism 150 to facilitate engagement of the cartridge 112 with the second pump. The controller 168 may also be configured to halt an ongoing delivery protocol including any axial advancement or cycling of the delivery element 156 at this time to avoid removal of cartridge 112 during delivery of fluid to the patient 127.

During removal of the cartridge 112 from the first pump 114, the ball feature 194 on the rack or drive shaft 190 may snap through the lateral opening 198 in the coupling element 196 until the delivery mechanism 132 of the cartridge 112 is free of the drive mechanism 150 of the first pump 114. The removal of the infusion cartridge 112 from the first pump device 114 may require a certain degree of force imparted by the patient 127 such that inadvertent removal or uncoupling of the infusion cartridge 112 from the pump device 114 is avoided. The finger grips 218 or other three-dimensional feature on the outer housing 130 of the infusion cartridge 112 may aid a patient 127 in the removal of a cartridge 112 from the pump device 114. As discussed above, once the attachment and receiving mechanisms 176 and 178 are uncoupled, the first pump device 114 may send a signal to the second pump device such that the second pump device may configure itself in preparation for receiving the infusion cartridge 112. Such a signal may be a radiofrequency signal, for example. In some embodiments, the drive shaft 190 of the drive mechanism 150 of the second pump device may be adjusted in an axial direction in accordance with the data sent by the first pump 114.

In some cases, the axial position of the drive shaft 190 of the second pump may be adjusted to the proper position such that when the infusion cartridge 112 is inserted into the slot of the second pump device the ball feature 194 of the rack 190 may be directly inserted through the lateral opening 198 on the coupling element 196 without causing axial displacement of the coupling element 196. The coupling element 196 then snaps over the ball 194 in a top-down direction. In some embodiments, rather than adjusting the rack 190 to match an axial position of the rack 190 of the first pump, the rack 190 of the second pump may instead be fully proximally retracted upon the initiation of a transfer process. In such a process, the infusion cartridge 112 may be inserted into the slot 122 of the second pump without any mechanical engagement between the coupling element 196 of the delivery mechanism 132 or the ball 194 of the drive mechanism 150.

Once the cartridge 112 is engaged with the pump 114, the controller 168 may then instruct the drive shaft or rack 190 of the drive mechanism 150 to advance in a distal direction until pushing the spool 156 of the delivery mechanism 132 to a hard stop 226 within the bore 220. Once the spool 156 is upon the hard stop 226, further axial advancement of the drive shaft 190 in a distal direction will force the ball feature 194 of the drive shaft 190 into the socket 196 of the spool or delivery element 156 until it snaps into place and is mechanically captured by the socket 196. If a glucose meter 20 is being stored within the slot 122 of the second pump device, it may be removed prior to inserting the infusion cartridge 112 into the slot 122 and replaced into the slot 122 of the first pump device 114.

The patient's infusion set 125 may remain connected to the infusion cartridge 112 via the set connector 232 during transfer between the first and second pump devices. The sterility of the infusion cartridge 112 and the infusion set 125 is maintained regardless of how many times the infusion cartridge 112 is removed and re-inserted into a pump device 114. Neither the drive mechanism 150 nor the attachment mechanism 132 of the pump devices 114 breaks the sterile field of the fluid reservoir 126. Similarly, connection between the pneumatic tap 179 and the port 182 of the receiving element does not break the sterile field of the fluid reservoir 126. The insulin or other medicament is contained within the fluid reservoir 126 which may be a closed sterile environment that is not broken or exposed during repeated installations between the first and second pump devices 114.

Figure 18:
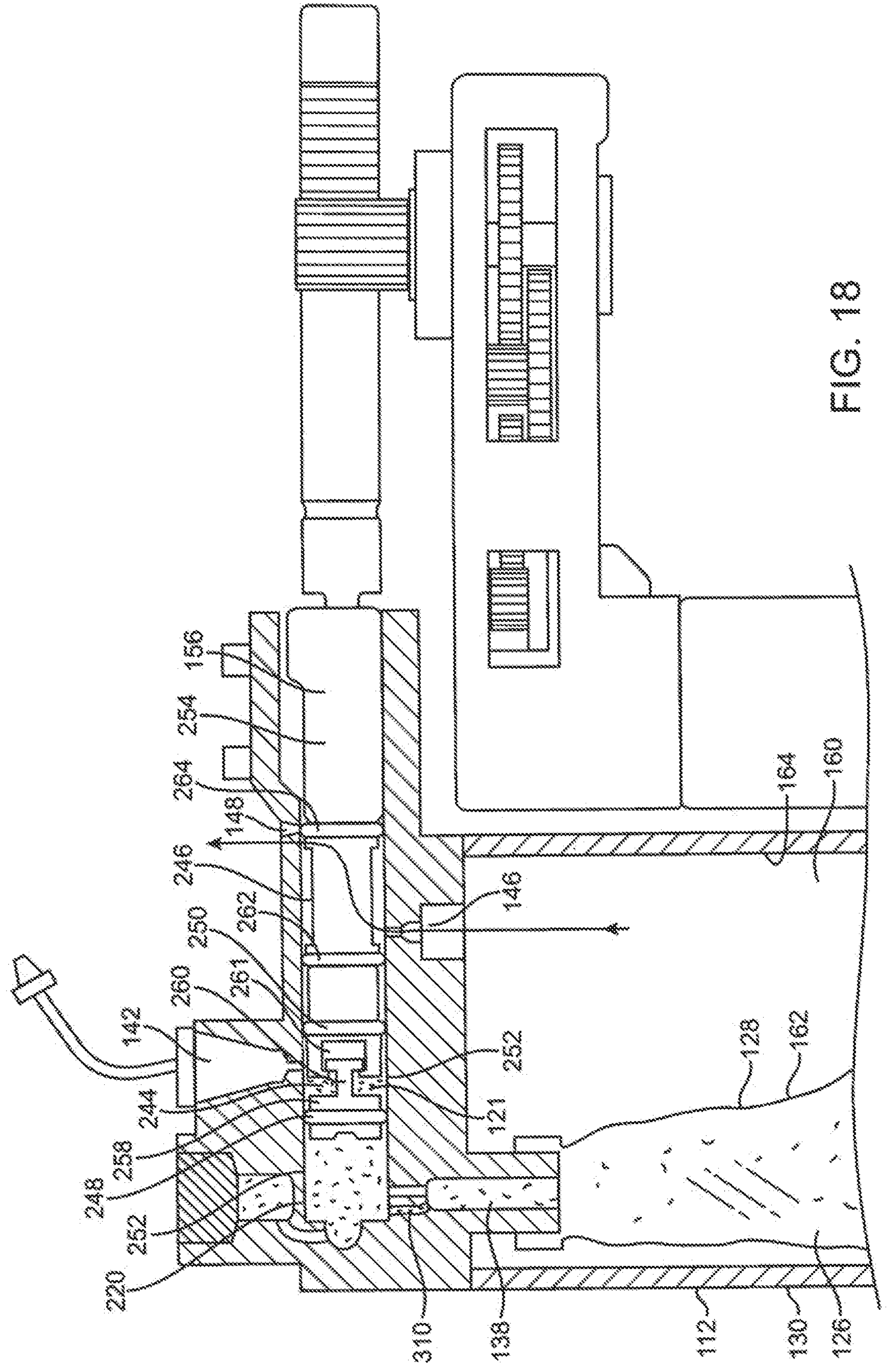
FIG. 18 is a section view of the delivery mechanism embodiment of FIGS. 12A and 12B with the spool of the delivery mechanism positioned prior to delivery of fluid from the expandable volume of the spool and with a vent channel established for the vented volume of the cartridge.

Referring to FIGS. 14-17, the embodiment of the delivery mechanism 132 shown in FIG. 12A is shown in a fluid delivery cycle sequence wherein fluid from the interior volume of the reservoir 126 is drawn into the bore 220 of the delivery mechanism 132 and dispensed from the dispense outlet port 142. The dispense cycle embodiment shown in FIGS. 14-17 illustrates a dispense cycle without a venting of the vented volume 160 of the infusion cartridge 112 of the pump system 110. FIG. 18 shows an optional venting step wherein a vent second volume 234 of the delivery mechanism 132 is disposed in communication with a vent inlet port 146 and a vent outlet port 148 of the delivery mechanism 132. The dispense and vent method embodiments discussed herein may also be combined with one or more methods and devices for measuring and/or confirming a volume of fluid dispensed or flow from a delivery mechanism 132. Venting of the volume of the shell 130 surrounding the reservoir may be useful in order to prevent pressure build up of the fluid in the reservoir 126 which might then force fluid 121 past seals of the system to a patient 127.

Such devices and methods for measuring and/or confirming a volume of material dispensed and the like from a delivery mechanism 132 or flow metering device are discussed in co-pending, commonly owned U.S. patent application Ser. No. 12/714,299, filed Feb. 26, 2010, by M. Rosinko et al., titled Methods and Devices for Determination of Flow Reservoir Volume, which is incorporate by reference herein in its entirety. The methods and devices discussed therein include measuring a pressure increase in a vented volume of a fluid reservoir cartridge between the rigid shell and flexible membrane of the fluid reservoir as discussed herein. Such pressure measurements may be used to determine or confirm an amount of fluid dispensed, as well as detect malfunctions in the components of a delivery mechanism 132 or drive mechanism 150 of a pump system 110.

Other methods and devices used for calculating and measuring flow volumes dispensed are discussed in U.S. Pat. No. 7,008,403, filed on Jul. 19, 2002, by Scott Mallett, titled Infusion Pump and Method for Use, U.S. Pat. No. 7,341,581, filed on Jan. 27, 2006, by Scott Mallet, titled Infusion Pump and Method for Use, U.S. Pat. No. 7,374,556, filed on Jan. 31, 2006, by Scott Mallett, titled Infusion Pump and Method for Use, 2007/0264130, filed on May 4, 2007, by Scott Mallett, titled Infusion Pumps and Method for Use, and 2009/0191067, filed on Jan. 25, 2008, by Paul DiPerna, titled Two Chamber Pumps and Related Methods, which are all incorporated by reference herein in their entirety. Some embodiments discussed in these references include the use of the ideal gas law or Boyle's law, for determination of a volume of material dispensed from a device 110 or reservoir 126 thereof. Such methods and devices may be used in conjunction with or as part of suitable embodiments 10 or 110 discussed herein.

Referring again to FIG. 14, a portion of the fluid reservoir cartridge 112 including a delivery mechanism 132 illustrated in FIG. 12A is shown in section as well as a portion of a drive mechanism 150 of an infusion pump. The disposable fluid cartridge 112 includes the delivery mechanism 132 which has a delivery mechanism body 236 and a bore 220 disposed in the delivery mechanism body 236. The bore 220, which may have a substantially round transverse cross section as shown in FIG. 14A, includes a distal end 238, a proximal end 240 disposed towards the drive mechanism 150 of the infusion pump 114, an interior volume 242, a reservoir inlet port 138, a fluid dispense port 142, a vent inlet port 146 and a vent outlet port 148. The spool 156, which may also have a substantially round transverse cross section, is slidingly disposed within the bore 220 and forms a collapsible first volume 244 and a vent second volume 246 with the bore 220.

The collapsible first volume 244 of the delivery mechanism 132 may be positionable to overlap the reservoir inlet port 138 independent of an overlap of the fluid dispense port 142. The collapsible first volume 244 may be formed between a first seal 248 around the spool 156, a second seal 250 around the spool, an outer surface of the spool body between the first and second seal 250 and an interior surface 252 of the bore 220 between the first and second seal 248 and 250. The first and second seals 248 and 250 are axially moveable relative to each other so as to increase a volume of the collapsible volume 244 when the first and second seals 248 and 250 are moved away from each other and decrease the collapsible volume 244 when the seals 248 and 250 are moved closer together.

The second seal 250 is disposed on a main section 254 of the spool 156 of the delivery mechanism 132 and moves in conjunction with movement of the rest of the spool. A proximal end 256 of the spool 156 is coupled to a ball portion 194 of a drive shaft 190 of the drive mechanism 150 of the pump device 114. The drive mechanism 150 includes a rack and pinion mechanism actuated by an electric motor 152 through a gear box 154. As such, the second seal 250 moves or translates axially in step with axial translation of the spool 156 and drive shaft 190. The first seal 248, however, is disposed on a distal section 258 of the spool 156 which is axially displaceable with respect to the main section 254 of the spool 156. The distal section of the spool 156 is coupled to the main section of the spool by an axial extension 260 that is mechanically captured by a cavity 261 in the main section 254 of the spool 156. This configuration allows a predetermined amount of relative free axial movement between the distal section 258 of the spool and the nominal main section 254 of the spool 156.

For some embodiments, a volume of a "bucket" of fluid dispensed by a complete and full dispense cycle of the spool 156 may be approximately equal to the cross section area of the bore 220 multiplied by the length of displacement of the captured axial extension of the spool 156 for the distal section 258. The complete bucket of fluid may also be dispensed in smaller sub-volumes in increments as small as a resolution of the drive mechanism 150 allows. For some embodiments, a dispense volume or bucket defined by the complete collapsible volume 244 of the delivery mechanism 132 may be divided into about 10 to about 100 sub-volumes to be delivered or dispensed. In some cases, the maximum axial displacement between the distal section and main section of the spool may be about 0.01 inch to about 0.04 inch, more specifically, about 0.018 inch, to about 0.022 inch.

For some embodiments, the bore 220 of the delivery mechanism may have a transverse dimension or diameter of about 0.04 inches to about 0.5 inches, more specifically, about 0.08 inches to about 0.15 inches. For some embodiments, the spool 156 may have a length of about 10 mm to about 40 mm, more specifically, about 15 mm to about 20 mm. The spool 156 and housing of the delivery mechanism 132 may be made from any suitable material or materials including polymers or plastics such as polycarbonate, PEEK, thermoplastics, cyclic olefin copolymer, and the like. In some cases, the seals disposed on the spool may have an outer transverse dimension or diameter that is slightly larger than that of the spool 156. In some instances, the seals on the spool may have an axial thickness of about 0.01 inches to about 0.03 inches and may be made from materials such as butyl, silicone, polyurethanes or the like having a shore hardness of about 65 A to about 75 A, more specifically, about 70 A.

In some instances, a vent second volume 246 of the delivery mechanism 132 may be formed by the spool 156 and bore 220 of the delivery mechanism 132. For some embodiments, the vent second volume 246 may be formed by a third seal 262 disposed around the spool 156 and a fourth seal 264 also disposed around the spool and axially separated from the third seal 264. The axial separation between the third and fourth seals 262 and 264 forming the vent second volume 246 may be greater than the axial separation between the vent inlet port 146 and vent outlet port 148 of the bore 220 in some instances. The vent second volume 246 is also formed by an outside surface 266 of the spool 156 between the third and fourth seal 262 and 264 and an inside surface 252 of the bore 220 between the third and fourth seal 262 and 264.

The vent second volume 246 may be axially displaceable with the movement of the spool 156 and may also be positionable by such axial displacement in order to simultaneously overlap the vent second volume 246 with the vent inlet port 146 and vent outlet port 148 of the bore 220. Such an overlap of both the vent inlet port 146 and vent outlet port 148 puts these ports in fluid communication with each other and allows an equilibration of pressure between the vented volume 160 of the reservoir cartridge 112 and the environment surrounding the vent outlet port 148. In most cases, the vent outlet port 148 will be in communication with the atmosphere and air will pass from the environment surrounding the vent outlet port 148, through the vent second volume 246 of the bore 220 and into the vent volume 160 to replace the fluid dispensed subsequent to the last vent cycle. When the vent inlet port 146 and vent outlet port 148 do not share a common volume formed by the spool and bore of the delivery mechanism 132, they are typically isolated and no venting of the vented volume takes place.

Figure 14:
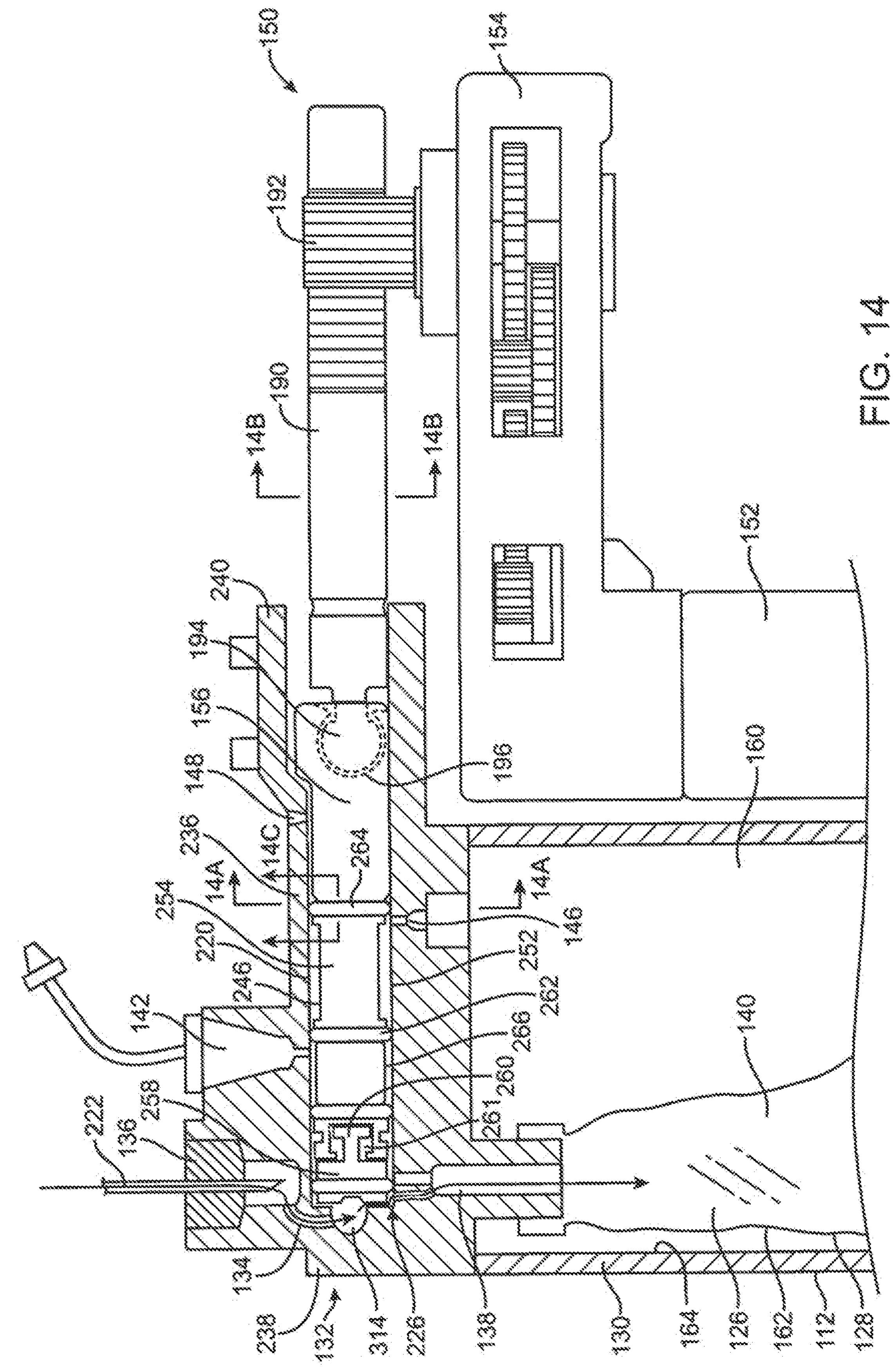
FIG. 14 is a section view of the delivery mechanism embodiment shown in FIGS. 12A and 12B with the spool of the delivery mechanism positioned at a distal hard stop for filling of the expandable reservoir.
Figure 14A:
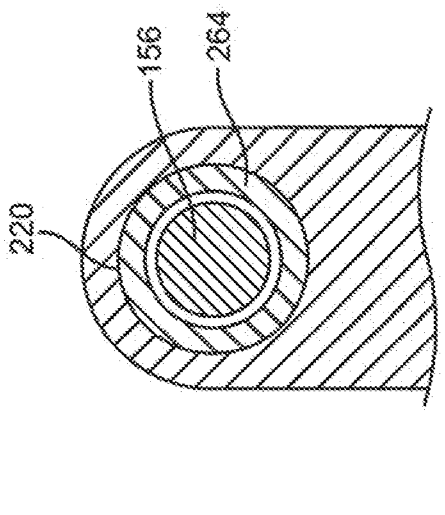
FIG. 14A is a transverse section view of the delivery mechanism of FIG. 14 taken along lines 14A-14A of FIG. 14.
Figure 14B:
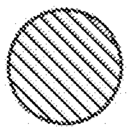
FIG. 14B is a transverse section view of the delivery mechanism of FIG. 14 taken along lines 14B-14B of FIG. 14.

A collapsible fluid reservoir 126 of the infusion cartridge 112 shown in FIG. 14 may be bounded by or disposed within a flexible membrane or layer 128. The fluid reservoir 126 may include an interior volume 140 in fluid communication with the reservoir inlet port 138 of the bore 220 of the delivery mechanism 132. A top portion of the flexible membrane or layer 128 may be clamped or otherwise sealed to an extension or boss 268 of the reservoir inlet port 138 that extends into the cartridge 112. In this configuration, the interior volume 140 of the collapsible fluid reservoir 126 may be isolated or sealed from the surrounding environment except for the reservoir inlet port 138 which is in fluid communication with the bore 220 of the delivery mechanism 132. A substantially rigid shell 130 may be disposed about the collapsible fluid reservoir with an interior volume that contains the collapsible fluid reservoir. The vented volume 160 of the cartridge 112 is disposed between an outer surface 162 of the flexible membrane 128 and an interior surface 164 of the rigid shell 130. The vent inlet port 146 is in fluid communication with the vented volume 160 and the bore 220 of the delivery mechanism 132. The vent inlet port 146 is disposed proximally of the reservoir inlet port 138 for the embodiment of the delivery mechanism 132 shown.

In operation, the spool 156 and the particular volumes formed between the spool 156, the bore 220 and the circumferential seals 248, 250, 262 and 264 disposed on the spool of the delivery mechanism 132 are typically translated in a proximal and distal direction in order to move the volumes into and out of communication with the various ports of the bore 220. This axial movement in alternating proximal and distal directions of the spool 156 within the bore 220 may be used to put the various ports in fluid communication with translatable volumes of the delivery mechanism 132 and other ports of the mechanism. For reliable operation, it may be desirable in some circumstances for the spool 156 and the circumferential seals 248, 250, 262 and 264 disposed about the spool 156 to move smoothly within the bore 220 of the delivery mechanism 132 while maintaining a seal between an outside surface 266 of the spool 156 and an inside surface 252 of the bore. It may also be desirable for the seals 248, 250, 262 and 264 disposed on the spool 156 to move axially back and forth within the bore 220 while maintaining a seal and with a minimum of friction. Achieving these features of the spool 156 may be facilitated with the use of particular seal configurations or gland configurations used to house the seals of the spool embodiments.

Figure 14C:
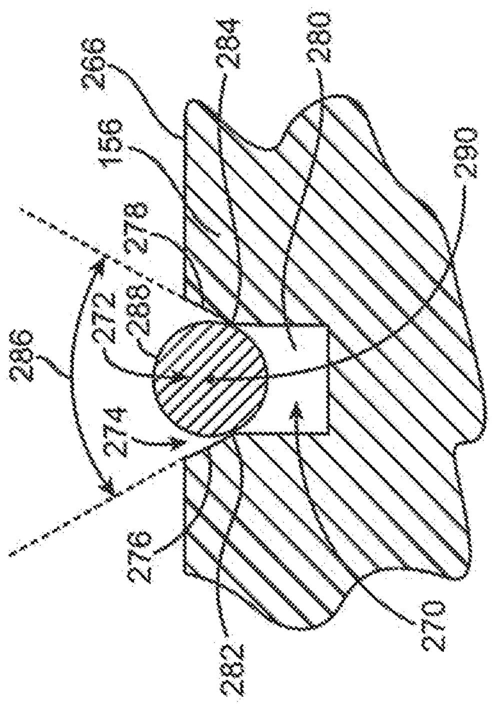
FIG. 14C is a transverse section view of the delivery mechanism of FIG. 14 taken along lines 14C-14C of FIG. 14.

Referring to FIG. 14C, a specialized seal gland 270 is shown that may be used to form a dynamic seal between the spool 156 and bore 220 of the delivery mechanism 132 using an o-ring type seal. The gland may be useful for achieving positive displacement in an infusion pump delivery mechanism 132. Such a gland configuration may be particularly useful in achieving a reliable seal while accommodating various manufacturing tolerances of a bore 220, a spool 156 and seals 248, 250, 262 and 264 such as o-ring type seals, quad ring type seals or any other suitable type of seal that may be used in a circumferential groove of a spool 156 or the like. The configuration shown may also be useful for minimizing the effects of static friction and seal compliance on dispense volume error by minimizing seal width and minimizing variability due to the manufacturing tolerances of the components of the delivery mechanism 132. The configuration may achieves some or all of these benefits by utilizing a gland 270 that includes a seal contact surface that may include angled edges and an overflow channel.

The angled surfaces or edges may be configured to compress an o-ring semi-axially and rely on the elastic memory of the seal or o-ring material to create a dynamic seal. The angled surfaces or any other suitable configuration may provide both axial stability of the seal as well as outward radial support of the seal to provide positive and sealing contact with an inside surface of the bore or any other appropriate sealing surface. The mixed radial and axial support provided by the angles edges or surfaces may also be useful for allowing substantially equal distribution of tension of the seal around the gland which may also provide a centering function of the body of the seal with respect to a longitudinal axis of the spool or other sealed element. The o-ring or seal may be sealed around at least one of the angled edges or surfaces and an inside surface of the bore 220 to prevent an axial flow of fluid past the seal. The overflow channel provides a volume of the gland adjacent the seal that accommodates a flow of excess seal material when the seal is compressed between two elements. A typical grooved gland used for o-ring type seals may force a flow or overflow of seal material into the gap between the two sealed elements resulting in excessive or inconsistent friction or stiction between the elements. The overflow channel provides a volume for the excess seal material to flow into instead of a gap between sealed surfaces. The gland embodiment shown in FIG. 14C may be used for any suitable seal embodiment discussed herein including seals 248, 250, 262 and 264. The gland may be useful for providing a reliable seal between the spool 156 and bore 220 with consistent frictional resistance between these elements while accommodating a significant variation or tolerance in the sizes of the components. The configuration of the gland 270 may also aid in the assembly of the o-ring type seal with the spool 156 as the angled surfaces or edges of the gland 270 tend to have a centering influence on the seal being inserted into the gland 270. A seal disposed in a gland such as gland 270 also tends to have a good axial stability without flowing into the gap between sealed surfaces. For infusion pumps such as pump system 110, the stable axial position of the seal with respect to the spool provides for more accurate metering of fluid being dispensed as well as more consistent friction or resistance between the spool 156 and bore 220.

FIG. 14C shows an o-ring seal including a gland 270 for seating an o-ring 272. The gland 270 has an outer circumferential groove 274 extending circumferentially around a longitudinal axis of a cylindrical body of the spool 156 of the delivery mechanism 132. The circumferential groove 274 may include an angled first edge 276 or surface and an angled second edge 278 or surface opposite the angled first edge 276. An inner overflow channel 280 may be disposed below the angled channel 274 formed by the angled first and second edges or surfaces 276 and 278. An o-ring embodiment 272 is disposed in the gland 270 with a first circumferential band 282 of the o-ring 272 resting on the first angled edge 276 and a second circumferential band 284 of the o-ring 272 resting on the second angled edge 278 of the angled channel 274 of the gland. The o-ring 272 is also shown in FIG. 14C resting above the overflow channel 280 with the o-ring 272 in a substantially uncompressed state. For the embodiment shown, the overflow channel 280 provides a circumferential volume in the gland 270 for the material of the o-ring 272 to flow into rather than exert excessive force against an inside surface of the bore 220 if the o-ring 272 has a particularly large section for the application, the bore 220 is at a small end of the tolerance specification or the like. The overflow channel 280 and angled channel 274 configuration of the gland 270 are configured to accommodate tolerance variations in the components of the spool 156, bore 220 and seals 248, 250, 262 and 264 of the delivery mechanism 132.

Figure 14D:
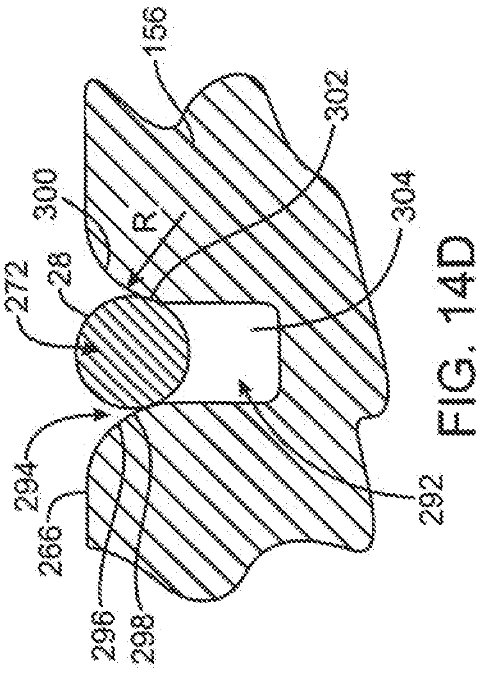
FIG. 14D is a transverse section view of another embodiment of the delivery mechanism of FIG. 14 taken along lines 14C-14C of FIG. 14.

For some gland embodiments 270, the angled first and second edges 276 and 278 may form a total inclusive angle with each other of about 20 degrees to about 60 degrees, as indicated by the arrow 286 in FIG. 14C. For the embodiment shown, an outer surface 288 of the o-ring 272 rests above a nominal outer surface 266 of the cylindrical body of the spool 156 and does not extend substantially into the overflow channel 280 when the o-ring 272 is in an uncompressed state. However, a center 290 of the seal element cross section of the o-ring 272 is disposed below the nominal outer surface 266 of the cylindrical body of the spool 156 when the o-ring 272 is in a substantially uncompressed state. For the embodiment shown, the overflow channel 280 of the gland 270 has a substantially straight-walled configuration. The gland embodiment 292 shown in FIG. 14D includes an outer circumferential groove 294 having a radius 296 on a first edge 298 and a radius 300 on a second edge 302. An overflow channel 304 is disposed below the first radiused edge 298 and second radiused edge 302. The overflow channel 304 shown in FIG. 14D also has a substantially straight-walled configuration. The gland embodiments of 220 and 292 FIGS. 14C and 14D each have first and second edges that provide a combination of axial and radial support to the outer surface 288 of the o-ring 272 disposed in the gland 270 or 292. The o-ring is disposed in these gland embodiments 270 and 292 with an outer surface 288 of the o-ring 272 disposed above the nominal surface 266 of the spool 156 or other sealed structure within with the gland is being utilized. For some such gland embodiments 270 or 292, the volumetric percent gland fill may be about 70 percent to about 90 percent where the volumetric percent gland fill is the volume of an o-ring 272 to be used in a particular gland 270 or 292 divided by the volume of the gland 270 or 292 as a whole.

Figure 14E:
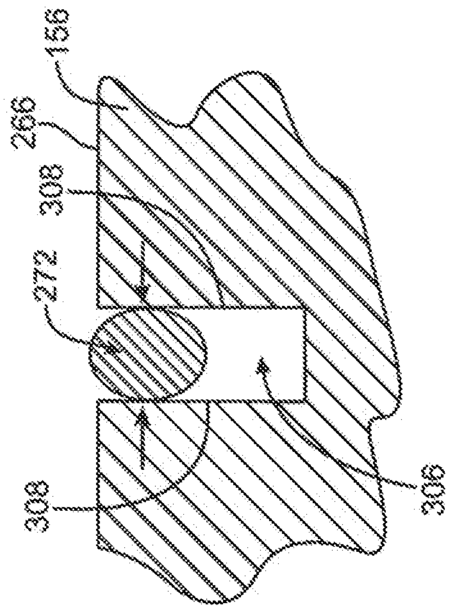
FIG. 14E is a transverse section view of another embodiment of the delivery mechanism of FIG. 14 taken along lines 14C-14C of FIG. 14.

Some gland embodiments, such as the gland 306 shown in FIG. 14E, utilize only axial compression or support of the o-ring disposed in the gland 306 and would essentially have a total angle of the groove of up to about 5 degrees, more specifically, about 0 degrees to about 3 degrees. Such a gland 306 may be configured as a straight-walled groove 308 that may be sized to have a volumetric percent gland fill similar to that of the embodiments of FIGS. 14C and 14D discussed above. Such a gland embodiment 306 may also be configured to provide a predetermined amount of axial compression on the o-ring 272. For some such embodiments, the percent compression of the o-ring 272/gland seal 306 may be about 60 percent to about 85 percent where the percent compression is determined by the width of the groove 308 of the gland 306 divided by the thickness of the o-ring 272 of the seal. For any of the gland embodiments discussed above, there is a predetermined percentage of axial support or compression of the o-ring 272 and a useable overflow channel component of the gland.

In use, referring again to FIG. 14, once the reservoir cartridge 112 of the infusion pump system 110 has been installed or otherwise snapped into place in the slot 122 of the pump device 114, the interior volume 140 of the collapsible reservoir 126 may then be filled with a desired fluid 121 for dispensing. In order to fill the reservoir 126, the spool 156 may be translated by the drive mechanism 150 to a hard stop position 226 as shown in FIG. 14. In the hard stop position 226 the first seal 248 is disposed proximally of a relief port 310, the relief port 310 being disposed in fluid communication between a distal end 238 of the bore 220 and the reservoir volume 140. In the hard stop position, the first seal 248 is also disposed distally of the reservoir inlet port 138. In the hard stop position, a distal end 316 of the spool 156 is contacting a distal end 238 or shoulder portion 312 of the distal end 238 of the bore 220 to prevent any further distal displacement of the spool 156.

A reservoir fill port 134 is disposed on a top portion of the bore 220 substantially opposite the bore 220 of the reservoir inlet port 138. With the spool 156 and seals 248, 250, 262 and 264 thereof so positioned, a patient may then obtain an amount of a desired fluid to be dispensed. In some cases, if the desired fluid to be dispensed is insulin or other suitable medicament, the patient 127 typically stores the insulin in a refrigerated glass container. The insulin is then accessed with a hypodermic needle 222 of a syringe device and drawn into an interior volume of the syringe (not shown). The tip of the hypodermic needle 222 of the syringe may then be pushed through a septum membrane 136 that seals the reservoir fill port 134 as shown and fluid manually dispensed from the interior volume of the syringe, through the hypodermic needle 222, through a bubble trap volume 314 in the bore 220 of the delivery mechanism 132 and into the interior volume 140 of the collapsible reservoir 126 of the cartridge 112 as shown by the arrow 318 in FIG. 14.

As discussed above with regard to other embodiments of the delivery mechanism 132, the vented volume 160 of the cartridge 112 disposed between an outside surface 162 of the flexible membrane 128 of the collapsible reservoir 126 and an inside surface 164 of the rigid shell 130 may include or be in operative communication with a pressure sensor 158 (not shown). The pressure sensor 158 may be used to monitor the pressure within the vented volume 160 during the filling of the collapsible reservoir 126. The controller 168 of the pump system 114 may be programmed with information regarding the fixed volume of the rigid shell 130 of the cartridge 112 and configured to calculate the volume of fluid loaded into the collapsible reservoir 126 based on the pressure rise within the rigid shell 130 upon filling of the collapsible reservoir 126. The data regarding the volume of fluid loaded into the collapsible reservoir 126 may be stored and used to calculate and display data later in the use cycle such as fluid remaining in the collapsible reservoir 126 and the like.

Once the collapsible reservoir 126 contains a desired amount of a fluid 121 to be dispensed, a dispense cycle may be initiated by driving the spool 156 with the drive mechanism 150 based on commands from a controller 168 of the pump device to a position with the collapsible first volume 244 in communication with the reservoir inlet port 138. The had stop position shown in FIG. 14 is such a position. If the spool 156 has been driven to this hard stop position 226 in a distal direction from previous proximal position, the friction generated between the first seal 248 of the spool 156 and the inside surface 252 of the bore 220 will have collapsed the collapsible volume 244 of the delivery mechanism 132 with the first seal 248 and second seal 250 in a least axially separated state. In this state, the collapsible volume 244 has a minimum volume. Such a state of the delivery mechanism 132 is shown in FIG. 14. Once in this pre-fill position, the spool 156 may then be driven so as to axially separate the first and second seals 248 and 250 (and the main section 254 of the spool 156 and distal section 258 of the spool 156) of the collapsible first volume 244 and draw fluid into the first volume 244 through the reservoir inlet port 138 from the reservoir 126 as shown by the arrow 320 in FIG. 15. As the fluid 121 is drawn into the collapsible volume 244, the pressure within the vented volume 160 decreases. As previously discussed, this drop in pressure may be used in accordance with the ideal gas law to determine the amount of material taken from the collapsible reservoir 126. An unexpected reading based on the magnitude of the translation of the main section 254 of the spool 156 may also be used to detect a failure of a portion of the delivery mechanism 132 in some cases.

Figure 9E:
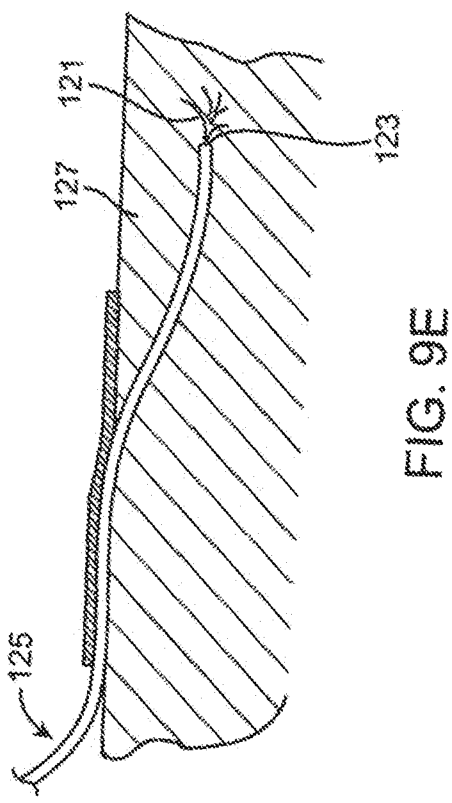
FIG. 9E illustrates an enlarged view in partial section of a distal end of an infusion line of the infusion pump system of FIG. 9D disposed subcutaneously in the patient.
Figure 9D:
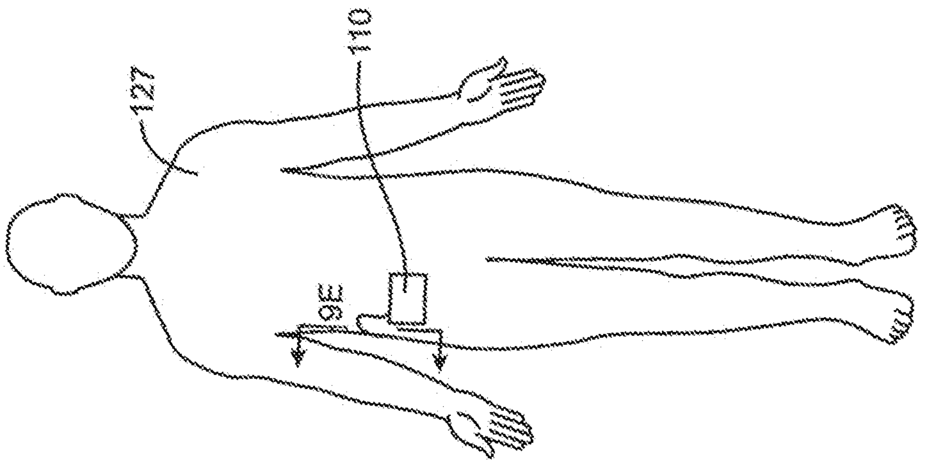
FIG. 9D illustrates an embodiment of an infusion pump system in operative communication with a patient.
Figure 15:
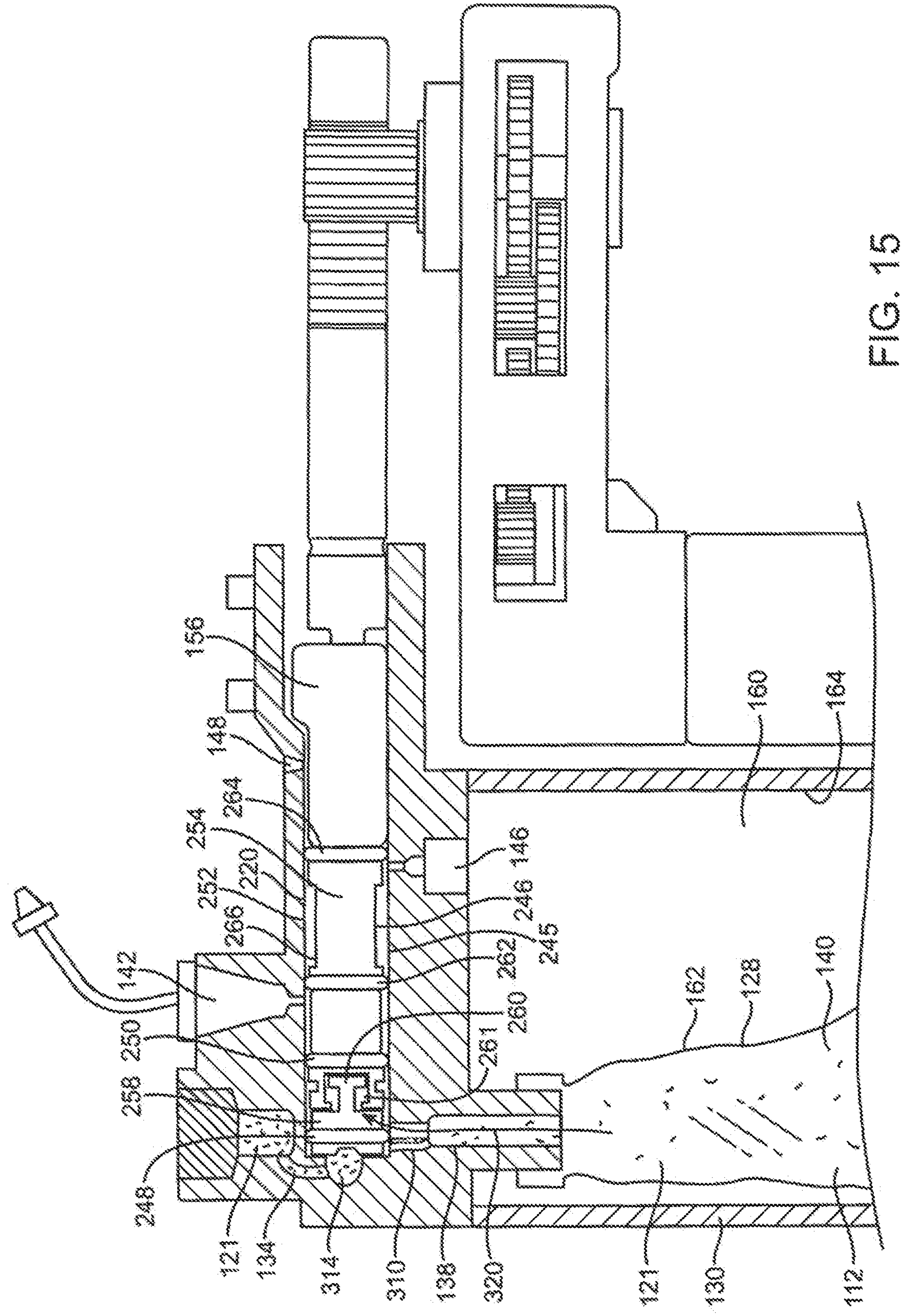
FIG. 15 is a section view of the delivery mechanism embodiment of FIGS. 12A and 12B with the spool of the delivery mechanism positioned for filling of a collapsible volume of the spool.
Figure 15A:
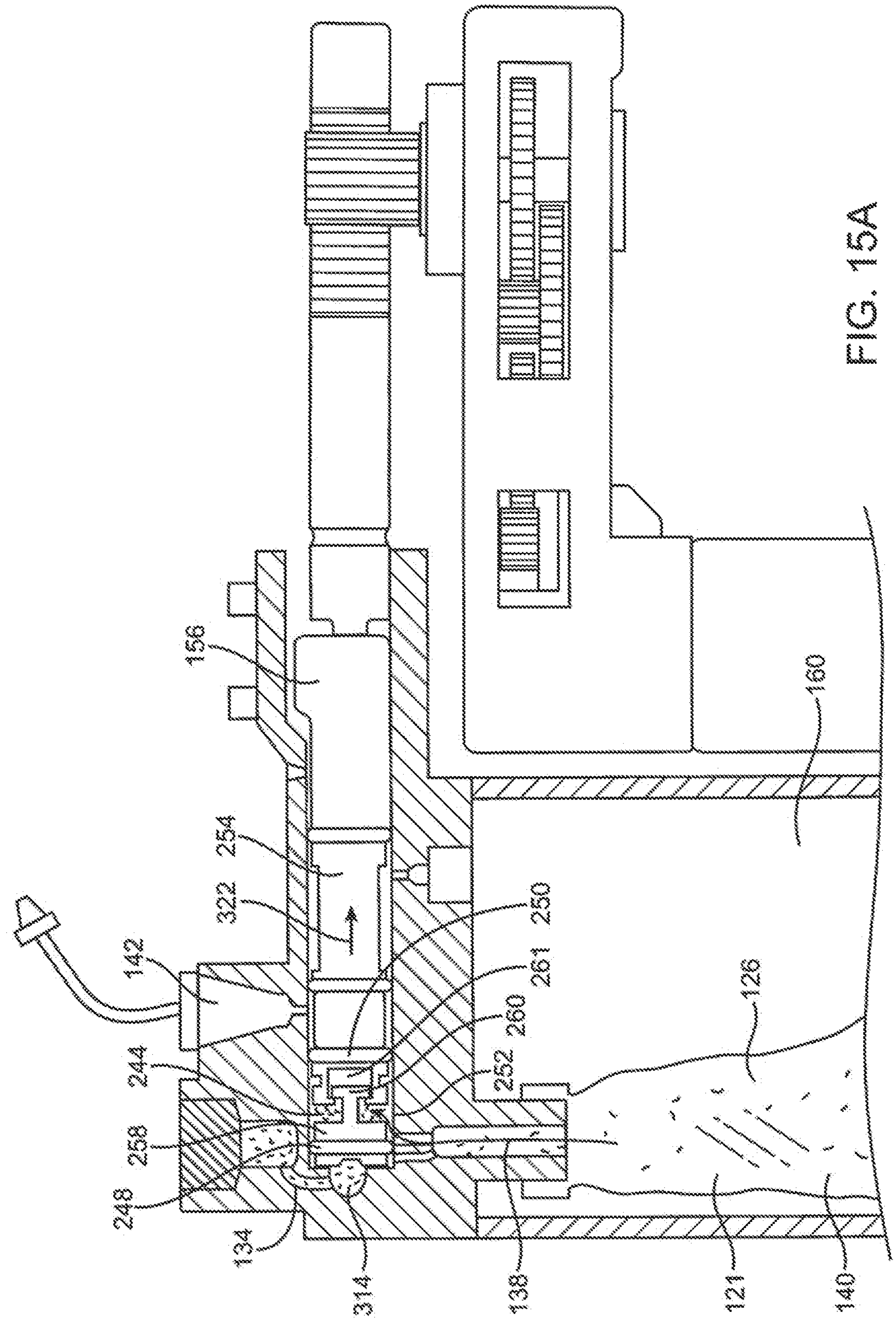
FIG. 15A is a section view of the delivery mechanism embodiment of FIGS. 12A and 12B with the spool of the delivery mechanism positioned after filling of the collapsible volume of the spool.
Figure 15B:
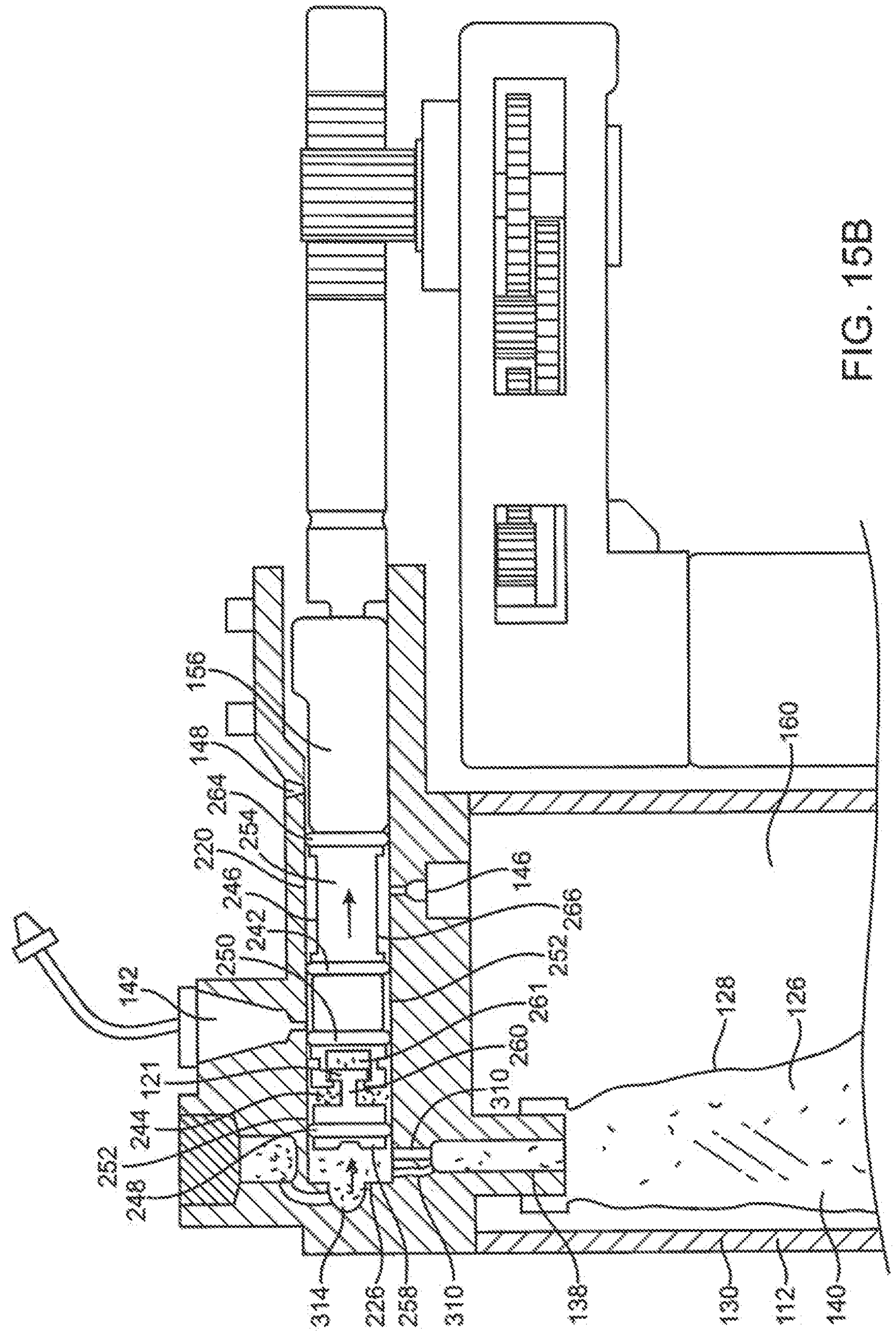
FIG. 15B shows the spool of FIG. 15A with the collapsible volume of the device full of fluid being displaced proximally towards the dispense port of the device.

The collapsible volume 244 of the delivery mechanism 132 may be completely filled by proximally retracting the main section 254 and second seal 250 of the spool 156 relative to the first seal 248 and distal section 258 of the spool 156 as shown by arrow 322 on spool 156 in FIG. 15A. Once filled, the spool 156 may then be driven in a proximal direction as shown in FIG. 15B wherein there are two seals 248 and 250 disposed in the bore 220 between the reservoir inlet port 138 and relief port 310 and the dispense port 142. As shown by arrow 22 and arrow 324 in FIG. 15B, both the main section 254 and distal section 258 of the spool 156 are proximally retracted together. The captured axial extension of the distal section 258 by the main section 254 pulls the distal section along without axial displacement between the main section 254 and distal section 258 of the spool 156. The dispense port may be in fluid communication with a subcutaneous portion of a patient's body 127 as shown in FIGS. 9D and 9E. The delivery mechanism 132 configuration illustrated in FIGS. 14-18 always includes at least one seal 248 or 250 disposed in the bore 220 between the reservoir volume 140 and material 121 disposed therein and the dispense port 142 in order to prevent a free flow condition wherein the material 121 in the reservoir 126 is in uninterrupted communication with the patient's body 127.

Figure 16:
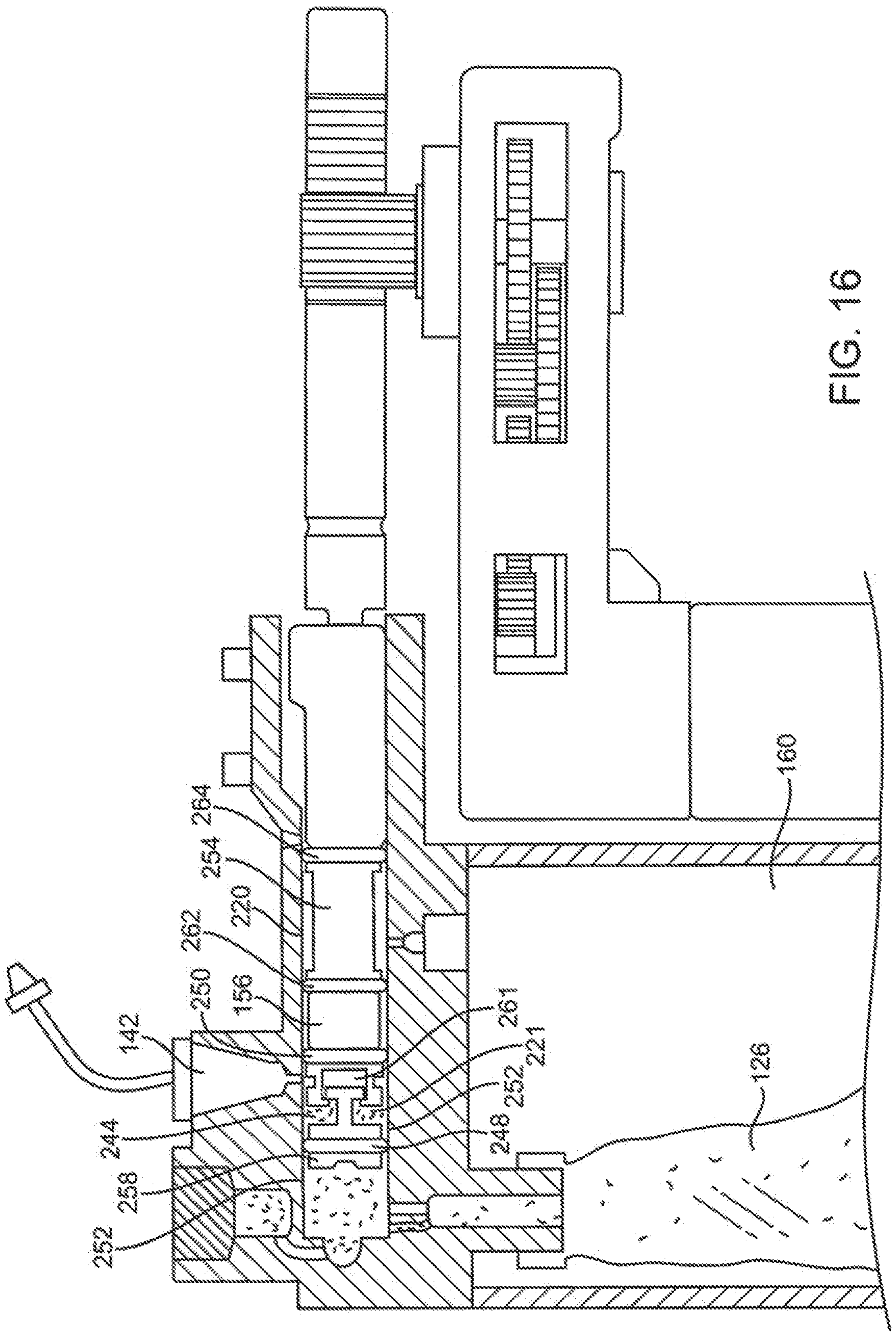
FIG. 16 is a section view of the delivery mechanism embodiment of FIGS. 12A and 12B with the spool of the delivery mechanism positioned prior to delivery of fluid into the dispense port from the collapsible volume of the spool.
Figure 17:
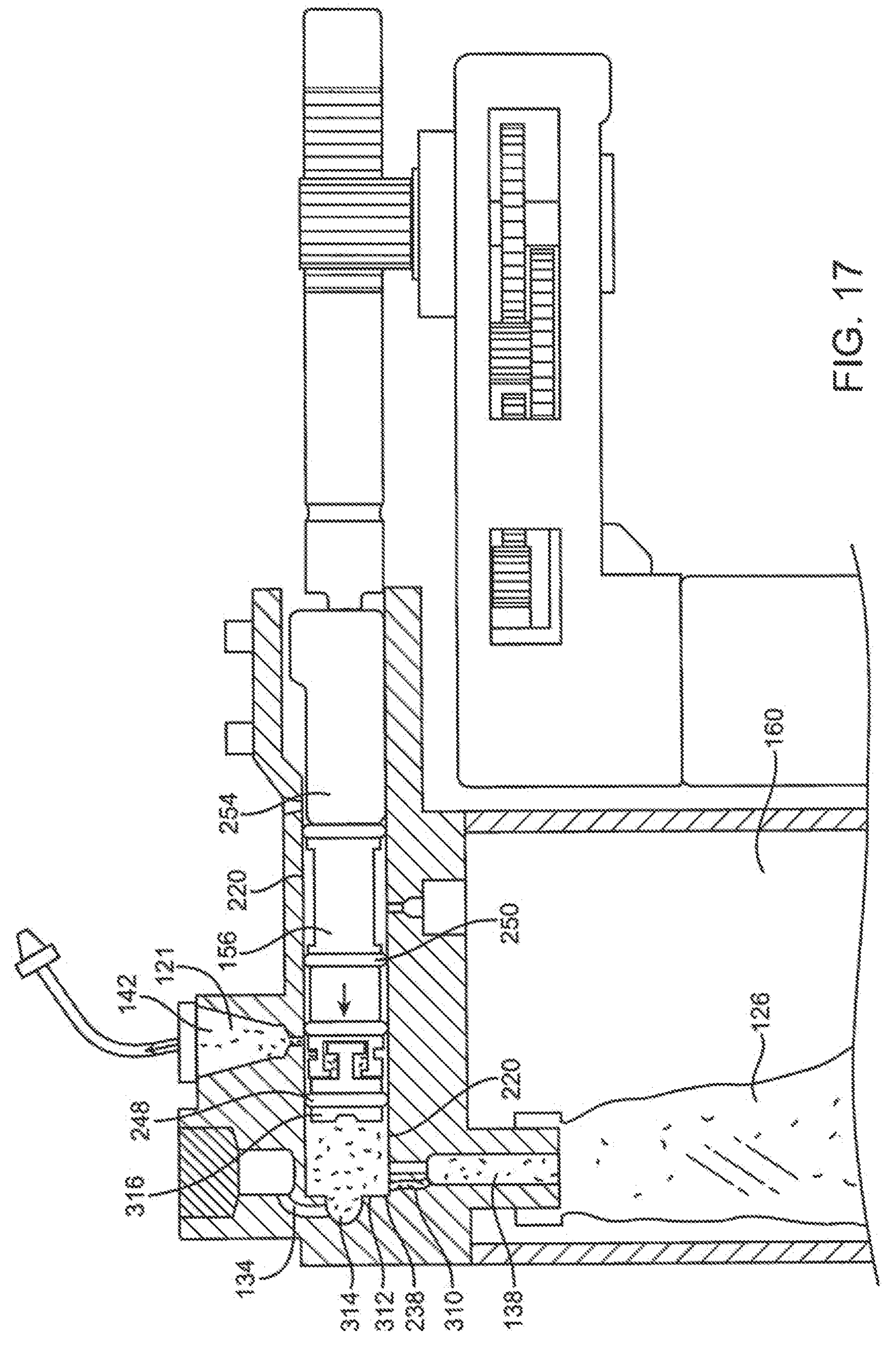
FIG. 17 is a section view of the delivery mechanism embodiment of FIGS. 12A and 12B with the spool of the delivery mechanism positioned after delivery of fluid from the collapsible volume of the spool into the dispense port.

Once filled, the spool 156 and filled collapsible volume 244 may be proximally displaced with the drive mechanism 150 to a position with the collapsible first volume 244 in communication with the fluid dispense port 142 of the bore 220 as shown in FIG. 16. In the configuration shown in FIG. 16, the collapsible first volume 244 of the delivery mechanism 132 is in fluid communication with the fluid dispense port 142, but the vent second volume 246 is only in fluid communication with the vent inlet port 146 and not the vent outlet port 148. Thus, in the position shown, the spool 156 of the delivery mechanism 132 is configured to dispense the fluid 121 in the collapsible volume 244 without venting of the vented volume 160 of the cartridge 112. This arrangement allows one or more dispense cycles to be carried out independent of venting of the vented volume 160.

Once the spool 156 is positioned as shown in FIG. 16, the main section of the spool 156 may then be axially driven in a distal direction by the drive mechanism 150 with the distal section 258 of the spool remaining stationary or substantially stationary. This axial distal movement of the main section 254 as indicated by arrow 326 on the spool 156 shown in FIG. 17, serves to at least partially collapse the collapsible first volume 244. Collapsing the first volume 244 of the delivery mechanism 132 dispenses fluid from the collapsible first volume 244 through the fluid dispense port 142 as shown by the arrow 328 in FIG. 17. For some embodiments, the axial distance of the translation between the first seal 248 and second seal 250 may be about 0.015 inches to about 0.025 inches. In some instances, the bore 220 may have an inner transverse dimension or diameter of about 0.10 inches to about 0.20 inches.

After filling of the collapsible volume 244 of the delivery mechanism 132 as shown in FIG. 16, if venting of the vented volume 160 is desired, the spool 156 may be driven by the drive mechanism 150 to a position with the vent second volume 234 in simultaneous communication with the inlet vent port 146 and vent outlet port 148 as shown in FIG. 18. This arrangement allows the vented volume 160 of the reservoir cartridge 112 to vent as shown by the arrow 330 in FIG. 18. In such circumstances, the vent second volume 234 arrives at the same pressure as the vent outlet port 148 and vented volume 160. In some instances, the vent outlet port 148 may be at ambient atmospheric pressure and the vented volume 160 is brought to ambient atmospheric pressure during every venting cycle.

In some cases, the vented volume 160 of the cartridge is vented about every 2 dispense cycles to about every 10 dispense cycles. In some cases, the vented volume 160 may be vented about every 3 dispense cycles to about every 7 dispense cycles. However, any desired interval of venting cycles to dispense cycles may be used. For some embodiments, the venting of the vented volume 160 of the infusion cartridge 112 may be triggered by the detection or measurement of a pressure difference threshold in the vented volume 160. That is, if the pressure measured in the vented volume 160 of the infusion cartridge 112 is above or below a predetermined valued relative to the ambient pressure, the controller 168 will initiate a venting cycle to vent the vented volume 160 and equalize the pressure in the vented volume 160. For some embodiments, the magnitude of such a threshold pressure difference may be up to about 1 psi gauge, more specifically, up to about 0.1 psi gauge.

FIGS. 19A-19E illustrate an embodiment of a spool 340 of a delivery mechanism 342 that includes a sliding seal configuration for the collapsible first volume 344 of the delivery mechanism 342. The delivery mechanism 342 may have some or all of the same features, dimensions, materials and methods of use as those of any other delivery mechanism discussed herein, and particularly delivery mechanism 132. In addition, it should be noted that some or all of the suitable features, dimensions, materials and methods of use of the delivery mechanism 342 may be used or incorporated into any other infusion system, or components thereof, discussed herein.

In some cases, the collapsible first volume 344 of the delivery mechanism 342 includes a volume bounded by at least one distal seal 346 that is axially displaceable relative to a slide section of the spool body 348 and which may form a substantially fluid tight seal between an outside surface 350 of the seal 346 and an inside surface 252 of the bore 220. A fluid tight seal may also be formed between an outside surface 352 of a slide portion 354 of the spool 340 and an inside surface or inside diameter 356 of the seal. More specifically, the delivery mechanism 342 of an infusion pump system 358 may include the bore 220 disposed in the delivery mechanism 132 body and the spool 340 disposed in the bore 220 which is axially displaceable within the bore 220. The delivery mechanism 342 also includes a collapsible volume 344 bounded by an outside surface 358 of the spool 340, an inside surface 252 of the bore 220, the distal seal disposed between the spool 340 and the bore 220 and a proximal seal 360 disposed and sealed between the spool 340 and the bore 220. The proximal 360 seal is axially fixed relative to the spool 340 but displaceable relative to an inside surface 252 of the bore 220. The slide portion 354 of the spool 340 may be disposed in a central aperture 362 of the distal seal 346.

An outer surface of the aperture 362 of the distal seal 346 may form a substantially fluid tight seal over an outside surface 352 of the slide portion 354 of the spool 340, while also being axially displaceable over the slide portion 354 once the friction there between is overcome. The distal seal 346 also forms a seal between an outside surface 350 of the distal seal 346 and the inside surface 252 of the bore 220 while being axially displaceable within the bore 220 once the friction between the distal seal 346 and surface 252 of the bore 220 is overcome. The slide portion 254 of the spool 340 may be a substantially cylindrical section of the spool 340 which as a smooth and uniform outside surface 352. The slide portion 354 may be bounded at both the proximal end 364 and distal end 366 of the slide portion 354 by a proximal shoulder portion 368 and a distal shoulder portion 370 respectively. The shoulder portions 368 and 370 may serve to limit the axial translation of the distal seal 346 over the slide portion 354 of the spool 340. The separation of the shoulder portions 368 and 370 may serve to determine the maximum and minimum volume of the collapsible volume 344 of such a spool embodiment 340. In some embodiments, the friction between inside surface 252 of bore 220 and distal seal 346 is greater than friction between outside surface 352 of slide portion 354 of spool 340 and aperture 362 of the distal seal 346.

In some instances, the proximal and distal seals 346 and 360 may include an o-ring. In some embodiments, the spool 340 includes an elongate cylindrical member having a transverse dimension of about 0.5 mm to about 10 mm, In some cases, the maximum axial displacement of the distal seal 346 between the proximal and distal shoulder portions may be about 0.01 inch to about 0.04 inch, more specifically, about 0.018 inch, to about 0.022 inch. For some embodiments, the bore 220 of the delivery mechanism 342 may have a transverse dimension or diameter of about 0.04 inches to about 0.5 inches, more specifically, about 0.08 inches to about 0.15 inches. For some embodiments, the spool 340 may have a length of about 10 mm to about 40 mm, more specifically, about 15 mm to about 20 mm. The spool 340 and housing of the delivery mechanism 342 may be made from any suitable material or materials including polymers or plastics such as polycarbonate, PEEK, thermoplastics, cyclic olefin copolymer, and the like. In some cases, the seals disposed on the spool 342 may have an outer transverse dimension or diameter that is slightly larger than that of the spool 156. In some instances, the seals on the spool 342 may have an axial thickness of about 0.01 inches to about 0.03 inches and may be made from materials such as butyl, silicone, polyurethanes or the like having a shore hardness of about 65 A to about 75 A, more specifically, about 70 A.

Figure 19A:
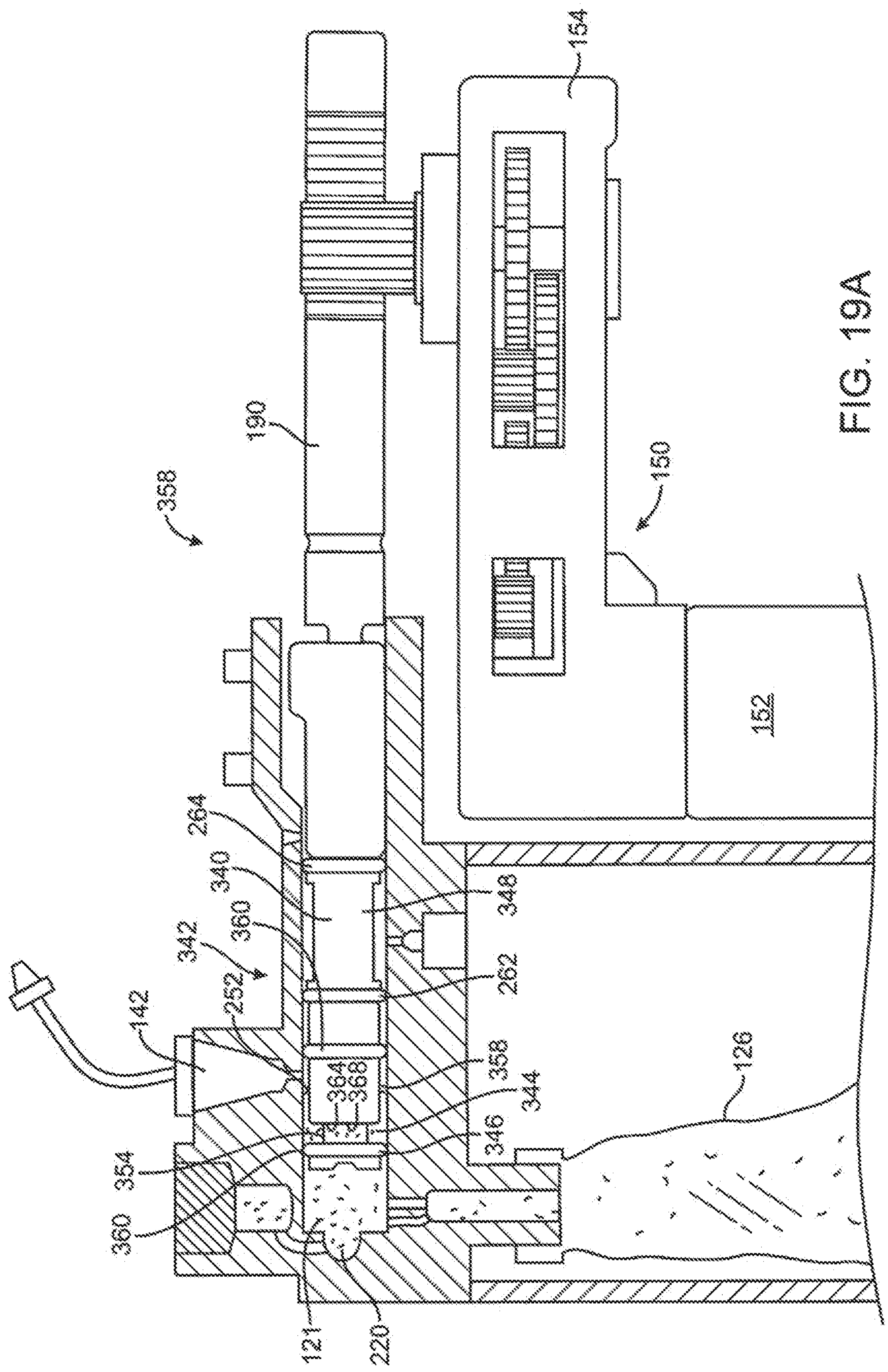
FIG. 19A is a section view of a delivery mechanism embodiment having an expandable volume formed from a sliding seal and with a spool of the delivery mechanism positioned prior to delivery of fluid from the expandable volume of the spool with a vent channel remaining closed.

In use, the spool embodiment 340 incorporating the sliding seal arrangement shown in FIG. 19A may operate similarly to the spool configuration 156 shown in FIG. 14 and discussed above. FIG. 19A shows the delivery mechanism embodiment 342 with the spool 340 in a pre-dispense configuration with the collapsible volume 344 disposed between the proximal and distal seals 346 and 360 filled with a fluid 121 to be dispensed. The collapsible volume 344 of the device may be filled by the same sequence as that shown in FIGS. 14-18 above with regard to spool embodiment 156. In particular, the collapsible volume 344 may be distally advanced and positioned to be in fluid communication with reservoir inlet port 138. In this position, the collapsible volume 344 will be initially in a collapsed state with the distal seal 346 and proximal seal 360 as close together as possible. In other words, the distal seal 346 would be disposed near or against the proximal shoulder portion 368. The spool 340 may then be proximally retracted so as to proximally retract the proximal seal 360 from the distal seal 346 and thereby expand the collapsible volume 344 drawing the fluid 121 into the collapsible volume from the reservoir 126 through the reservoir inlet port 138.

During proximal withdrawal of the spool 340 and proximal seal 360, the distal seal 346 may remain substantially stationary with respect to the bore 220 due to the static frictional force between an inside surface of the bore and an outside surface of the distal seal 346. This process also may require that the slide portion of the spool moves axially in a proximal direction through an inner diameter of the annular distal seal 346 while maintaining a fluid tight sealed condition therebetween. It may also require that the static frictional force between the inside surface of the bore 220 and outside surface of the distal seal 346 is greater than the frictional force between the slide portion 354 of the spool and inside aperture or diameter of the distal seal 346. In this way the spool 340 and proximal seal can translate within the bore 220 while the distal seal 346 remains stationary. The proximal withdrawal and filling of the collapsible volume 344 may continue until the distal seal 346 contacts the distal shoulder portion 370 of the spool 340. Thereafter, the spool 340, distal seal 346 and proximal seal 360 may be proximally translated in unison until the collapsible volume is disposed in fluid communication with the dispense port 142.

Once the collapsible volume 344 is disposed in fluid communication with the dispense port 142, the filling process for the collapsible volume 344 discussed above may be reversed. In this case, the spool 340 is distally advanced along with the proximal seal 360 while the distal seal 346 again remains substantially axially stationary. This has the effect of collapsing the collapsible volume 344 and dispensing the fluid 121 from the dispense port 142. It should also be noted that for the dispense function to proceed, the frictional force between an outside surface of the distal seal 346 and inside surface of the bore 220 must be greater than the force equal to the pressure of the fluid 121 within the collapsible volume 344 multiplied by the area of the bore 220. The same condition holds true for the spool embodiment 156 discussed above. The pressure within the collapsible volume 344 during a dispense cycle may depend on several factors including the viscosity of the fluid 121, the size and cross sectional area of the various ports 138 and 142, and the speed with which the spool 340 is translated. For some embodiments, these parameters may be selected such that the pressure of the fluid 121 within the collapsible volume 344 may be up to about 20 psi, more specifically, up to about 10 psi, in some cases. If the pressure of the fluid 121 within the collapsible volume 344 exceeds the force of frictional engagement of the distal seal 346 with the surface of the bore 220, the distal seal will be displaced along with the spool 340, at least to some extent. The controller of the pump device may be configured to measure pressure within the volume of the shell 130 as discussed above and detect an increase in pressure during the dispense stroke of the spool 340 or 156. Such a pressure change may be an indication of a clog in the dispense port 142 or fluid lumen of the infusion kit or line disposed and sealed between the dispense port 142 and patient 127. If such a clog is detected, an auditory, vibratory, or visual signal may be generated to warn the patient of the clog. All three types of signals or warnings could be generated as well. The pressure within the shell 130 may be monitored by the controller 168 generally in order to verify the performance of the axial movements of spool 156 or 340.

Figure 19B:
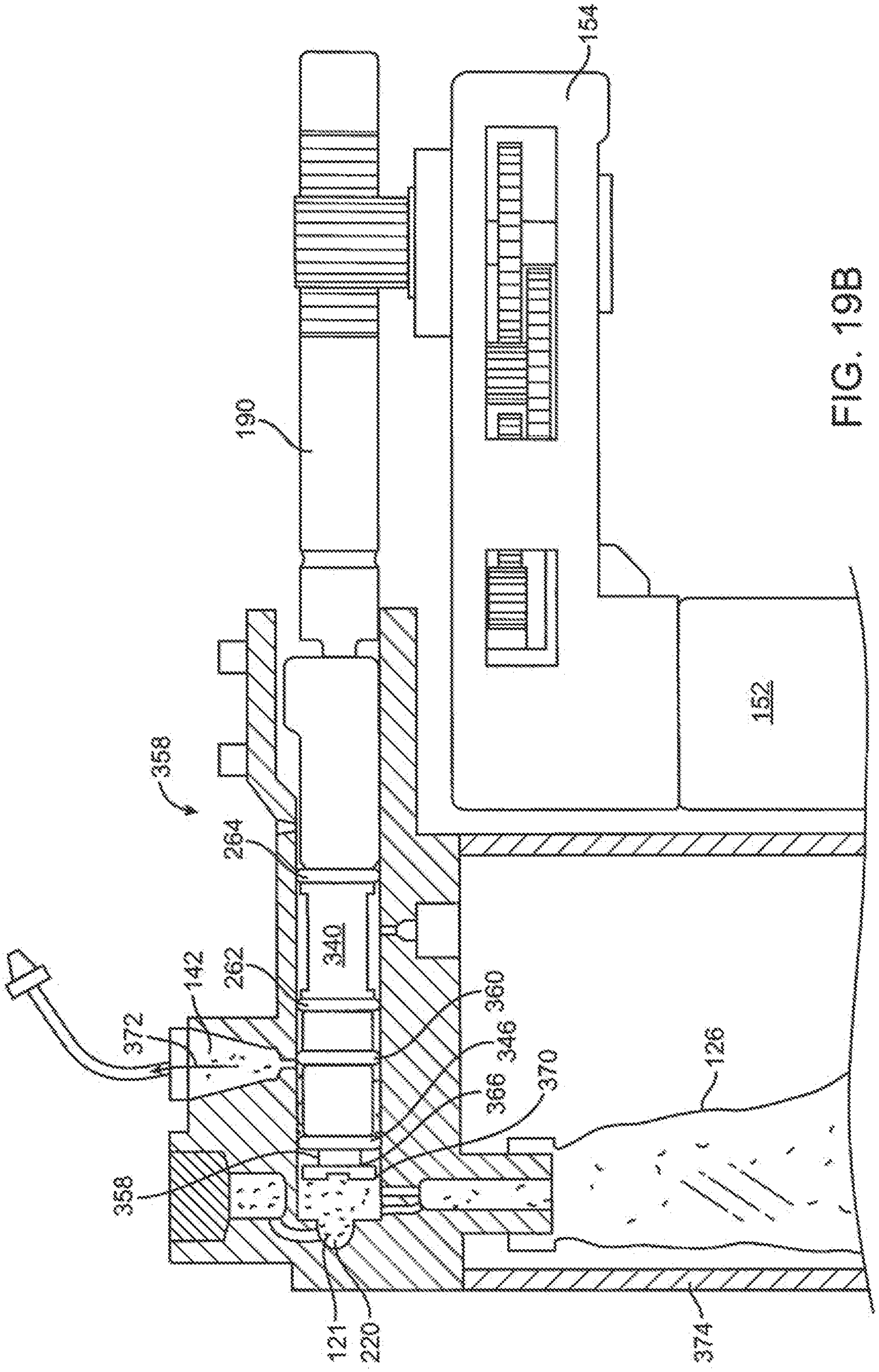
FIG. 19B is a section view of the delivery mechanism embodiment of FIG. 19A with the spool of the delivery mechanism positioned after delivery of fluid from the expandable volume of the spool.
Figure 19E:
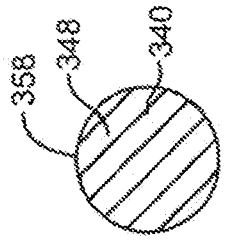
FIG. 19E is a transverse section view of the delivery mechanism of FIG. 19C taken along lines 19E-19E of FIG. 19C.
Figure 19D:
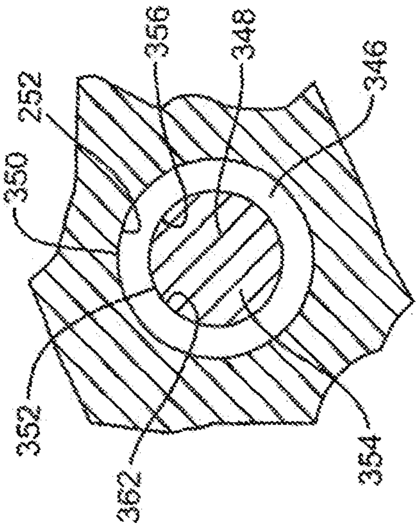
FIG. 19D is a transverse section view of the delivery mechanism of FIG. 19C taken along lines 19D-19D of FIG. 19C.
Figure 19C:
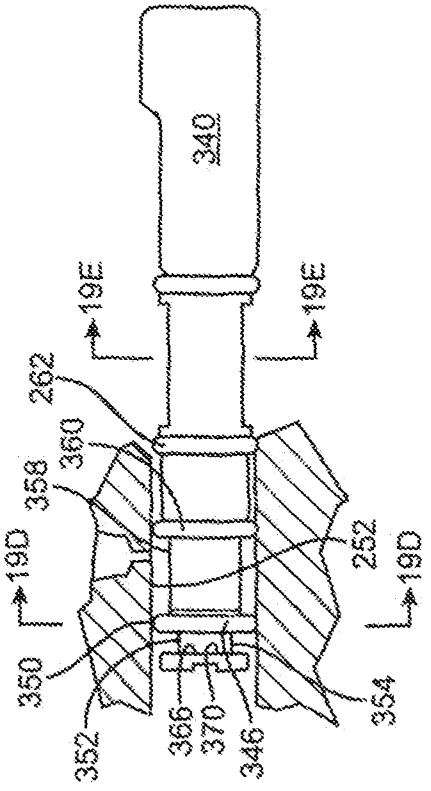
FIG. 19C is a section view of the delivery mechanism of FIG. 19B broken away for purposes of illustration.

FIG. 19B shows the spool 340 after the fluid 121 in the collapsible volume 344 has been collapsed by axial translation of the spool 340 and proximal seal 360 while the distal seal 346 has remained substantially stationary with respect to the bore 220 and dispense port 142. As a result, the fluid 121 in the collapsible volume 344 has been dispensed from the dispense port 142 as shown by the arrow 372 in FIG. 19B. The spacing of the proximal and distal seals 346 and 360, as well as the maximum and minimum translation of the proximal and distal seals 346 and 360 relative to each other may be the same as discussed above with regard to the spool embodiment 156 of FIG. 14. Venting of the vented volume 160 of the cartridge 374 may also be carried out in the same manner with the spool embodiment 340 of FIG. 19A-19E as was discussed above with regard to venting of the vented volume 160 of cartridge 112.

Figure 20:
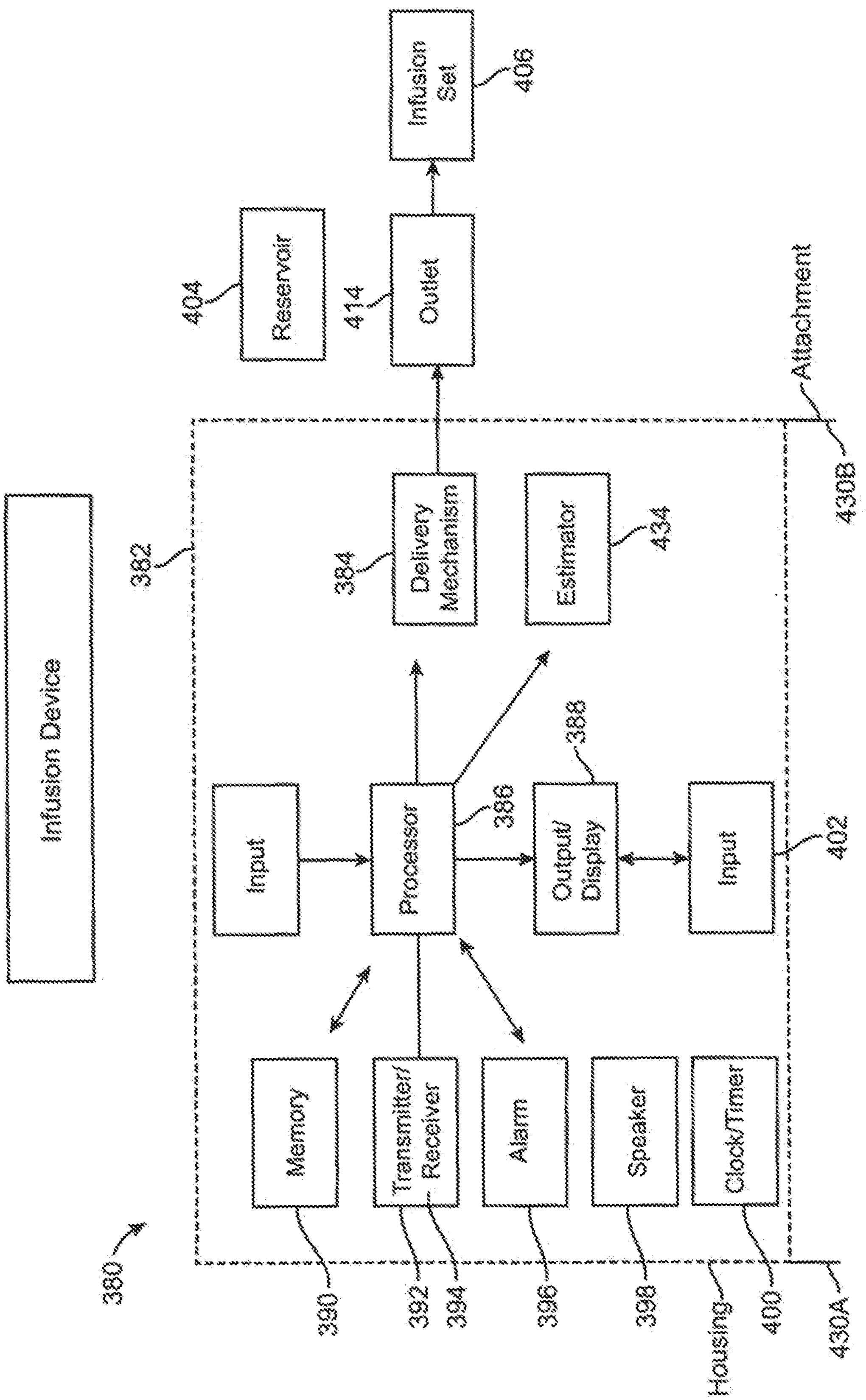
FIG. 20 is a block diagram representing an exemplary infusion pump device.

Referring to FIG. 20, a schematic representation of a portable infusion device 380 for delivering a quantity of fluid to a body is shown. In some embodiments, the portable infusion device 380 may comprise an insulin or other medicament portable infusion device such as the pump devices discussed above. In addition, some or all of the suitable features of the device 380 shown in FIG. 20 may be included with any of the pump devices discussed above. The portable infusion device 380 may include a housing 382 which may be of any suitable shape and any suitable size. For instance, the housing 382 may be extended and tubular, and further may be in the shape of a square, rectangle, circle, cylinder, or the like and may be dimensioned so as to be comfortably associated with a user and/or hidden from view, for instance, within or under the clothes of a user. The housing 382 may be configured to receive or contain components including one or more of a delivery mechanism 384, a processor 386, a display 388, memory 390, transmitter 392, receiver 394, an alarm 396, a speaker 398, a clock/timer 400, and an input device 402. In certain embodiments, the housing 382 may be configured for being associated with a removable reservoir 404 and/or an infusion set 406.

For example, in certain embodiments, the portable infusion device 380 includes a delivery mechanism 384. The delivery mechanism 384 may be any suitable type of mechanism including the delivery mechanisms 90 and 132 discussed above. For some embodiments, the delivery mechanism 384 may include a typical drive mechanism, such as a drive mechanism that includes a drive screw coupled to a motor. In such an instance, the drive mechanism may be configured for being operably coupled to a reservoir, such as a syringe based reservoir, and the housing may be sized to include at least a portion of the drive mechanism and the reservoir. In some instances, the delivery mechanism 384 may include a hydraulics mechanism, pneumatic mechanism, step motor, continuous motor, or the like.

Figure 21:
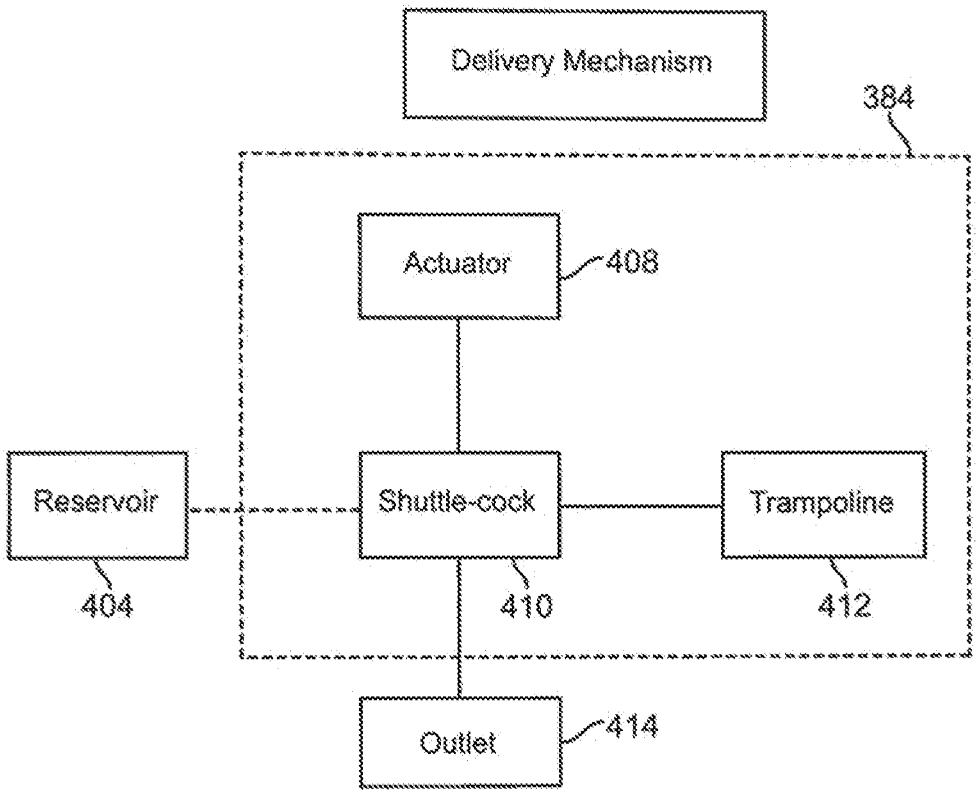
FIG. 21 is a block diagram representing an exemplary delivery mechanism of an infusion pump embodiment.

In some embodiments, such as the embodiment depicted in FIG. 21, the delivery mechanism 384 may include or more of an actuator 408, a shuttlecock 410, and/or one or more trampolines 412. The actuator 408 functions to move or otherwise actuate the shuttlecock 410. The shuttlecock 410 translates within a translation chamber. The translation chamber may communicate with a reservoir, the one or more trampolines, and an outlet orifice. The shuttlecock 410 may be configured such that as it translates in a given direction, e.g., a forward direction, in the translation chamber, a fluid in the reservoir is forced into and through the shuttlecock, in such a manner so as to contact one or more of the trampolines 412, causing the trampoline 412 to extend from a rest position to an extended position. For instance, the trampoline 412 may be fabricated from a material that is capable of extending in response to a force, such as the driving force that expels the fluid from the reservoir, through the shuttlecock, and onto a surface of the trampoline. As the shuttlecock translates in a second given direction, e.g., rearwards, the extended trampoline returns to its rest position thereby expelling any fluid contained thereon through the shuttlecock and out through a suitably configured outlet.

For certain embodiments, the shuttlecock 410 may be configured such that as it translates forwards and rearwards within the translation chamber, it regulates the flow of a fluid from the reservoir outwards away from the translation chamber outlet 414. The shuttlecock, therefore, can have any suitable shape or size and be of any suitable configuration so long as it is capable of translating within the translation chamber and thereby regulating the flow of a fluid from the device. In certain embodiments, the shuttlecock has an extended body that includes one or more openings, which openings pass through the entire width and/or length of the shuttlecock. The openings may be positioned within the shuttlecock such that they line up with one or more of a corresponding opening in the reservoir and/or the trampoline surface. Hence, as the shuttlecock 410 translates in one direction and at least one opening aligns with a corresponding opening in the reservoir, fluid is expelled inwards through the shuttlecock 410 to contact the surface of the trampoline 412 causing it to extend thereby storing a quantity of fluid thereon, and as the shuttlecock 410 translates in another direction and at least one opening therein aligns with the extended trampoline 412, the stored fluid is expelled away from the trampoline as it moves toward its rest position, through the shuttlecock 410, and out of the translation chamber.

The actuator or drive mechanism 408 may be configured for actuating or otherwise effecting the translation of the shuttlecock 410. The actuator 408 may be any mechanism that is capable of causing the translation of the shuttlecock 410. For instance, the actuator 408 may include an electric coil, a ferrite member, a nitinol member, a lever arm, corresponding magnets or electric magnets or dipoles, and the like.

Figure 22:
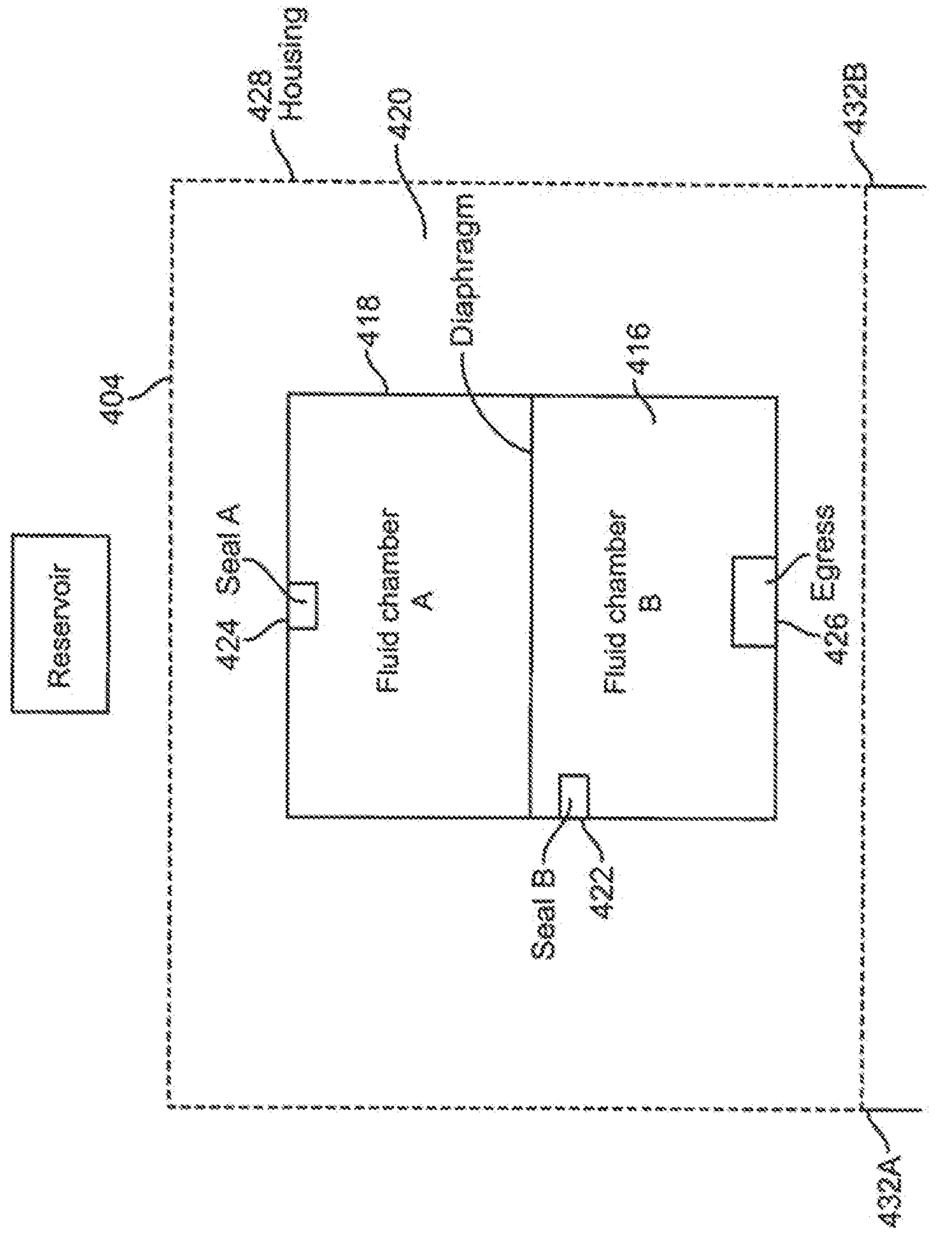
FIG. 22 is a block diagram representing an reservoir embodiment associated with an infusion pump embodiment.

As shown FIG. 22, the portable infusion device 380 may include or otherwise be associated with a reservoir 404. The reservoir embodiment 404 may be configured for storing a fluid, such as a liquid or a gas. The reservoir 404 may have any suitable shape and size configured for receiving and storing a fluid 121 and releasing the same in response to a force, such as an applied pressure. For instance, the reservoir may be configured such as those typically known in the art and described above. For example, the reservoir may be a mini-syringe including a barrel for storing the fluid and a plunger for applying pressure to the fluid within barrel which pressure effects the expulsion of the fluid from the barrel. As indicated above, where a drive mechanism 150 is included, the drive mechanism 150 may be operably coupled to the reservoir, such as the plunger, to exert a force in the plunger and thereby effect expulsion of the fluid from within the barrel. In such an instance, the housing of the portable infusion device may be configured to contain at least a portion of the reservoir and/or attendant drive mechanism, e.g., within the bounds of the housing.

In certain embodiments, such as that depicted in FIG. 22, the reservoir 404 may not include a barrel and/or plunger, but rather may include two or more chambers, such as a first fluid chamber 416, for storing a first fluid, and a second fluid chamber 418, for storing a second fluid. The fluid chambers 416 and 418 may be separated one from the other by a liquid gas interface, diaphragm or other moveable boundary 420, such that if a pressure is introduced into one chamber and acts upon the boundary that pressure is directly transferred into the other chamber. In certain embodiments, the moveable boundary includes a piston that is configured for regulating the interaction between the chambers. Each of the fluid chambers may additionally include one or more resealable or pregnable seals and/or valves 422 and 424.

For instance, the reservoir 404 may include a first chamber 416 that is configured for storing a liquid, such as a medicament to be delivered to a body. The second chamber 418 may be configured for storing a gas, such as air, carbon dioxide, or the like. The chambers additionally may be configured to store the fluid under pressure, such as atmospheric or high pressure. The boundary, such as a diaphragm 420, may be made from an elastic material that is substantially impermeable to the fluids in either chamber, but configured for being displaced from a resting position to an extended position, such as in response to an increase in pressure. Accordingly, as the second chamber 418 is filled with the gas, the diaphragm 420 is displaced, which displacement causes the pressure in the first chamber 416 to increase. The chambers may include one or more additional openings for the passage of the fluid into or out of the chamber. For instance, the first chamber 416 may include an opening or egress 426 for allowing the fluid, e.g., a liquid, stored within the chamber 416 to be expelled from the chamber 416 through the egress or dispense port 426.

As indicated above, the egress 426 may be configured so as to communicate with the shuttlecock translation chamber and/or shuttlecock 410 and/or one or more openings therein. The egress 426 may further be configured for opening and closing or otherwise regulating the amount of fluid that is allowed to pass there through. In this manner, the reservoir 404 interacts with the delivery mechanism 384 to effectuate the delivery of a stored fluid from the reservoir 404, through the delivery mechanism 384, and out of the portable infusion device 380, e.g. via infusion set 406.

In further embodiments, a third chamber may also be included. For instance, the third chamber may be in fluid communication or otherwise associated with the second chamber, such as via a solenoid valve. In certain embodiments, the reservoir is configured in such a manner that the amount of fluid delivered by the first chamber is directly calculated by a transfer of an amount of gas, e.g., from one chamber to another, such as by the amount of gas transferred from the third to the second chamber.

For example, the total volume of the second and/or third chambers may be fixed. As gas is transferred from the third chamber to the second chamber, an increase in volume in the second chamber results in a corresponding decrease in volume of the third chamber. This transfer of fluid results in a pressure being exerted on the diaphragm resulting in the expulsion of fluid from the first chamber, wherein the amount of fluid expelled from the first chamber is directly proportional to the increase in volume of the second chamber. Sensors may be included in the second and third chambers so as to determine the pressure transfer of the gas in the second and third chambers.

Specifically, since the volume of the third chamber is known and fixed, the ideal gas law and the principle of conservation of mass may be applied to determine the volume of gas in the second chamber. Since the combined volume of the second and first chambers is known and fixed, the volume of the first chamber is determined from the calculated volume of the second. The flow rate of the fluid from the first chamber is determined by calculating the volume of fluid in the second chamber at two instances in time and dividing the change in volume by the time between measurements. See, for instance, U.S. Pat. No. 7,374,556 incorporated by reference herein in its entirety. The processor may be employed for determining the dispensing of fluid from the first chamber, based upon the pressures sensed by the pressure sensor(s), e.g., in the second and third chambers. See, for instance, FIG. 23.

As indicated in FIG. 22, the chambers 416 and 418 of the reservoir 404 may include one or more seals and/or valves e.g. 422 and 424, such as a solenoid valve. The seals and/or valves may be configured for allowing a fluid to be added to a lumen of the chamber, thereby allowing the passage of the fluid into the chamber, while at the same time preventing the passage of the fluid back out of the chamber, once the fluid has entered into the chamber. In certain embodiments, a valve is included wherein the valve is capable of regulating the flow of the fluid into and/or out of the chamber, for instance, in a controlled manner.

Further, as indicated in FIGS. 20 and 22, the reservoir 404 may include a housing 428, wherein at least partially within the bounds of the housing the first and second chambers 416 and 418 are contained. The housing may be coextensive with the housing of the portable infusion device, or the housing 428 of the reservoir 404 may be separate there from, e.g., a separate and distinct component. For instance, as depicted, the housing 428 of the reservoir 404 is a separate component from the housing 382 of the portable infusion device 380. For example, the housing 382 of the portable infusion device 380 may include an attachment mechanism 430A and 430B, and the housing 428 of the reservoir 404 may include a corresponding attachment mechanism 432A an 432B, wherein the attachment mechanisms are configured for interacting with one another in such a manner that the housing 382 of the portable infusion device 380 is capable of being removably coupled to the housing 428 of the reservoir 404, thereby allowing the reservoir 404 to be attached and detached from the portable infusion device 380.

The attachment mechanism may have any shape and configuration, that is capable of removably attaching the housing 428 of the reservoir 404 with the housing 382 of the portable infusion device 380. In certain embodiments, the attachment is a rail system including corresponding grooves that allow the reservoir to be slidably coupled to the portable infusion device. In other embodiments, the attachment is a snap system that includes corresponding male and female parts that allow the reservoir to snap into place in operable contact with the portable infusion device. Hence, in certain instances, the reservoir and/or associated housing form a removable cartridge. Further, in certain embodiments, the reservoir itself is a cartridge that fits into a separate reservoir housing, which housing may then be attached, e.g., removably, to the housing of the portable infusion device.

Figure 23:
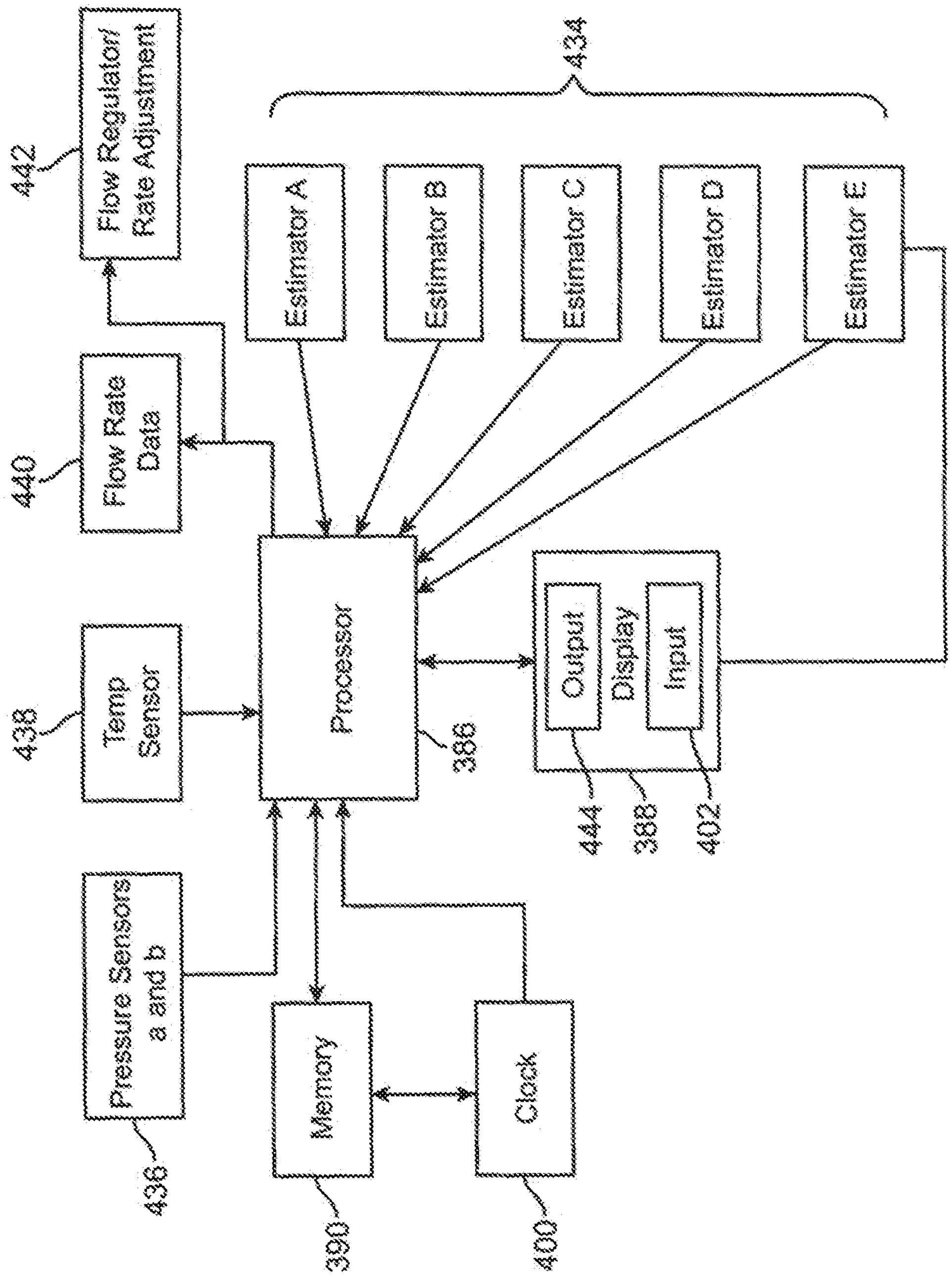
FIG. 23 is a block diagram representing functioning of a processor embodiment of an infusion pump.

As shown in FIG. 23, the portable infusion device 380 may include a processor 386. The processor 386 functions for controlling the overall functions of the portable infusion device 380. Specifically, the processor 386 includes programming that functions to control the device 380 and its components. The programming may comprise computer instructions stored in memory or firmware components that, when executed by the processor 386, provide the processing and features described herein. For instance, the processor 386 may communicate with, e.g., send signals to and/or receives signals from, and/or otherwise control one or more of the delivery mechanism 384, reservoir 404, estimators 434, output mechanisms (e.g., display) 388, memory 390, transmitter 392, receiver 394, alarm(s) 396, speaker 398, clock 400, and the like. The programming that is executed by the processor 386 may be referred to herein as the "program" or "programming" of the device.

Accordingly, the processor may include programming that it can execute to control the speed of shuttlecock translation, the release of fluid from the reservoir, the data to be displayed by a display, the data to be transmitted via the transmitter, the one or more alarms, etc. The processor may also include programming that allows the processor to receive signals and/or other data from an input device, receiver, various sensors (such as a sensor that may be included as a part of the device or used in conjunction therewith, for instance, a blood glucose monitor and/or a blood glucose sensor, and the like) and to store the same in a memory. The memory can be any type of memory capable of storing data and communicating that data to one or more other components of the device, such as the processor.

For instance, the memory may be one or more of a Flash memory, SRAM, ROM, DRAM, RAM, EPROM, dynamic storage, and the like. For instance, the memory may be coupled to the processor and configured to receive and store input data and/or store one or more template or generated delivery patterns. For example, the memory may be configured to store one or more personalized (e.g., user defined) delivery profiles, such as a profile based on a user's selection and/or grouping of various input factors (as described below); past generated delivery profiles; recommended delivery profiles; one or more traditional delivery profiles, e.g., square wave, dual square wave, basal and bolus rate profiles; and/or the like. The memory may also be configured for storing user information, history of use, compliance, an accessible calendar of events, and the like.

The processor may also include programming to allow the processor to make a recommendation. For instance, the processor may include one or more estimator functionalities 434 that enable the processor 386 to receive data from various sources, parse the data, collate the same, and generate an estimate based on the same. For instance, the processor may be configured to receive user input data and/or data from one or more sensors or other external source, which data the processor can process and thereby use to generate an estimate, such as an estimate of an amount of fluid to deliver to a body, a rate of fluid delivery, and/or a specific fluid delivery profile. For example, the processor may be configured to process data pertinent to a current or predicted condition and to generate an estimate, represented as an amount, rate, profile, etc. of fluid to be delivered based on that data, which estimate may then be displayed to a user, thereby allowing the user to interact with the estimate to accept, decline, and/or otherwise modify the estimate.

Specifically, as shown in FIG. 23, the processor 386 receives inputs from many of the other various components of the device 380. As indicated above, the portable infusion device may include one or more sensors, such as one or more pressure sensors 436A and 436B, a temperature sensor 438, a clock 400, and the like. For instance, as indicated above, the processor 386 may be configured for receiving pressure sensor data, which data may be processed to determine a flow rate 440 and/or further used to control a flow regulator 442 (e.g., a valve of the reservoir, a motor of the actuator) so as to make flow rate adjustments 442 and/or recommendations of the same for user consideration and evaluation. For example, the processor may receive pressure data from the sensors, e.g., pressure sensors 436A and 436B, which may be included in the second and third chambers (if included), and use that data to determine an amount of fluid being delivered from the device and/or a flow rate, which data in turn may be used to regulate and/or otherwise adjust the rate of flow, for instance, by communicating with one or more solenoids associated with the chambers e.g., through various electronic switches controlled by the processor.

For instance, the processor 386, and other processors discussed herein, may include estimator programming 434, such as estimators A-E (or a larger number as desired), enabling the processor 386 to adjust the amount and/or flow rate, etc. of a fluid from the device 380. For example, the portable infusion device 380 may include an interface that allows a user such as a patient to interact with the programming of the processor to determine an amount of fluid to be delivered, a rate of delivery, a delivery profile, and/or the like. In certain embodiments, the portable infusion device is configured for receiving user information about a users present or predicted conditions. Such information may include the amount of insulin already present in the body, e.g., insulin on board; blood glucose level; trending glucose level; insulin sensitivity/insensitivity; glycemic index; metabolism; metabolic rate; stress level; physiological conditions, e.g., age, health, sickness, diurnal cycles, etc; measurable parameters: hormones, steroids, etc.; pharmacokinetics of the medicament, e.g., age of insulin, decay rate, etc.; food to be ingested, e.g., carbohydrates, proteins, fat; activity; use history; calendared events; environment, e.g., temperature, humidity, pressure, etc.; and the like. One or more of these factors may be entered into the device, for instance, by an input device. The processor 386 includes programming configured for receiving such user input information, such as that discussed above, parsing and collating the information to generate an output, and presenting that output to a user, such as on display 388.

Figure 24:
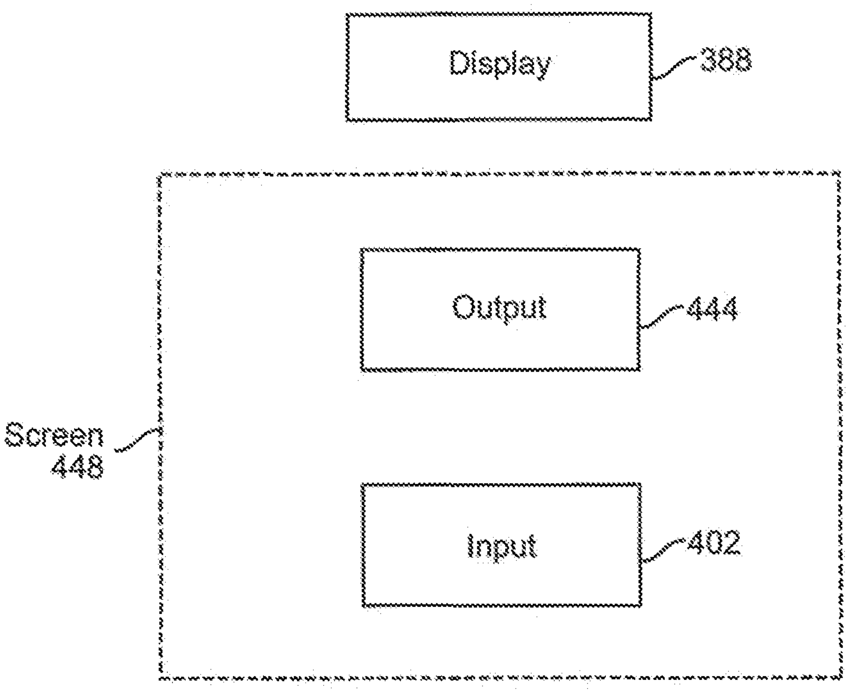
FIG. 24 is a block diagram representing a display of an infusion pump embodiment.

As can be seen with respect to FIG. 24, the portable infusion device may include a display 388, which display may be operable through an input/output interface. The display 388 may also include an input device 402. The display 388 may be any form of display capable of receiving data from the processor and displaying that data, for instance, receiving the data through an interface and displaying the data on a display screen, e.g., an LCD, LED, and/or plasma screen. The display 388 may be an interactive display and include a screen 448, wherein the screen may further include a touch screen, or touch sensitive, input device 402. For instance, the screen may be a capacitance or resistive touch screen.

A unique complication that may be present with respect to diabetic users is that they often build up calluses on the tips of their fingers as a result of blood glucose testing, which may be problematic for capacitive-based touch screen configurations. For example, calluses may prevent or hinder the transfer of energy that the capacitive screens use to receive directions. Accordingly, in certain embodiments, the touch screen may be a resistive based touch screen. The touch screen, or touch sensitive display, may be configured to display screens or pages that allow the user to input data fields, e.g., select variable inputs, so as to allow the program to produce a suggested delivery amount, rate, profile, and/or the like in an intuitive, manipulable, and/or graphic representation, thereby allowing the user to interact with the screen to shape the characteristic/form of the delivery amount, rate, and/or graphic delivery profile, e.g., by manipulating the delivery estimate or pattern displayed on the screen to effectuate the actual delivery. The portable infusion device may additionally include a keyboard or other device known in the art for data entry, which such devices may be separate from the screen and/or display.

Information provided by the portable infusion device may be presented on the display screen as any number of objects, including one or more numerical values, a range, a value or range that is presented in the form of a drop-down menu, a toggle that can be adjusted by the user, a graphical representation or an animated graphic, and the like. For instance, in certain embodiments the value is a range of values that are presented on a screen of the display as a toggle, wherein the toggle may be adjusted upwards or downwards by the user swiping a finger over the screen to select the appropriate value range, e.g. appropriate range of amounts of medicament such as insulin to be delivered and/or the appropriate rate of medicament delivery. In certain instances, the values presented in the range may be adjusted by the processor 170 based on various characteristics of the user, such as age, sex, weight, height, insulin sensitivity, etc.

Additionally, in certain instances, the value estimate may be displayed in graphical form; for instance, as an interactive graphic interface, such as where the value to be displayed is a delivery profile. In some circumstances, a possible advantage of the disclosed portable infusion devices is that the programming of the processor and the touch screen functionality permit the portable infusion device to receive user inputs pertaining to a wide variety of variables, such as those described above. The variables may be used to generate a graphic representation of a delivery profile that may be manipulated by the user to change the delivery profile, with or without various predetermined parameters. This represents a movement away from the static stair step delivery modules that are based more on the limitations of archaic pumping mechanisms and that have a limited ability to correlate with the actual present or future medicament needs of a user. Hence, rather than locking a user into a delivery profile that resembles, for example, a square stair step wave or a dual wave profile, as is commonly employed in the art, the delivery profiles of the present portable infusion device may be represented as a series of adjustable graphs.

For example, where the fluid to be delivered is insulin, a portable infusion device of the present disclosure may be configured to receive user and/or external, e.g., sensor, inputs to calculate current or predicted insulin on board for the user, and may further make calculations to determine a predicted rate of decay for the same. The portable infusion device programming may in turn use this information, along with other information, such as user input information, e.g., current blood glucose level, stress level, or activity level, to generate a delivery profile that more resembles the actual insulin requirements of a user. In this manner, a portable infusion device of the present disclosure generates a delivery profile that models the amount of glucose in the blood, such that a user will have enough insulin to deal with the present blood sugar but not so much of an excess that medical complications arise.

Specifically, in many current infusion pumps, two typical infusion rates are possible: a basal rate, wherein insulin is being delivered at a constant rate; and a bolus rate, wherein prior to ingesting food a bolus of insulin is delivered to account for the amount of sugar to be ingested. In practice, the user enters the amount of carbohydrates they are about to ingest, their carb ratio (the volume of insulin programmed to be delivered for every particular number of carbohydrates predicted to be consumed by the user), and based on this information the infusion pump will generate an estimate of a bolus amount of insulin to be delivered. If accepted by the user, e.g., by depressing a button, the then-current basal delivery mode is suspended and the bolus delivery rate is initiated.

As discussed, there are several shortfalls in such calculations. For instance, the amount of insulin to be delivered should model the amount of glucose in the blood as well as the predicted amount of glucose to be ingested, and/or the insulin sensitivity of the user. These amounts are further affected by factors such as the user's emotional state, activity level, physical conditions, etc; and further, the food to be ingested often include other components, e.g., fat and protein, in addition to carbohydrates, which are generally not of high importance in the calculations performed by current devices. Although the presently disclosed portable infusion devices consider the amount of carbohydrates a user is to ingest as well as their carb ratio, they also may consider a wide variety of other variables that may be input by the user or other external sources, such as by sensors, and the like. That is, the suggested delivery profile that is generated by the processor may include as input values such as amount of carbs, user carb ratio, user's emotional state, activity level, physical conditions, etc. Hence, the suggested delivery profile that is produced by a portable infusion device of the present disclosure more closely represents the amount of insulin to be delivered over time at the time that amount of insulin is expected to be needed, thus more closely matching the amount of insulin on board at any given time with the amount of glucose present in the blood for that time.

Therefore, rather than merely having two basic delivery modes or profiles, such as a basal delivery profile that may be suspended and replaced by a bolus delivery profile, e.g., prior to when a user is about to eat, the delivery profiles of the present portable infusion devices may include a plurality of bolus delivery profiles that may be used in any combination to deliver a series of boluses. These profiles may be adjusted over time to account for a changing variety of variables such as insulin on board, food ingested, decay rates for both the insulin on board and insulin delivered, carb ratio, and the like. The boluses may be of equal size or of different sizes, in accordance with the delivery profile. In this manner, the present portable infusion devices are capable of more closely controlling the level of insulin in the bloodstream, and generating delivery patterns that resemble actual insulin needs rather than delivery patterns that are based on the limitations provided by the pump's mechanical delivery mechanisms.

For instance, due in part to their unique delivery mechanism(s) and/or programming, the portable infusion devices of the disclosure may be configured for delivering a series of multiple reduced size bolus deliveries of a fluid, such as insulin, so as to finely control the amount of that fluid in the blood, e.g., the amount of insulin on board (IOB). Thus the total amount of the fluid, e.g., insulin, delivered is an integrated amount determined by the graphical shape of the delivery profile curve for the series of multiple bolus deliveries. For example, the graphical shape of the delivery profile curve may represent the amount of insulin delivered over a period of time, where the x-axis of the graph represents the time, e.g., hours, minutes, actual time in user's time zone, etc., and the y-axis represents the amount of insulin, e.g., in units. Therefore, the rate of insulin delivery may be easily represented by a graph having a slope defining the delivery rate and the area under the graph totaling generally the amount of fluid delivered, or to be delivered, to the user. Hence, in this manner, the portable infusion device may more closely control the fluid, e.g., the amount of the medicament, such as insulin, in the user's blood stream by generally constantly modulating the boluses of the fluid being delivered. In addition, or alternatively, the modulation of boluses may be done on a non-constant basis, e.g., rapidly, intermittently, periodically, etc., as generally desired by a user.

The mechanisms, processors, and programs employed by current infusion pumps cannot account for the data input and/or to make the calculations and determinations sufficient to enable fine manipulations of the suggested delivery profile(s). Accordingly, although portable infusion devices described herein are capable of generating square or dual wave bolus delivery patterns, because of the dynamics of the systems described herein, such patterns are capable of being manipulated, even in real-time, by a user via, e.g., a touch screen display, so as to be adjusted according to any of a number of variables, as described above. For example, due in part to the programming of the present devices, the portable infusion devices described herein may calculate necessary volumes of insulin to deliver to a user in order to at least attempt to maintain a user's target blood glucose level, which is generated by accounting for various parameters entered by the user or external sources.

In this manner, for instance, with respect to insulin, a desired ideal delivery profile may be generated so as to match the insulin to be delivered with the amount of glucose in the blood given the present or predicted future conditions of the user taking into account such parameters as meals, meal complexities, exercise, absorption/clearance rates, decay rates, and the like. A benefit of the programming described herein may be that it allows for predicted events and provides for real-time corrections to medicament delivery if those predicted events so not correlate with or anticipate current conditions. Thus, the devices disclosed herein allow for generally predictive events so that an appropriate amount of insulin can be available in the blood at the time needed to account for the changing conditions of the user, and/or can be corrected real time. For example, the present devices allow for an estimate of medicament amount, rate, profile, etc. that will be needed in the future so that an appropriate amount of the medicament, e.g., insulin, needed to accomplish a desired function, such as process the now current glucose present in the blood, is generally readily available to the user.

Specifically, in some exemplary situations, the user may input data into the device pertaining to a meal to be consumed. The processor will process that information to generate an insulin delivery pattern, wherein the amount of insulin to be delivered is modeled on the predicted amount of glucose to be present at the time of its entering the bloodstream based on the inputted data and/or data accessed via the memory or remotely via, e.g., a network, for calculating the amount of insulin required. Hence, in such a situation, the portable infusion device system may account for such variables as the type and amount of food to be ingested, the amount of glucose, other sugars and carbohydrates, proteins and fat associated with such food, the decay rate of insulin, as well as the rate at which the food ingested is metabolized by the body for the food ingested. The data to be entered into the system of the device, therefore, may include one or more of the complex composition, as described above, of the meal (e.g., which may be a value range based on low, medium, or high complexity), and/or may include the amounts of carbohydrates, proteins, and fats to be consumed. The users current blood glucose level and/or glycemic index may then be input or may be calculated, the insulin duration and/or food (e.g., carbohydrate, protein, fat) absorption rates may be calculated, current or predicted activity levels, and variables related to present physiological conditions (e.g., stress levels) may be input into the device, any or all of which data may be used by the processor to generate a delivery profile that more closely represents desirable or ideal curve for insulin on board (IOB) over time, which is the amount of insulin remaining in a user's body over time due to any bolus deliveries of insulin to the user. The delivery profile generated may then be accepted and/or manipulated by the user, for instance, in an exemplary situation where the user predicts that he or she will be exercising within a certain period of time but never does. Accordingly, the delivery profile may be represented as a graph, such as a graph that displays the amount of insulin to be delivered over time, which graph may be capable of being graphically manipulated by a user.

For instance, the graphic representation may be a bar graph that indicates an amount of insulin to be delivered over a certain time interval, such as a four minute increment, for a given period of time, e.g., 1 hour, wherein each bars represents an aliquot of insulin to be delivered within the 4 minute time increments, and the height of the bar equals the amount of insulin to be delivered within that time frame, and further wherein the height of the bars may be manipulated by a user in response to present or predicted conditions. For example, in one embodiment, a series of bolus amounts of insulin to be delivered e.g., every four minutes, for a given time period, e.g. 1 hour, may be calculated, wherein the upper limit for the total amount of insulin to be delivered is fixed, but each individual bar, representing an amount of insulin to be delivered in a given 4 minute increment, is adjustable within a given range, so as to allow a user to have greater control of the amount of insulin being delivered over the given time period.

In some instances, a first graph may be displayed wherein the user is notified of the amount of insulin that is presently "on board" and expected to be "on board" over a given time period. A second graph may then be displayed showing a suggested amount of insulin to be delivered over a given time period, e.g. overlaid with the first graph or shown sequentially thereafter. The shape of this second graph may be capable of user manipulation, if desired. In certain embodiments, the systems disclosed herein may allow for complete manipulation of medicament delivery by a user with no limits, or, for safety and/or regulatory reasons may provide a range of data within which the medicament delivery may be so manipulated or altered. The user may, e.g., be prompted before making any or all such changes if they, for instance, calculated by the system to be dangerous, non-optimal, etc., such as with a message prompting the user to select a button before making such change and/or reading a message with information regarding possible effects of such manipulation before making such change. Alternative "lock out" features temporarily disabling the ability for such manipulation may be used as well as alarms or notification functionality for storing and/or transmitting data associated with such user-generated changes to a clinician, parent, etc. In some embodiments, although the shape of the graph is capable of being manipulated so as to change the delivery profile, the total area under the curve, and therefore the total amount of insulin to be delivered over time, is not changed.

In other embodiments, as indicated above, the graph may be a series of bars, wherein the width of each bar represents a time period, the height of each bar represents an amount of insulin to be delivered, and the number of bars represent a given time period for delivery. In such an instance, each individual bar may be capable of being manipulated, and in certain embodiments, the total amount of insulin to be delivered for the overall period could be limited such that an increase in one bar results in an a subsequent decrease in another bar for the given overall period. Additionally, a bar graph could be displayed wherein the insulin on board is represented as a function of activity, wherein the bars represent the amount of suggested insulin to be delivered, e.g., in 4 minute increments, and the bars are capable of being manipulated with respect to the amount of exercise to be engaged in. In such an instance, a decrease in activity level may require an increase in the amount of insulin to be delivered.

In another embodiment, the graphic representation may be a triangle bounded by three points that are variably selected, e.g., food to be ingested, historic blood glucose level, and activity level, wherein the output would be a given amount of glucose to be delivered over a given period of time, and further wherein the shape of the triangle may be modulated by the user to change the delivery profile. In a further embodiment, a delivery rate may be set forth graphically in a series of step, the steps could then be overlaid by a suggested rounded wave, and the user can manipulate the screen so as to configure the steps to model the shape of wave, e.g., rounding out the steps.

It is to be noted that although the above examples have been set forth with respect to the amount of insulin to be delivered in view of certain variables, such as time, activity level, user history, and the like, equivalent graphical representations could be set forth with respect to any of the above described variables. Further, although various graphical representations have been set forth, such as generally wave-from shaped graph, bar graphs, and generally triangular shaped graphs, such graphical representations are not meant to be limited hereby as other graphical representations could be used to convey the relationships between the various factors herein, and thus, the disclosed graphical representations are not meant hereby to be limiting.

As indicated above, the graphical representations are capable of being manipulated, for instance, by a user interacting with the device in such a manner as to produce a change in a characteristic of the graph. For instance, where the screen of the display is a touch screen, or touch sensitive display, the user may interact with the screen, e.g., by use of a finger, stylus, or other such instrument, so as to cause a change in the displayed representation. Hence, in certain embodiments, the display may be configured in any suitable manner that allows for the representation of data, which data may then be acted upon by a user so as to effect a change in the displayed representation. For example, in certain embodiments, the display is configured for displaying various forms of graphs, which graphs may be capable of being manipulated by a user's interaction therewith. Additionally, in certain embodiments, the display is configured for displaying a toggle representing a given quantity, which toggle may be scrolled through for the selection by the user of a determined representation of the quantity to be selected.

For instance, where the display is configured for graphical representation, the graphic representation may be configured for manipulation by a user touching or otherwise "clicking" the representation and dragging the representation in a predefined manner so as to change the form, e.g., height, width, shape, etc. of the representation. For example, where the graphical representation is a bar, the height or width of the bar may be adjusted by clicking on the appropriate dimension and manipulating it to adjust that chosen dimension. Where the graphical representation is a curve or wave, the curve or wave may be clicked and the shape thereof may then be manipulated, for instance, by dragging a finger across the screen in a predetermined manner. As the graphical curve or wave is manipulated by the user, data values corresponding to the curve values are changed.

Figure 54:
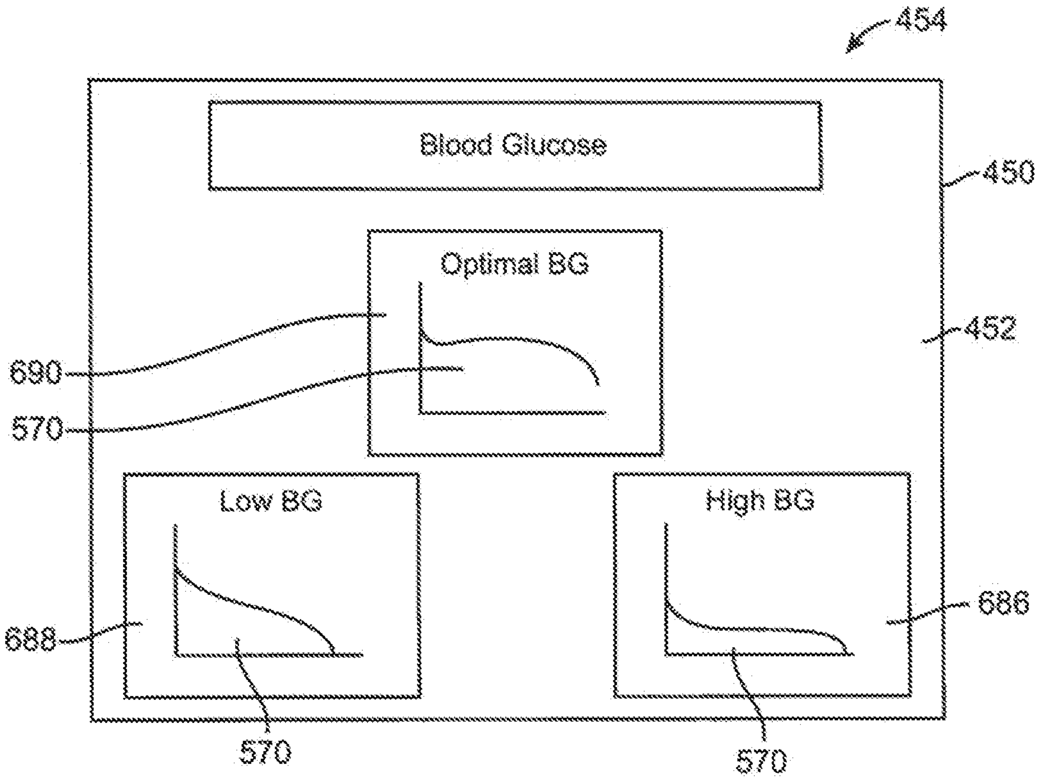
FIG. 54 illustrates a screen which displays multiple graphs simultaneously on a touch screen display.

FIG. 54 illustrates an example of multiple graphs being simultaneously displayed on the touch screen display, which include a BG graph, an IOB graph and a target BG graph. Any one of the graphs may be configured for manipulation by a user, such that a user may modify the slope of any one of the graphs in order to ultimately modify the rate amount of insulin in the body of the user over a period of time. Furthermore, user manipulation of one graph may or may not automatically cause modifications to one or more additional graphs and/or settings. Any number of graphs displaying various data may be simultaneously displayed on the touch screen display to enable a user to directly modify any one of the displayed modifiable graphs.

Some embodiments may include a configuration wherein the graph includes a handle and spline, wherein the graph is capable of being manipulated by tapping the handle and moving the same to effect a change in the spline. Hence, in such manners as these, the graphs of the display, in certain embodiments, are capable of being manipulated, which allows a user to change, e.g., in real time, the delivery pattern of a fluid, for instance, so as to account for present conditions and/or future predictions, such as actual exercise levels and/or actual amounts to be eaten vs. predicted exercise levels and/or amounts actually eaten. In certain embodiments, the graphic representations may also include an auto correct feature, such as a feature that allows for a best-it curve correction, such as, e.g., an auto correct button.

Accordingly, the device may receive information from a user input and/or sensor or monitor input and based on this information may make a calculation of an amount of glucose present or about to be present in the blood. The results of these calculations can then be used generate an amount or rate of insulin to be delivered over a given period of time, which rate may be represented as a graph, such as a graph that can be manipulated by the user. Once the suggested amount, rate, delivery profile, or the like is presented to the user, the system may require the user to take an affirmative action, such as depressing a confirmation screen, before the device will deliver the medicament in response to the user's affirmative action.

Figure 25:
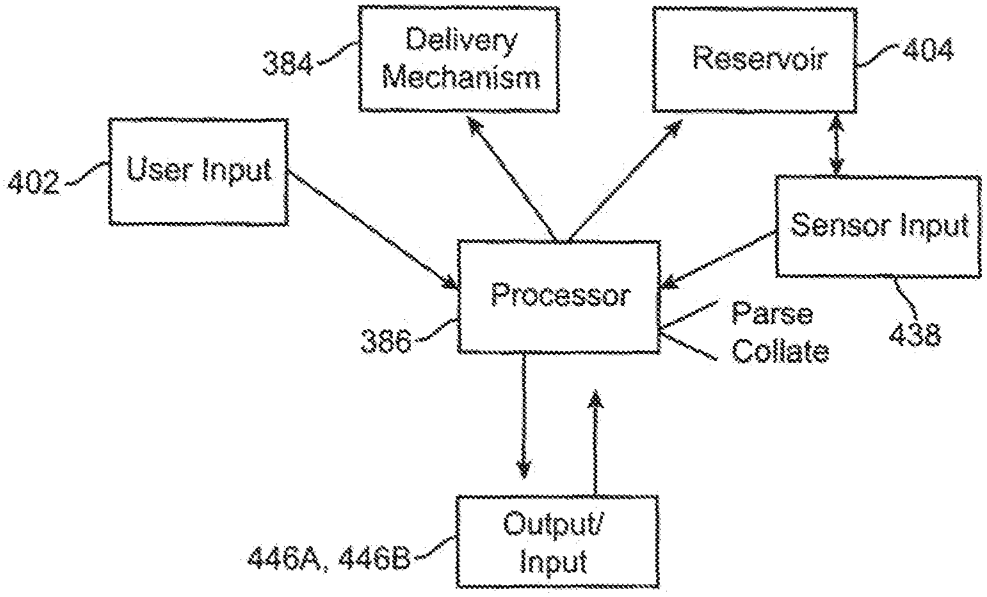
FIG. 25 is a block diagram representing functioning of a processor of an infusion pump embodiment.

For instance, in some exemplary embodiments, as can be seen with respect to FIG. 25, the processor 386 may be configured for receiving user input 402 as well as sensor input 438 and generating an output 446A, such as an estimated amount or rate of fluid to be delivered, which output may be presented on a display of the device, such as in a toggle or graphic format. The output 446A may further be of such a configuration that a user response may be required, for instance, by tapping a screen of the display as, for instance, selecting an object or symbol of the display to indicate a confirmation of the user's acceptance of the estimate, which confirmation serves as additional user input 446B that signals the processor 386 to initiate the delivery mechanism 384 so as to translate within the translation chamber and the reservoir 404 to expel fluid into the translation chamber and thereby begin delivery of the fluid in accordance with the confirmed amount and/or rate. As indicated above, the reservoir 404 may include one or more sensors that can send the processor information with which the processor can determine the amount and rate of delivery and adjust the same as necessary in accordance with the user instructions, thus, allowing a feedback loop whereby the actuator may be deactivated and/or the egress of the reservoir closed once the appropriate amount of fluid has been delivered. Other selections of objects and symbols on the display may provide confirmation of selection or acceptance of the corresponding displayed values of the object or symbol.

The portable infusion device 380 of the disclosure may also include one or more of a suitably configured power source; wire or wireless communication capability, such as for the remote sending and receiving of data, e.g., a transmitter and/or receiver, WIFI connection, infrared or bluetooth communication device, USB or SD port, flash drive port, or the like; GPS functionality; phone functionality; warning and/or alarm programming; music storage and replay functionality, e.g., an MP3 player; a camera or video mechanism; auto scaling capabilities, and/or one or more video type games. A USB connection may be used to charge the device and may allow the portable infusion device to display information from a program being run by the processor on the device onto the connected computer's monitor. Therefore, this may allow a portable infusion device to interact with any computer having a USB connector for at least downloading data onto the computer for subsequent use of the data, e.g., upload onto the internet, save data in computer's memory, view and/or modify device data using word processing, store the data in various media file formats, etc. This also relieves users from having to load installation software onto a computer prior to at least downloading data from the portable infusion device onto the computer.

The device may also include an accelerometer, for instance, which may be used for changing presented estimates, wherein instead of scrolling through a menu of options or using a numerical keypad, values can be input or changed via the accelerometer, such as by gesturing with or otherwise shaking the device. Further, the processor of the device may include additional programming to allow the processor to learn user preferences and/or user characteristics and/or user history data, for instance, to implement changes in use suggestions based on detected trends, such as weight gain or loss; and may include programming that allows the device to generate reports, such as reports based upon user history, compliance, trending, and/or other such data. Additionally, a device of the disclosure may include a power of or suspend function for suspending one or more functions of the device, such as suspending a delivery protocol, and/or for powering off of the device or the delivery mechanism thereof.

Some embodiments of an infusion system may include a portable infusion device, as described above and a remote commander device. In such an instance, the portable infusion device may include a suitably configured receiver and/or transmitter for communication with an external device such as a remote commander, as well as programming for directing the use of the device; and the remote commander may additionally include a suitably configured receiver and/or transmitter for communication with an external device such as a portable infusion device, as well as programming for directing the use of the device. For instance, the remote commander may include one or more of the functionalities described herein above with respect to the portable infusion device.

For example, the remote commander may include a processor, a memory, a transmitter and/or receiver, an input mechanism, an output mechanism, e.g., a display, a clock, a timer, an alarm, an estimator, and the like. Hence, in certain embodiments, the portable infusion device may include a transmitter that receives commands, e.g., infusion commands, from the processor and transmits the commands (e.g., to a remote commander or vice-versa). Similarly, the remote commander may include a transmitter that receives commands, e.g., infusion commands, from its processor and transmits the commands (e.g., to a portable infusion device or vice-versa). In such an instance, the portable infusion device and/or remote commander may also include a receiver that receives commands, such as remotely/wirelessly generated commands, and communicates the commands to the processor. Accordingly, the remote commander may include the appropriate hardware and software necessary for producing these functionalities in the remote commander, such as that described above with respect to the portable infusion device. The portable infusion device itself or the remote commander may also include programming that includes an initiating command request, whereby the user has to interact with the device, such as by tapping a screen, e.g., on a display of the portable infusion device or remote commander, so as to accept an infusion recommendation before the remote commander signals the portable infusion device and/or before the portable infusion device accepts the command and begins infusion of the fluid.

Some embodiments may be directed to a system for generating an estimate of an amount of fluid to be delivered to a body and for delivering the amount of fluid to the body of a user in accordance with the generated estimate. The system may include a remote commander and a portable infusion device. For instance, the system may include a remote commander configured for generating the estimate of the amount of fluid to be delivered to the body, and for communicating instructions for the delivery of the amount of fluid to the portable infusion device. Accordingly, the remote commander may include one or more of: a processor, for generating an estimate of an amount of fluid to be delivered to a body in response to user input data; a data input interface for communicating with the processor, wherein the data input interface is configured for receiving user input data; a memory coupled to the processor; for receiving and storing user input data; a display for displaying the estimate of an amount of a fluid to be delivered; and a transmitter for transmitting a command to a portable infusion device, wherein the command instructs the portable infusion device to deliver an amount of fluid in accordance with the generated and confirmed estimate.

Further, the system may include a portable infusion device that is configured for delivering the amount of fluid to the body in accordance with the estimate generated by the remote commander. The portable infusion device may include one or more of a reservoir, for storing the fluid; a delivery mechanism, for effecting the delivery of the fluid; a receiver for receiving instructions, e.g., commands, from the transmitter of the remote commander; and a processor, for instructing the reservoir and/or delivery mechanism to deliver the amount of fluid to the body of a user in accordance with the received instructions, e.g., the generated estimate.

Additionally, the housing of the device, e.g., the housing of the portable infusion device and/or reservoir and/or remote commander (if included), may be configured for containing at least a portion of one or more of a stylus, a lancet, and/or glucose sensing strips or other glucose sensing components. Additionally, the device may include a removable skin or other cover configured for protecting the device from the environment and/or breakage due to mishandling. One or more of these may also be included in a kit of the present disclosure.

Some embodiments may be directed to a method for using the above portable infusion device and/or remote commander so as to deliver an amount of a fluid, such as an estimated amount of fluid to a body of a user. The method may include providing an infusion device and/or remote commander, as described above, for instance, where the infusion device includes one or more of a reservoir, for storing the fluid; a delivery mechanism, for delivering the fluid; a processor, for generating an estimate of an amount of fluid to be delivered to the body in response to user input data, and for controlling the delivery mechanism; a data input interface for communicating with the processor, wherein the data input interface is configured for receiving user input data; a transmitter and/or a receiver, for transmitting and receiving commands; and a display for displaying the estimate of an amount of a fluid to be delivered. If a remote commander is provided, the remote commander may include one or more of a processor, for controlling the remote commander and/or generating an estimate of an amount of fluid to be delivered to the body in response to user input data; a data input interface for generating commands and communicating with the processor, wherein the data input interface is configured for receiving user input data, such as a user command; a transmitter and/or a receiver, for transmitting and receiving commands; and a display for displaying the command and/or an estimate of an amount of a fluid to be delivered.

The method may further include inputting externally supplied values into the data input interface, such as a data input interface of the portable infusion device and/or remote commander wherein the data input interface is configured for receiving the user input data and communicating that data to the processor and the processor is configured for receiving the user input data and/or generating an estimate of an amount of a fluid to be delivered to the body of the user, and further configured for communicating the estimate to the display and/or to the portable infusion device or remote commander (if included). For instance, the user input data may include one or more of a blood glucose level, a stress level, a physiological condition, a complexity of a meal to be ingested, an activity level, a user history profile, or the like. The method may additionally include one or more of receiving the generated estimate of an amount of fluid to be delivered on a display of the portable infusion device and/or remote commander; receiving a request for a user input on a display of the device, such as wherein the request requires the user make a selection before delivering the amount of fluid to the body of the user; and making a selection based on the estimate; wherein, once the selection is made (if required) the device delivers the quantity of fluid to the body in response to the selection.

Some embodiments may be directed to a kit which kit may include a device and/or a system for the infusion of a medicament as described herein above. Specifically, the kit may include one or more of a portable infusion device, a reservoir, a remote commander, as well as instructions for using the same, and may include an aliquot of the medicament, e.g., insulin to be delivered, as well as infusion set tubing. The instructions may be in written, audio, or pictorial form and may be included in a written manual and/or on an instruction CD or DVD, MP3 file, or accessible via a network. In certain embodiments, a training video may be included, for instance, on a separate DVD or other medium, may be accessible via a network, or may be included as programming on the portable infusion device and/or remote commander. For instance, in certain embodiments, the portable infusion device and/or remote commander may include a training module. The training module may be included as programming accessible by the processor of the device, wherein the software is configured to instruct a user in the proper use of the device.

In certain embodiments, the programming may be interactive, thus, the software may include steps of tasks (e.g., such as loading a reservoir, entering data, or using an estimator) that must be accomplished to show mastery of the use of the device and/or may include additional programming that prevents a user from moving on to the next step before mastering the present steps, such programming may be automatically erasable after the tasks of the steps have been completed thereby expanding available memory. The programming may include one or more of an automated mascot, an electronic protocol, preloaded or downloadable video training, as well as instructions for how to use the device and/or specific features of the device. Additionally, the remote commander and/or portable infusion device may include one or more indicators and/or alarms, such as an alarm that indicates when a command, e.g., a user input, is being received, has been received, and/or is being or has been implemented by one or both of the remote commander and portable infusion device. The indicator and/or alarm may be a visual indication, auditory indication, tactile indication, and the like.

It should be noted that some or all of the suitable features, dimensions, materials and methods of use of the GUI 166 may be used or incorporated into any other infusion system, or components thereof, discussed herein. As discussed in an embodiment above, the screen of the display 450 may be a touch screen 450. For example, a touch screen 450 may have a 320×240 pixel QVGA display, 16 bit color depth, and a rectangular shaped display area having a diagonal length of 2.5 inches. However, the touch screen 452 display 450 of the portable infusion device 110 may have any variation of display characteristics and configurations, e.g., 128×64 to 1280×1024 pixel resolution, 16 to 32 bit color depth, and a diagonal display 450 length of 1 to 3 inches. The user may interact with the touch screen 452 by touching the touch screen 452 (e.g., by use of finger, stylus, or other such instrument), so as to cause a change in the display representation. The user-interactive touch screen 452 also assists in providing the user with a user-friendly graphical user interface (GUI) 454, which can be used in GUI 166 in the embodiment discussed above. In addition, the GUI 454 may be used in combination with any of the infusion device embodiments described herein for controlling the delivery of one or more fluids to a user, or patient. User-friendly GUI 454 embodiments discussed herein may include any means and/or methods for interacting with the portable infusion device 110, or any device associated with the portable infusion device 110, through direct manipulation or commands.

One possible advantage of some portable infusion device 110 embodiments may be the ability to provide a user with generally improved usability. This has been achieved by integrating a user-centered GUI 454 design that may provide an interface having at least one display screen representation or page 456 that reduces user-error and enhances the efficiency and user satisfaction of the device 110. It may be a benefit for some embodiments to offer generally complex programs in a portable infusion device 110 for assisting in the delivery of insulin that best serve the user's insulin needs. As discussed above, in order to optimize the delivery of insulin to best serve the user's insulin needs, a number of factors must be taken into account for determining the user's present and predicted future insulin needs. Therefore, the GUI 454 of the portable infusion device 110 may provide a user with enhanced usability for interacting with the device 110 in order to customize deliveries of insulin that best meet the insulin needs of the user.

Some embodiments of the portable infusion device 110 may also include multiple other capabilities in addition to delivering one or more medicaments (i.e., insulin). For example, the portable infusion device may be capable of interacting with a personal computer (PC) for uploading and downloading data, various file types (e.g., JPEG, PDF) and programs. The portable infusion device 110 may also access and send information wirelessly to a PC or other electronic device (e.g., printer, memory storage device). These functions, for example, may be particularly beneficial to a user for sending and receiving information to a physician, or uploading new or upgrading current programs onto the portable infusion device 110. Furthermore, the portable infusion device 110 may have instructions, or accessible by the user and/or processor 170 for converting information on the device 110 into various file formats, e.g., portable document format (PDF), word processing documents, JPEG, etc., which may be distributed and shared among various electronic devices. The GUI 454 of the portable infusion device assists in improving the usability of at least these capabilities. In addition, some GUI 454 embodiments may be available to a user by downloading a software application onto the user's cell phone and/or PDA, which would allow the user to use their cell phone or PDA as a remote commander to the portable infusion device 110.

Some GUI 454 embodiments discussed herein, including the GUI 454 shown in FIG. 9A, may use a generally intuitive interface for an improved user experience of a portable infusion device 110. A user interacting with some embodiments of the GUI 454 may experience improved usability over past and current infusion devices. Therefore, some embodiments of the GUI 454 may offer an improved user efficiency, user satisfaction, and reduction in user error when operating the portable infusion device 110. In addition, a user interacting with the GUI 454 of the portable infusion device may find learning to use the device to be generally simple due, at least in part, to a generally intuitive interface such that operating the device 110 may be intuitive and/or learned by simply observing the device 110.

With improved usability, a user may be enticed to interact with the portable infusion device 110 in order to use the device to a greater degree than what is typically experienced with past and present infusion devices. In some cases, there is a need for portable infusion devices with improved usability so that users do not simply "set-it-and forget-it," as what is often done with other infusion devices because users may find them too difficult, time consuming, and/or confusing to operate. When a user "sets-it and forgets-it," the user of the infusion devise relies on a small number of generally generic delivery profiles that do not fully represent the user's present and future insulin needs. Therefore, some of the GUI 454 embodiments discussed herein may at least improve upon some of the past and present deficiencies of infusion devices by providing a portable infusion device with improved user friendliness.

In addition, some of the GUI 454 embodiments discussed herein may at least improve a physician and/or clinician's ability to respond to a patient's needs. For example, a user of the portable infusion device may inform a physician of a problem the user has been experiencing, e.g., chronic fatigue, mood swings, large swings in BG levels, etc. The physician may then analyze any of the delivery profiles 458 programmed in the user's device 110 to determine which of the settings to modify in order to try and improve the user's wellbeing. For instance, by viewing the delivery profiles 458, the physician may be able to determine that one of the delivery profile settings is programmed too low, which may have been contributing to not enough insulin being delivered to the user. Therefore, the physician may then directly modify the setting, e.g., increase the setting value, that was determined to be programmed too low. As will be discussed in more detail below, some embodiments of the GUI 454 enable a user, or the user's physician, to view multiple settings across multiple time spans within at least one delivery profile 458, which may be displayed on a single touch screen 452 display 450 (as shown by way of example in FIG. 49). Furthermore, from this condensed view of information, a user or physician may directly manipulate one or more of the settings displayed on the touch screen 452 display 450. This condensed view, and the added benefit of enabling direct manipulation of the settings displayed in the condensed view, may further improve a physician's ability to respond efficiently and effectively to a patient's needs.

At least a part of the GUI 454 includes an information architecture 460 and a hierarchy of pages (or display representations) 456 that assist the portable infusion device 110 in interacting with the user by collecting and displaying information, as well as guide a user on how to use the device 110. The information architecture 460 may provide a general roadmap for accessing a variety of programs and information accessible by the control unit, or processor 170, of the portable infusion device 110. A user is generally able to interact with the GUI 454 to set up, for example, customizable insulin delivery profiles 458 based on the user's current and predicted future insulin needs. This may be accomplished, at least in part, by a user navigating through one or more infusion workflows, or protocols embedded within a program accessible by the processor 170 of the portable infusion device 110.

An infusion workflow 464, or protocol, may be at least part of a program that, when executed by the processor, assists a user to at least program or control the portable infusion device 110 and/or at least one operation comprising enter, change, confirm, or view various information within the device 110. Any part of a workflow 464 or protocol may include any number of queries for prompting the user to enter, modify, or confirm information, which are typically presented to the user on the display.

For example, a program accessible by the processer that includes an infusion workflow 464 or protocol may enable a user to program the portable infusion device to deliver insulin to the user. In addition, an infusion workflow 464, or protocol, may present the user with a number of understandable queries for allowing the user to enter, confirm or modify information regarding the physiological conditions of the user. For instance, queries presented to a user during the execution of a program may enable a user to set various settings within the portable infusion device (e.g., the time, date, or one or more alarms) and/or enter information about a users present or predicted conditions (e.g., blood glucose level, physiological conditions, food to be ingested, etc).

In some embodiments, the linear approach of a workflow 464, or protocol, for programming the portable infusion device is at least limited. As an alternative approach, the user is instead provided with a virtual form 462 displayed on the touch screen 452 display 450 for the user to complete. A virtual form 462 enables a user to directly select and manipulate one or more parts of a displayed virtual form 462, with each part generally representing a setting. In this way, a user is not required to navigate through a generally linear workflow 464 or protocol and/or prompted with a series of queries. Instead, the user is presented with generally a single page 456 where the user completes the virtual form 462 in order to initiate a programmed delivery of insulin, as will be discussed in greater detail below and shown by way of example in FIGS. 53A-53C and 48-49.

Some GUI page 456 or screen representation embodiments of the GUI page hierarchy enable a user to easily access and view one or more settings and information within the portable infusion device. A single page 456 may include one or more objects 466 simultaneously presented on the touch screen 452, where an object 466 may be any number of text, numbers, graphs, pictures, video, or combination thereof which display understandable information to a user. The information may have been entered by a user and/or presented by the portable infusion device 110, and may at least be one of information regarding the amount of insulin already present in the body, e.g., insulin on board; blood glucose level; trending glucose level; insulin sensitivity/insensitivity; glycemic index; metabolism; metabolic rate; stress level; physiological conditions, e.g., age, health, sickness, diurnal cycles, etc; measurable parameters: hormones, steroids, etc.; pharmacokinetics of the medicament, e.g., age of insulin, decay rate, etc.; food to be ingested, e.g., carbohydrates, proteins, fat; activity; use history; calendared events; environment, e.g., temperature, humidity, pressure, etc.; and the like. An object 466 may represent any number of information without departing from the scope herein, and may also be in the form of a pictogram to generally intuitively represent, for example, a program, file, user, setting, status, profile, action or other entity discussed herein.

Furthermore, any object 466 may be a soft key so that when the user touches the object soft key, the "selection" of the object 466 is communicated to the processor. How the processor 170 interprets the selection of an object 466 depends, at least in part, on which program is currently executing and what the selected object 466 represents. For instance, selection of an object 466 may be processed by the processor 170 such that the user is given an opportunity to modify displayed information, or the user may be directed to another page 456 within the GUI page hierarchy. Various examples of programs, workflows 464, displayed objects 466, and user selections of objects 466 displayed on the portable infusion device 110 display 450 will be described in more detail below.

By way of one example, an object 466 displayed on the touch screen 452 may represent the number of units of insulin programmed to be delivered to the user. In addition, this object 466 may be a soft key so that when the user selects the object 466, the user is given the opportunity to modify the number of units of insulin programmed to be delivered to the user. The number may be modified by a variety of operations. For example, the display may show a virtual keyboard or keypad 500 for actuation, or may receive input through multi-touch techniques, or may receive input through actuation of a physical button or keypad (not shown). One possible advantage of some embodiments may be that multiple objects 466 may be simultaneously displayed on the touch screen 452 of the portable infusion device 110, including any one of which may be a soft key, so that any one of the multiple modifiable objects 466 simultaneously displayed may be directly manipulated by a user. Moreover, the user can view values of multiple parameters, such as parameters comprising a delivery profile 458, on a single display screen 450 or page 456. Therefore, a user is not limited to having to scroll through more than one page 456 to view, enter, or change, for example, a value, range, graph, or any object 466 representing any number of information entered by the user or presented by the portable infusion device 110.

GUI 454 embodiments of the portable infusion device may serve multiple purposes, including informing the user about various settings, activities, and/or statuses relating to the device, as well as providing a means for the user to enter, confirm, and/or modify displayed settings and/or values. Furthermore, the GUI 454 may also provide the user with video or animated graphics to enhance the ability to instruct or inform a user and improve usability. For example, animated graphics and/or video may be displayed on the touch screen 452 to assist in instructing the user on how to operate the portable infusion device 110, such as load insulin into the device 100.

The GUI 454 of the portable infusion device 110 may also include any number of features for assisting in preventing the user from entering, changing, or accepting any information that may be incorrect. For example, the user may be presented with confirmation pages and/or queries where the user is required to confirm one or more presented information. Some GUI embodiments of the portable infusion device may also prevent the user from selecting one or more objects 466 displayed on the touch screen 452 in order to prevent the user from selecting or entering incorrect information, as will be discussed in more detail below. Some GUI embodiments of the portable infusion device may prevent unauthorized access to accommodate at least privacy, HIPPA regulations, and/or other concerns. For example, passwords, biometric sensors, etc., could be incorporated in the portable infusion device system as well as encrypted processors and data transmission to assist in added security and/or privacy of the device.

GUI 454 embodiments may also interact with a variety of pre-programmed or user programmed alarms integrated in the portable infusion device 110 for at least assisting in alerting the user and/or preventing user error. For instance, the portable infusion device may utilize the GUI 454 to present important information to the user as to the status of the device (e.g., battery life, remaining medicament in the cartridge, occlusion in the fluid line, etc). For example, the portable infusion device 110 may warn the user by changing one or more colors on the display screen 450 of the portable infusion device 110 to alert the user. Alternatively, or in combination, the portable infusion device 110 may alert the user by sounding an alarm (e.g., a beeping noise) or vibrating the device. The user may program the portable infusion device 110 to alert the user for various reasons relating to at least one of a physiological measurement and/or a portable infusion device status. For example, in the context of insulin delivery, a user may program the portable infusion device to alert the user when a predetermined amount of insulin, e.g., one hundred units, fifty units, twenty-five units, or any number of units of insulin remain in the portable infusion device for dispensing.

Figure 26:
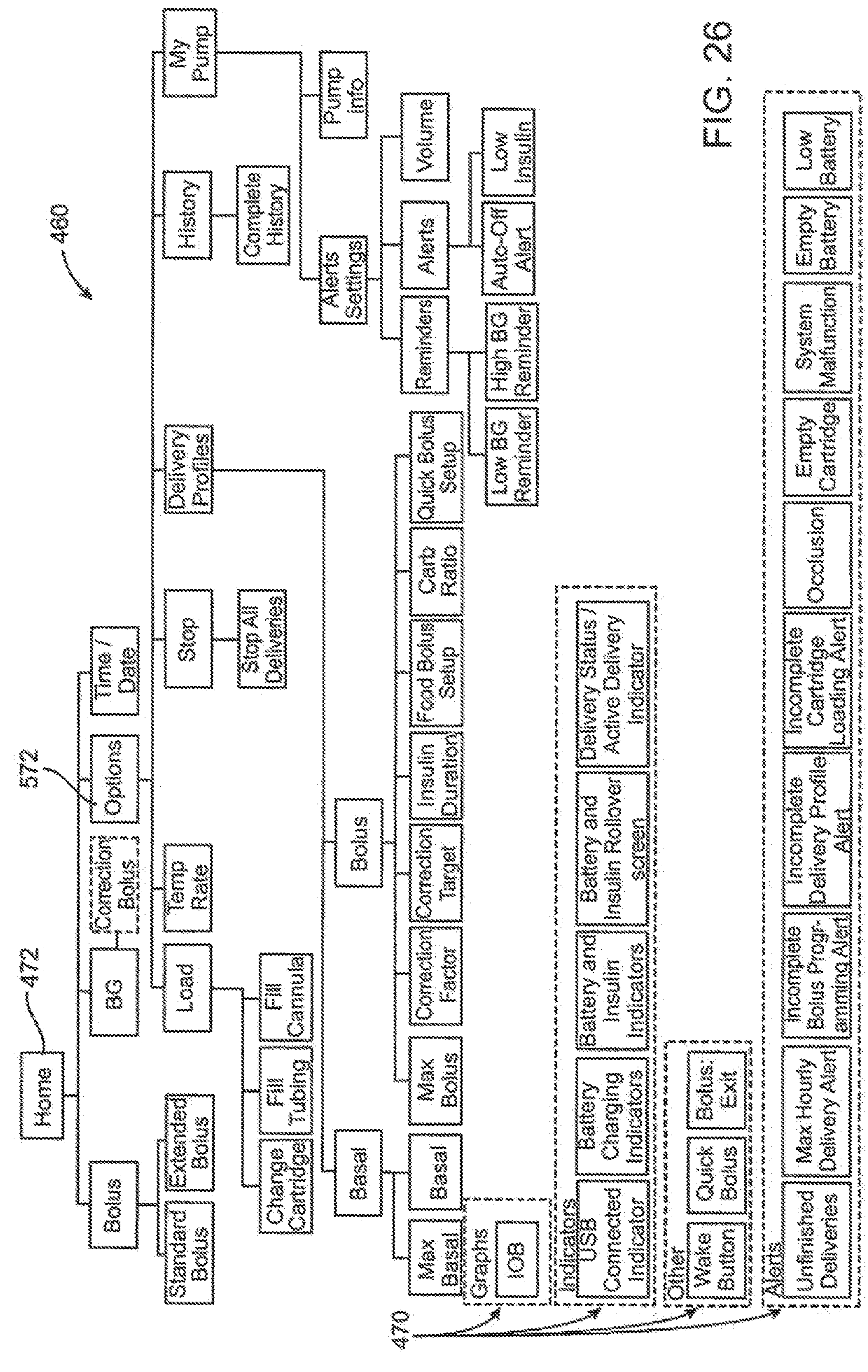
FIG. 26 is an embodiment of information architecture representing a part of a GUI page or screen hierarchy of portable infusion device embodiments discussed herein.

Turning now to the figures, FIG. 26 illustrates one embodiment of an information architecture 460, which illustrates at least a part of the GUI page 456 hierarchy, the interconnectedness of information within the device 110, and programmable settings of the portable infusion device 110 accessible by a user. Generally, in FIG. 26, the display screen 450 of each page 456 at a level of the hierarchy includes display objects 466 representing all of the objects 466 in the hierarchy level immediately below so that selecting one page will produce a screen or page 456 display with objects 466 that will allow navigation to the next lower level. In general, each display 450 will also include at least one object 466 for selection to return to the previous level in the hierarchy, and/or a physical "back" button may provide the same functionality. The information architecture 460 illustrated in FIG. 26, although shown in a configuration suitable for delivery of medicament such as insulin, is not meant to be exhaustive, and is, instead, a broad exemplary representation of some of the information and settings of the portable infusion device 110 accessible by a user. In addition, and shown surrounded in dashed-lines at the bottom of FIG. 26, the portable infusion device may include a number of various GUI features and functions 470, e.g., graphs, indicators, alerts, etc., which may be generally embedded and accessible by a user within the information architecture 460.

Figure 27:
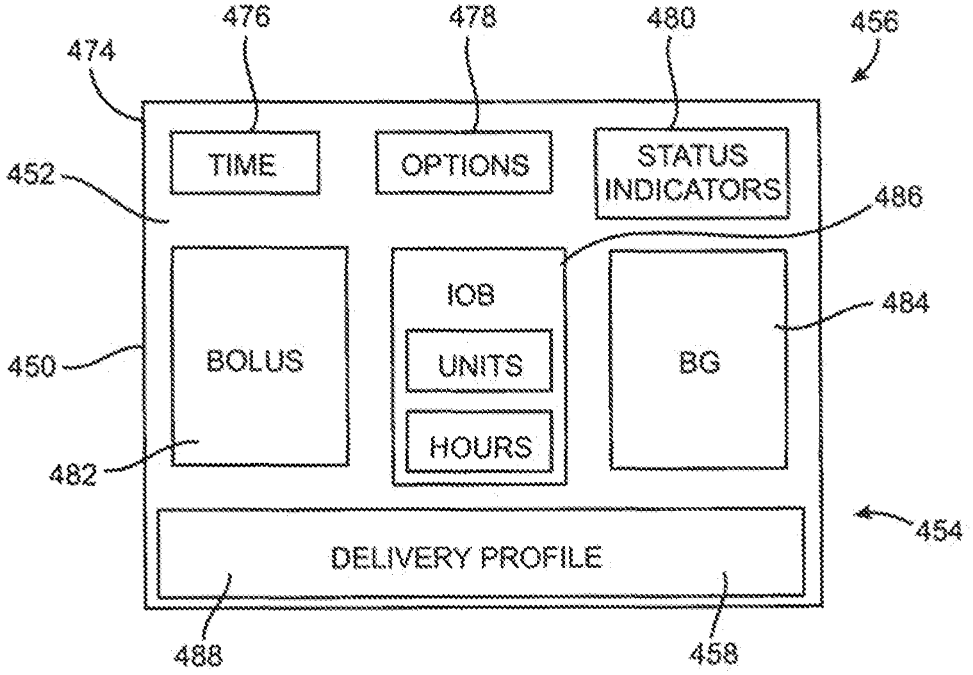
FIG. 27 is an embodiment of a screen shot of a home screen page of the GUI page hierarchy of the portable infusion device.

The "home" 472 location of the FIG. 26 information architecture 460 may represent a home screen page 474 on the display screen 450, as shown by way of example in FIG. 27. The home location 472 of the information architecture 460, or the home screen page 474, generally serves as the starting point for a user to access any information, program, or setting embedded within the information architecture 460, or GUI page 456 hierarchy. The home screen 474 is typically the screen representative or page 456 that is displayed to the user upon applying power or switching on the device 110. Any information displayed in the information architecture 460 may be displayed in at least part of a page 456 within the GUI page 456 hierarchy.

FIG. 27 illustrates one embodiment of a home screen page 474 displaying various objects 466, including a time object 476 (displaying the time and date), options object 478 (a menu option), a status indicator object 480 (displaying device status information, e.g., battery life), bolus delivery object 482 (initiates a bolus delivery program), blood glucose (BG) object 484 (directs user to deliver insulin based on BG level), insulin on board (IOB) object 486 (displays how much insulin remains in user's body over a period of time due to the delivery of one or more boluses), and a delivery profile object 488 (displays various information regarding insulin delivered to user). Any one of the displayed objects 466 on the home screen page 474 may be a soft key so that when a user selects any one of the objects 466, such as by touching the object with a finger or stylus, the processor 170 receives the selection and performs operations that execute instructions and/or receive further input, so the user is able to at least do one or more of the following; modify the object 466, be directed to a new page 456, or initiate a workflow 464 or protocol of a program. GUI 454 embodiments may provide a user with the ability to view and/or select multiple objects 466 simultaneously displayed on the touch screen 452 display 450 of the portable infusion device 110. In contrast, a user of an infusion device 110 without the capability of simultaneously displaying multiple selectable objects 466 would have to maneuver though multiple display screen representations 456 to accomplish what is readily available on a single page 456 of the present GUI page 456 hierarchy.

Figure 28:
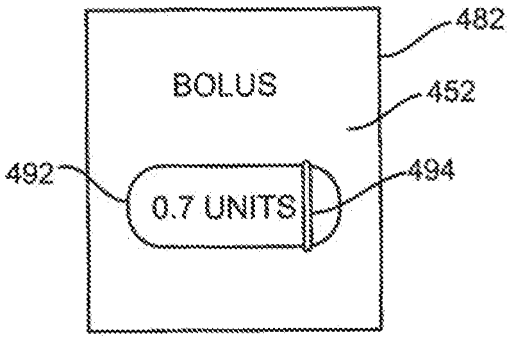
FIG. 28 illustrates an embodiment of a bolus object.

FIG. 28 illustrates an embodiment of a bolus object 482, which may be displayed on at least the home screen page 474. The bolus object 482 may be a soft key so that when selected by the user the processor initiates execution of a bolus delivery program that allows a user to setup a bolus delivery of insulin. Furthermore, the bolus delivery program may include a bolus workflow 490 or protocol which may, in combination with the processor 170 and memory 172 of the portable infusion device 110, present the user with pages 456 or screen representations having a number of queries and information for setting up an appropriate bolus of insulin to be delivered to the user.

In addition, once a bolus delivery has been setup, a bolus object 482 may also include a bolus status indicator 492 that provides feedback to the user regarding the programmed bolus delivery of insulin. For example, the status indicator 492 may provide feedback as to how much of the bolus has been delivered to the user. The bolus status indicator 492 may display the total bolus volume of insulin to be delivered (shown by way of example as 0.7 units). The bolus status indicator may also provide animated feedback, such as an animated indicator line 494 or bar that moves in a generally intuitive manner such that the status of the bolus delivery is generally understood by the user. Furthermore, feedback may be provided to a user for any number of reasons and may be portrayed to a user in various configurations, e.g., one or more blinking lights, color changes on the display 450, etc.

For example, the animated indicator line 494 may travel from one side to the other of the bolus status indicator 492 as the bolus is delivered to the user. By way of further example, as the animated indicator line 494 moves, the color on one side of the animated indicator line 494 may be a different color than the other side such that it is generally intuitive to a user as to the status of the bolus delivery. Therefore, the bolus status indicator 492 may provide efficient and user-friendly information that is easily accessible for a user to view and understand the status of a insulin being delivered.

Figure 29:
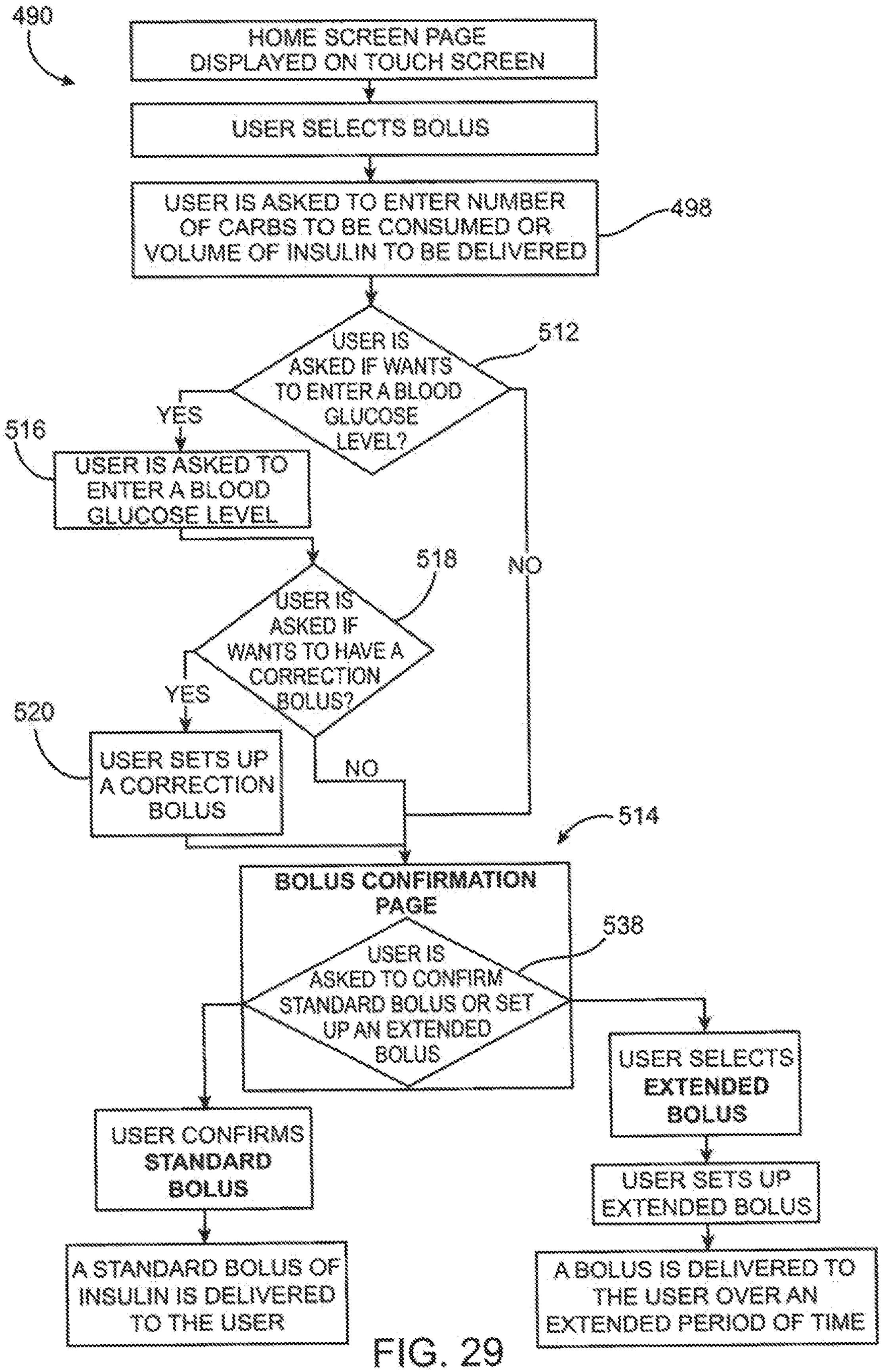
FIG. 29 is a flow diagram illustrating a method of programming the delivery of a bolus.
Figure 31:
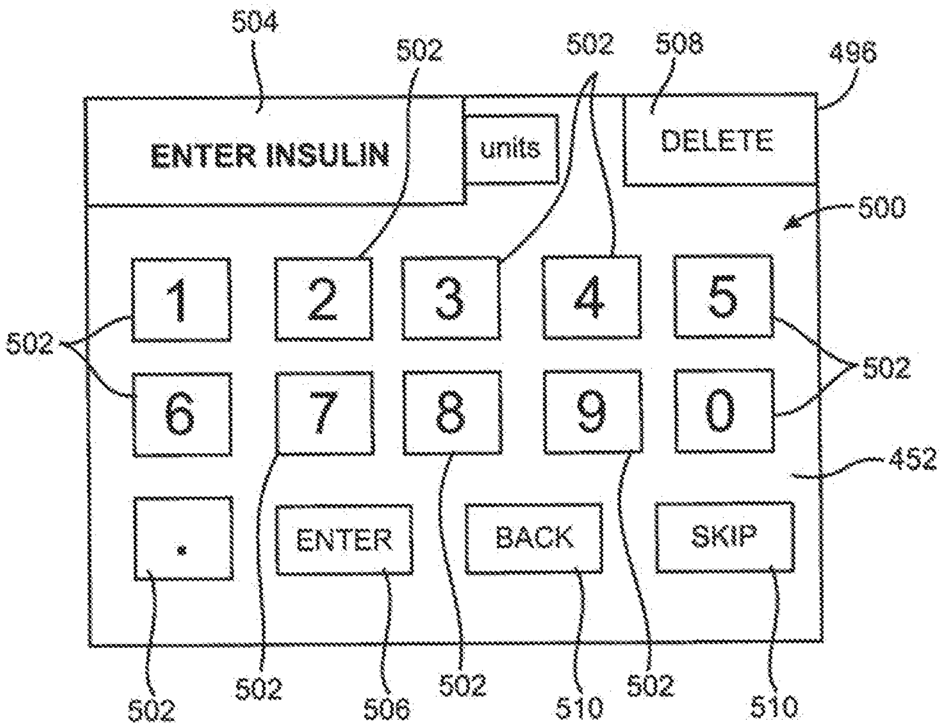
FIG. 31 is a screen shot of a virtual keypad displayed on the touch screen display for data entry.

FIG. 29 illustrates one embodiment of a bolus workflow 490 comprised of a number of interrelated pages 456 and pages displaying queries for enabling the user to program the portable infusion device 110 to deliver an appropriate bolus of insulin. The bolus workflow 490 may be initiated from the home screen page 474 in response to the user selecting the bolus object 482 soft key on the touch screen 452. Once the user selects the bolus object soft key 482, the processor 170 may load a bolus delivery program that provides instructions to the processor 170 for guiding a user through the bolus workflow 490. For instance, once the processor 170 is executing the bolus delivery program, the program will present the user with a page such as the insulin entry page 496 as illustrated in FIG. 31, that provides the user with a first query 498 of the bolus workflow 490. The first query 498 of the bolus workflow 490 may ask the user to either enter the approximate amount of carbohydrates (e.g., in grams) the user predicts to consume, or the volume of insulin (e.g., in units) the user would like delivered as shown in FIG. 31.

A user may enter the amount of carbs or volume of insulin in order to assist in programming the portable infusion device to deliver generally an appropriate bolus of insulin based on the amount of food the user has predicted to consume, which may also be referred to as the food or meal bolus. If the device 110 is programmed for the user to enter the number of carbs, the processor 170 may use a carb ratio (the amount of insulin delivered for every X number of carbohydrates consumed) to determine the food bolus of insulin to deliver to the user. In addition, a user may program the device 110 to prompt the user to enter any one or more of a variety of information to determine an appropriate food bolus, which may generally depend on the type of information the user wants to enter. For example, the user may program the device 110 to prompt the user to enter a blood glucose level and the number of carbs predicted to be consumed for programming a food bolus. Therefore, the portable infusion device 110 enables a user to customize the device 110 regarding what type of information the user will be prompted to enter for programming at least a bolus of insulin.

FIG. 31 illustrates one embodiment of a virtual keypad 500 which may be displayed on the touch screen 452 for allowing a user to input information. A virtual keypad 500 may include one or more user-interactive virtual keys 502 that enable a user to select one or more of the virtual keys 502 to enter information associated with each virtual key 502. A virtual keypad 500 may be presented to a user on the display 450 anytime the user selects to enter or modify, or is requested to enter or modify, any one of the multiple settings and/or entries stored on the portable infusion device 110. One or more virtual keys 502 illustrated in FIG. 31 are shown as relating generally to various numbers and a decimal.

Figure 35:
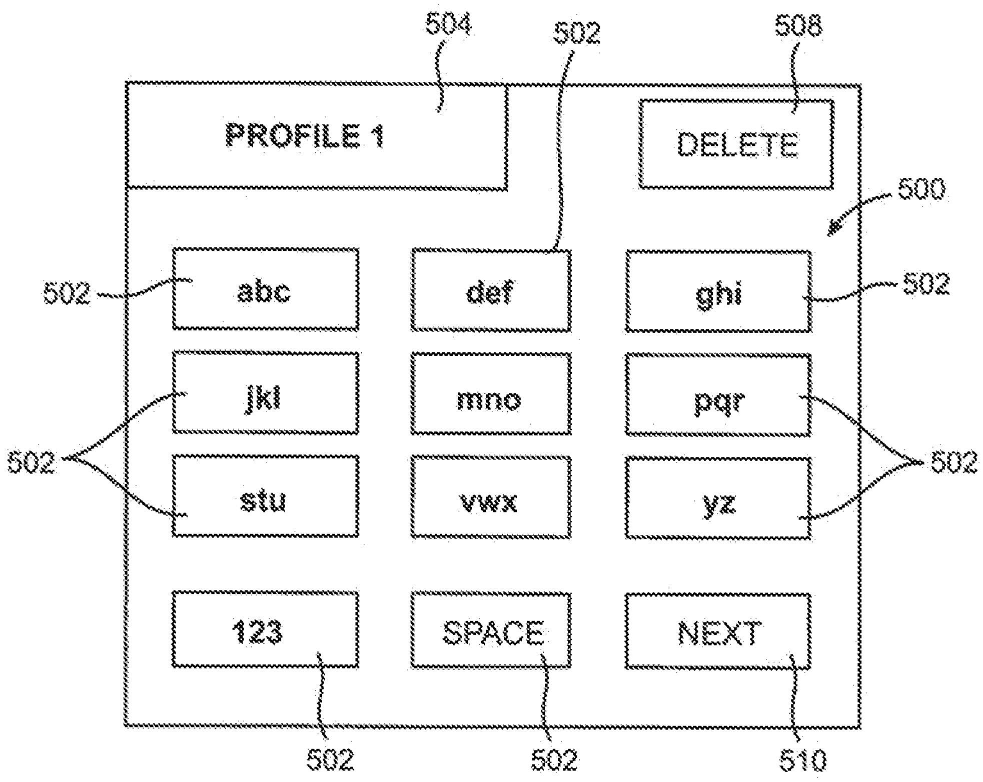
FIG. 35 is a screen shot of an embodiment of a virtual keypad displayed on the touch screen display for entering text.

Additionally, and shown by way of example in FIG. 35, a virtual keypad or keyboard 500 may include one or more virtual keys 502 relating to one or more letters and/or numbers. A virtual key 502 relating to one or more various input, e.g., number, letter, symbol, etc., as shown in some of the virtual keys 502 in FIG. 35, a may perform various interactions with these virtual keys 502 to cause a particular input to be made. For example, a user may sequentially tap, or select, a virtual key 502 one or more times to cause various entries to be made. By way of further example, a user may touch a virtual key 502 one time to input the letter "a," or may touch the same virtual key 502 two times to input the letter "b." Any number of user interactions with virtual keys 502 to cause various types and forms of input may be used to at least improve usability of the portable infusion device 110.

For instance, a virtual keypad 500 may be presented with queries in the text entry field 504 (such as the "enter insulin" query presented in the test field in FIG. 31) which may allow a user intuitively to respond to the query by selecting one or more of the virtual keys 502. As the user selects a virtual key 502, the information associated with the selected virtual key 502 is displayed in the text entry field 504. This provides the user with the ability to view the information selected and decide to delete or enter the selected information. Therefore, the virtual keypad 500 offers a user an efficient and intuitive means for entering information.

Although the virtual keypad 500 illustrated in FIG. 31 shows an "enter insulin" query in the text entry field 504, any number of text may be displayed in the text entry field 504 for either prompting or requesting information from a user. Furthermore, the virtual keys 502 may display and relate to any one of several types of user input, e.g., letters, numbers, symbols, text, pictograms, etc. for allowing a user to enter a variety of information into the portable infusion device 110. Additionally, an enter object 506, a delete object 508, and one or more navigation objects 510 (e.g., back, skip, next) may be presented as part of, or in combination with, the virtual keypad 468 for allowing a user to navigate to another page. Navigation objects 510, e.g., back, skip, and next, assist in enabling the user to easily navigate through a series of interconnected pages 456, such as in the bolus delivery workflow 490, and may be presented on any page within the GUI page 456 hierarchy.

Figure 30:
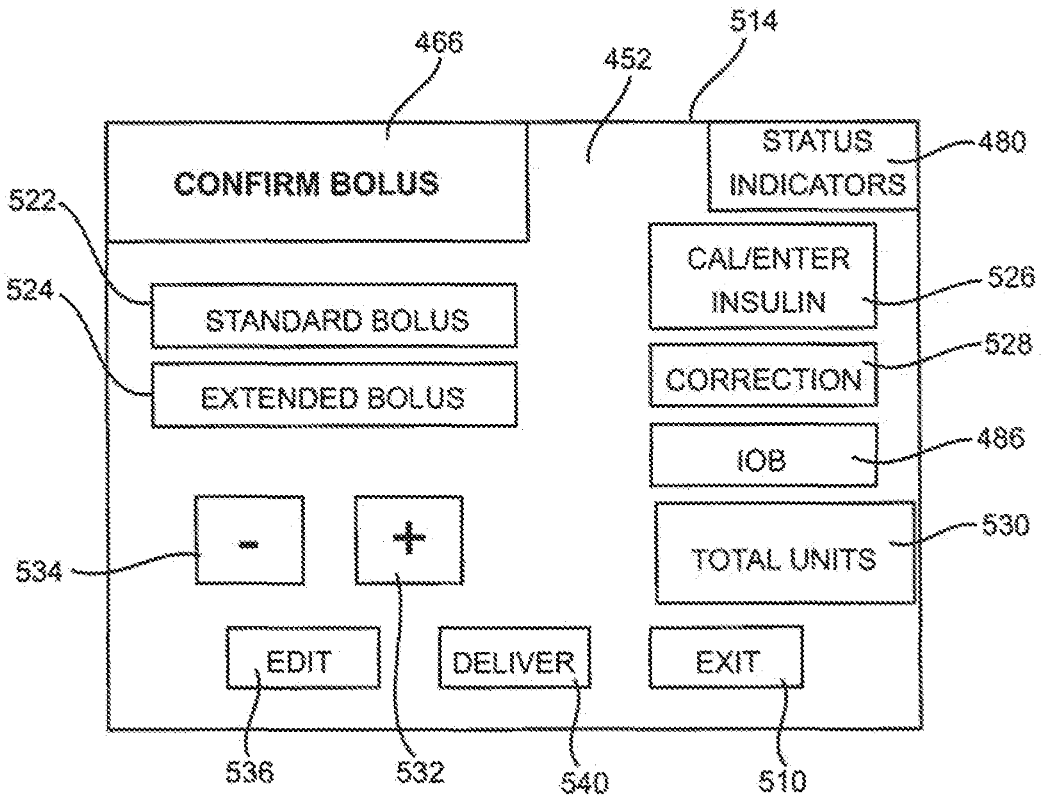
FIG. 30 is an embodiment of a bolus confirmation page of the GUI page hierarchy.

As illustrated in FIG. 29, once the user either skips or enters a selected entry in response to the first query 498 of the bolus workflow 490, the user is presented with a second query 512. The second query 512 asks the user if the user would like to enter a blood glucose level into the system. If the user chooses not to enter a blood glucose level, the user is directed to a bolus confirmation page 514, as shown in FIG. 30. If the user chooses to enter a blood glucose level, the user is directed to a third query 516 where the user is asked to enter a blood glucose level. A user would then enter a blood glucose level that the user, for example, obtained from a blood glucose measuring tool. As discussed above, the user may be presented with a virtual keypad 468 for entering a blood glucose level.

Alternatively, the portable infusion device 110 may include a feature that either continuously or selectively reads the user's blood glucose level directly. If the portable infusion device 110 includes such a feature, the user would not have to enter a blood glucose level and would not be presented with the third query 516. Instead, the blood glucose monitoring feature would input the user's blood glucose level automatically into a workflow or protocol, as necessary, or simply require the user to confirm a blood glucose level gathered from the blood glucose monitoring feature.

The fourth query 518 of the bolus workflow, may ask the user whether the user would like a correction bolus. A correction bolus may be used to deliver additional insulin in order to reach the user's programmed target BG level (the BG level the user would generally optimally like to have). If the user chooses not to have a correction bolus, the user is directed to a bolus confirmation page 514, as shown in FIG. 30. If the user chooses to have a correction bolus, the user is directed to a fifth query 520 asking the user to enter an appropriate correction bolus, or confirm a stored correction bolus.

Once the user has either skipped or entered information for at least one of the first five queries 498, 512, 516, 518, 520 of the bolus workflow 490, the user is presented with a bolus confirmation page 514. FIG. 30 illustrates one embodiment of a bolus confirmation page displaying a standard bolus object 522, extended bolus object 524, status indicator object 480, cal/enter insulin object 526, correction bolus object 528, IOB object 486, and total units object 530—any one of which display information either entered or confirmed by the user, or processed by the processor 170 based on any one of an entered, sensed, stored or confirmed information. More specifically, the standard bolus and extended bolus object 522 and 524 may be selected by a user for initiating a standard or extended bolus delivery of insulin, respectively. The status indicator object 480 may provide information to the user regarding the status of the portable infusion device 110, which will be discussed in greater detail below. The cal/enter insulin object 526 may display the amount of insulin calculated based on the expected consumption of carbohydrates or the number of units of insulin to be delivered entered by the user. The IOB object 486 may display information to a user regarding the amount of insulin that has been delivered to the user in the form of a bolus, and the general amount of time the user's body will need in order to metabolize that insulin.

One benefit of embodiments discussed herein may be that any one of the objects presented on the bolus confirmation page 514 may be a soft key for allowing a user to modify any one of the objects as well as decide whether a standard or extended bolus is the appropriate delivery profile. For example, the total units object 530 displayed on the bolus confirmation page 514 may be a soft key so that when a user touches, or selects, the total units object 530, the user is then able to modify the total units of insulin programmed to be delivered.

By way of further example, if the user touches the total units object 530, the user may be directed to a new page 456 displaying a virtual keypad 500 to enable a user to enter an appropriate number. Once the user enters an appropriate number, the user would then be directed back to the bolus confirmation page 514. Alternatively, the user may not be directed away from the bolus confirmation page 514 to modify an object. For example, a user may touch either the total units object 530 on the bolus confirmation page 514 and be given a visual or audible indicator (e.g., flashing total units object, a color change of the total units object, and/or an audible indicator) to inform the user that the total units of insulin may be altered. The user may then touch the "plus" object 532 or "minus" object 534 (as shown in FIG. 30) to cause the total units of insulin to incrementally increase or decrease, respectively. A plus object 532 and minus object 534 may be displayed on any page 456 necessary, and may be displayed instead of, or in combination with, a virtual keypad 500 for entering information. One advantage of the virtual keypad 500 is that the user may enter a value for a setting with greater resolution in comparison to selecting "plus" and "minus" objects 532 and 534 on the touch screen 452 display 450 that are set to increase or decrease, respectively, at generally specific increments.

By way of another example, a user may select the edit object 536 soft key on the bolus confirmation page 514 which allows the user to alter one or more subsequently touched objects 466 displayed on the bolus confirmation page 514. An edit object 536 soft key may be displayed on any page 456 in the GUI page hierarchy for modifying one or more modifiable objects 466, as described above. Furthermore, any modifiable object displayed on the touch screen 452 display 450 of the portable infusion device 110 may be selected and modified by a user using any method and/or means described herein.

As discussed above, the bolus confirmation page 514 displays more than one modifiable object generally related to the programmed delivery of a bolus of insulin to a user. One possible advantage of some GUI embodiments of the portable infusion pump may be the ability to view and directly modify more than one modifiable object displayed on the touch screen 452. Because GUI 454 embodiments may be able to display multiple settings that may be directly manipulated by the user, the user is not required to memorize stored entries and navigate through multiple pages 456 to at least view or modify a setting. The ability of the GUI 454 of the portable infusion device 110 to provide this feature may improve the usability of the device and reduce user error.

In addition, the bolus confirmation page 514 also offers the user the option to select a standard or extended bolus by touching either the standard bolus object 522 or extended bolus object 524, respectively. As illustrated in the bolus workflow 490 example FIG. 29, a sixth query 538 is generally presented on the bolus confirmation page, which asks the user to choose between a standard or extended bolus of insulin. Generally, a standard bolus delivers the programmed volume of insulin immediately upon completion of the bolus delivery set-up, and an extended bolus allows a user to program the portable infusion device to deliver the bolus over a defined duration.

If the user chooses a standard bolus (e.g., by selecting the standard bolus object 522 followed by the deliver object 540), the user may then be presented with a bolus delivery confirmation page where the total units of insulin to be delivered to the user is displayed along with a countdown timer 542 and a cancel object. The countdown timer 542 may begin at any time duration, either set by the user or pre-programmed in the portable infusion device 110, to allow the user some time to cancel the delivery of the bolus, e.g., by selecting the cancel object. The countdown timer appears on the display 450 and begins to countdown to zero at about the same time the bolus delivery confirmation page appears on the touch screen 452. By way of further example, the countdown timer 542 may begin at five seconds, thus giving the user about five seconds to decide whether to select the cancel object to cancel the programmed bolus delivery of insulin.

Once the countdown timer 542 counts down to zero time, the processor 170 instructs the delivery mechanism 384 or 132 of the portable infusion device 110 to deliver the programmed bolus of insulin to the user. If an emergency exists, for example, and the user wants to attempt to stop the insulin being delivered to the user after the countdown timer reaches zero, the user may hard-stop the portable infusion device by powering off the device. The countdown timer 542, along with the displayed total volume of insulin to be delivered and a cancel object 544, may provide a user with a further opportunity, in addition to the bolus confirmation page, to generally ensure a proper amount of insulin is being delivered to the user. A countdown timer 542, along with a cancel object 544, may be displayed to a user on the touch screen 452 display 450 prior to any delivery of insulin to a user and is not limited to only prior to the delivery of a standard bolus. It may be a benefit of some embodiments to provide the user with multiple opportunities to view and modify insulin delivery settings in order to at least improve the usability and reduce user error of the portable infusion device 110.

Figure 32:
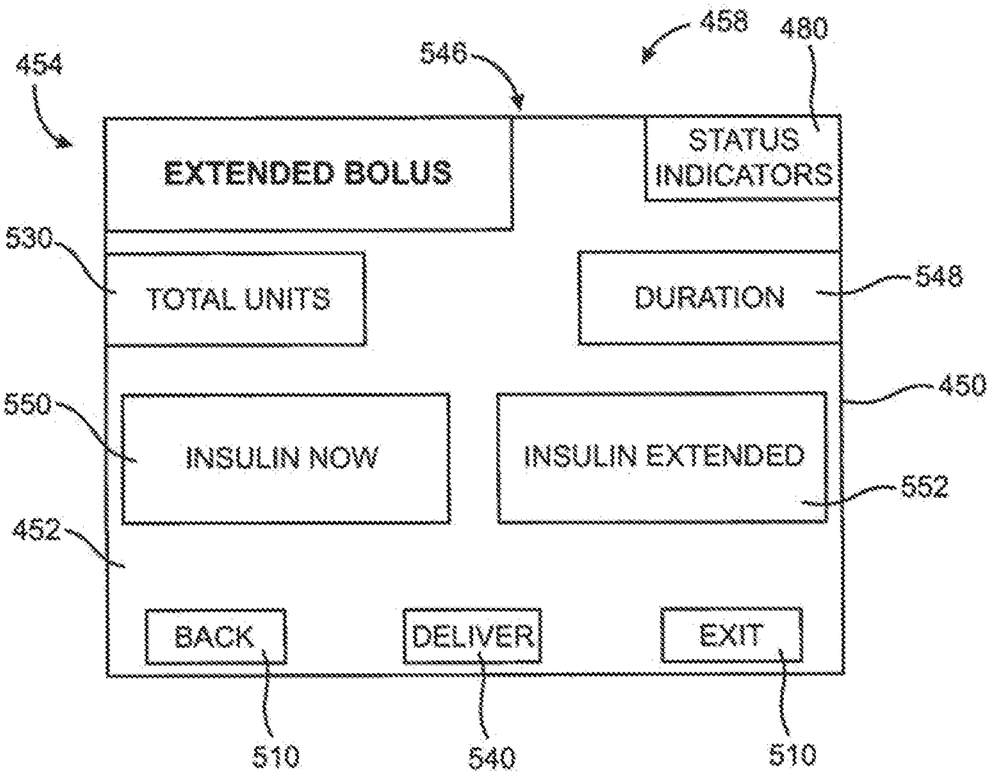
FIG. 32 is a screen shot of an embodiment of an extended bolus setup page.

Alternatively, to the standard bolus, the user may choose to have an extended bolus delivered (e.g., by sequentially selecting the extended bolus object 524 followed by the deliver object 540 on the bolus confirmation page 514). The user may then be directed to an extended bolus setup page 546 where the user is presented with multiple modifiable objects representing settings relating to the delivery of an extended bolus. FIG. 32 illustrates one example of an extended bolus setup page 546, including a total units object 530 (displaying the total units of insulin to be delivered), duration object 548 (displaying the duration that an extended bolus will be delivered), insulin now object 550 (displaying the units of insulin to be delivered generally immediately after setup of the extended bolus), and an insulin extended object 552 (displaying the units of insulin to be delivered over the defined duration)—any one of which may be a soft key, so that when selected a user can modify the selected object. Any one of the modifiable objects may be modified by at least any one of the methods described herein for modifying an object, e.g., selecting user-interactive plus and minus objects 532 and 534 to increase or decrease, respectively, object 466 values; direct user entry by way of selecting one or more of a letter, number, or symbol displayed on the touch screen 452 display 450 in the form of a virtual keypad 500; or user selection of an edit object 536 whereby subsequent object selections allows the user to modify the objects 466.

A user who decides to have an extended bolus of insulin delivered may define a number of units to be delivered immediately upon completion of the extended bolus delivery setup, as well as a defined number of units delivered over a defined duration. This customizable delivery profile may benefit the user by delivering insulin generally more equivalent to the user's insulin needs over a period of time, which may be due to any one of the various factors influencing a body's insulin needs, as described above.

One advantage of a portable infusion pump 110 for medicament delivery in general and specifically in the context of insulin is the ability to deliver such complex and customizable insulin delivery profiles 458 to a user that would be extraordinarily difficult, if not impossible, to achieve with standard syringe delivery methods currently used by a significant number of diabetics. As the complexity and customization of insulin delivery devices increase in order to provide users with improved delivery profiles, so may the user errors. Again, it may be a benefit of some embodiments to provide a GUI 454 with improved usability, which include the ability to simultaneously present multiple modifiable settings for a user to either view or modify. Therefore, this may allow embodiments of the portable infusion device 110 to provide the user with complex insulin delivery profiles 458 that generally better serve the user's insulin needs, while also reducing user error by providing the user with condensed and easily modifiable information pertinent to the delivery profiles 458.

Figure 33:
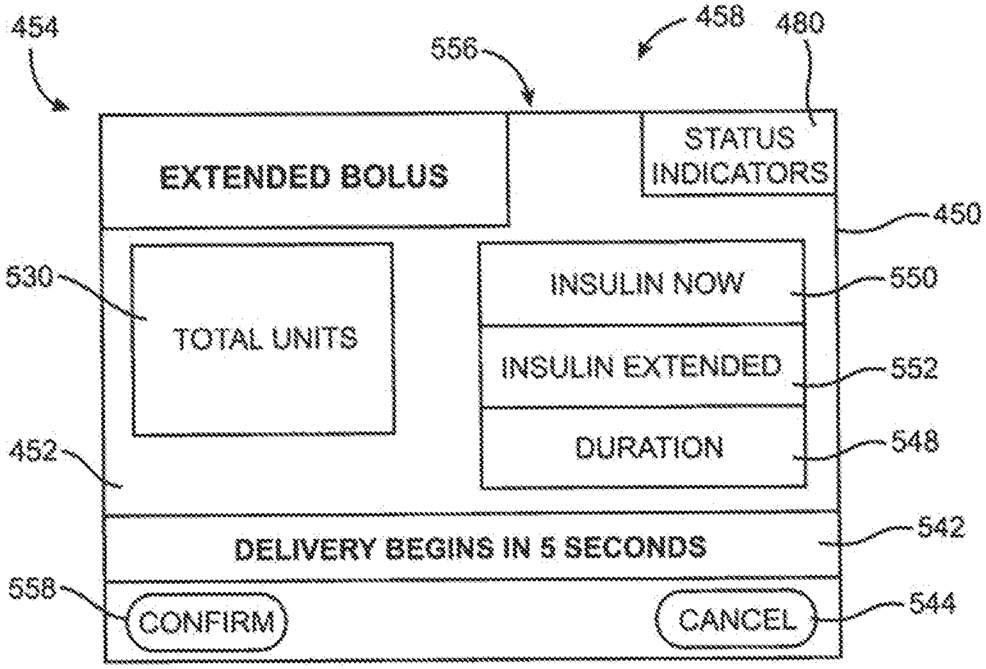
FIG. 33 is a screen shot of an embodiment of an extended bolus confirmation page.

Similar to the standard bolus setup described in the example above, once a user has completed viewing and modifying any information presented on the extended bolus setup page 546, the user may select the deliver object 540 to initiate the delivery of the extended bolus. As illustrated in FIG. 33, the user may then be presented with an extended bolus delivery confirmation page 556 where information pertinent to the programmed extended bolus is displayed (e.g., total units of insulin, units of insulin to be delivered generally immediately after delivery setup, units of insulin to be delivered over an extended duration, the duration over which the extended bolus will be delivered, etc.). In addition, a confirm object 558 and cancel object 544 are displayed to allow a user to either confirm or cancel the extended bolus programmed in the portable infusion device for delivery. The user may select the confirm object 558 to initiate delivery, at which time a countdown timer 542 appears on the touch screen 452 (as shown in FIG. 33) and gives the user another opportunity to select the cancel object 544 to cancel the programmed delivery of insulin, as described above. Once the countdown timer 542 counts down to zero, the processor 170 instructs the delivery mechanism of the portable infusion device 110 to deliver the programmed extended bolus of insulin to the user.

Another feature of the portable infusion device 110 for assisting in preventing an undesired volume of insulin delivered to a user is referred to herein as the dynamic error prevention feature 560. The dynamic error prevention feature 560 of embodiments may assist in preventing a user from incorrectly selecting one or more objects 466 displayed on the touch screen 452 display 450. For example, and illustrated in the insulin delivery example of FIG. 34, a virtual numeric keypad 500 may be displayed on a display screen 450 which include number and symbol object soft keys (displayed as virtual keys 502) for user selection. However, any one of the virtual keys 502 may be deactivated such that when a user touches the deactivated object 562, it is generally not communicated to the processor 170 as an entry. At least one object appearing on the display 450 will be a soft key so that when selected, the processor 170 will be informed of the selection for subsequent processing. The deactivated objects 562 may ensure that a user does not accidently enter in a value that is too large or too small based on information known by the portable infusion device 110, for example, either as pre-programmed or user defined limits. The de-activation and activation of objects 466 presented on the touch screen 452 for user selection is dynamic and may change subsequent one or more selections by a user on the touch screen 452.

For instance, in the context of insulin delivery, the user may have programmed the portable infusion device 110 to limit the allowable volume of insulin to be delivered over a specified duration. Therefore, if the user programmed the portable infusion device 110 not to allow more than twenty-five units of insulin to be delivered over the period of an hour, the virtual keyboard 500 would not allow the user to initially select any of the virtual keys 502 corresponding to a value greater than two. If the user selected a virtual key 502 displaying a one or a two, the number would appear, for example, in the text field 504 on the display 450. However, if the user attempted to select an object 466 displaying a number three, or greater than three, either no number would appear in the test field 504 and/or a warning may be displayed on the display 450 for informing the user that the selection is not acceptable. Because this feature is dynamic, after the user selects an acceptable entry, the deactivated and activated objects may change. Therefore, if the user selects an object 466 displaying a one or a two, as described above, any object 466 displaying a number less than or equal to five would be activated for user selection while any object 466 displaying a number greater than five would be deactivated. Therefore the user would be prevented from entering a value greater than twenty-five, as previously defined by the user. Furthermore, after the user selects a second acceptable entry, at least all of the numeric virtual keys 502 would be deactivated such that the user would only be able to select the delete 508, enter 506, back 510 or skip 510 objects in order to prevent the user from selecting an entry greater than twenty-five. Therefore, the dynamic error prevention feature 560 assists in preventing the user from entering an undesired value, and may be used to generally limit a user's available selections on the touch screen 452 display 450. In addition, the dynamic error prevention feature 560 advantageously assists in relieving the user from having to read an error message and then go back and re-enter a new setting value. This may benefit the user by eliminating time wasted due to entering values that are programmed to be unacceptable.

The dynamic error prevention feature 560 may also improve usability by relieving the user from having to recall what had been previously determined to be appropriate limits of various settings, for example, while being consulted by a physician. Therefore, a physician, physician's assistant, nurse, certified diabetes educator, etc., may assist a user of the portable infusion device to store acceptable parameters to any number of settings modifiable by a user so that a user does not later attempt to program a user modifiable setting that is out of the user's appropriate range.

In addition, some GUI 454 embodiments may display the activated and deactivated objects such that they are visually distinct from each other to a user viewing the display. For example, the deactivated objects 562 may appear darker in color and/or less illuminated than the objects acceptable for selection. The visual distinction may assist in preventing a user from wasting time attempting to select objects that are deactivated and unable to select this may improve the efficiency and user satisfaction of the portable infusion device 110.

Figure 34:
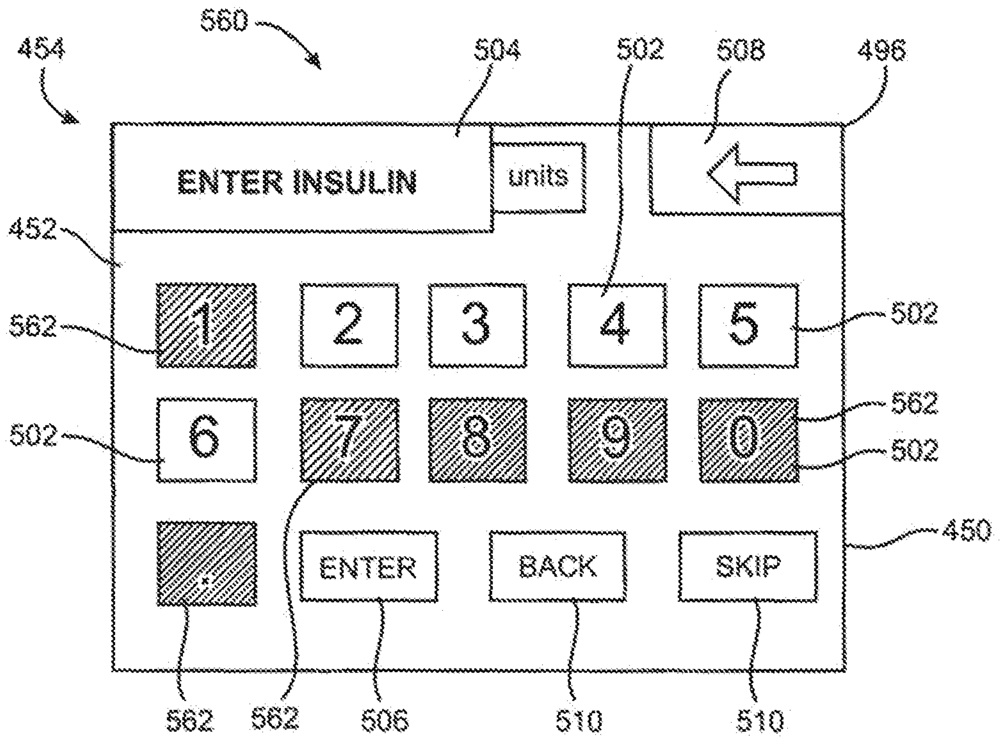
FIG. 34 is a screen shot of an embodiment of a virtual keypad employing a dynamic error prevention feature.

FIG. 34 illustrates an example of the dynamic error prevention feature 560 in the context of insulin delivery by showing a virtual keypad 500 displayed on the touch screen display. The virtual keys 502 displaying a decimal and numbers less than two and greater than six are displayed darkened relative to other objects (shown schematically in FIG. 34 as hash marks) in order to visually indicate to a user that those objects are unacceptable for selection. Objects displaying numbers two through six are displayed in higher relative contrast or in different colors, brightness levels, or combinations thereof, in order to visually indicate to a user that those objects are acceptable for selection. Any number of visual or audible indicators may be used to assist in making objects acceptable for selection distinct from objects not acceptable for selection without departing from the scope herein.

Figure 36:
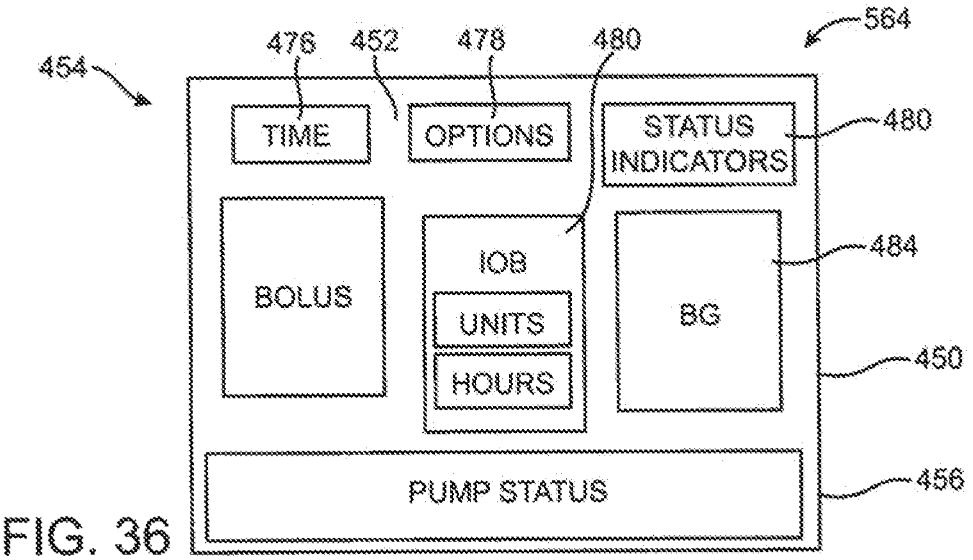
FIG. 36 is a screen shot of a home screen page embodiment.
Figure 37:
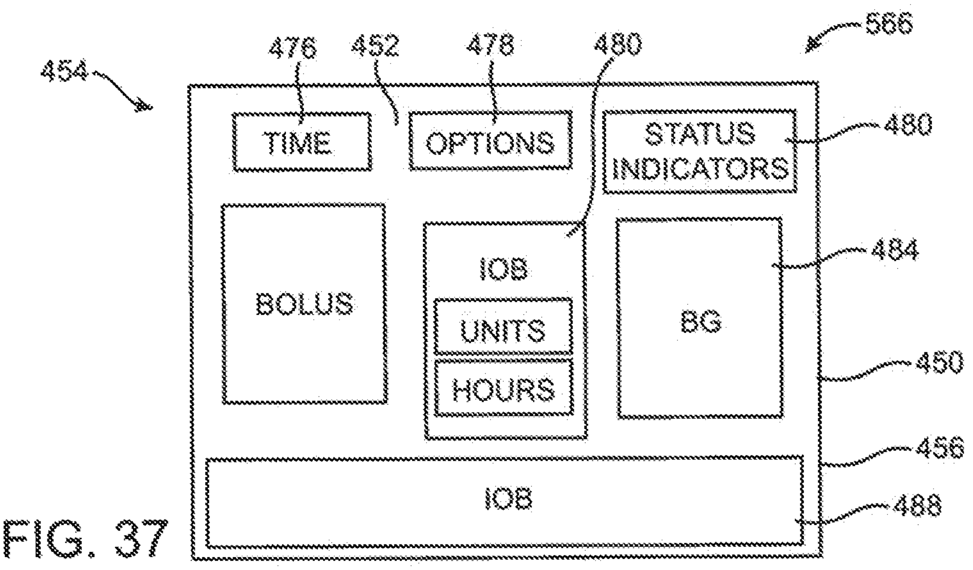
FIG. 37 is a screen shot of a home screen page embodiment.
Figure 38:
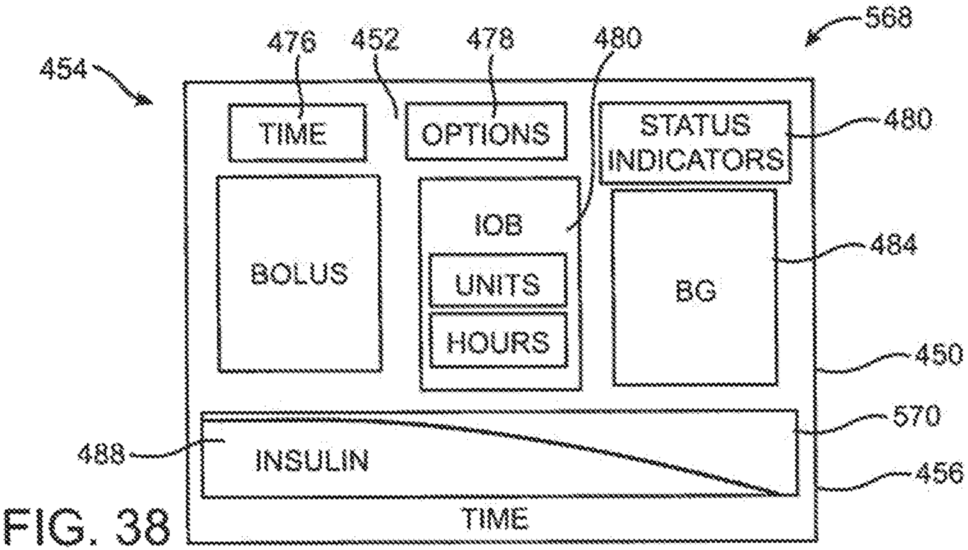
FIG. 38 is a screen shot of a home screen page embodiment.

FIGS. 36-38 illustrate additional embodiments of the home screen page 564, 566 and 568 that may be displayed on the touch screen display of the portable infusion device in the context of insulin delivery. A user may select among various configurations and/or displayed information to have as the user's home screen page, which may be continually changed as desired or necessary. For instance, the user may select from a variety of delivery profile objects 488 that may be displayed, for example, in the bottom portion of the display screen 450, such as the pump status object shown in FIG. 36. The ability for a user to generally customize the information presented on the home screen page generally improves the usability of the portable infusion device.

A delivery profile object 488 may display one or more items of information relating to the history, current status, and/or programmed future status of the delivery of insulin from the portable infusion device 110. In addition, the one or more items of information displayed within a delivery profile object 488 may be presented in numerical, textual, graphical and/or symbolic form. Additionally, as described above, where at least a part of the display 450 is configured for graphical representation 570, the graphic representation 570 may be configured for manipulation by a user touching or otherwise "clicking" the representation 570 and dragging the representation 570 in a predefined manner so as to change the form, e.g., height, width, shape, etc. of the representation.

A delivery profile object 488 may display information relating to the status of the pump, where the user is informed that all deliveries have been stopped, or what name or type of delivery profile 458, or personal profile, is currently being delivered to the user. As illustrated by way of example for insulin delivery in FIG. 37, the delivery profile object 488 (shown labeled as "IOB") may display information relating to the amount of insulin that has, and will be, in the user's body as a result of one or more boluses of insulin delivered to the user over a given amount of time. Furthermore, the IOB information may be displayed in numerical, textual, graphical and/or symbolic form. FIG. 38 illustrates an example in the context of insulin delivery of the user's IOB information displayed in graphical form 570 in the delivery profile object. By presenting this information in graphical form 570, a user may at least easily visualize the decay rate of insulin remaining in the user's body over a generally defined duration of time (based on the personal and/or delivery profiles of insulin programmed to be delivered to a user over the defined duration of time).

In general, a user may select among different home screen page representations and configurations for displaying various information in a variety of forms, e.g., graphical, numerical, textual, symbolical. This feature enables the user to customize the home screen page 474, 564, 566, 568 so that it generally displays information that is of particular interest to the user. Additionally, it allows the user some freedom to select what information the user would like to view in combination on the display screen 450. As discussed above, it may be a benefit of some embodiments to provide the user with the ability to view multiple selectable and/or modifiable objects 466 simultaneously displayed on the display screen 450 for comparing and directly manipulating one or more of the displayed information. A user may access a setup screen or initiate an administrative process that provides the user with options 572 for setup, as indicated in the hierarchy of FIG. 26.

Figure 39:
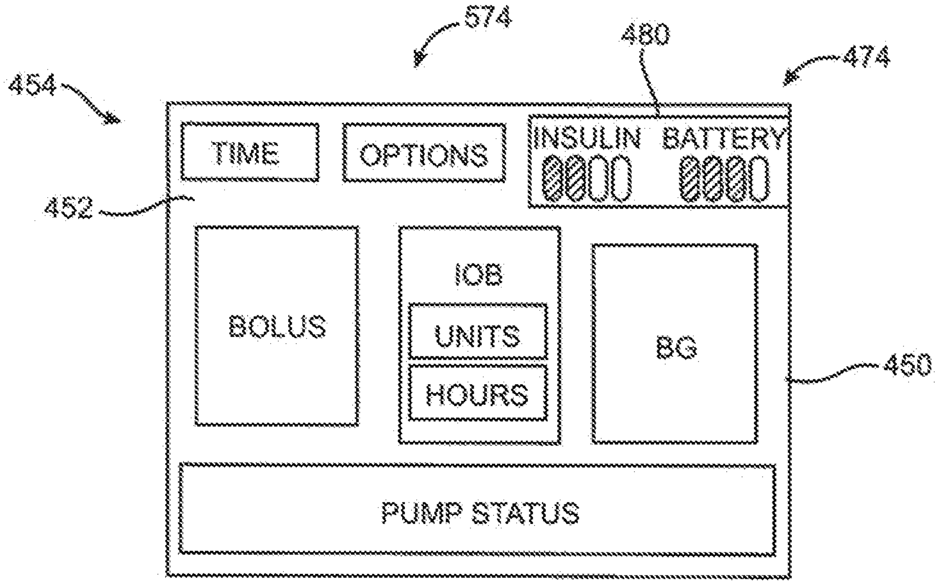
FIG. 39 is a screen shot of a home screen page embodiment.
Figure 40:
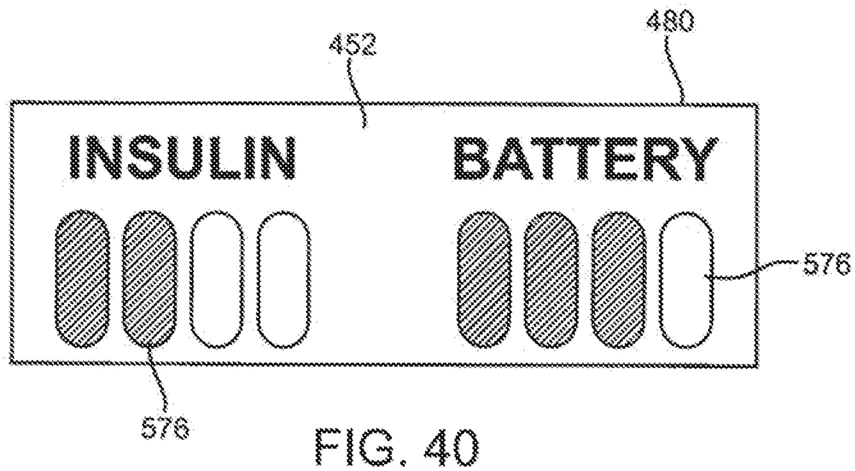
FIG. 40 is an enlarged view of a status indicator object displayed on a page of the GUI page hierarchy.

FIG. 39 illustrates an embodiment of a home screen page 574 further illustrating an embodiment of a device status indicator 480. A device status indicator 480 for insulin delivery that may be advantageously configured such that it is compact enough to be displayed on most pages 456 of the GUI 454 page 456 hierarchy and provide generally more vital information regarding the status of the device 110. For example, and as shown in FIGS. 39 and 40, a device status indicator 480 may display information regarding device 110 conditions, such as the amount of insulin and battery power remaining in the portable infusion device. A device status indicator may display any variation of numbers, text, and/or symbols for indicating to a user the status of various device conditions. Additionally, a device status indicator 480 may show one or more indicator bars 576 that may, for example, light up and/or change color to indicate to a user the condition of each status.

For instance, when the portable infusion device 110 is generally fully charged, all four of the indicator bars 576 may be a particular color and/or illuminated such that it is generally intuitive to a user that the portable infusion device 110 is fully charged. As the portable infusion device 110 consumes power, one or more indicator bars 576 may change in appearance, such as its color, brightness, or it may no longer illuminate. This change in appearance allows the user intuitively to understand that the portable infusion pump is no longer fully charged, as well as approximately how much battery life remains (e.g., percentage of full charge or time remaining) in the device. In addition to symbolic identifiers, such as indicator bars 576, any number of numerical, textual, symbolic and/or graphical representations may be displayed in the delivery status indicator for informing a user as to the status of any number of conditions of the portable infusion device.

Some portable infusion device embodiments may also alert a user (e.g., sound a noise, vibrate the device, flash the display screen) when the status of any number of device conditions reach a pre-programmed or user-defined condition level, or condition state. For example, the user may program the portable infusion device 110 to alert the user when the cartridge contains less than fifty units of insulin. By way of further example, the portable infusion device may also alert a user by any means described herein to inform the user when a programmed delivery of insulin is interrupted for any reason; that the maximum allowable delivery of insulin for a user has been reached, that a user profile and/or insulin delivery profile setup information is incomplete, that the insulin cartridge was not correctly loaded into the housing, that the insulin cartridge is empty, that there is an occlusion preventing delivery, that the system is malfunctioning, and/or any condition appropriate for alerting a user as to the status of the portable infusion device 110. Any one of the alerts may be customized by the user to alert at user-defined condition levels, or conditional states, in generally any way that the user prefers (e.g., vibrate the device, sound a noise, flashing display, etc.). As broadly illustrated by way of example in the information architecture 460 in FIG. 26, a user may setup one or more of the alerts discussed herein by selecting the options object 478 on the home screen page 474, then selecting the "my pump" object 578 on the options page. The user may then be directed to a "my pump" (not shown) page where a user may select an alert settings object, which may then direct a user to setting up one or more alert settings, as discussed above.

Figure 44:
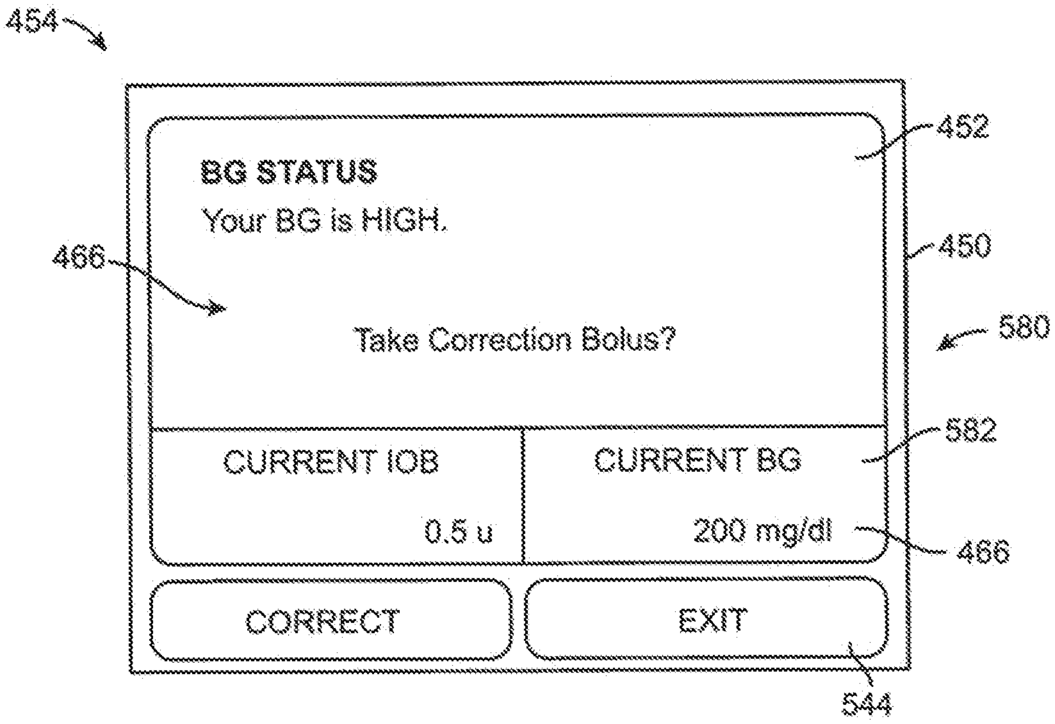
FIG. 44 is a screen shot of a blood glucose status page embodiment.

FIG. 44 illustrates one example of an alert page 580 which may appear on the display screen 450 alone or in combination with any of the alerts described above to alert a user as to any number of conditions. An alert page 580 may include one or more text, graphics, animation and/or video for informing a user as to the alert being made. Additionally, different features and/or colors may be applied to particular information displayed on the display screen for emphasizing the information. For example, the current BG object 582 (displaying the user's current blood glucose level), as shown in FIG. 44, may be displayed in red in order to further direct the user's attention to the information causing the alert, such as a high blood glucose (BG). Furthermore, a user may be able to directly modify a displayed modifiable object associated with information either directly or indirectly related to the alert being made. Therefore, the user may be able to efficiently learn and repair (e.g., by selecting the correct object on alert page 580 to correct the error by any means described herein for entering and/or modifying a setting or value) the condition which caused the portable infusion device 110 to display an alert on an alert page 580

Figure 45:
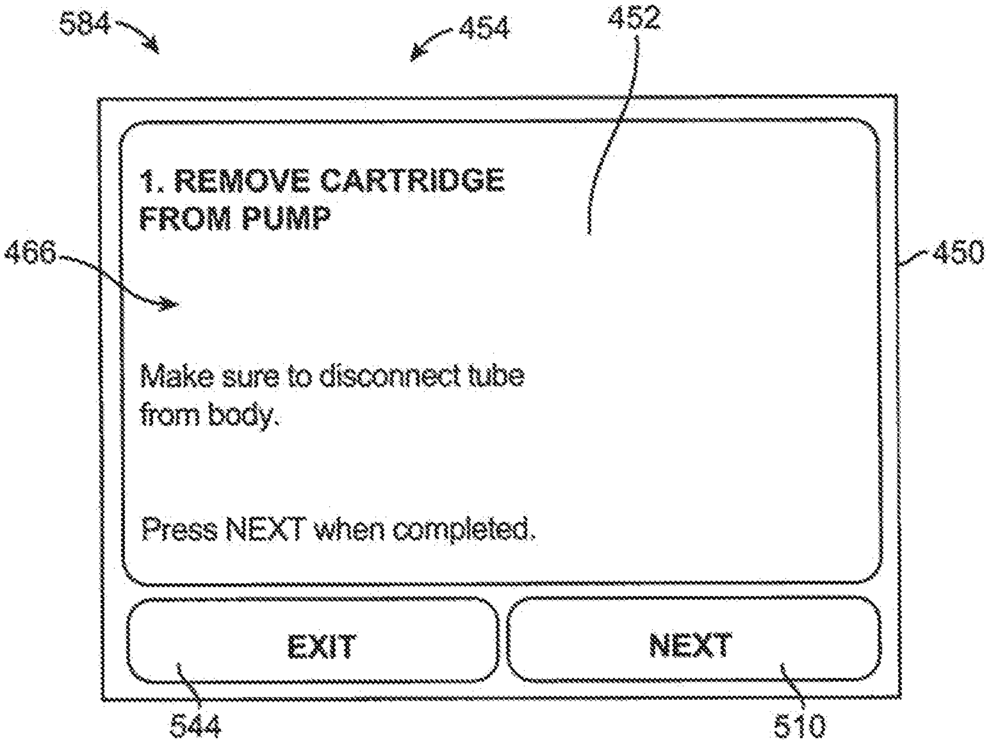
FIG. 45 is a screen shot of an instructional page embodiment for set up of a portable infusion pump.
Figure 46:
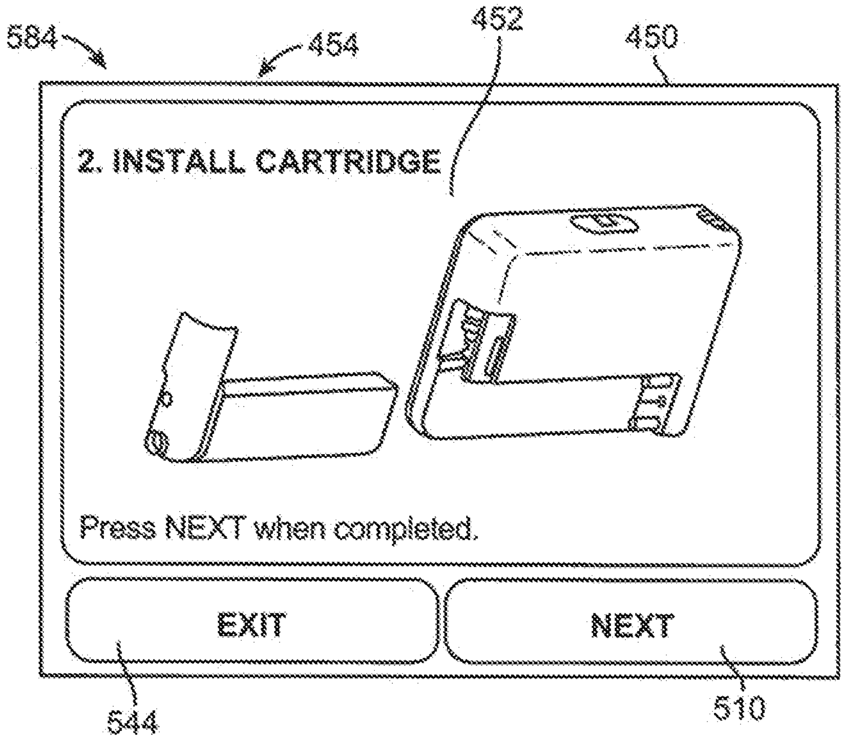
FIG. 46 is a screen shot of an instructional page embodiment for set up of a portable infusion pump.
Figure 47:
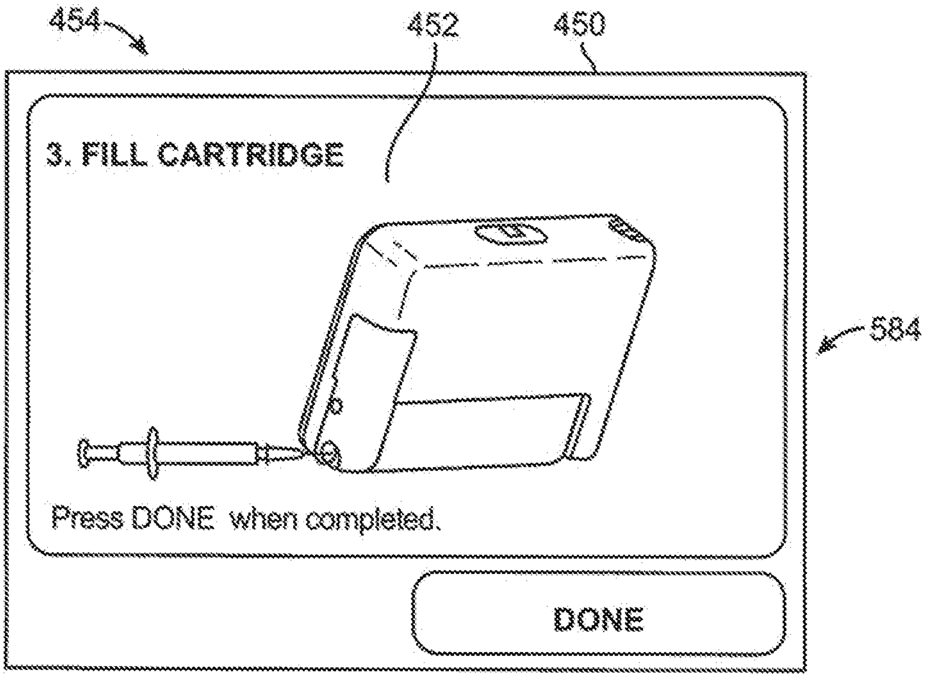
FIG. 47 is a screen shot of an instructional page embodiment for set up of a portable infusion pump.

FIGS. 45-47 illustrate display pages that show one example of an animation 584 for instructing a user on how to operate the portable infusion device 110. In particular, the animation 584 may include text and graphics, of which any may be animated on the display screen 450, for instructing a user on how to remove, install and fill a cartridge in a housing of the portable infusion device 110. An animation 584 may be an efficient and user-friendly means for assisting, instructing, and/or informing a user on how to operate the portable infusion device 110, which may enhance the usability of the device 110. Furthermore, audio may accompany any animation 584 for further assisting and/or instructing a user. Such audio may include, singly or in combination, voice, tones, music, vibrational alerts, etc. The portable infusion device 110 may present to a user any number of animated graphics and/or videos (with or without accompanied audio) for at least assisting, informing, and/or instructing a user on how to operate the device 110; what is wrong and how to fix a current malfunction of the device 110; the status of a programmed delivery of insulin; or any feature and or function associated with the portable infusion device, as described herein. The portable infusion device 110 may further include a help menu page (not shown) in the GUI page hierarchy whereby a user may select one or more listed animations and/or videos relating to, for example, operating the device. Animated graphics and/or videos may also appear at any time on the display screen 450 and are not limited to only when a user selects an animation 584 or video to appear on the display 450.

In addition, a selectable help object 466 may appear on any page within the GUI page 456 hierarchy that, when selected by a user, directs a user to a help page. The help page may be a generic help page, which may describe general instructions on how to use the device 110. Additionally, a help page may be tailored to the page 456 from which the help object 466 appeared on. For example, a user who selects a help object 466 on a bolus confirmation page 514 would be directed to a help page displaying at least information regarding how to set up the device 110 to deliver a bolus of insulin. Furthermore, one or more help objects 466 may be displayed on a single page being displayed on the touch screen 452 display 450, with each help object 466 relating to various help information, e.g., definitions of settings, instructions on how to execute a function, etc.

Figure 41:
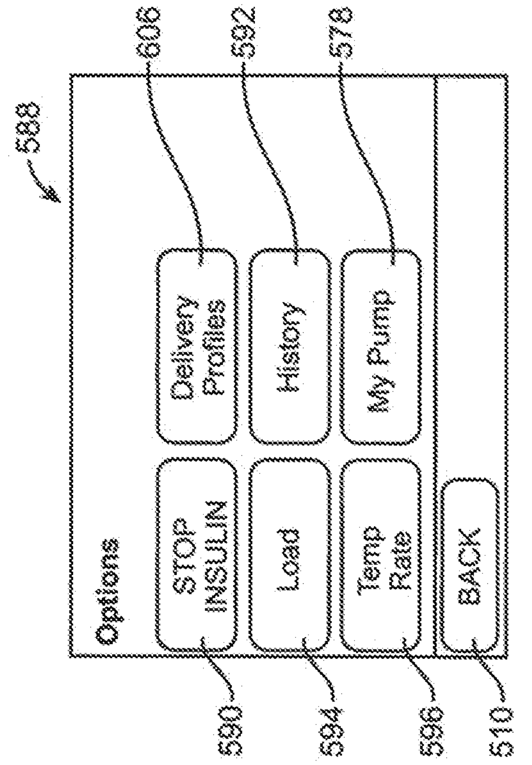
FIG. 41 is a screen shot of an options page embodiment.

FIG. 41 illustrates an embodiment of an options page 588, for insulin delivery, which may be accessed once a user, for example, selects the options object 478 on the home screen page 474 (refer to FIGS. 26 and 27). The options page 588 includes a list of objects 466 that, when selected, direct a user to various settings, operations, functions and information of the portable infusion device 110. For instance, the options page 588 may include a stop insulin object 590, which allows a user to stop the active delivery of insulin to the user upon selection of the stop insulin object 590. Alternatively, the stop insulin object 590 may be a resume insulin object (not shown) for allowing a user to resume the delivery of insulin from the device to the user upon selection of the resume insulin object.

The options page 588 may also include a history object 592 that, when selected by a user, directs a user to be able to view one or more history profiles that may include any number of information relating to a delivery of insulin that was made to a user (e.g., time and duration insulin was delivered, units of insulin delivered, physiological conditions recorded, etc.). Generally, any information entered by the user, processed by the processor 170, or sensed by the device 110 may be stored in memory 172 and recalled by the user in one or more history profiles.

Additionally, the options page 588 may list a load object 594 that, when selected by a user, may direct a user on how to load and unload a cartridge into a housing of the portable infusion device 110; fill the infusion tubing with fluid to be delivered to a user; and fill a cannula with fluid to be delivered to a user. Generally, selection of the load object 594 by a user allows a user to prepare the device 110 for proper delivery of insulin after loading a cartridge into the housing of the portable infusion device 110. As mentioned above, video and or animation 584 may be displayed on the touch screen 452 display 450 for assisting in informing and instructing a user on how to do any of the aforementioned tasks, with or without audio accompaniment.

A user may also select the temp rate object 596 on the options page 588 to allow a user to set a percentage of the current basal rate to be delivered for a temporary period of time. For example, a user may want to program a temp rate of eighty percent for a period of two hours because the user is planning to exercise for an hour. After the defined period of time is over, the portable infusion device 110 returns to the basal rate that was set prior to activation of the temp rate.

Figure 42:
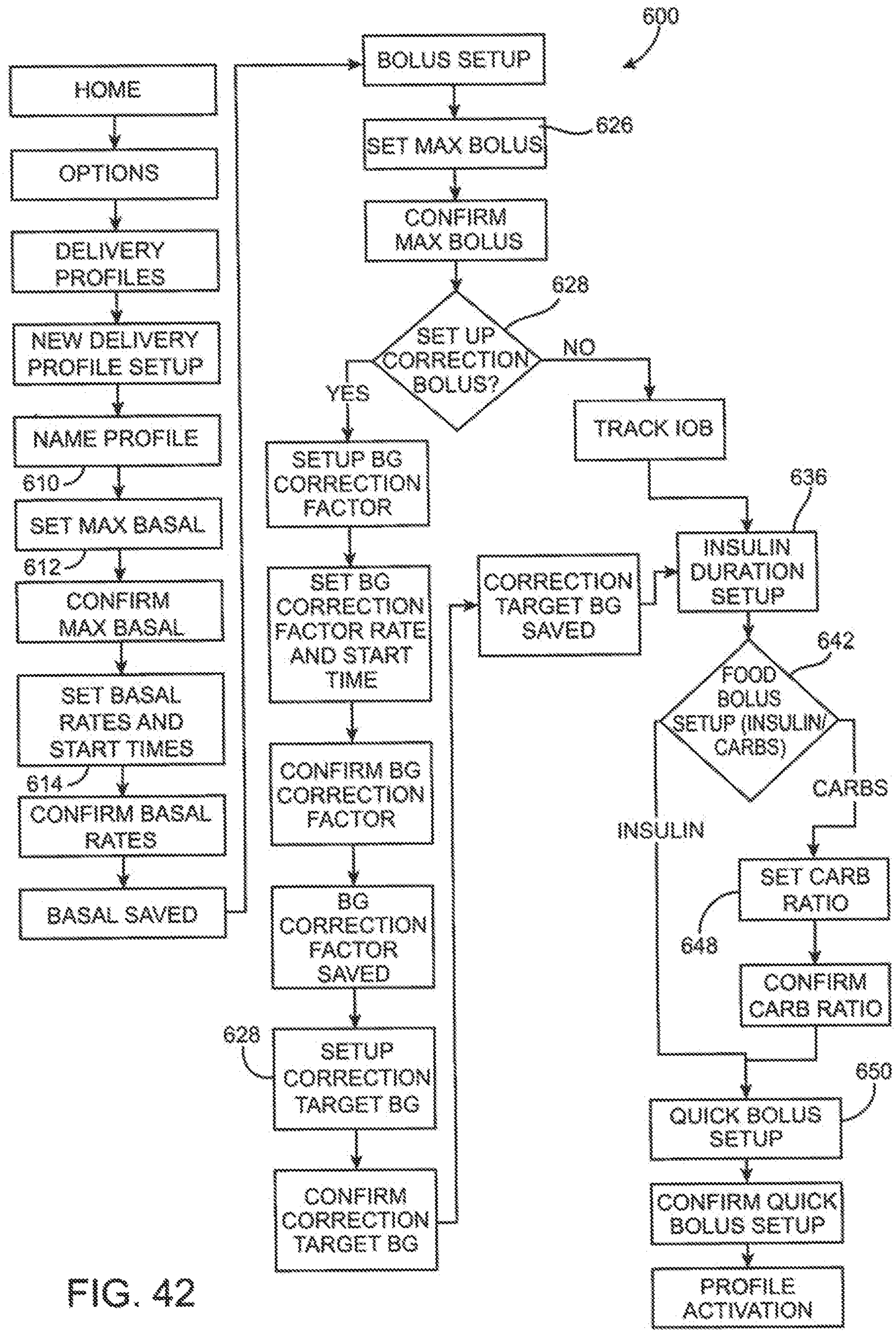
FIG. 42 is a flow diagram of a delivery setup process embodiment for a portable infusion pump.

The options page 588 also allows a user to initiate the programming of one or more delivery profiles 458. Depictions of various delivery profile setup pages 598 are shown in FIGS. 42A-42L. A reference to "FIG. 42" without a letter suffix will be understood to be a reference to the delivery profile workflow 600 generally. FIG. 42 illustrates one example of a delivery profile workflow 600 in an insulin delivery context that may direct a user to setting up a new delivery profile 458, which includes a number of queries, confirmations, and opportunities for a user to view and modify information regarding a delivery profile 458. A delivery profile 458 allows a user to customize the delivery of insulin, based on a number of settings, over a twenty-four hour period, which may be referred to as a personal delivery profile 604. However, a user may choose to activate any one personal delivery profile 604 at any time, but only one personal delivery profile 604 may generally be activated at a time. Furthermore, a personal delivery profile 604 may be comprised of one or more time segments 602. Each time segment 602 may define one setting for the defined period of time, as will be discussed in more detail below.

Figure 42A:
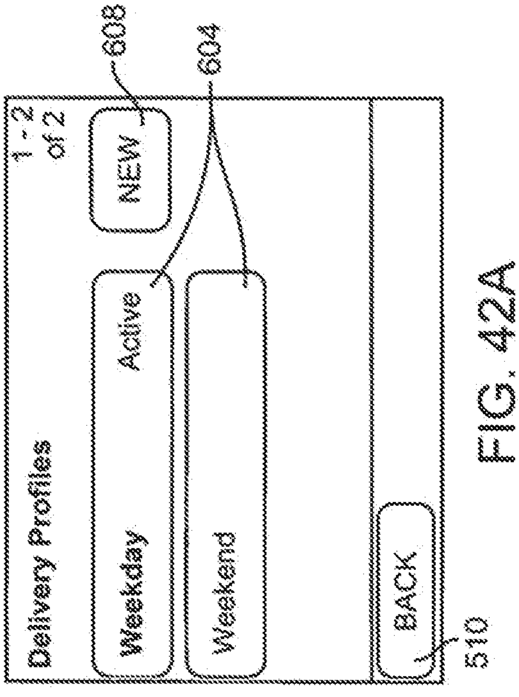
FIG. 42A is a screen shot of a data entry page embodiment for creation of a delivery profile.

By way of example, and broadly shown in FIG. 42, a user may initiate the setup of a new delivery profile 458, or personal delivery profile 604, by selecting the options object 478 on the home screen page 474, followed by the personal delivery profiles object 606 on the options page 588. To initiate the setup of a new personal delivery profile 604, the user may select the new object 608, as illustrated in FIG. 42A. Alternatively, a user may select one of the listed personal delivery profiles 604, if one exists, to be the active delivery profile. If the user selects to program a new personal delivery profile 604, the user may be prompted with a first query 610 to name the profile. A virtual keypad 500 containing lettered virtual keys 502 for allowing the user to select one or more virtual keys 502 may be displayed on the touch screen 452 to allow the user to name the personal delivery profile 604. The user may then be prompted with a second and third query 612, 613 to set a max basal value (the largest volume allowed for a basal) and a basal rate value (the rate at which the basal is delivered to the user), respectively. A virtual numeric keypad 500 may appear on the touch screen 452 display 450 for allowing a user to enter values to in response to the second and third, or any, query 612, 613. Alternatively, or in addition, a custom setup page, such as the basal rate setup page 616 illustrated by way of example in FIG. 42B may be displayed on the display screen 450 for allowing a user to set the basal rate and basal delivery start time. Each time a user completes defining a basal rate time segment 602, the user may select the add object 618 to define additional basal rate time segments 602.

In some embodiments, the max basal may be programmed in the device 110 to be a factor of the programmed standard basal rate. For example, once a standard basal rate has been programmed in the device 110 for a particular user, the device would generally automatically determine a max basal based on the programmed basal rate. By way of further example, the max basal may be calculated to be 1.5 to 3 times the standard basal rate, or profile basal rate. This may provide an additional safety feature by preventing a user from delivering too large of a bolus from the device 110.

Figure 42B:
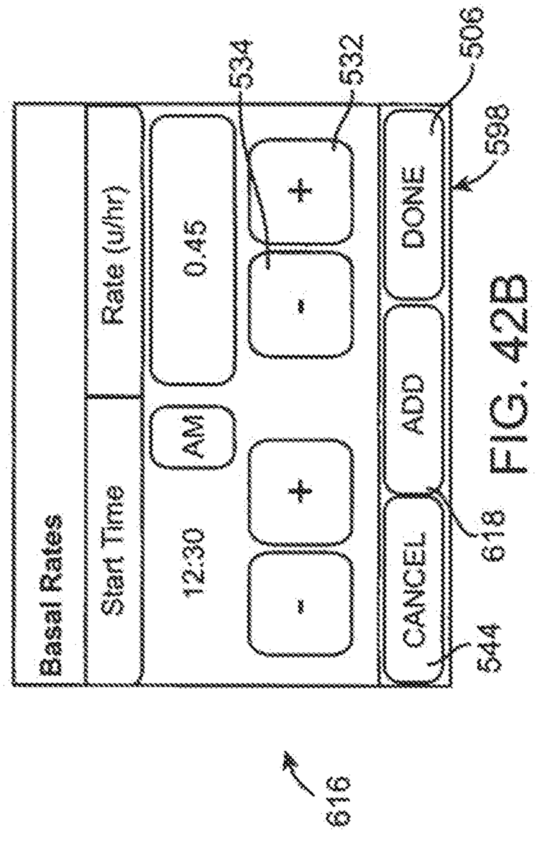
FIG. 42B is a screen shot of a basal rate setup page embodiment for creation of a delivery profile.
Figure 42C:
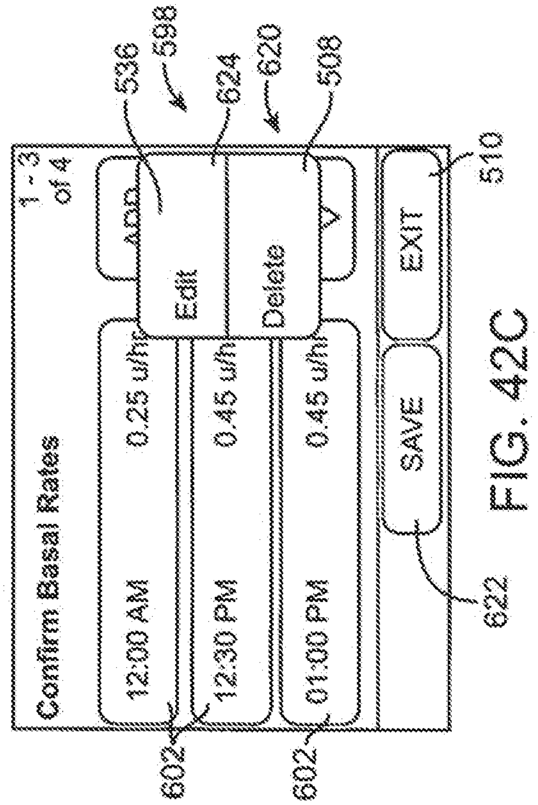
FIG. 42C is a screen shot of a basal confirmation page embodiment for creation of a delivery profile.

FIG. 42C illustrates an example of a basal rate personal profile confirmation page 620 displayed to a user to view the one or more basal rate time segments 602 defined by the user for the new delivery profile. A user may select any one of the listed basal rate time segments 602 to further edit or delete a time segment 602, or the user may select the save object 622 to save the programmed basal rate time segments 602 and move on to the next query in the delivery profile workflow. Selection of a save object 622 on any page 456 generally informs the processor 170 to store one or more information into memory 172. For example, and illustrated by way of example in FIG. 42C, a pop-up menu 624 may appear on the touch screen 452 display 450 when a user selects any one of the listed basal rate time segments 602 displayed on the personal profile basal rate confirmation page 620. A user may select any one of the listed options displayed in the pop-up menu 624, or the user may select, for example, any part of the touch screen 452 display 450 outside of the pop-up menu 624 to cause the pop-up menu 624 to close. Furthermore, a user may continue to add basal rate time segments 602 by selecting an add object 618 on a confirmation page, which may direct a user back to a setup page, such as the basal rate setup page 616, as shown in FIG. 42B. For example, a user may define sixteen different basal rate time segments 602 for any given personal delivery profile 604, which may allow a single personal delivery profile's 604 basal rate to vary up to sixteen times over a given twenty-four hour period.

Figure 42E:
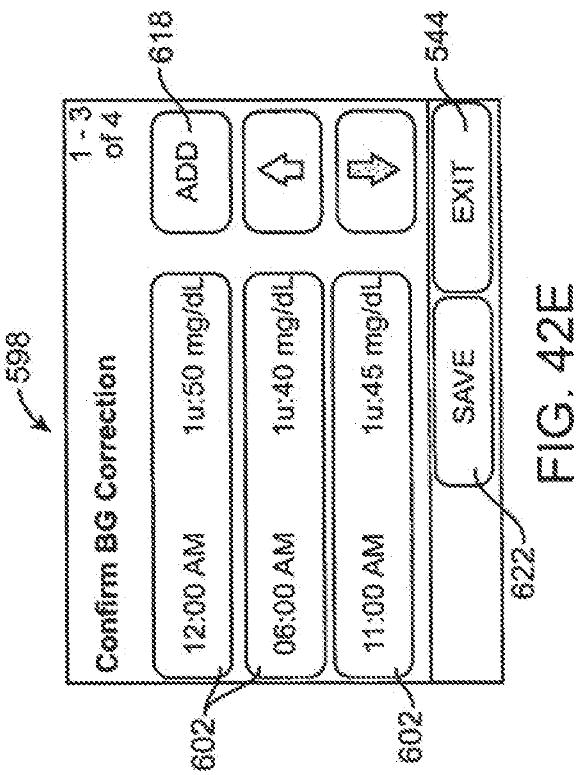
FIG. 42E is a screen shot of a blood glucose correction factor confirmation page embodiment.
Figure 42D:
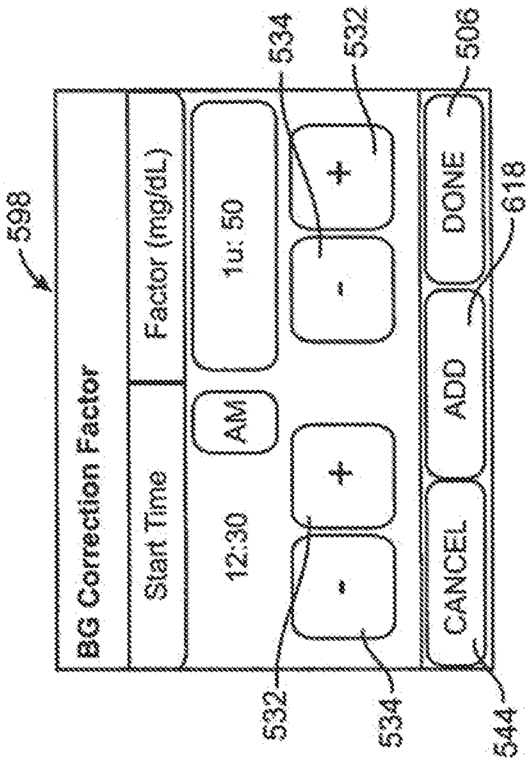
FIG. 42D is a screen shot a blood glucose correction factor setup page embodiment.

As illustrated in FIG. 42, once a user has confirmed and saved at least one basal rate time segment 602 for the new personal delivery profile 604, the user is prompted with generally a fourth query 626 asking the user to define and confirm a max bolus. Once the user has defined a max bolus, the user may then be presented with generally a fifth query 628 asking whether the user would like to setup one or more correction bolus time segments 602. A correction bolus may be defined as the amount a user's blood sugar will go down in response to the delivery of a unit of insulin. If the user chooses to setup a correction bolus, the user is presented with a series of queries asking the user to setup and confirm one or more BG correction factor time segments 602, as shown in FIGS. 42, 42D and 42E, respectively. The steps described above for a user to set up, confirm and add one or more basal rate time segments 602 are essentially identical to the steps for setting up, confirming and adding one or more BG correction factor time segments 602 such that it will not be repeated here for the sake of simplicity.

Figure 42G:
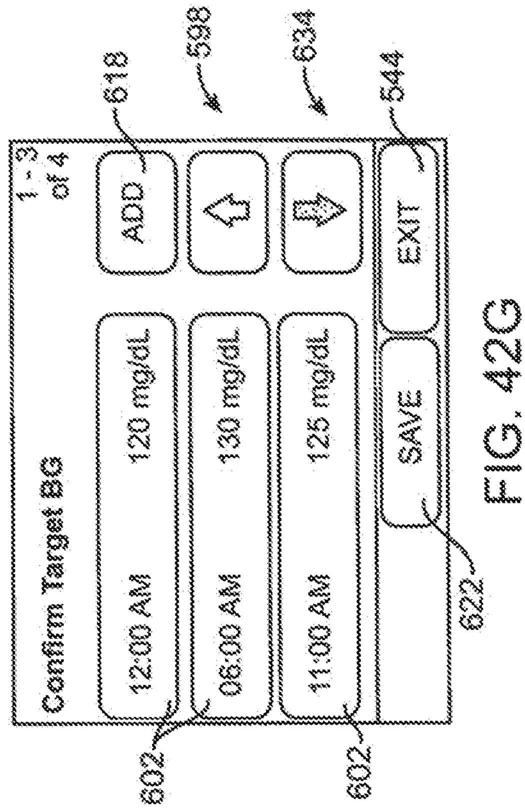
FIG. 42G is a screen shot of a target blood glucose confirmation page embodiment.
Figure 42F:
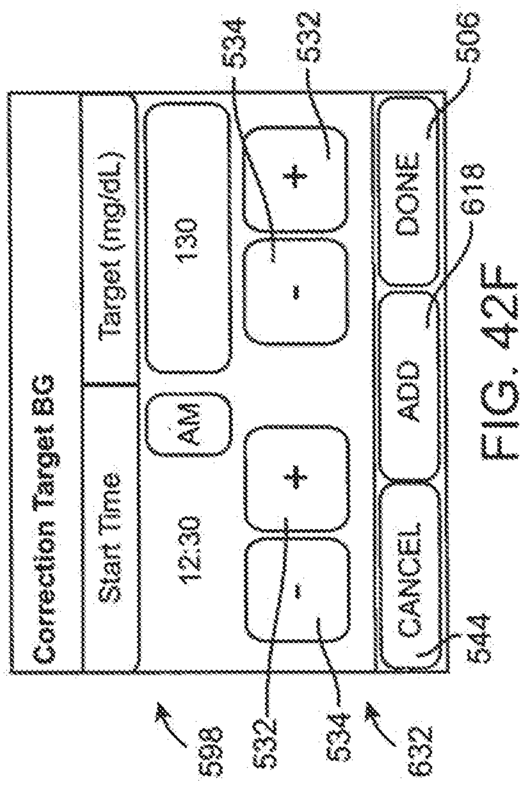
FIG. 42F is a screen shot of a blood glucose target correction setup page embodiment.

As illustrated in FIG. 42, once a user has saved at least one BG correction factor time segment 602 for the new personal delivery profile 604, the user is prompted with generally a sixth query 628 asking the user to define and confirm one or more correction target BG time segments 602. A target BG may be defined as what the user would prefer their BG level to be. The user is presented with a correction target BG setup page 632 and target BG confirmation page 634, as shown in FIGS. 42F and 42G, respectively. The steps described above for a user to set up, confirm and add one or more basal rate time segments 602 are essentially identical to the steps for setting up, confirming and adding one or more target BG time segments 602 such that it will not be repeated here for the sake of simplicity.

As illustrated in the personal delivery profile workflow 600 in FIG. 42, if the user elects not to setup a correction bolus, the user's "insulin on board" (IOB) will automatically be approximately tracked using various information (e.g., the rate at which the user's body metabolizes insulin, the amount of insulin delivered to the user over a period of time. etc.) entered into an algorithm accessible by the processor 170.

Figure 42H:
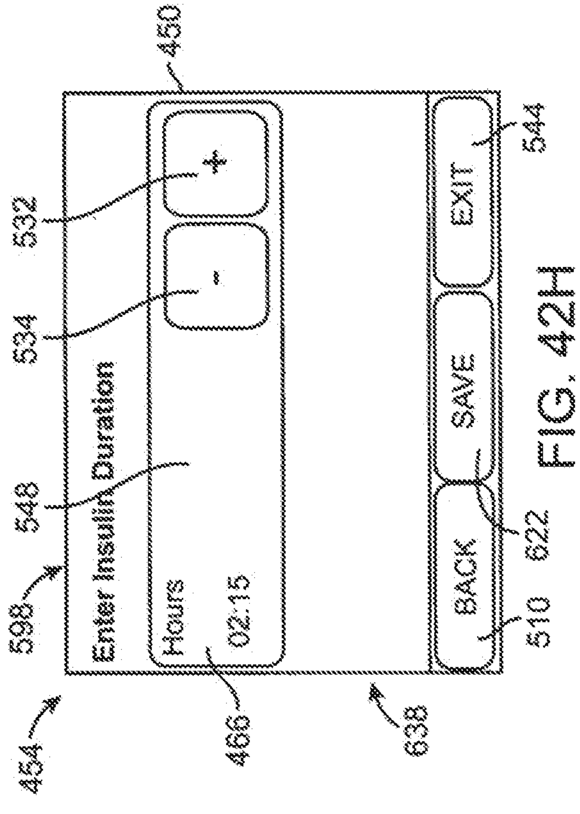
FIG. 42H is a screen shot of an insulin duration data entry page embodiment.

The final steps of setting up a new personal delivery profile 604 include defining an insulin duration and a bolus delivery value, as illustrated in the personal delivery profile workflow 600 in FIG. 42. A user may be presented with generally a seventh query 636 to setup an insulin duration, which approximately defines the time it takes for the user to metabolize a bolus of insulin. FIG. 42H illustrates one embodiment of an insulin duration setup page 638 where a user may enter or modify the number of hours and minutes it takes the user to metabolize a bolus of insulin.

Figure 42I:
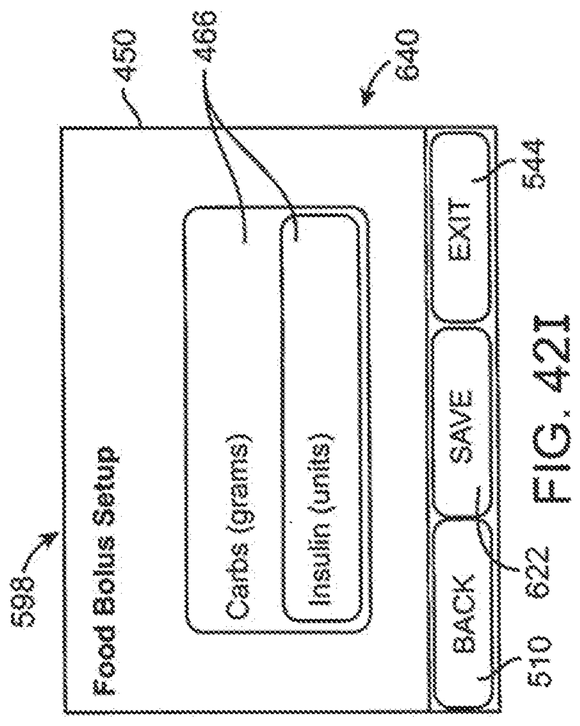
FIG. 42I is a screen shot of a food bolus set up page embodiment.
Figure 42J:
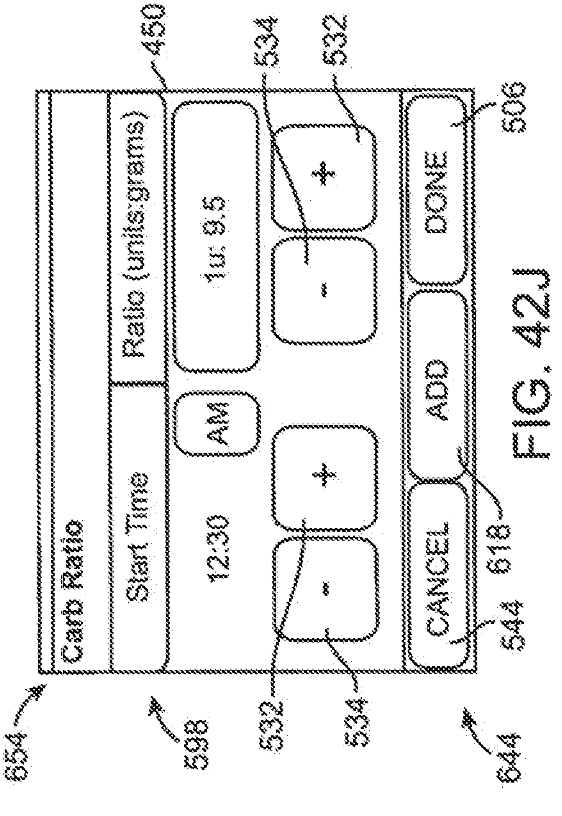
FIG. 42J is a screen shot of a carbohydrate (carb) ratio set up page embodiment.
Figure 42K:
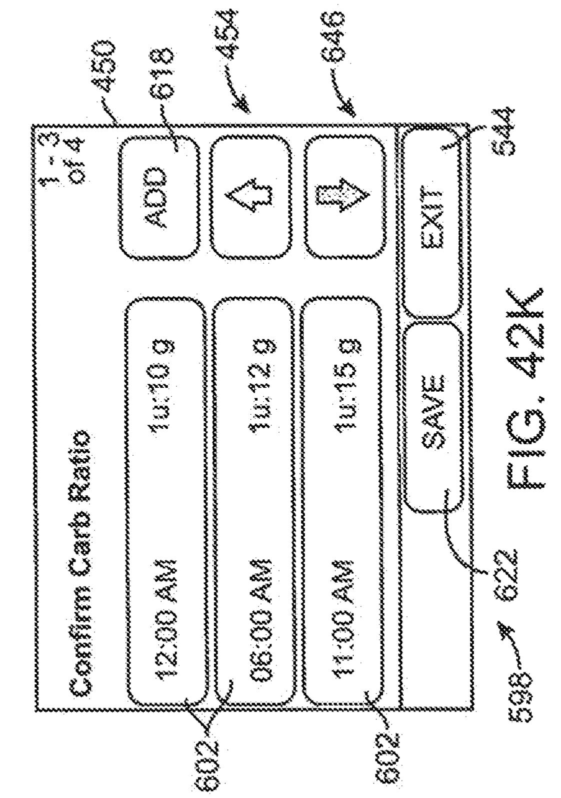
FIG. 42K is a screen shot of a carb ratio confirmation page embodiment.

The user may then be directed to a food bolus setup page 640, as illustrated in FIG. 42I, which may also be generally the eighth query 642 in the personal delivery profile workflow 600. From the food bolus setup page 640, a user may select a bolus delivery value based on the quantity (e.g., number of) of carbohydrates the user predicts to consume, or the user can choose to directly enter the total units of insulin to be delivered in the bolus. If the user chooses to base bolus delivery values on the predicted amount of carbohydrates to be ingested (in e.g., grams), the user may then be directed to a carb ratio setup page 644 and subsequent confirmation page 646, as illustrated in FIGS. 42J and 42K, respectively, and shown generally as the ninth query 648 in the personal delivery profile workflow 600. The user is then able to define at least one carb ratio time segment 602 (defined as the number of carbs a user must ingest for the device to deliver a single unit of insulin during the specified time segment 602) for the new personal delivery profile 604. The steps described above for a user to set up, confirm and add one or more basal rate time segments 602 are essentially identical to the steps for setting up, confirming and adding one or more carb ratio time segments 602 such that it will not be repeated here for the sake of simplicity.

The final steps a user may make in setting up a new personal delivery profile 604, for some embodiments, such as those illustrated here in the insulin delivery context, may be to select to have the quick bolus feature "on" or "off," which may also be the tenth query 650 in the personal profile delivery workflow 600. If the user chooses to turn the quick bolus feature "on," the user must define the increment of a quick bolus (either in grams of carbohydrates, or units of insulin). A quick bolus, as will be discussed in more detail below, allows a user efficiently to deliver a bolus quickly defined by the user. By way of example, the portable infusion device 110 may include a hard button (not shown) positioned at a convenient location for the user to simply press at least once to activate the delivery of a quick bolus to the user. Once the user has defined the quick bolus increment, the user has generally completed setting up the new personal delivery profile 604 and is able to save the personal delivery profile 604 for either immediate use or to be activated at a later time. By way of example, the portable infusion device 110 may be able to save any number of different personal delivery profiles 604 for a user to save and select for activating at any time. In one embodiment, the portable infusion device may be able to save up to 10 or more different delivery profiles. In another embodiment, the portable infusion device may be able to save up to 8 different delivery profiles. In yet another embodiment, the portable infusion device may be able to save up to six different delivery profiles.

As mentioned above, the portable infusion device 110 may include a quick bolus delivery function which allows a user to quickly deliver a bolus of insulin to a user. Depictions of various quick bolus delivery configuration pages 652 are shown in FIGS. 43A-43D. A reference to "FIG. 43" without a letter suffix will be understood to be a reference to the delivery configuration workflow generally. FIG. 43 illustrates one example of a quick bolus delivery workflow 651, which includes actions performed by a user for delivering a quick bolus of insulin to a user. For example, the quick bolus may be initiated by a user pressing and holding down a hard button (which may be referred to as the "wake" or "bolus" button) conveniently positioned on the portable insulin device 110. An embodiment of the home screen page may or may not be displayed on the touch screen 452 display 450 when the quick bolus delivery is initiated, and is not necessary for activating the delivery of a quick bolus.

Figure 43A:
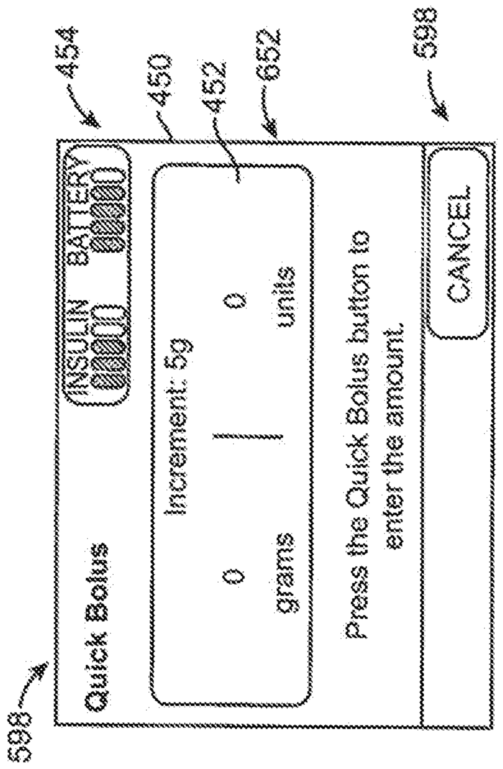
FIG. 43A is a screen shot of a quick bolus data entry page embodiment.
Figure 43B:
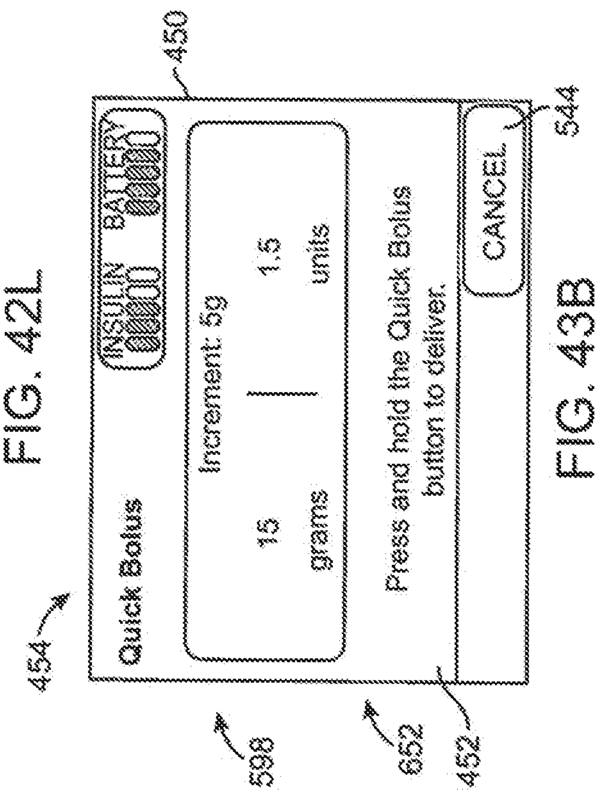
FIG. 43B is a screen shot of a quick bolus data entry page embodiment.
Figure 43C:
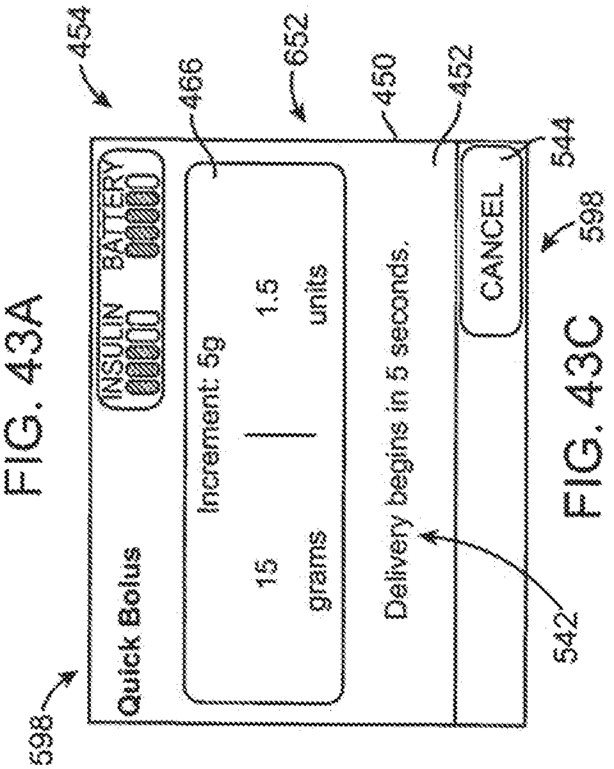
FIG. 43C is a screen shot of a quick bolus quick bolus data entry confirmation/delay page embodiment.
Figure 43:
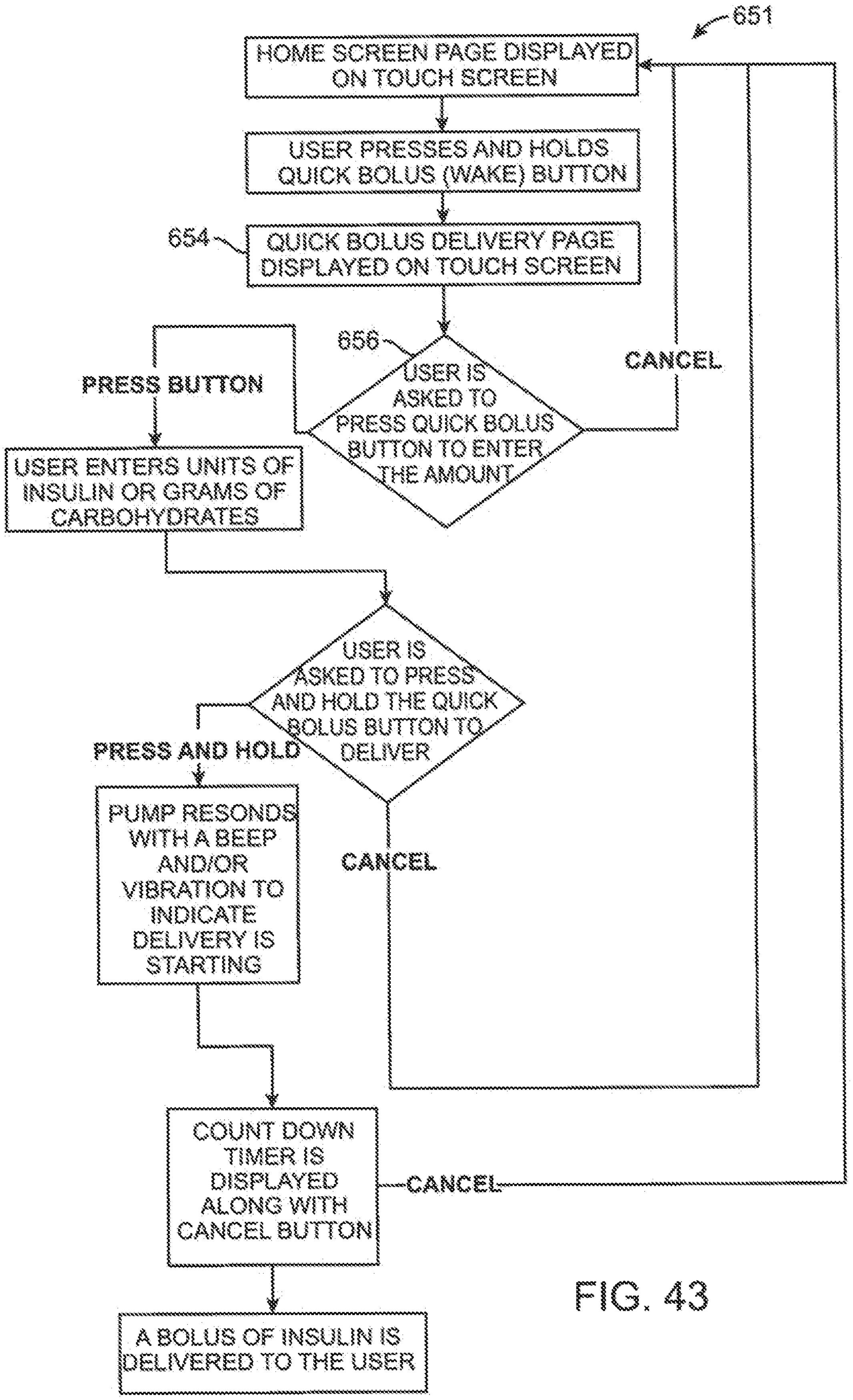
FIG. 43 is a flow chart of quick bolus set up process embodiment.
Figure 43D:
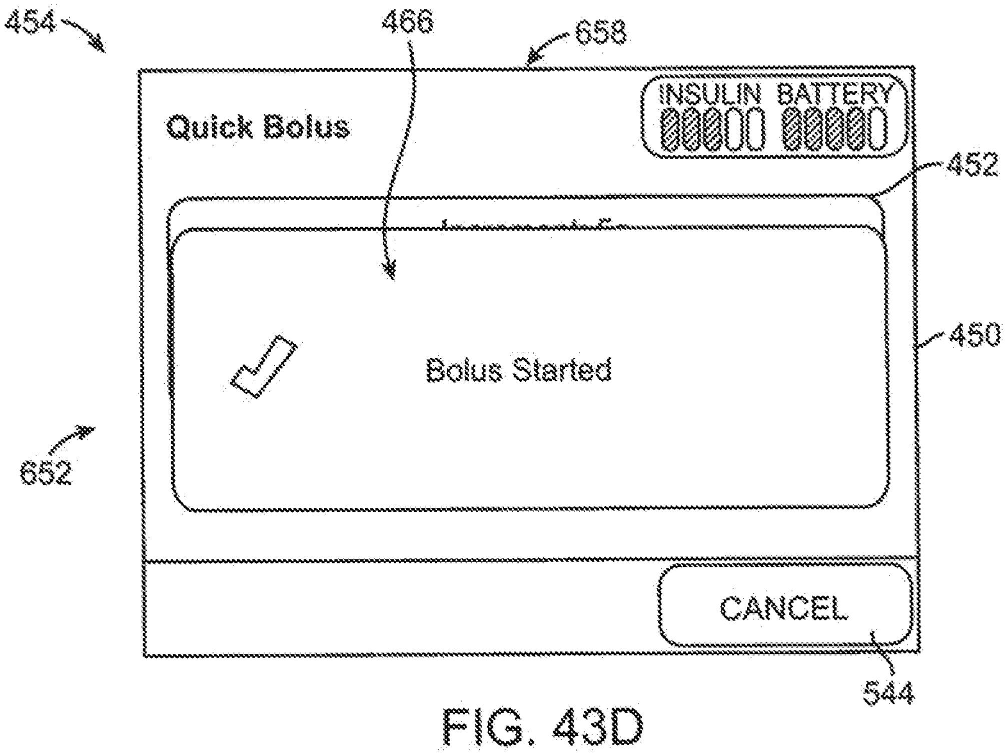
FIG. 43D is a screen shot of a bolus confirmation page embodiment.

Once the user presses and holds the hard button, a quick bolus delivery configuration page 652 is displayed on the touch screen 452 display, as illustrated in FIG. 43A. The user may then be presented with a first query 654 generally asking the user to press the hard button one or more times to increase the number of grams of carbs the user predicts to ingest. Each time the user presses the hard button in response to the first query 654, the grams of carbs and units of insulin increase by the quick bolus increment defined by the user in the currently activated personal delivery profile 604. The currently activated personal delivery profile 604 also includes a saved carb ratio which allows the appropriate units of insulin for delivery to be calculated.

For example, a user may have defined a quick bolus increment to be five grams, and a carb ratio of 0.5 units of insulin for every five grams of carbs. Therefore, each time the user presses the hard button in response to the first query 654 of the quick bolus workflow 651, the grams of carbohydrate increase by five grams and the units of insulin increase by 0.5 units. Therefore, if the user presses the hard button three times in response to the first query 654 of the quick bolus workflow 651, the quick bolus programmed to be delivered to the user would be 1.5 units of insulin, as shown by way of example in FIG. 43B.

Once the user has completed defining the number of units to be delivered in the quick bolus, the user is prompted with a second query 656, as illustrated in FIG. 43, asking the user to press and hold the hard button to initiate the delivery of the quick bolus. The user may then cancel the delivery, or press and hold the hard button to initiate the delivery of the quick bolus. The portable infusion device 110 provides the user with a notification (e.g., vibrate the device, an audible alert noise) to notify the user that the quick bolus delivery has been initiated. A countdown timer 542 is also initiated, as shown by way of example in FIG. 43C, to allow a user one or more seconds to select the cancel object and cancel the delivery of the quick bolus. A quick bolus confirmation page 658 may be presented to the user, as illustrated by way of example in FIG. 43D, as the actual delivery of insulin is initiated to the user.

Alternatively, a user may define a quick bolus increment in terms of units of insulin so that each time a user presses the hard button in response to the first query of the quick bolus workflow 654, the quick bolus volume is increased by the defined units of insulin. Therefore, a user may define a quick bolus increment to be one unit, so that each press of the hard button in response to the first query 654 in the quick bolus workflow 651 increases the quick bolus by one unit. Although described by way of example as pressing a hard button, any number of user interactions with the portable infusion device 110 may be completed by the user to define and initiate a quick bolus. A quick bolus may be defined while programming one or more personal delivery profiles 604 so that when a particular personal delivery profile 604 is activated, the volume of a quick bolus depends on what the user programmed the volume of a quick bolus to be for that particular personal delivery profile 604. Alternatively, the device 110 may have a universal quick bolus volume that may be defined by the user, which is not dependent upon the currently activated personal delivery profile 604. Instead, when the user activates the delivery of a universal quick bolus, the volume of the quick bolus will always be the same, regardless of which personal delivery profile 604 is activated. This may be an additional safety feature of the portable infusion device 110, because it generally relieves the user from having to at least be aware and recall what personal delivery profile 604 is currently active and what the volume for the quick bolus was programmed for the active personal delivery profile 604. For example, with a universal quick bolus, the user may be able to know that each time the user presses the hard button while setting up a quick bolus, the volume increases by five units, regardless of which personal delivery profile 604 is currently active.

An additional feature of the portable infusion device 110 includes a bolus delivery delay feature, which allows a user to at least define a bolus delivery volume, as well as define a delay in time before the bolus is delivered. For example, once a user has defined the bolus delivery (either by way of entering predicted carb intake or directly entering units of insulin), a user may either define a later time to start the bolus delivery (e.g., bolus delivery starts at 2:00 pm), or a time delay (e.g., bolus delivery starts in one hour). This feature may be particularly beneficial to children who may be more sensitive to bolus deliveries and may need an adult to assist in the setup of a bolus delivery, which may be more appropriately delivered at a later time (e.g., while the child is at school).

Figure 42L:
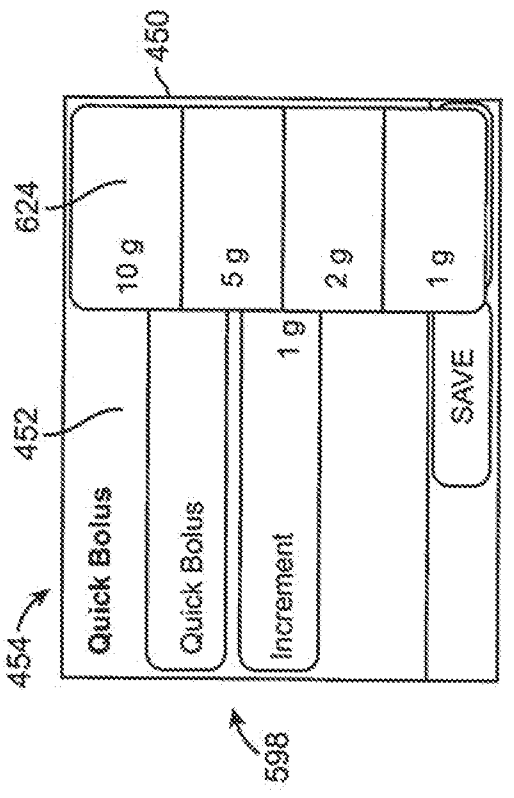
FIG. 42L is a screen shot of a quick bolus data entry page embodiment.

Another feature of some embodiments allows a user to set up a personal delivery profile 604, as was described and illustrated in FIGS. 42-42L, but instead of setting one or more time segments 602 for each setting of a personal delivery profile 604 (e.g., basal rate, BG correction factor, carb ration, target BG), the user may define each setting within a single time segment 602.

Figure 48:
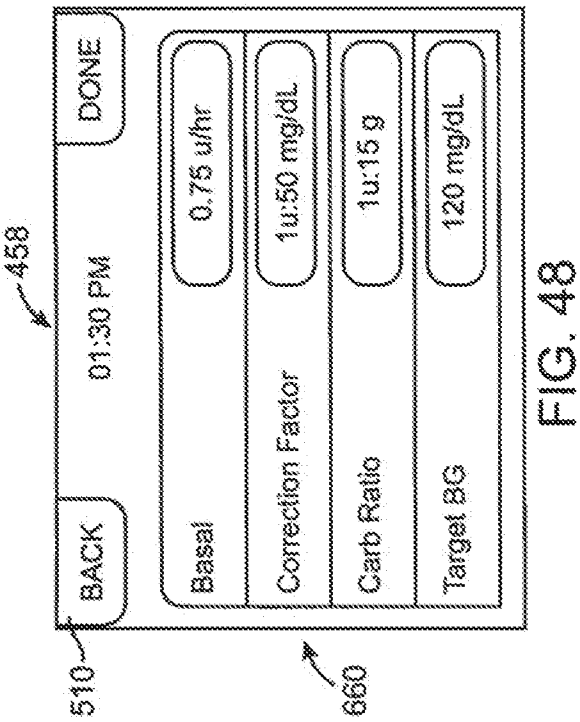
FIG. 48 is a screen shot of a delivery profile time segment setup page embodiment.

FIG. 48 illustrates one example of a personal delivery profile time segment setup page 660 where the multiple personal delivery profile 604 settings are displayed (for editing or confirmation) within a single time segment 602, or start time. For some configurations, the user may define multiple settings within a single time segment 602, thus eliminating the need to define time segments 602 for each setting. Additionally, the user may scroll down the touch screen 452 display 450 (e.g., by dragging a finger in a downward direction or selecting either the up object 662 or down object 664) to cause additional settings and or information regarding the personal delivery profile 604 to appear (e.g., max bolus, quick bolus). From the personal delivery profile time segment setup page 660, a user may define and/or modify any one of the personal delivery profile 604 settings for the time segment 602. The segment of time itself may also be defined and/or modified.

Figure 49:
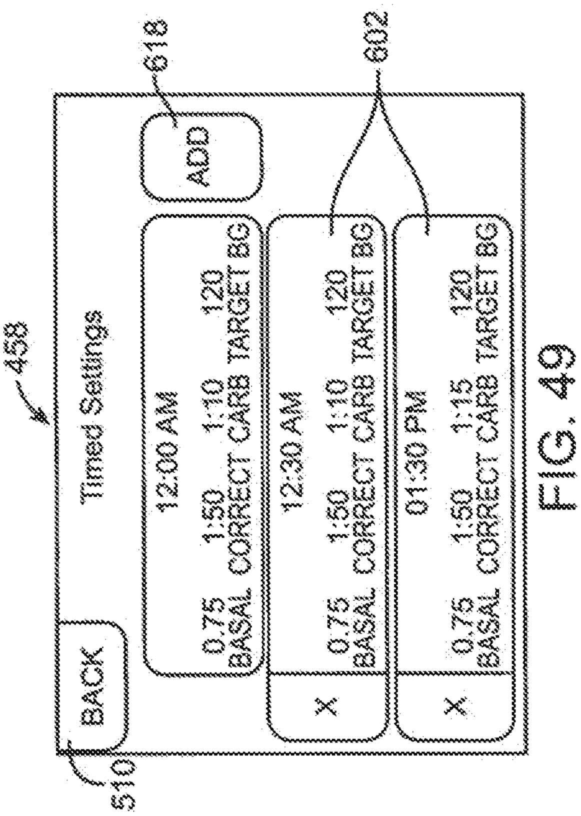
FIG. 49 is a screen shot of a delivery profile time segment confirmation page embodiment.

FIG. 49 illustrates an embodiment of a personal delivery profile confirmation page 666 displaying one or more personal delivery profile 604 settings for each time segment 602. It is one advantage of the portable infusion device 110 to offer a user with a condensed view of multiple personal delivery profile 604 time segments 602 and their associated settings, as shown in the personal delivery profile confirmation page 666 illustrated by way of example in FIG. 49. For example, a user may be able to view and compare multiple personal delivery profile 604 settings over multiple time segments 602 on a single touch screen 452 display 450. Furthermore, a user may simply scroll down the touch screen 452 display 450 (e.g., by dragging a finger in a downward direction or selecting either the up object 662 or down object 664) to cause additional time segments 602 to be displayed on the display screen 450. The user may edit, delete and add additional time segments 602 directly from the personal delivery profile confirmation page 666.

Figure 50A:
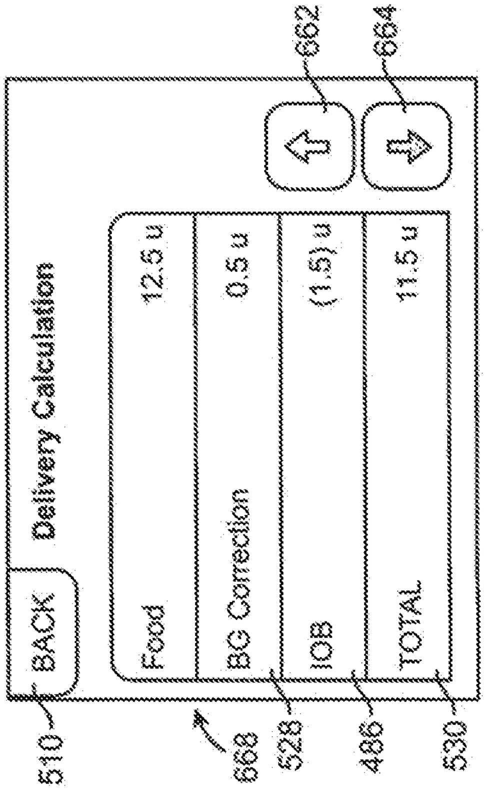
FIG. 50A is a screen shot of a delivery calculation page embodiment.

FIG. 50A illustrates an example of a delivery calculation page 668 displaying one or more variable setting used to calculate the total units of insulin programmed to be delivered to a user. A user may access a delivery calculation page 668, for example, by selecting a "view calculations" object 670 appearing on a page 456 within the GUI page 456 hierarchy, as shown by way of example in FIG. 53A. A delivery calculation page 668 may list any number of modifiable values and/or settings used for calculating the total units of insulin programmed to be delivered to a user. For example, variables used to calculate the total units of insulin may include the number of units of insulin necessary for the number of carbs to be ingested by the user; the number of units of insulin necessary to reach a defined target BG level; and the number of units of insulin currently in the user's body.

Figure 50B:
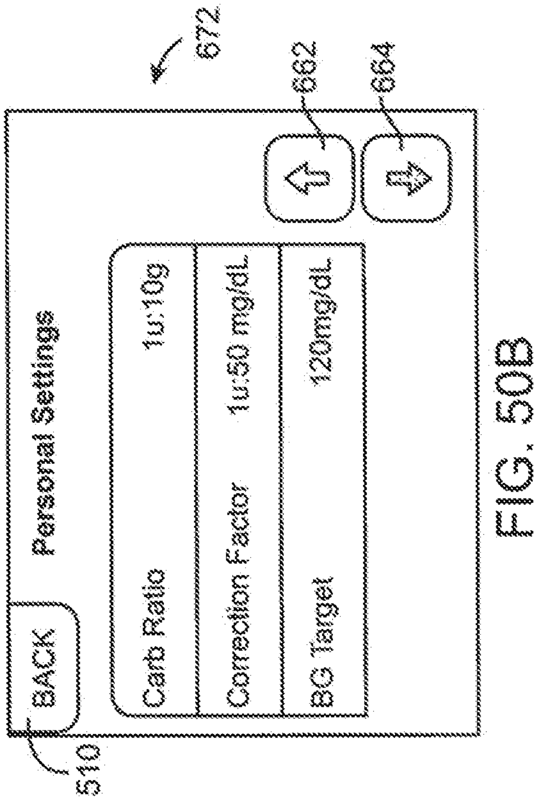
FIG. 50B is a screen shot of a person settings page embodiment.

Furthermore, and shown by way of example in FIG. 50B, a user may scroll down a delivery calculation page 670 to view a personal settings page 672. The personal settings page 672 may list one or more settings (e.g., carb ratio, BG correction factor, target BG) that may also have been used to determine the total units of insulin programmed to be delivered to a user. At least one of the settings displayed on the delivery calculation page 670 and personal settings page 672 may be directly modified by a user using any of the methods described herein for modifying a value displayed on the touch screen 452 display 450. Therefore, a user may at least view and modify any one of the settings listed on either the delivery calculation page 670 or personal settings page in order to modify the total units of insulin programmed to be delivered to a user.

Figure 51:
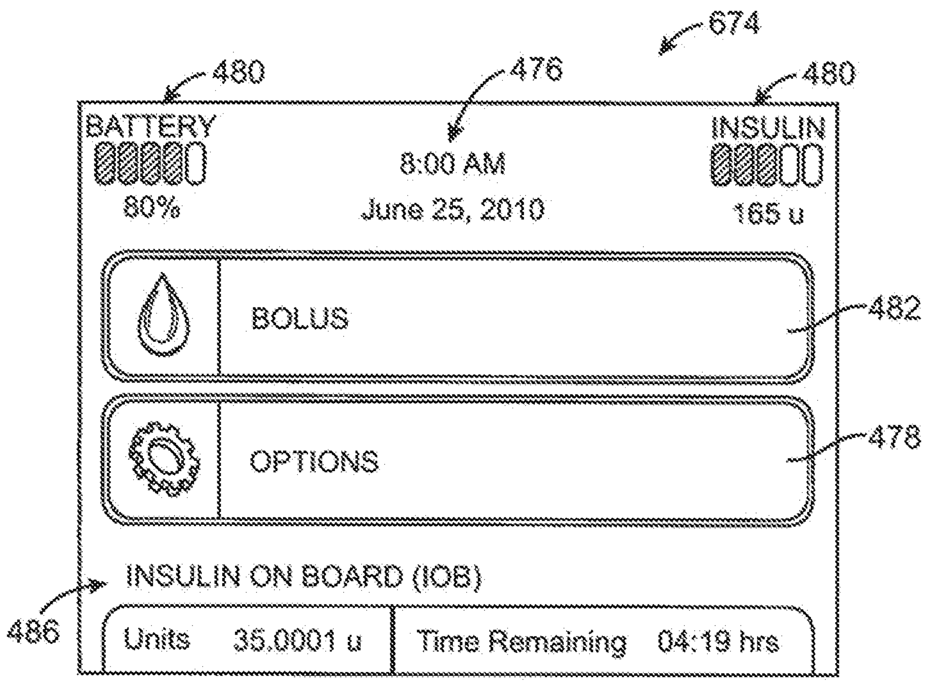
FIG. 51 is a screen shot of another embodiment of a home screen page.

FIG. 51 illustrates an additional embodiment of a home screen page 674 that may be displayed on the touch screen 452 display 450 of the portable infusion device 110. In this particular embodiment, the home screen page has been configured to include one or more status indicator objects 480, a bolus object 482, an options object 478, and an IOB object 486, of which any object may be a soft key so that the user may select any one of the selectable objects. For instance, a user may select the options object 478, which may direct the user to an options page 588, as described above and illustrated by way of example in FIG. 41. Additionally, any one of the status indicator objects 480 may be selected to either view or modify, as described above. Furthermore, the IOB object 486 may display the units of insulin remaining from the delivery of one or more bolus deliveries of insulin to the user. The IOB object 486 may also display the time remaining for the body of the user to metabolize the remaining bolus units of insulin. In addition, a user may select the bolus object, which may direct a user to a bolus setup page for setting up a bolus delivery of insulin.

Figure 53A:
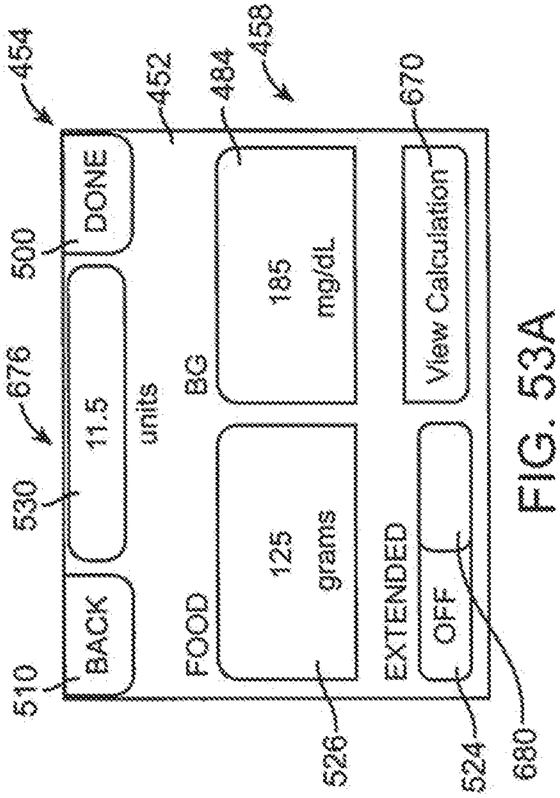
FIG. 53A is a screen shot of another embodiment of a bolus set up page.

FIG. 53A illustrates another embodiment of a bolus setup page 676 that may be displayed on the touch screen 452 display 450 of the portable infusion device 110. The bolus setup page 676 is shown as including a food bolus object 678, a BG object 484, a view calculation object 670, an extended bolus object 524, and navigation object 510, e.g., back, skip, next, of which any object may be a soft key so that the user may select any one of the selectable objects. This embodiment of the bolus setup page 676 may be configured to enable the user to simply select any one of the settings to enter or modify a value. For example, the user may select the food bolus object 526 to enter the number of grams of carbs the user predicts to consume. As discussed above, a virtual keypad 500 may be displayed on the touch screen 452 display 450 for enabling a user to enter the number of grams of carbs, or any means for entering or modifying a value described herein. Once the user enters the number of carbs, the user is then directed back to the bolus setup page 676.

One embodiment of the virtual keypad 500 may include one or more mathematical symbol virtual keys 502, e.g., plus sign, minus sign, multiplication sign, division sign, etc., to enable the virtual keypad 500 and processor 170 to function as a virtual calculator. For example, a virtual keypad 500 with one or more mathematical symbols displayed on the display screen 450 may enable a user to enter more than one entry and instruct the processor 170 to, for example, add, subtract, multiply, and/or divide the user entries. For instance, a user may be presented with a virtual calculator for enabling a user to enter and add more than one amount of carbs making up at least a part of a meal the user intends to consume. This feature may improve usability of the device 110 and reduce user error by simplifying the means by which a user determines the total number of carbs that make up a meal the user intends to consume, in addition to generally relieving the user from having to perform the calculations that may be necessary to determine the total number of carbs. As mentioned above, a virtual keyboard 500 including one or more mathematical virtual key 502 symbols may be presented to a user for various reasons and opportunities for a user to instruct the processor 170 to perform one or more calculations.

Figure 53B:
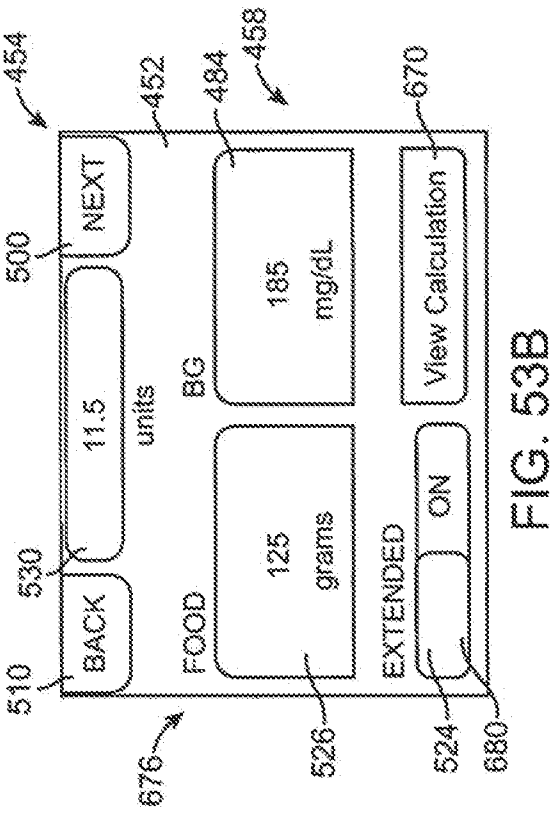
FIG. 53B is a screen shot of another embodiment of a bolus set up page.

In addition, from the bolus delivery setup page 676 a user may choose to program an extended bolus, as illustrated in FIGS. 53A and 53B showing a virtual slide button 680 exposing either "on" or "off" in response to a user selecting to either program or not program an extended bolus, respectively. A user may select to program an extended bolus, e.g., by sliding a finger over the virtual slide 680 button to cause the virtual slide button 680 to move and display the "on" and then selecting the next object, as illustrated in FIG. 53B, which may direct a user to an extended bolus setup page 682. Once the user completes setting up an extended bolus on the extended bolus setup page 682, the user is directed back to the bolus setup page.

Figure 53C:
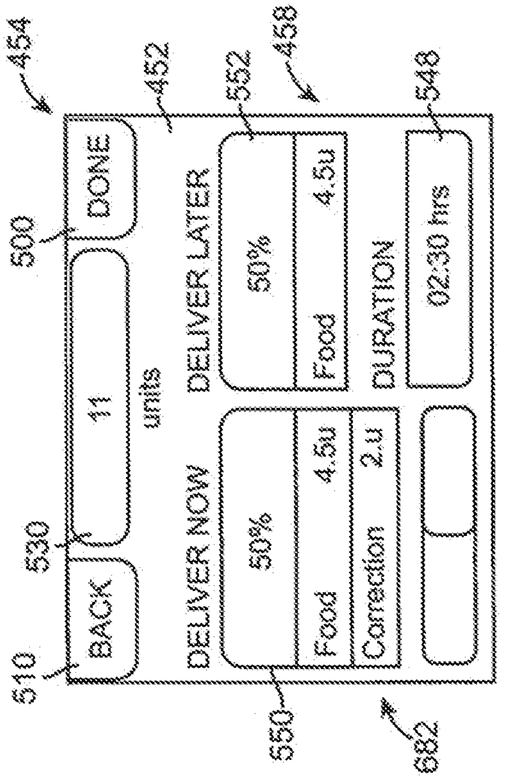
FIG. 53C is a screen shot of another embodiment of an extended bolus set up page.

FIG. 53C illustrates another example of an extended bolus setup page 682 that may be displayed on the touch screen 452 display 450 of the portable infusion device 110. The extended bolus setup page 682 is shown as including a deliver now object 550 (how much insulin is programmed to be delivered generally immediately after the user initiates the extended bolus delivery), a deliver later object 552 (how much insulin is programmed to be delivered over an extended period of time), a food bolus object 526 (how much insulin is programmed to be delivered to a user based generally on the amount of food, or carbs, the user predicts to consume), a duration object 548 (over what period of time the extended bolus will be delivered), and navigation objects 510, e.g., a back, next, done. Any of the objects displayed on the extended bolus setup page 682 may be a soft key for enabling a user to select any one of the objects. Furthermore, and similar to the bolus delivery setup page 676, a user may select any one of the selectable objects displayed on the touch screen 452 display 450 to enter or modify any of the settings using any means described herein for modifying selectable objects, e.g., entering a value by selecting virtual keys 502 on a virtual keypad 500 displayed on the touch screen 452 display 450.

As described above, once the user completes setting up an extended bolus on the extended bolus setup page 682, the user may select the done object 506 on the extended bolus setup page 682 to be directed back to the bolus delivery setup page 676. Once the user is directed back to the bolus delivery setup page 676, the user may either modify any of the settings displayed on the touch screen 452, select the back object 510 to be directed to a previous page, or select the done object 506 to initiate delivery of the extended bolus.

Alternatively, a user may not have selected to setup an extended bolus, e.g. by positing the virtual slide button 680 to allow the "off" to be displayed as shown in FIG. 53A, and may have, instead, selected the done object 506 after entering or modifying one or more settings on the bolus delivery setup page 676 to initiate delivery of a standard bolus.

Therefore, the embodiment of the bolus delivery setup page 676 illustrated in FIGS. 53A and 53B enable a user to setup a bolus delivery without navigating through a generally linear workflow 464 or a series of queries. Instead, the user may select any one of the selectable settings displayed on the single bolus delivery setup page 676 on the touch screen 452 display 450 to either enter or modify one or more of the bolus delivery settings.

Figure 52:
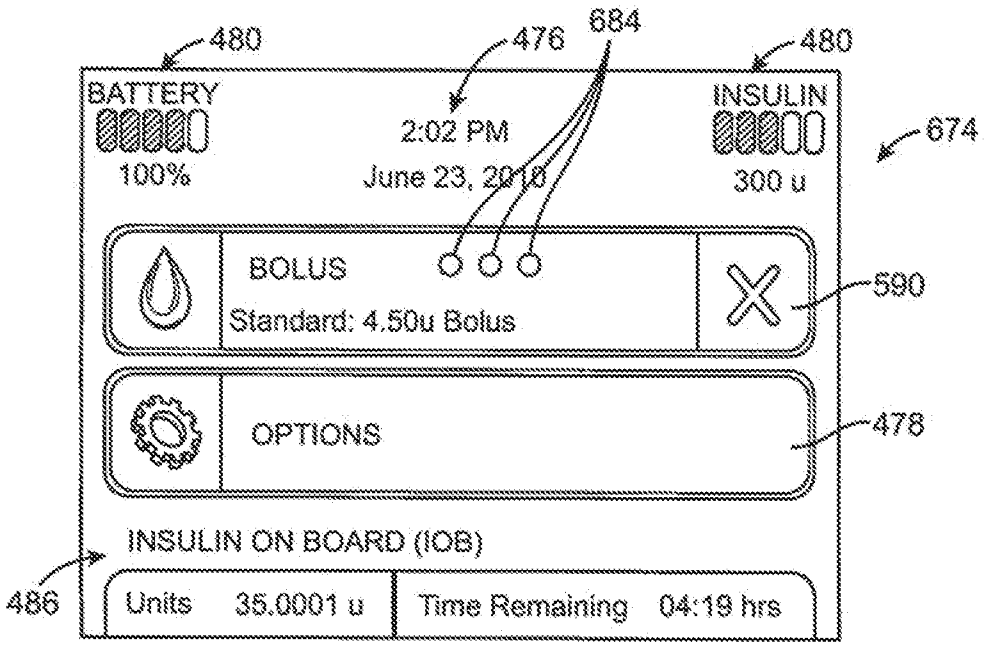
FIG. 52 is a screen shot of another embodiment of a home screen page.

Once the user has completed setting up either a standard or extended bolus and has confirmed delivery of the bolus, the user may be directed back to a home screen page 674. FIG. 52 illustrates the home screen page 674 which includes one or more delivery status indicators and a stop insulin object 590. The one or more delivery status indicators 684 may visually change, e.g., color, brightness, etc., either separately or in unison so that it is generally obvious to a user that the delivery of the bolus has at least been initiated. In addition, when the delivery status indicators 684 stop visually changing, it may be obvious to a user that the delivery of the bolus is complete.

Additionally, and shown by way of example in FIG. 52, another embodiment of a stop insulin object 590 may be displayed on the home screen 674 page. A stop insulin object 590 may only appear on the home screen page 674 after a delivery has been initiated, and remain displayed until the delivery has been completed. This feature enables a user to easily access and stop a programmed delivery of insulin while there is generally an opportunity to do so. Having the stop insulin object 590 on the home screen page 674 may improve the user's safety by enabling the user to select the stop insulin object 590 to stop delivery more quickly than having to navigate through one or more additional pages, which may decrease the amount of unwanted insulin delivered to the user.

As discussed above, the GUI 454 may display various information in graphical form, and the graphic representation 570 may be configured for manipulation by a user touching or otherwise "clicking" the representation and dragging the representation in a predefined manner so as to change the form, e.g., height, width, shape, etc. of the representation. For example, where the graphical representation 570 is a bar, the height or width of the bar may be adjusted by clicking on the appropriate dimension and manipulating it to adjust that chosen dimension. Where the graphical representation 570 is a curve or wave, the curve or wave may be clicked and the shape thereof may then be manipulated, for instance, by dragging a finger across the screen in a predetermined manner.

FIG. 54 illustrates an example of multiple graphs 570 simultaneously displayed on the touch screen 452 display 450, which may collectively inform a user as to the range and optimal levels of a user's BG programmed into the portable infusion device 110. The graphs 570 simultaneously displayed may include a high blood glucose (BG) graph, a low BG graph and an optimal BG graph. However, any number of graphs 570 representing various information may be simultaneously displayed on the touch screen 452 display 450 of the portable infusion device 110. Furthermore, the graphs 570 shown in FIGS. 54 and 55 are illustrated for example purposes and do not limit the shape, e.g., slope, geometry, etc., or configuration of the graphical representations shown or discussed herein.

In addition, the information represented by at least one of the graphs 570 may be used to calculate and determine additional settings. For instance, the high BG graph 686 may display the range of a user's acceptable high BG levels over a period of time, the low BG graph 688 may display the range of acceptable low BG levels over a period of time, and the optimal BG graph 690 may display the range of optimal BG levels over a period of time. For example, a user's high BG level range may influence the occurrence and amount of correction boluses delivered to a user. Therefore, a user may modify, for example, the programmed high BG level range in order to modify the occurrence and amount of correction boluses programmed to be delivered to the user.

Figure 55:
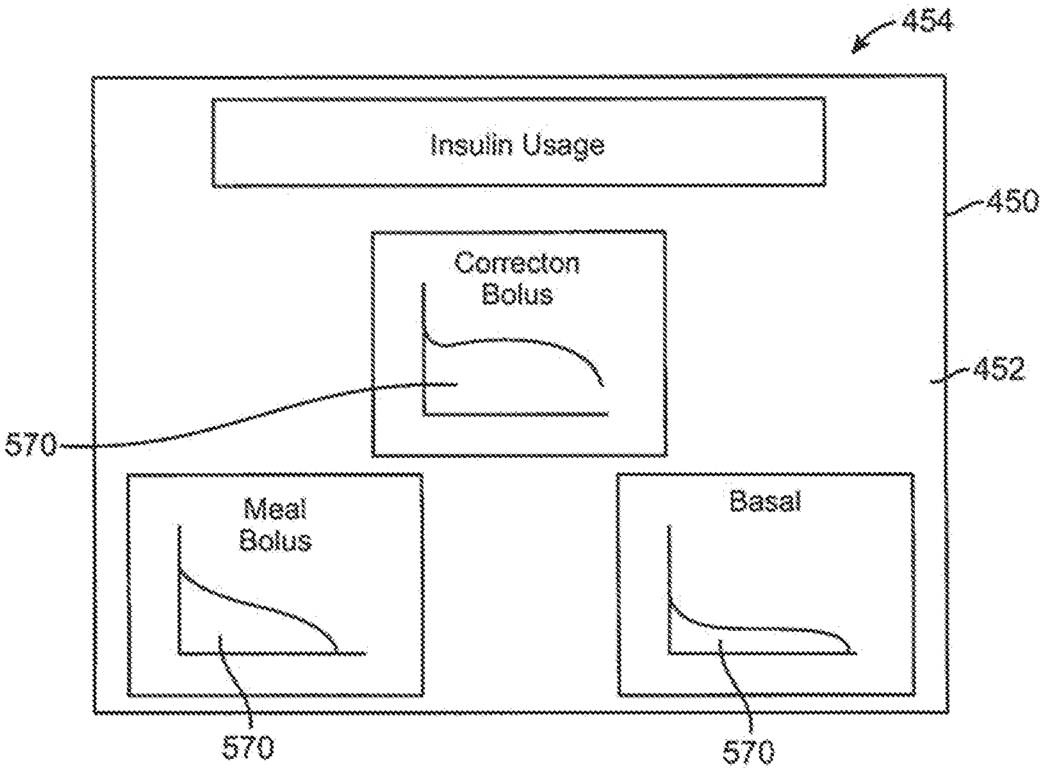
FIG. 55 illustrates a screen which displays multiple graphs simultaneously on a touch screen display.

FIG. 55 illustrates another example of multiple graphs 570 simultaneously displayed on the touch screen 452 display 450, which may collectively inform a user as to the composition of insulin programmed to be delivered to a user. For instance, and shown by way of example in FIG. 55, a correction bolus graph 692 may display what percent of the insulin programmed to be delivered to a user over a period of time is a correction bolus. In addition, a meal bolus graph 694 may display what percent of the insulin programmed to be delivered to a user over a period of time is a meal bolus (based on a user's carb ratio), and a basal graph 696 may display the basal delivery rate of insulin programmed to be delivered to a user over a period of time. The simultaneously displayed graphs 570 may provide a user with a simplified way to at least view, compare, and/or modify various programmed information over a period of time.

Furthermore, any one of the graphs 570 may be configured for manipulation by a user, such that a user may modify the range of any one of the graphs 570. For example, a user may want to modify the high BG range, e.g., by selecting and dragging a part of the high BG graph 686, in order to decrease the percentage of correction bolus comprising the total amount of insulin delivered to a user over a period of time. Therefore, modification of one graph 570 may generally cause modification to one or more additional graphs 570, which may result in improved usability of the portable infusion device 110 for a user to at least manage their insulin therapy.

With regard to the above detailed description, like reference numerals used therein may refer to like elements that may have the same or similar dimensions, materials and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" may refer to one of or a plurality of the elements it modifies (e.g., "a reagent" can mean one or more reagents) unless it is contextually clear either one of the elements or more than one of the elements is described. Although the present technology has been specifically disclosed by representative embodiments and optional features, modification and variation of the concepts herein disclosed may be made, and such modifications and variations may be considered within the scope of this technology.

Certain embodiments of the technology are set forth in the claim(s) that follow(s).

The invention claimed is:

1. A portable infusion pump system, comprising:

a portable infusion pump including a reservoir configured to contain a medicament and a pumping mechanism configured to deliver the medicament in the reservoir to a user;

a remote control device configured to remotely control the portable infusion pump, the remote control device including a display and at least one processor configured to:

receive a numerical value for a bolus calculation;

calculate a bolus based at least in part on the numerical value;

display the calculated bolus adjacent the numerical value on the display; and transmit an operating command to the portable infusion pump to cause the portable infusion pump to deliver the calculated bolus to the user.

2. The portable infusion pump system of claim 1, wherein the at least one processor of the remote control device is configured to present one or more objects on the display and wherein the numerical value is received in response to selection of one of the one or more objects.

3. The portable infusion pump system of claim 2, wherein the display is a touchscreen display and the one or more objects are touch-selectable.

4. The portable infusion pump system of claim 2, wherein the one or more objects includes a food object and wherein the at least one processor of the remote control device is configured to utilize the numerical value as an amount of carbohydrates.

5. The portable infusion pump system of claim 2, wherein the one or more objects includes a blood glucose object and wherein the at least one processor of the remote control device is configured to utilize the numerical value as a blood glucose level.

6. The portable infusion pump system of claim 2, wherein the at least one processor of the remote control device is further configured to:

present a virtual numeric keypad on the display in response to selection of the one of the one or more objects, and receive the numerical value via the virtual numeric keypad.

7. The portable infusion pump system of claim 1, wherein the at least one processor of the remote control device is further configured to present a view calculation object adjacent the calculated bolus, the view calculation object being selectable to display on the display how the calculated bolus was calculated based on the numerical value.

8. The portable infusion pump system of claim 1, wherein the at least one processor of the remote control device is further configured to:

present a selectable stop insulin object on the display while the calculated bolus is being delivered;

receive user input selecting the stop insulin object while the calculated bolus delivery is being delivered; and transmit an operating command to the portable infusion pump to stop delivery of the calculated bolus in response to the selection of the stop insulin object.

9. The portable infusion pump system of claim 1, wherein the at least one processor of the remote control device is further configured to:

present a plurality of discrete bolus status indicator objects on the display after transmitting the operating command to the portable infusion pump to cause the portable infusion pump to deliver the calculated bolus to the user;

change an appearance of the plurality of discrete bolus status indicator objects while the calculated bolus is being delivered; and stop changing appearance of the plurality of discrete bolus status indicator objects when the calculated bolus delivery is completed.

10. The portable infusion pump system of claim 9, wherein changing the appearance of the plurality of discrete bolus status indicator objects includes changing a color of the bolus status indicator objects to indicate that the calculated bolus delivery is ongoing.

11. The portable infusion pump system of claim 1, wherein the remote control device is a cell phone.

12. A non-transitory computer readable medium storing instructions that, when executed by a processor, cause a device to:

receive a numerical value for a bolus calculation;

calculate a bolus based at least in part on the numerical value;

display the calculated bolus adjacent the numerical value on a display; and transmit an operating command to a portable infusion pump to cause the portable infusion pump to deliver the calculated bolus to the user.

13. The non-transitory computer readable medium of claim 12, further comprising instructions that, when executed by the processor, cause the device to present one or more objects on the display and wherein the numerical value is received in response to selection of one of the one or more objects.

14. The non-transitory computer readable medium of claim 13, wherein the display is a touchscreen display and the one or more objects are touch-selectable.

15. The non-transitory computer readable medium of claim 13, wherein the one or more objects includes a food object and further comprising instructions that, when executed by the processor, cause the device to utilize the numerical value as an amount of carbohydrates.

16. The non-transitory computer readable medium of claim 13, wherein the one or more selectable objects includes a blood glucose object and further comprising instructions that, when executed by the processor, cause the device to utilize the numerical value as a blood glucose level.

17. The non-transitory computer readable medium of claim 13, further comprising instructions that, when executed by the processor, cause the device to:

present a virtual numeric keypad on the display in response to selection of the one of the one or more objects, and receive the numerical value via the virtual numeric keypad.

18. The non-transitory computer readable medium of claim 12, further comprising instructions that, when executed by the processor, cause the device to present a view calculation object adjacent the calculated bolus, the view calculation object being selectable to display on the display how the calculated bolus was calculated based on the numerical value.

19. The non-transitory computer readable medium of claim 12, further comprising instructions that, when executed by the processor, cause the device to:

present a selectable stop insulin object on the display while the calculated bolus is being delivered;

receive user input selecting the stop insulin object while the calculated bolus delivery is being delivered; and transmit an operating command to the portable infusion pump to stop delivery of the calculated bolus in response to the selection of the stop insulin object.

20. The non-transitory computer readable medium of claim 12, further comprising instructions that, when executed by the processor, cause the device to:

present a plurality of discrete bolus status indicator objects on the display after transmitting the operating command to the portable infusion pump to cause the portable infusion pump to deliver the calculated bolus to the user;

change an appearance of the plurality of discrete bolus status indicator objects while the calculated bolus is being delivered; and stop changing appearance of the plurality of discrete bolus status indicator objects when the calculated bolus delivery is completed.

* * * * *